US011538996B2

(12) United States Patent
Voges et al.

(10) Patent No.: US 11,538,996 B2
(45) Date of Patent: Dec. 27, 2022

(54) MATERIALS FOR ORGANIC ELECTROLUMINESCENT DEVICES

(71) Applicant: Merck Patent GmbH, Darmstadt (DE)

(72) Inventors: Frank Voges, Bad Duerkheim (DE); Teresa Mujica-Fernaud, Darmstadt (DE); Elvira Montenegro, Weinheim (DE)

(73) Assignee: MERCK PATENT GMBH, Darmstadt (DE)

( * ) Notice: Subject to any disclaimer, the term of this patent is extended or adjusted under 35 U.S.C. 154(b) by 510 days.

(21) Appl. No.: 16/562,496

(22) Filed: Sep. 6, 2019

(65) Prior Publication Data

US 2020/0006657 A1 Jan. 2, 2020

Related U.S. Application Data

(63) Continuation of application No. 16/079,151, filed as application No. PCT/EP2017/000079 on Jan. 24, 2017, now Pat. No. 10,454,041.

(30) Foreign Application Priority Data

Feb. 23, 2016 (EP) .................................. 16156960

(51) Int. Cl.
| | | |
|---|---|---|
| *H01L 51/00* | (2006.01) | |
| *C07C 211/56* | (2006.01) | |
| *C07C 211/61* | (2006.01) | |
| *C07C 25/22* | (2006.01) | |
| *C07C 17/269* | (2006.01) | |
| *C07C 17/35* | (2006.01) | |
| *H01L 51/50* | (2006.01) | |
| *C07D 307/91* | (2006.01) | |
| *C07C 25/18* | (2006.01) | |
| *C07D 209/86* | (2006.01) | |
| *C07D 333/76* | (2006.01) | |
| *C07C 211/54* | (2006.01) | |
| *C07D 411/12* | (2006.01) | |
| *C07C 17/263* | (2006.01) | |

(52) U.S. Cl.
CPC .......... *H01L 51/006* (2013.01); *C07C 17/263* (2013.01); *C07C 17/269* (2013.01); *C07C 17/35* (2013.01); *C07C 25/18* (2013.01); *C07C 25/22* (2013.01); *C07C 211/54* (2013.01); *C07C 211/56* (2013.01); *C07C 211/61* (2013.01); *C07D 209/86* (2013.01); *C07D 307/91* (2013.01); *C07D 333/76* (2013.01); *C07D 411/12* (2013.01); *H01L 51/008* (2013.01); *H01L 51/0059* (2013.01); *H01L 51/0061* (2013.01); *H01L 51/0072* (2013.01); *H01L 51/0073* (2013.01); *H01L 51/0074* (2013.01); *H01L 51/5096* (2013.01); *H01L 51/5056* (2013.01); *H01L 51/5092* (2013.01); *Y02E 10/549* (2013.01)

(58) Field of Classification Search
CPC ............... H01L 51/006; H01L 51/0059; H01L 51/0061; H01L 51/0072; H01L 51/0073; H01L 51/0074; H01L 51/008; H01L 51/5096; H01L 51/5056; H01L 51/5092; H01L 51/5088; C07C 17/263; C07C 17/269; C07C 17/35; C07C 25/18; C07C 25/22; C07C 211/54; C07C 211/56; C07C 211/61; C07D 209/86; C07D 307/91; C07D 333/76; C07D 411/12; Y02E 10/549

See application file for complete search history.

(56) References Cited

U.S. PATENT DOCUMENTS

| | | |
|---|---|---|
| 2011/0193074 A1 | 8/2011 | Lee et al. |
| 2015/0065730 A1* | 3/2015 | Montenegro ......... C07C 211/58 548/440 |
| 2015/0179948 A1 | 6/2015 | Zeng et al. |
| 2016/0276600 A1* | 9/2016 | Park ...................... C09K 11/025 |
| 2018/0026187 A1 | 1/2018 | Park et al. |
| 2018/0033966 A1 | 2/2018 | Park et al. |
| 2018/0212149 A1* | 7/2018 | Pfister .................. C07D 209/86 |
| 2018/0219156 A1* | 8/2018 | Mujica-Fernaud .......................... H01L 51/0052 |
| 2018/0370938 A1* | 12/2018 | Voges ................... C07C 211/61 |

FOREIGN PATENT DOCUMENTS

| | | |
|---|---|---|
| CN | 102216269 A | 10/2011 |
| CN | 104114672 A | 10/2014 |
| CN | 104995185 A | 10/2015 |
| CN | 105218302 A | 1/2016 |
| CN | 106796996 A | 5/2017 |

(Continued)

OTHER PUBLICATIONS

Demeter et al., "The influence of aryl substitution on the photophysics of 1-aryl-fluorenones", Tetrahedron Letters, vol. 38, No. 29, 1997, pp. 5219-5222.

(Continued)

*Primary Examiner* — Ahmed N Sefer

(74) *Attorney, Agent, or Firm* — Faegre Drinker Biddle & Reath LLP

(57) ABSTRACT

The present invention relates to a process to produce compounds of the formula (1) which are suitable for use in electronic devices, as well as to intermediate compounds of formula (Int-1) and compounds of formula (1-1) and (1-2) obtained via the process. These compounds are particularly suitable for use organic electroluminescent devices. The present invention also relate to electronic devices, which comprise these compounds.

13 Claims, No Drawings

(56) References Cited

FOREIGN PATENT DOCUMENTS

| | | |
|---|---|---|
| CN | 107922312 A | 4/2018 |
| EP | 2947079 A1 | 11/2015 |
| JP | 2015-513530 A | 5/2015 |
| KR | 10-2015-0051662 A | 5/2015 |
| KR | 10-1520955 B1 | 6/2015 |
| KR | 10-1530885 B1 | 6/2015 |
| KR | 10-1530886 B1 | 6/2015 |
| KR | 10-2015-0136032 A | 12/2015 |
| KR | 101614740 B1 | 4/2016 |
| WO | WO-2013120577 A1 | 8/2013 |
| WO | 2015/022051 A1 | 2/2015 |
| WO | WO-2017016632 A1 | 2/2017 |
| WO | WO-2017026727 A1 | 2/2017 |

OTHER PUBLICATIONS

International Search Report for PCT/EP2017/000079 dated Sep. 14, 2017.
Written Opinion of the International Searching Authority for PCT/EP2017/000079 dated Sep. 14, 2017.

* cited by examiner

MATERIALS FOR ORGANIC ELECTROLUMINESCENT DEVICES

CROSS-REFERENCE TO RELATED APPLICATIONS

This application is a continuation of U.S. patent application Ser. No. 16/079,151 filed Aug. 23, 2018, which is a national stage application (under 35 U.S.C. § 371) of PCT/EP2017/000079, filed Jan. 24, 2017, which claims benefit of European Application No. 16156960.3, filed Feb. 23, 2016, both of which are incorporated herein by reference in their entirety.

The present invention relates to materials for use in electronic devices, in particular in organic electroluminescent devices, and to electronic devices comprising these materials. The present invention also relates to a process for the preparation of these materials and to the intermediate compounds that are prepared with the process.

BACKGROUND OF THE INVENTION

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organo-metallic complexes which exhibit phosphorescence instead of fluorescence (M. A. Baldo et al., *Appl. Phys. Lett.* 1999, 75, 4-6).

In accordance with the prior art, the hole-transport materials used in the hole-transport layer or in the hole-injection layer are, in particular, triaryl-amine derivatives which frequently contain at least two triarylamino groups or at least one triarylamino group and at least one carbazole group. These compounds are frequently derived from diarylamino-substituted triphenyl-amines (TPA type), from diarylamino-substituted biphenyl derivatives (TAD type) or combinations of these base compounds. Furthermore, for example, use is made of spirobifluorene derivatives which are substituted by one to four diarylamino groups (for example in accordance with EP 676461, U.S. Pat. No. 7,714,145).

In EP2814906, spirobifluorene derivatives substituted with a diarylamine group in position 1, 1', 8 or 8' are represented.

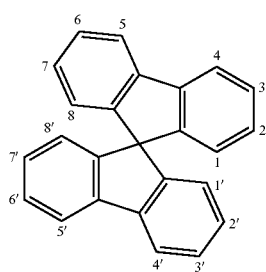

The use of spirobifluorene derivatives substituted in position 1, 1', 8 or 8' in OLEDs is interesting because it leads to OLEDs with good properties, in particular in terms of efficiency and operating voltage.

In the case of these compounds, there is still a demand for alternative materials that can be used in OLEDs devices in order to obtain devices with good properties, in particular in terms of efficiency.

However, it is difficult to synthesize such compounds because the positions 1, 1', 8 or 8' are difficult to access.

Therefore, there is also a demand for processes for the preparation of these compounds with higher reaction yields, in order to reduce the fabrication costs. There is also a demand for processes, which are easy to implement and which enable to obtain compounds with a high purity. The intermediate compounds play a key role in the synthesis of materials for OLEDs. It is important to have some intermediate compounds, which are stable, easy to synthesize and easy to purify in order to increase the efficiency of the synthesis of the OLED materials and thus, to decrease the costs of the synthesis. Intermediate compounds that are stable, easy to synthesize and easy to purify are even more interesting when then can be used in different kind of syntheses in order to obtain different kind of OLED materials.

BRIEF SUMMARY OF THE INVENTION

Thus, a first object of the invention is to provide a process for the preparation of spirobifluorene derivatives substituted with a larger group in position 1, 1', 8 or 8'. A second object of the invention is to provide such compounds, which are suitable for use in a fluorescent or phosphorescent OLED, in particular a phosphorescent OLED, for example as hole-transport material in a hole-transport or exciton-blocking layer or as matrix material in an emitting layer. A third object of the invention is to provide key intermediate compounds for the preparation of spirobifluorene derivatives substituted with a larger group in position 1, 1', 8 or 8'.

It has now been found that the process described below in greater detail achieve the first object and result in very good reaction yield for the preparation of spirobifluorene derivatives substituted with a larger group in position 1, 1', 8 or 8'. Furthermore, the intermediate compounds obtained through the different steps of the process described below are easily purified, which lead to a more efficient synthesis in terms of cost and time. The products of the synthesis also exhibit a very high purity. It has also been found that certain compounds described below achieve the second object of the invention and result in OLEDs with a very high efficiency. Finally, it has been found that the intermediate compounds described below achieve the third object of the invention and can be used in the preparation of spirobifluorene derivatives substituted with a larger group in position 1, 1', 8 or 8'.

DETAILED DESCRIPTION OF THE INVENTION

The present invention therefore relates to a process for the preparation of a compound according to formula (1), formula (1)

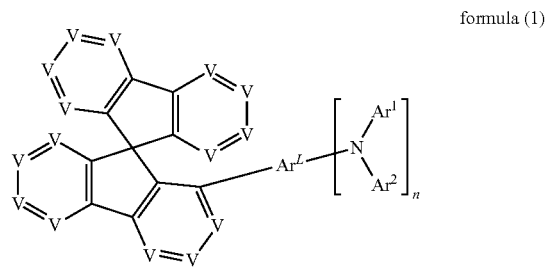

where the process comprises the following steps:
(a) Preparation of a compound of formula (Int-1) by a route (a-1) or by a route (a-2) as follows:

Route (a-1):

(a-1-1) Preparation of a compound of formula (p-3) by first a metalation reaction, preferably a lithiation reaction or a Grignard reaction, of a compound of formula (p-1), followed by a cyclization reaction, preferably under acidic conditions or using a Lewis acid, between a fluorenone derivative of formula (p-2) with a compound of formula (p-1i):

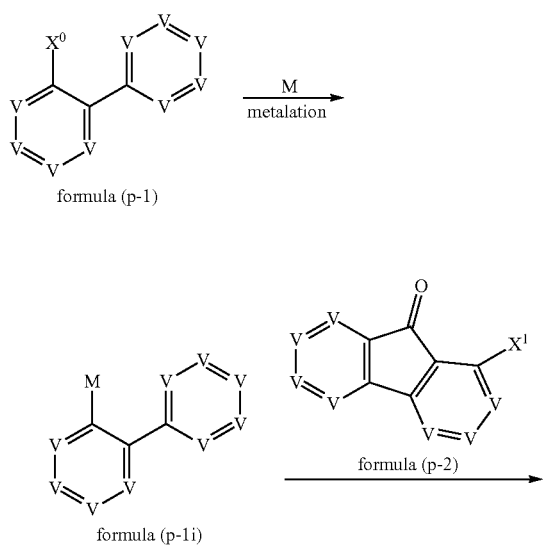

(a-1-2) Preparation of a compound of formula (Int-1) by a chemical reaction, preferably a Suzuki reaction, between a compound of formula (p-3) and a compound of formula (p-4):

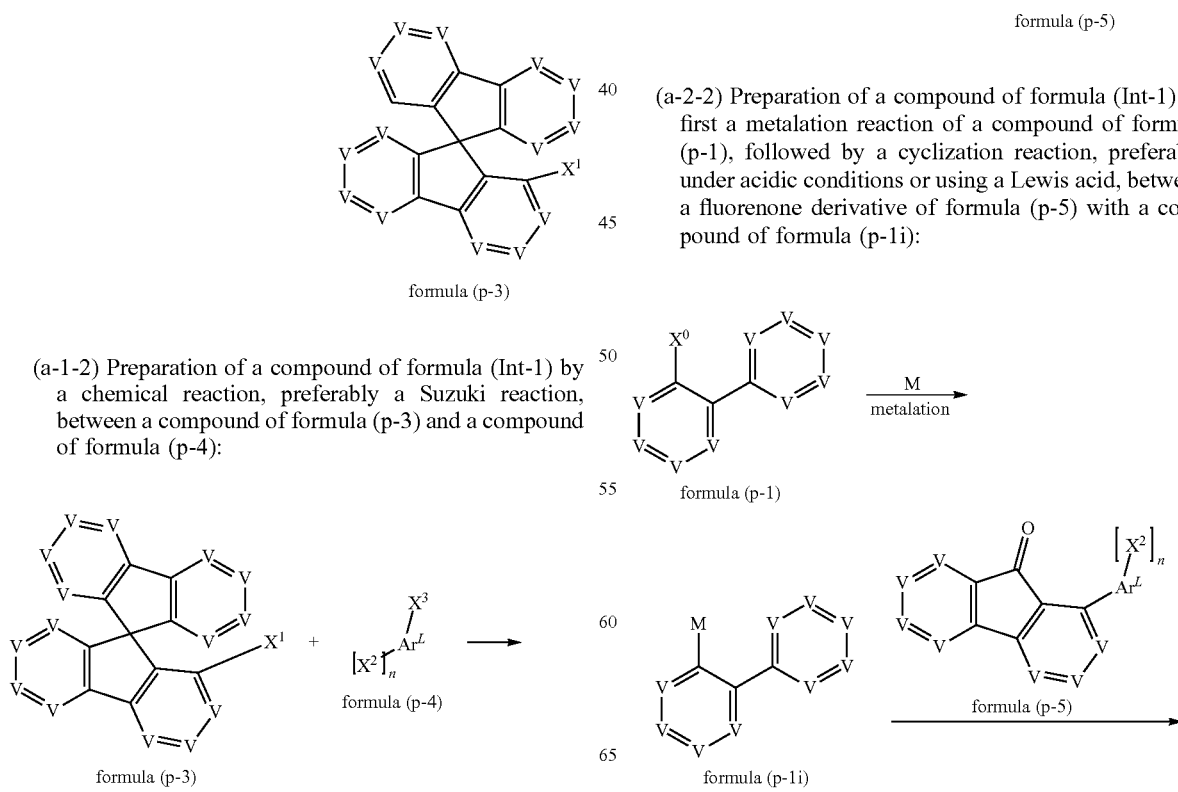

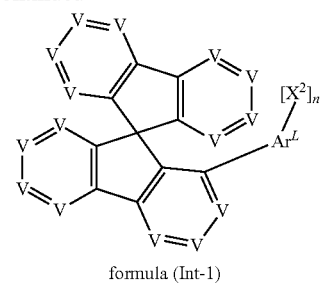

formula (Int-1)

Route (a-2):

(a-2-1) Preparation of a compound of formula (p-5) by a chemical reaction, preferably selected from a Suzuki reaction, between a fluorenone derivative of formula (p-2) with a compound of formula (p-4):

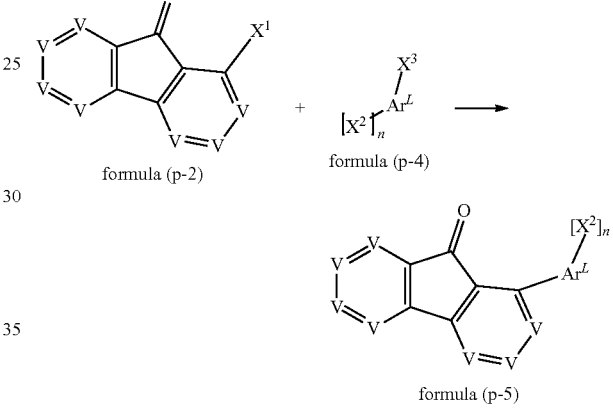

(a-2-2) Preparation of a compound of formula (Int-1) by first a metalation reaction of a compound of formula (p-1), followed by a cyclization reaction, preferably under acidic conditions or using a Lewis acid, between a fluorenone derivative of formula (p-5) with a compound of formula (p-1i):

-continued

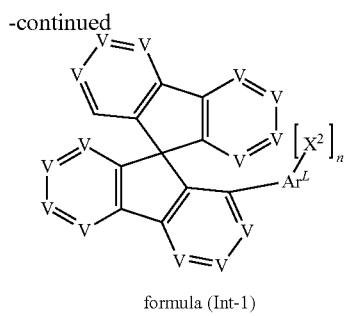

formula (Int-1)

(b) Preparation of a compound of formula (1) by a chemical reaction, selected from amination reactions, more preferably from Buchwald-Hartwig amination reactions, between a compound of formula (Int-1) with a compound of formula (p-6):

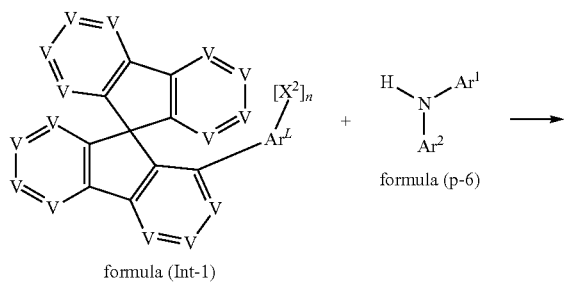

formula (Int-1)   formula (p-6)

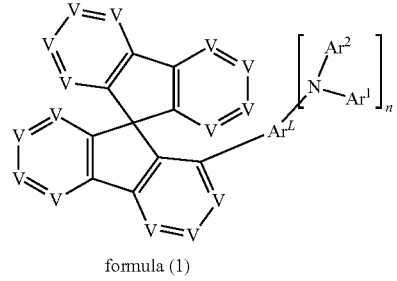

formula (1)

where the following applies to the symbols used above:

V is CR or N, with the proviso that there are maximum three N per 6-membered-ring, or two adjacent groups V (V—V or V=V) stand for a group of the formula (V-1) or (V-2),

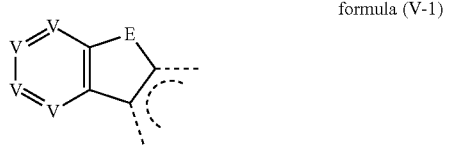

formula (V-1)

formula (V-2)

in which the dashed bonds indicate the linking to the spirobifluorene skeleton;

E is a divalent bridge selected from $N(R^0)$, $B(R^0)$, O, $C(R^0)_2$, $Si(R^0)_2$, $C=NR^0$, $C=C(R^0)_2$, S, S=O, $SO_2$, $P(R^0)$ and $P(=O)R^0$;

$Ar^L$ is an aromatic or heteroaromatic ring system having 5 to 40 aromatic ring atoms, which may in each case be substituted by one or more radicals $R^1$;

$Ar^1$, $Ar^2$ are, identically or differently, an aromatic or heteroaromatic ring system having 5 to 60 aromatic ring atoms, which may in each case also be substituted by one or more radicals $R^2$; $Ar^1$ and $Ar^2$ here may also be connected via a single bond or a divalent bridge selected from —$N(R^2)$—, —O—, —S—, —$C(R^2)_2$—, —$C(R^2)_2$—$C(R^2)_2$—, —$Si(R^2)_2$— and —$B(R^2)$—;

$R^0$, R, $R^2$ are selected on each occurrence, identically or differently, from the group consisting of H, D, F, CHO, CN, $C(=O)Ar^3$, $P(=O)(Ar^3)_2$, $S(=O)Ar^3$, $S(=O)_2Ar^3$, $N(Ar^3)_2$, $Si(R^3)_3$, $B(OR^3)_2$, $OSO_2R^3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^3$, where in each case one or more non-adjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $P(=O)(R^3)$, SO, $SO_2$, O, S or $CONR^3$ and where one or more H atoms may be replaced by D, F or CN, an aromatic or heteroaromatic ring system having 5 to 60 aromatic ring atoms, which may in each case be substituted by one or more radicals $R^3$, and an aryloxy group having 5 to 60 aromatic ring atoms, which may be substituted by one or more radicals $R^3$, where two adjacent substituents $R^0$, two adjacent substituents R or two adjacent substituents $R^2$ may optionally form a mono- or polycyclic, aliphatic ring system or aromatic ring system, which may be substituted by one or more radicals $R^3$;

$R^1$ is selected on each occurrence, identically or differently, from the group consisting of H, D, F, CHO, CN, $C(=O)Ar^3$, $P(=O)(Ar^3)_2$, $S(=O)Ar^3$, $S(=O)_2Ar^3$, $Si(R^3)_3$, $B(OR^3)_2$, $OSO_2R^3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^3$, where in each case one or more non-adjacent $CH_2$ groups may be replaced by $R^3C=CR^3$, $C\equiv C$, $Si(R^3)_2$, $Ge(R^3)_2$, $Sn(R^3)_2$, $C=O$, $C=S$, $C=Se$, $P(=O)(R^3)$, SO, $SO_2$, O, S or $CONR^3$ and where one or more H atoms may be replaced by D, F or CN, an aromatic or heteroaromatic ring system having 5 to 60 aromatic ring atoms, which may in each case be substituted by one or more radicals $R^3$, and an aryloxy group having 5 to 60 aromatic ring atoms, which may be substituted by one or more radicals $R^3$, where two adjacent substituents $R^1$ may optionally form a mono- or polycyclic, aliphatic ring system or aromatic ring system, which may be substituted by one or more radicals $R^3$;

$R^3$ is selected on each occurrence, identically or differently, from the group consisting of H, D, F, CHO, CN, $C(=O)Ar^3$, $P(=O)(Ar^3)_2$, $S(=O)Ar^3$, $S(=O)_2Ar^3$, $Si(R^4)_3$, $B(OR^4)_2$, $OSO_2R^4$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^4$, where in each case one or more non-adjacent $CH_2$ groups may be replaced by $R^4C=CR^4$, $C\equiv C$, $Si(R^4)_2$, $Ge(R^4)_2$, $Sn(R^4)_2$, $C=O$, $C=S$, $C=Se$, $P(=O)(R^4)$, SO, $SO_2$, O, S or $CONR^4$ and where one or more H atoms may be replaced by D, F, or CN, an aromatic or heteroaromatic ring system having 5 to 60 aromatic ring atoms, which may in each case be substituted by one or more radicals $R^4$, and an aryloxy group having 5 to 60 aromatic ring atoms, which may be substituted by one or more radicals $R^4$, where two adjacent substituents $R^3$ may optionally form a mono- or polycyclic, aliphatic ring system or aromatic ring system, which may be substituted by one or more radicals $R^4$;

$R^4$ is selected on each occurrence, identically or differently, from the group consisting of H, D, F, CN, a straight-chain alkyl, alkoxy or thioalkyl group having 1 to 20 C atoms or a branched or cyclic alkyl, alkoxy or thioalkyl group having 3 to 20 C atoms, where in each case one or more non-adjacent $CH_2$ groups may be replaced by SO, $SO_2$, O, S and where one or more H atoms may be replaced by D or F, and aromatic or heteroaromatic ring system having 5 to 24 C atoms;

$Ar^3$ is selected, identically or differently on each occurrence, from the group consisting of an aromatic or heteroaromatic ring system having 5 to 24 aromatic ring atoms, more preferably having 5 to 18 aromatic ring atoms, which may in each case also be substituted by one or more radicals $R^4$;

n is 1, 2 or 3;

$X^0$ is selected from Cl, Br or I;

$X^1$ is Cl, Br, I, trifluoromethanesulfonate ($CF_3SO_3$—), tosylate ($CH_3C_6H_4SO_3$—), mesylate ($CH_3SO_3$—), or —$B(OR^B)_2$;

$R^B$ is H, a straight-chain alkyl having 1 to 10 C atoms, where two substituents $R^B$ may form a monocyclic aliphatic ring system that may be substituted by an alkyl group having 1 to 3 C atoms;

$X^2$ is Cl, Br, I, trifluoromethanesulfonate ($CF_3SO_3$—), tosylate ($CH_3C_6H_4SO_3$—) or mesylate ($CH_3SO_3$—);

$X^3$ is Cl, Br, I or —$B(OR^B)_2$; with the proviso that one of the group $X^1$ or $X^3$ must stand for —$B(OR^B)_2$ but not both groups ($X^1$ and $X^3$) stand for —$B(OR^B)_2$ at the same time; and M is Lithium or Magnesium.

In routes (a-1-1) and (a-2-2), metalation reactions takes place.

These well-known reactions are performed under an inert atmosphere, for example under argon or nitrogen. The metalation in route (a-1-1) and (a-2-2) may be a lithiation reaction. Lithiation reactions generally take place at a temperature from −100° C. to 20° C., preferably from −78° C. to 0° C. Examples of suitable solvents for the lithiation reaction are THF, Dioxane, Dimethoxyethane and Cyclopentylmethylether. Examples of suitable organolithiums used in a lithiation reaction are n-Butyllithium, sec-Butyllithium and tert-Butyllithium. The metalation may be a Grignard reaction. Grignard reactions are well-known organic reactions, which generally take place at a temperature from −20° C. to 100° C., preferably from room temperature (more preferably 20° C.) to 40° C., in solvents like THF, Dioxane, Dimethoxyethane, Cyclopentylmethylether and toluene.

The metalation reaction in routes (a-1-1) and (a-2-2) is followed by the addition to the cold reaction media under an inert atmosphere of a fluorenone derivative, which leads to the formation of a tertiary alcohol. This is followed by a cyclization under acidic conditions or using a Lewis acid.

The cyclization reaction takes place at a temperature from 20 to 110° C., preferably from 30 to 90° C. Examples of suitable acids and Lewis acids are HCl, HBr, Orthophosphoric acid, $H_2SO_4$, $BF_3$, Methanesulfonic acid, Polyphosphoric acids, $FeCl_3$ and sulfonic acid resin (for example Amberlist®). Example of suitable solvents for the cyclization reaction are: THF, acetic acid, $CH_2Cl_2$, Toluene, Dioxane, $H_2O$ and $H_2SO_4$. Preferred suitable combinations of solvents and acids or Lewis acids for the cyclization reaction are the following ones: acetic acid with HCl or $H_2SO_4$, toluene with Amberlist, $CH_2Cl_2$ with Methanesulfonic acid or $BF_3$, Dioxane with HCl and THF with HCl.

The chemical reaction in routes (a-1-2) and (a-2-1) is preferably a Suzuki reaction, which is a well-known chemical reaction. The Suzuki reaction generally takes place at temperatures from room temperature (around 20° C.) to the reflux temperature of the solvent. Typical solvents for Suzuki reactions are toluene, THF, Dimethylformamide, Dioxane, Cyclopentylmethylether, Dimethylether, Xylene, Ethylenglycoldimethylether, Ethanol and water. Typical catalysators used in a Suzuki reaction are: Bis(triphenylphosphin)-Pd(II)-dichlorid, $PdCl_2$(dppf), Palladium Tetrakis, $Pd_2$(dba)$_3$-SPhos, $PdCl_2$(PCy)$_3$, $Pd(OAc)_2$—P(t-Bu)$_3$, $Pd(OAc)_2$-Tri-o-tolylphosphine and $Pd(OAc)_2$—S-Phos. Typical bases used in Suzuki reactions are: $Na_2CO_3$, $K_2CO_3$, CsF, Boron salts and hydrates, $K_3PO_4$, NaOH, KOH, KF, KAcO, $Cs_2CO_3$, KOtBu and $NEt_3$.

Alternatively, the process described below can be used for the preparation of the compounds of formula (1). This alternative process (linear synthesis) comprises the steps (a), (b) and (c):

(a) Preparation of a compound of formula (p-5) by a chemical reaction, preferably a Suzuki reaction, between a fluorenone derivative of formula (p-2) with a compound of formula (p-4):

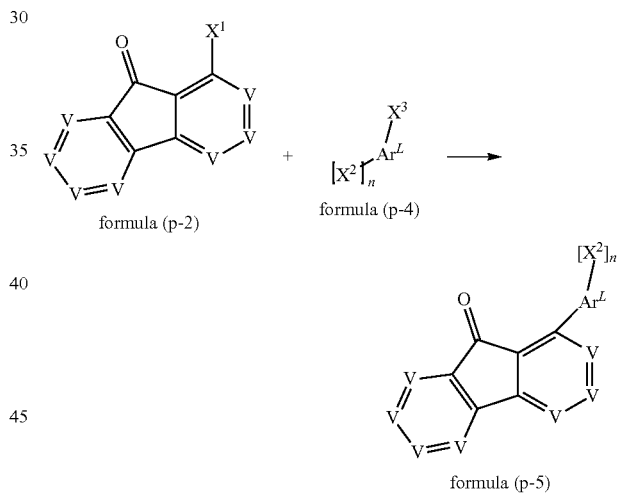

(b) Preparation of a compound of formula (Int-1') by a chemical reaction selected from amination reactions, more preferably from Buchwald-Hartwig amination reactions, between a compound of formula (p-5) and a compound of formula (p-6):

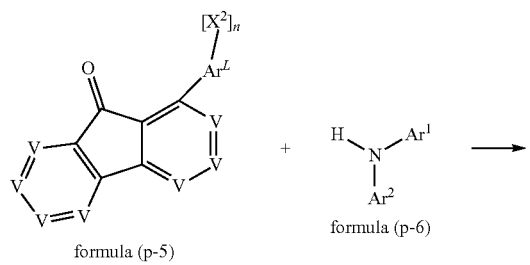

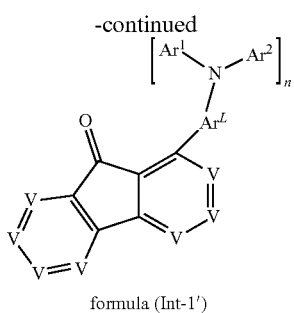

formula (Int-1')

(c) Preparation of a compound of formula (1) by a metalation reaction of a compound of formula (p-1), followed by a cyclization reaction, preferably under acidic conditions or using a Lewis acid, between the compound of formula (Int-1') with a compound of formula (p-1i):

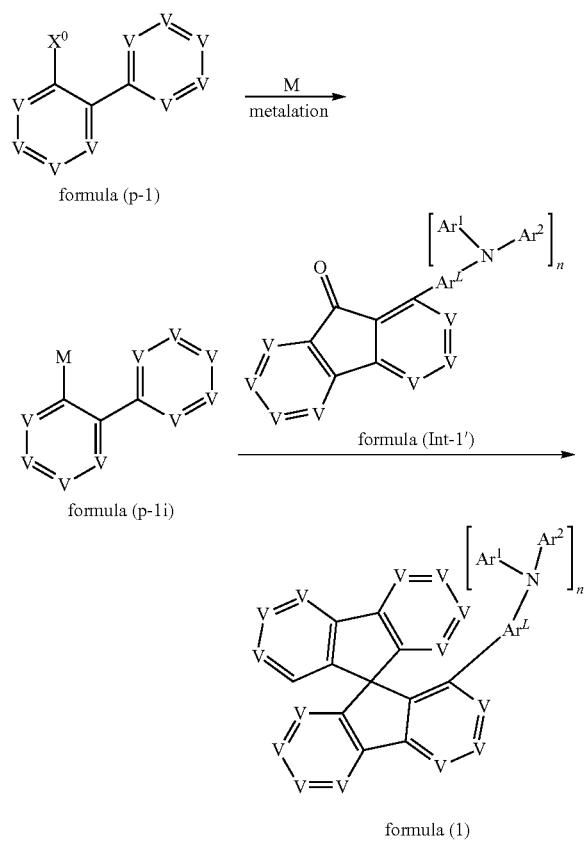

where the symbols and indices are the same as above.

Nevertheless, this alternative process is less interesting because it leads to specific intermediate compounds of formula (Int-1') that already bear the substituents $Ar^1$ and $Ar^2$. On the contrary, the intermediate compound of formula (Int-1) according to the invention do not bear any groups $Ar^1$ and $Ar^2$, so that they may be isolated and used in the last step of the process for the fabrication of different compounds of formula (1). Therefore, the alternative process leading to the formation of the intermediate compound of formula (Int-1') is not preferred.

In accordance with a preferred embodiment of the invention, n is equal to 1.

It is preferable that the group $-B(OR^B)_2$ stands for $-B(OH)_2$ or for a picanolboronester of the following formula ($R^B$-1):

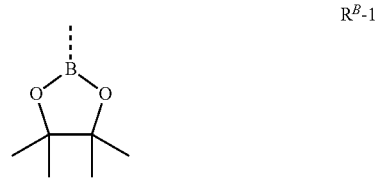

where the dashed bond indicate the bond to the group, which is substituted by $X^1$ or $X^3$.

In accordance with another preferred embodiment, $X^1$ is Cl, Br, or I and $X^3$ is $-B(OR^B)_2$. More preferably, $X^1$ is Cl and $X^3$ is a group ($R^B$-1) as depicted above.

It is preferred that $X^2$ is Br, Cl or I.

In accordance with a preferred embodiment, V is CR.

In accordance with a preferred embodiment, $R^0$ is selected on each occurrence, identically or differently, from the group consisting of H, D, F, CN, $Si(R^3)_3$, a straight-chain alkyl group having 1 to 10 C atoms or a branched or cyclic alkyl group having 3 to 10 C atoms, each of which may be substituted by one or more radicals $R^3$, an aryl or heteroaryl group having 5 to 18 aromatic ring atoms, which may in each case be substituted by one or more radicals $R^3$, where two or more adjacent substituents $R^0$ may optionally form a mono- or polycyclic, aliphatic ring system or aromatic ring system, which may be substituted by one or more radicals $R^3$.

In accordance with a preferred embodiment, R, $R^1$ and $R^2$ are selected, identically or differently on each occurrence, from the group consisting of H, D, F, CN, a straight-chain alkyl or alkoxy group having 1 to 10 C atoms or a branched or cyclic alkyl or alkoxy group having 3 to 10 C atoms, each of which may be substituted by one or more radicals $R^3$, where one or more non-adjacent $CH_2$ groups may be replaced by O and where one or more H atoms may be replaced by F, an aromatic or heteroaromatic ring system having 5 to 24 aromatic ring atoms, which may in each case be substituted by one or more radicals $R^3$.

In a very preferred embodiment of the invention, R, $R^1$ and $R^2$ are selected, identically or differently on each occurrence, from the group consisting of H, D, F, CN, a straight-chain alkyl having 1 to 5 C atoms or a branched or cyclic alkyl group having 3 to 6 C atoms, or an aryl or heteroaryl group having 5 to 18 aromatic ring atoms, which may in each case be substituted by one or more radicals $R^3$.

In accordance with a preferred embodiment, R, $R^1$ and $R^2$ are selected, identically or differently on each occurrence, from the group consisting of H, an aryl or heteroaryl group having 5 to 18 aromatic ring atoms, which may in each case be substituted by one or more radicals $R^3$.

In a preferred embodiment of the invention, $R^3$ is selected, identically or differently on each occurrence, from the group consisting of H, D, F, CN, a straight-chain alkyl or alkoxy group having 1 to 10 C atoms or a branched or cyclic alkyl or alkoxy group having 3 to 10 C atoms, each of which may be substituted by one or more radicals $R^4$, where one or more non-adjacent $CH_2$ groups may be replaced by O and where one or more H atoms may be replaced by F, an aromatic or heteroaromatic ring system having 5 to 24 aromatic ring atoms, which may in each case be substituted by one or more radicals $R^4$.

In a very preferred embodiment of the invention, $R^3$ is selected, identically or differently on each occurrence, from the group consisting of H, D, F, CN, a straight-chain alkyl having 1 to 5 C atoms or a branched or cyclic alkyl group having 3 to 6 C atoms, or an aryl or heteroaryl group having 5 to 18 aromatic ring atoms, which may in each case be substituted by one or more radicals $R^4$.

In accordance with another preferred embodiment, the group $Ar^L$ in formulae (p-4), (p-5), (Int-1), (Int-1') and (1) is selected from aromatic or heteroaromatic ring systems having 5 to 18 aromatic ring atoms, which may in each case also be substituted by one or more radicals $R^1$.

In accordance with a preferred embodiment, the group $Ar^L$ in formulae (p-4), (p-5), (Int-1), (Int-1') and (1) is selected from the groups of formulae ($Ar^L$-1) to ($Ar^L$-24),

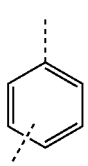

$Ar^L$-1

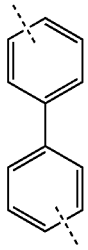

$Ar^L$-2

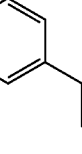

$Ar^L$-3

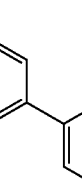

$Ar^L$-4

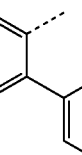

$Ar^L$-5

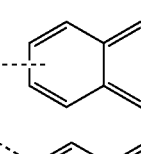

$Ar^L$-6

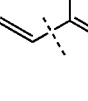

$Ar^L$-7

-continued

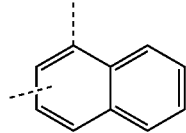

$Ar^L$-8

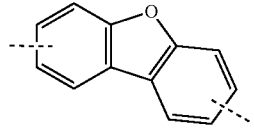

$Ar^L$-9

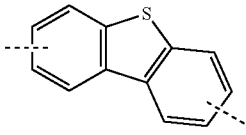

$Ar^L$-10

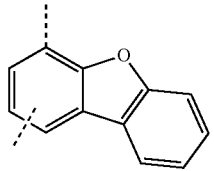

$Ar^L$-11

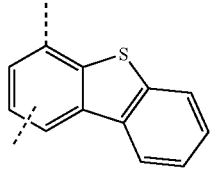

$Ar^L$-12

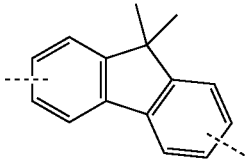

$Ar^L$-13

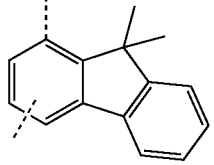

$Ar^L$-14

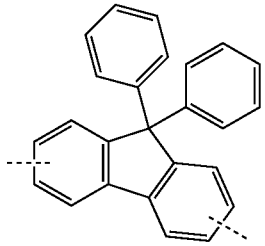

$Ar^L$-15

13
-continued

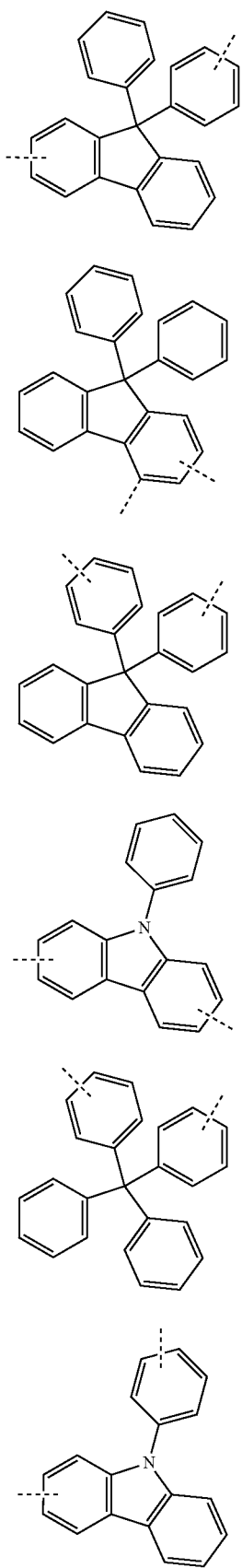

Ar$^L$-16

Ar$^L$-17

Ar$^L$-18

Ar$^L$-19

Ar$^L$-20

Ar$^L$-21

14
-continued

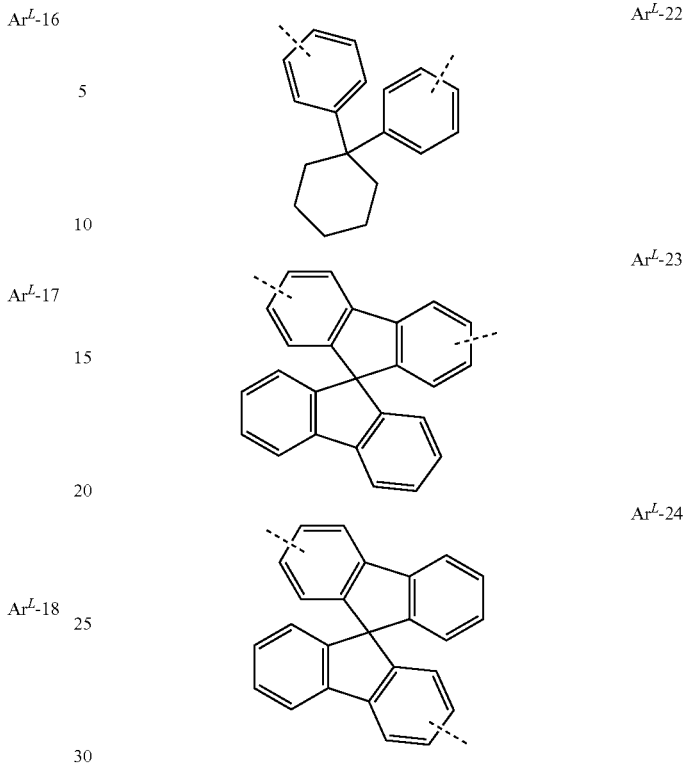

Ar$^L$-22

Ar$^L$-23

Ar$^L$-24 where the dashed bonds in (Ar$^L$-1) to (Ar$^L$-24) indicate,
when n=1,
  the bonds to the spirobifluorene skeleton and to the amine
    group NAr$^1$Ar$^2$ in formula (1);
  the bonds to the spirobifluorene skeleton and to the group
    X$^2$ in formula (Int-1);
  the bonds to the group X$^2$ and to the group —B(OR)$_2$ in
    formula (p-4);
  the bonds to the fluorenone skeleton and to the group X$^2$
    in formula (p-5);
  the bonds to the fluorenone skeleton and to the nitrogen of
    the group NAr$^1$Ar$^2$ in formula (Int-1'); and
when n=2, the dashed bonds in (Ar$^L$-1) to (Ar$^L$-24) indicate,
  in formula (1), the bonds to the spirobifluorene skeleton
    and to one of the amine group NAr$^1$Ar$^2$, whereas the
    second group NAr$^1$Ar$^2$ may be linked at each free
    position in formulae (Ar$^L$-1) to (Ar$^L$-24);
  in formula (Int-1), the bonds to the spirobifluorene skeleton and to one of the group X$^2$, whereas the second
    group X$^2$ may be linked at each free position in formulae (Ar$^L$-1) to (Ar$^L$-24);
  in formula (p-4), the bonds to the group X$^2$ and to the
    group —B(OR)$_2$, whereas the second group X$^2$ may be
    linked at each free position in formulae (Ar$^L$-1) to
    (Ar$^L$-24);
  in formula (p-5), the bonds to the fluorenone skeleton and
    to the group X$^2$, whereas the second group X$^2$ may be
    linked at each free position in formulae (Ar$^L$-1) to
    (Ar$^L$-24);
  in formula (Int-1'), the bonds to the fluorenone skeleton
    and to the nitrogen of the group NAr$^1$Ar$^2$, whereas the
    second group X$^2$ may be linked at each free position in
    formulae (Ar$^L$-1) to (Ar$^L$-24); and
when n=3, the dashed bonds in (Ar$^L$-1) to (Ar$^L$-24) indicate,
  in formula (1), the bonds to the spirobifluorene skeleton
    and to one of the amine group NAr$^1$Ar$^2$, whereas the second and third groups NAr$^1$Ar$^2$ may be linked at each free position in formulae (Ar$^L$-1) to (Ar$^L$-24);

in formula (Int-1), the bonds to the spirobifluorene skeleton and to one of the group X$^2$, whereas the second and third groups X$^2$ may be linked at each free position in formulae (Ar$^L$-1) to (Ar$^L$-24);

in formula (p-4), the bonds to the group X$^2$ and to the group —B(OR)$_2$, whereas the second and third groups X$^2$ may be linked at each free position in formulae (Ar$^L$-1) to (Ar$^L$-24);

in formula (p-5), the bonds to the fluorenone skeleton and to the group X$^2$, whereas the second and third groups X$^2$ may be linked at each free position in formulae (Ar$^L$-1) to (Ar$^L$-24);

in formula (Int-1'), the bonds to the fluorenone skeleton and to the nitrogen of the group NAr$^1$Ar$^2$, whereas the second and third groups X$^2$ may be linked at each free position in formulae (Ar$^L$-1) to (Ar$^L$-24);

and where the groups (Ar$^L$-1) to (Ar$^L$-24) may be substituted at each free position by a group R$^1$ but are preferably unsubstituted.

Among the groups (Ar$^L$-1) to (Ar$^L$-24), the groups (Ar$^L$-1), (Ar$^L$-2), (Ar$^L$-6), (Ar$^L$-7), (Ar$^L$-13), (Ar$^L$-20) and (Ar$^L$-23) are preferred.

Suitable groups Ar$^L$ in formulae (p-4), (p-5), (Int-1), (Int-1') and (1) are the groups of formulae (Ar$^L$-25) to (Ar$^L$-102), Ar$^L$-25

Ar$^L$-26

Ar$^L$-27

Ar$^L$-28

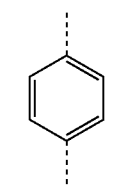

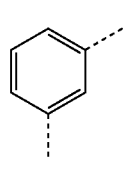

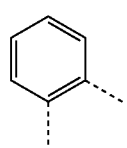

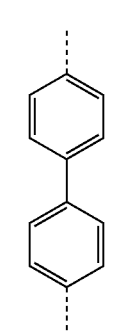

-continued

Ar$^L$-29

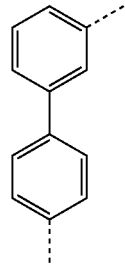

Ar$^L$-30

Ar$^L$-31

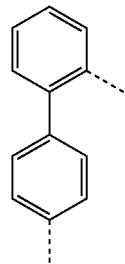

Ar$^L$-32

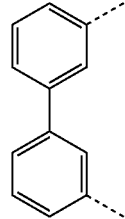

Ar$^L$-33

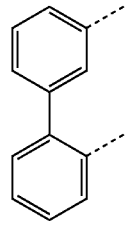

Ar$^L$-34

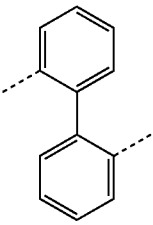

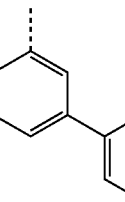

-continued
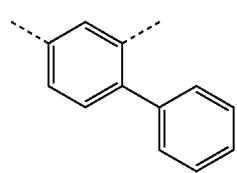
Ar^L-35
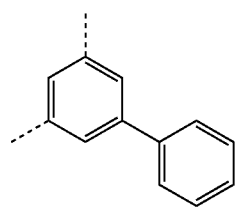
Ar^L-36
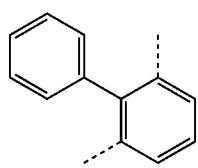
Ar^L-37
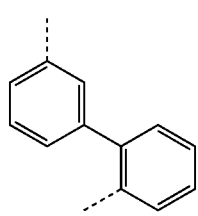
Ar^L-38
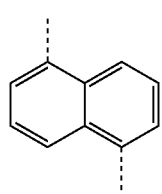
Ar^L-39
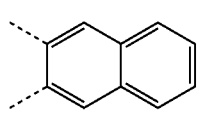
Ar^L-40
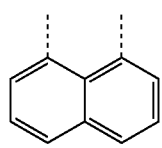
Ar^L-41
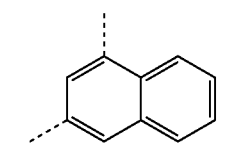
Ar^L-42
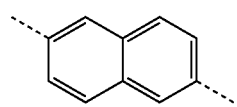
Ar^L-43
-continued
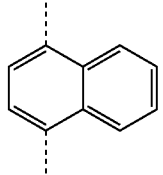
Ar^L-44
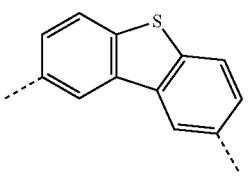
Ar^L-45
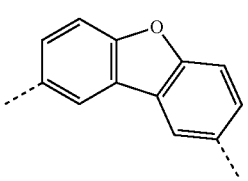
Ar^L-46
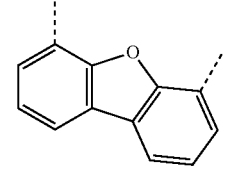
Ar^L-47
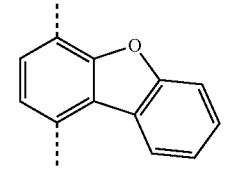
Ar^L-48
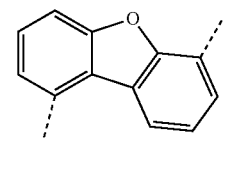
Ar^L-49
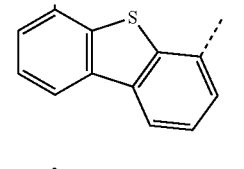
Ar^L-50
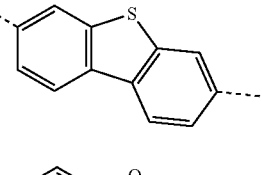
Ar^L-51
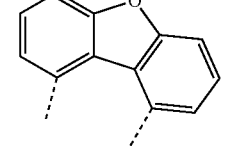
Ar^L-52

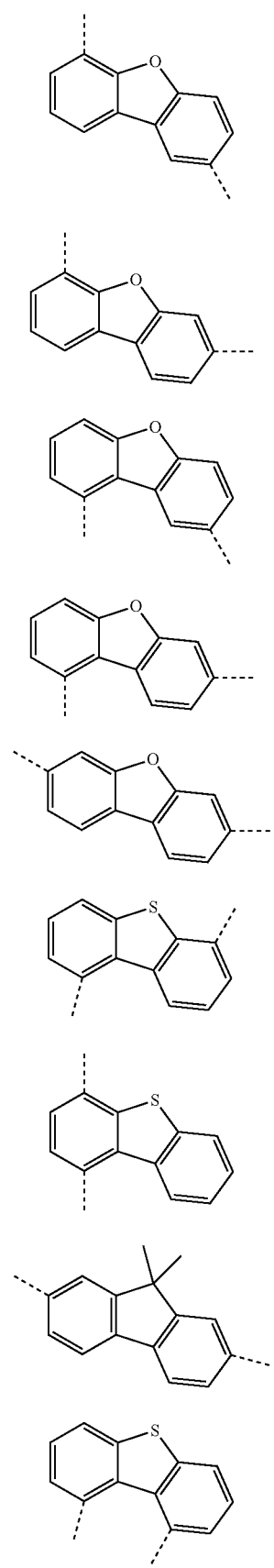
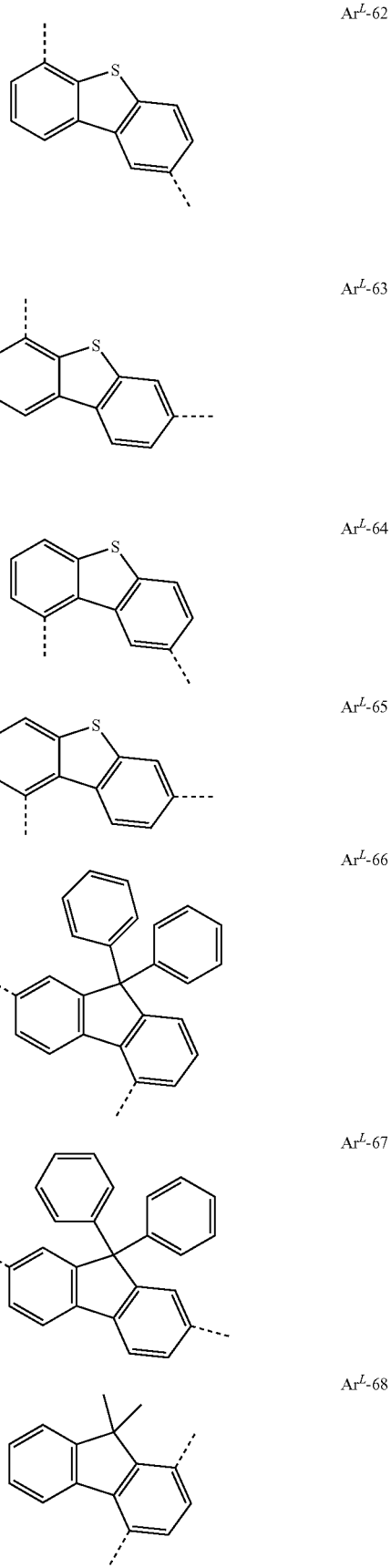

Ar<sup>L</sup>-69 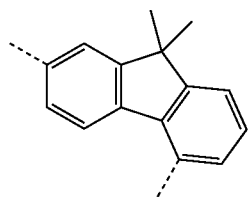
Ar<sup>L</sup>-70 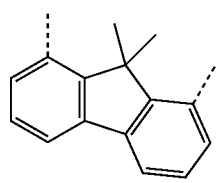
Ar<sup>L</sup>-71 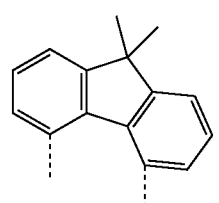
Ar<sup>L</sup>-72 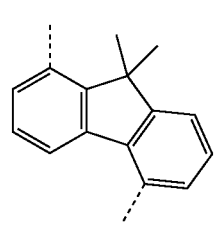
Ar<sup>L</sup>-73 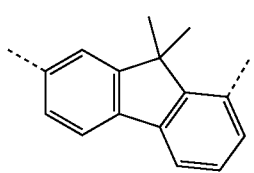
Ar<sup>L</sup>-74 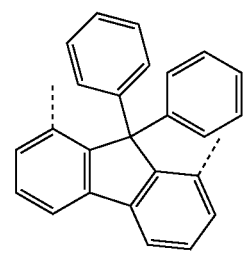
Ar<sup>L</sup>-75 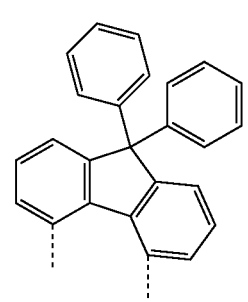
Ar<sup>L</sup>-76 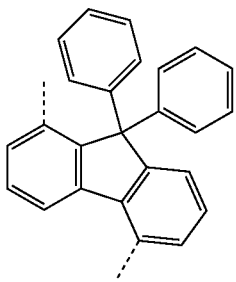
Ar<sup>L</sup>-77 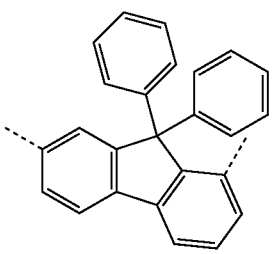
Ar<sup>L</sup>-78 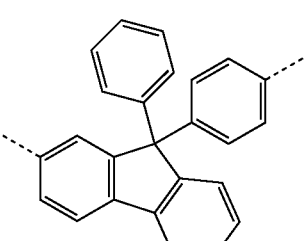
Ar<sup>L</sup>-79 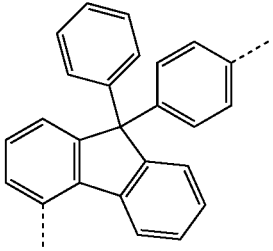
Ar<sup>L</sup>-80 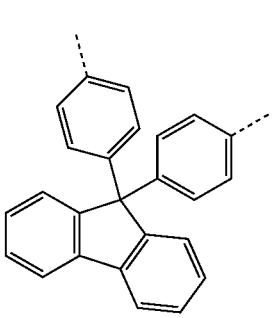

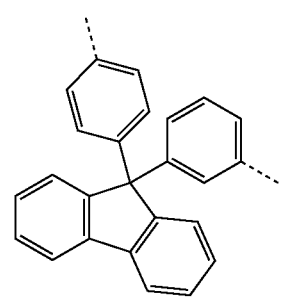 Ar^L-81
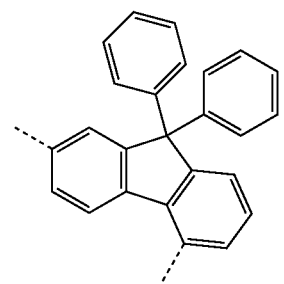 Ar^L-82
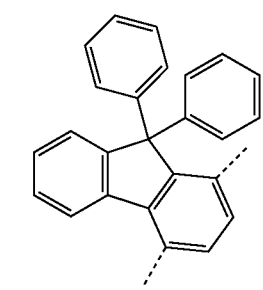 Ar^L-83
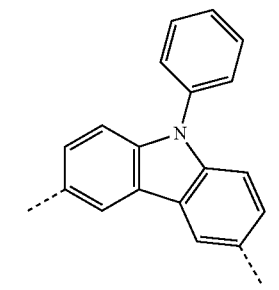 Ar^L-84
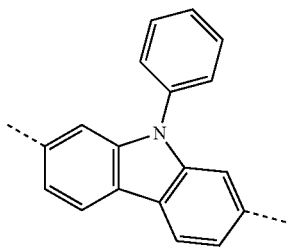 Ar^L-85
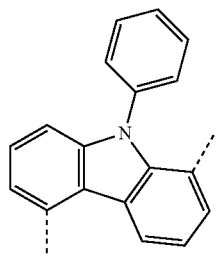 Ar^L-86
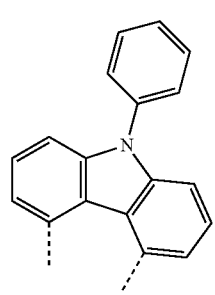 Ar^L-87
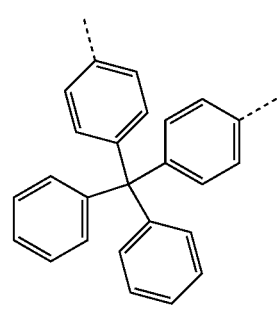 Ar^L-88
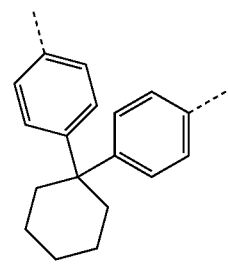 Ar^L-89
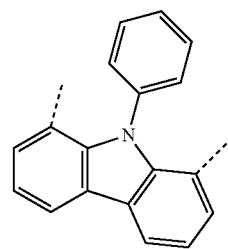 Ar^L-90

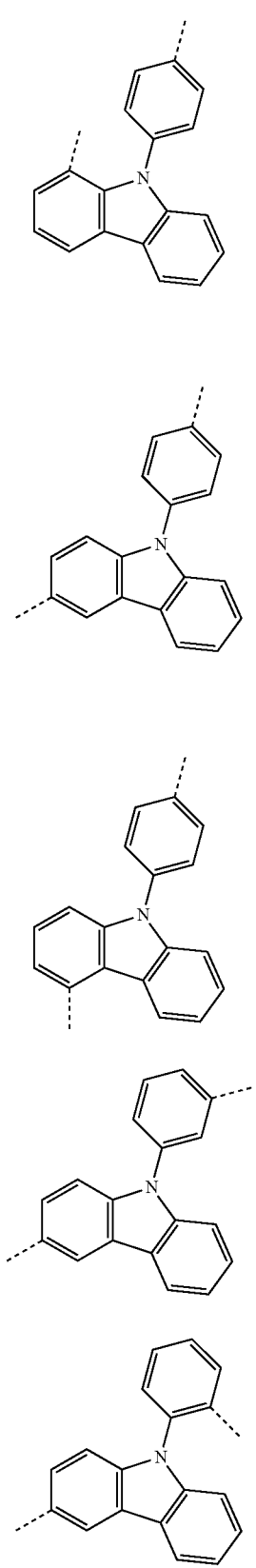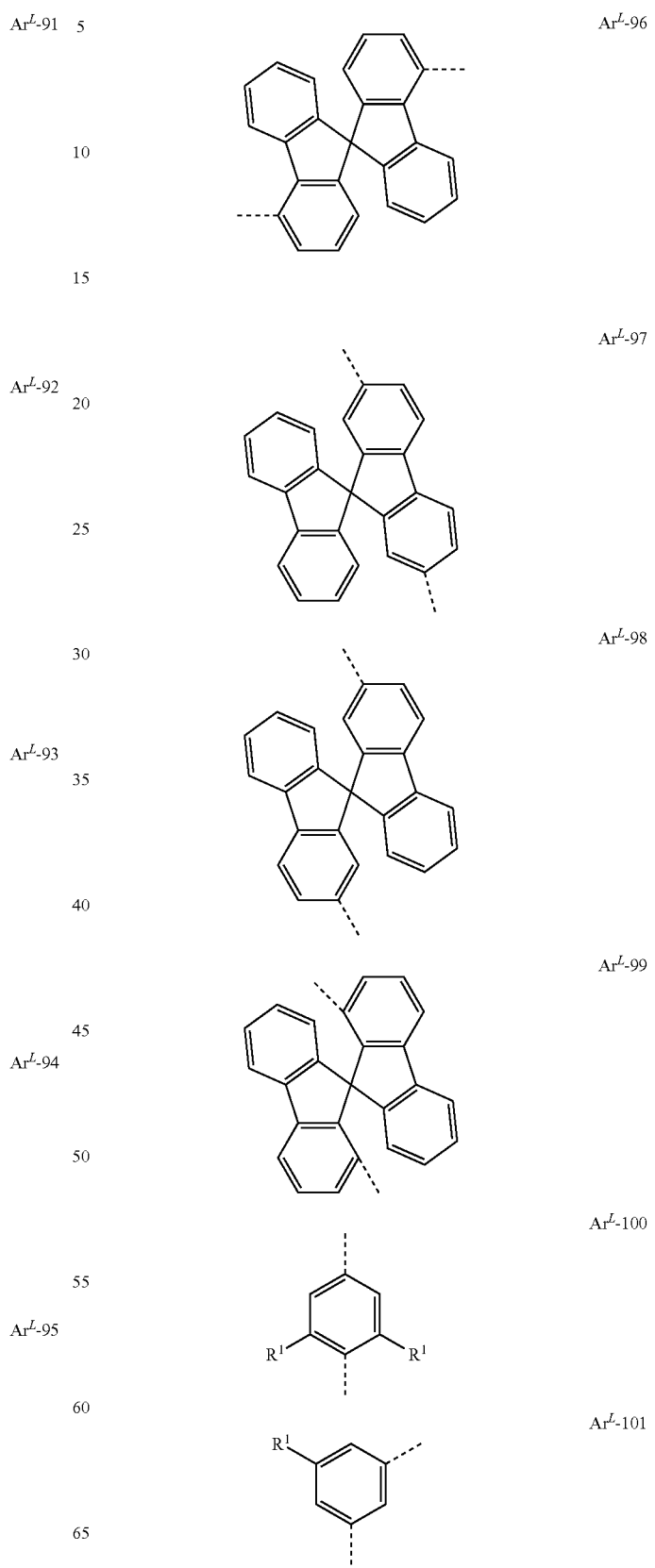

Ar^L-102

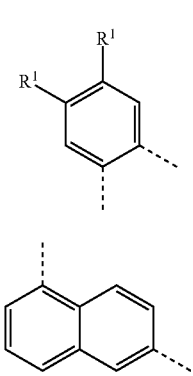

Ar^L-103 where the dashed bonds in (Ar^L-25) to (Ar^L-102) indicate,
when n=1,
  the bonds to the spirobifluorene skeleton and to the amine group NAr¹Ar² in formula (1);
  the bonds to the spirobifluorene skeleton and to the group X² in formula (Int-1);
  the bonds to the group X² and to the group —B(OR)₂ in formula (p-4);
  the bonds to the fluorenone skeleton and to the group X² in formula (p-5);
  the bonds to the fluorenone skeleton and to the nitrogen of the group NAr¹Ar² in formula (Int-1'); and
when n=2, the dashed bonds in (Ar^L-25) to (Ar^L-102) indicate,
  in formula (1), the bonds to the spirobifluorene skeleton and to one of the amine group NAr¹Ar², whereas the second group NAr¹Ar² may be linked at each free position in formulae (Ar^L-25) to (Ar^L-102);
  in formula (Int-1), the bonds to the spirobifluorene skeleton and to one of the group X², whereas the second group X² may be linked at each free position in formulae (Ar^L-25) to (Ar^L-102);
  in formula (p-4), the bonds to the group X² and to the group —B(OR)₂, whereas the second group X² may be linked at each free position in formulae (Ar^L-25) to (Ar^L-102);
  in formula (p-5), the bonds to the fluorenone skeleton and to the group X², whereas the second group X² may be linked at each free position in formulae (Ar^L-25) to (Ar^L-102);
  in formula (Int-1'), the bonds to the fluorenone skeleton and to the nitrogen of the group NAr¹Ar², whereas the second group X² may be linked at each free position in formulae (Ar^L-25) to (Ar^L-102);
when n=3, the dashed bonds in (Ar^L-25) to (Ar^L-102) indicate,
  in formula (1), the bonds to the spirobifluorene skeleton and to one of the amine group NAr¹Ar², whereas the second and third groups NAr¹Ar² may be linked at each free position in formulae (Ar^L-25) to (Ar^L-102);
  in formula (Int-1), the bonds to the spirobifluorene skeleton and to one of the group X², whereas the second and third groups X² may be linked at each free position in formulae (Ar^L-25) to (Ar^L-102);
  in formula (p-4), the bonds to the group X² and to the group —B(OR)₂, whereas the second and third groups X² may be linked at each free position in formulae (Ar^L-25) to (Ar^L-102);
  in formula (p-5), the bonds to the fluorenone skeleton and to the group X², whereas the second and third groups X² may be linked at each free position in formulae (Ar^L-25) to (Ar^L-102);
  in formula (Int-1'), the bonds to the fluorenone skeleton and to the nitrogen of the group NAr¹Ar², whereas the second and third groups X² may be linked at each free position in formulae (Ar^L-25) to (Ar^L-102);
and where R¹ in (Ar^L-100), (Ar^L-101) and (Ar^L-102) is selected from H, an aryl or heteroaryl group having 5 to 18 aromatic ring atoms.

Among the groups (Ar^L-25) to (Ar^L-102), the groups (Ar^L-25), (Ar^L-26), (Ar^L-27), (Ar^L-33), (Ar^L-40), (Ar^L-41), (Ar^L-60), (Ar^L-88) and (Ar^L-97) are preferred.

In accordance with a preferred embodiment, the groups Ar¹ and Ar² in formulae (p-6), (Int-1') and (1) are selected, identically or differently, on each occurrence from the groups of the following formulae (A-1) to (A-48),

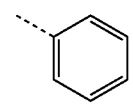

(A-1)

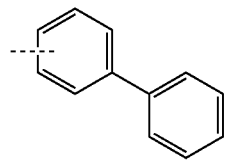

(A-2)

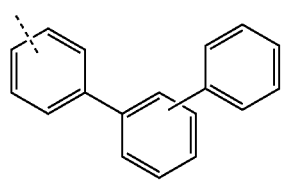

(A-3)

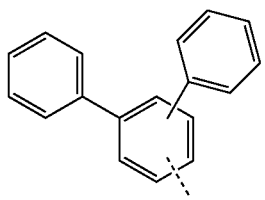

(A-4)

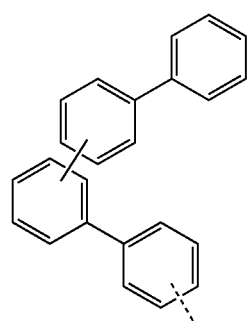

(A-5)

-continued
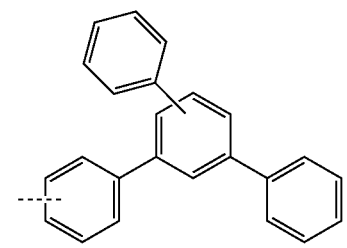
(A-6)
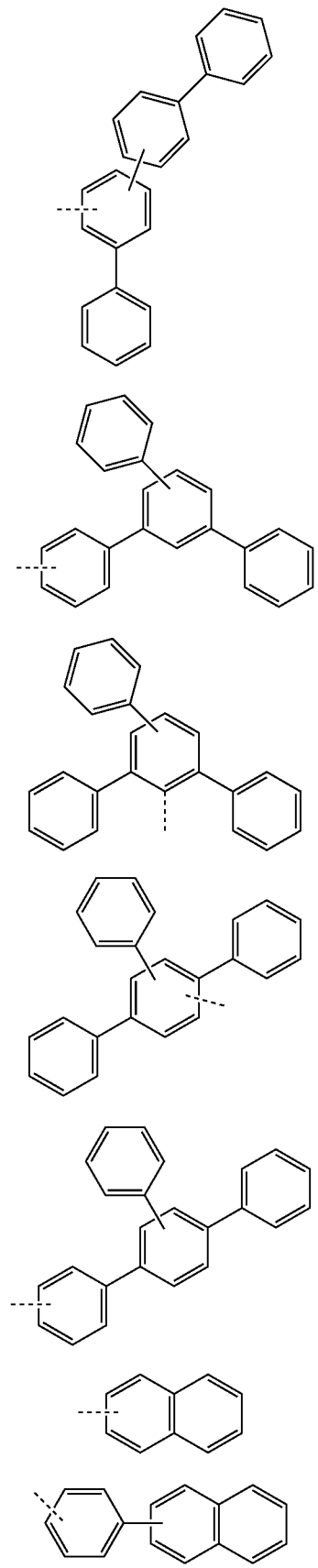
(A-7)
(A-8)
(A-9)
(A-10)
(A-11)
(A-12)
-continued
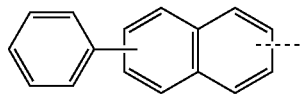
(A-13)
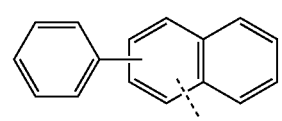
(A-14)
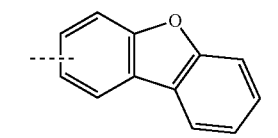
(A-15)
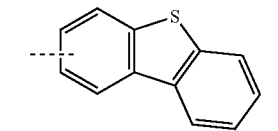
(A-16)
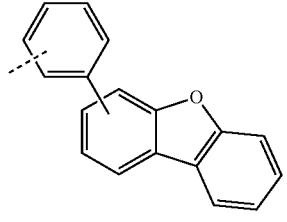
(A-17)
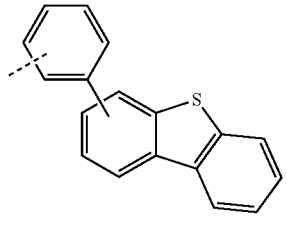
(A-18)
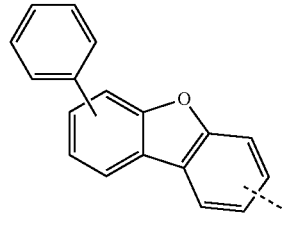
(A-19)
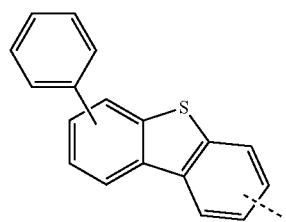
(A-20)

(A-21)
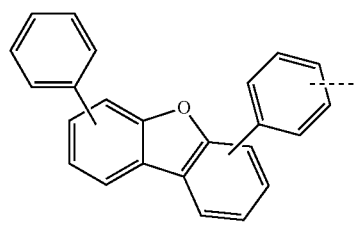
(A-22)
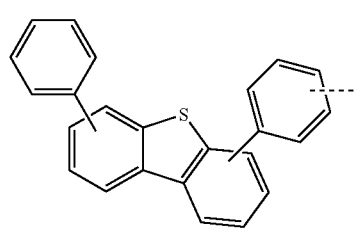
(A-23)
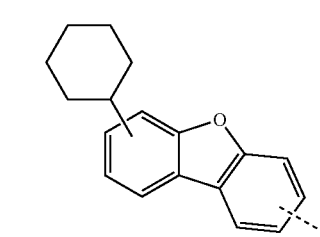
(A-24)
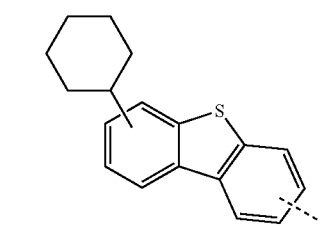
(A-25)
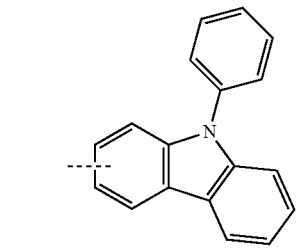
(A-26)
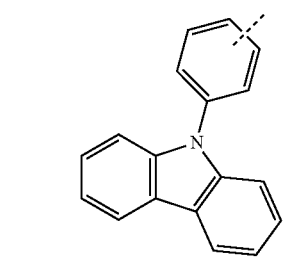
(A-27)
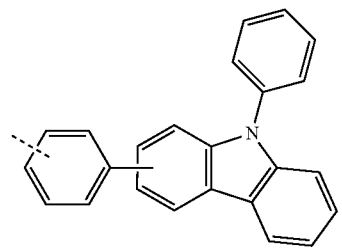
(A-28)
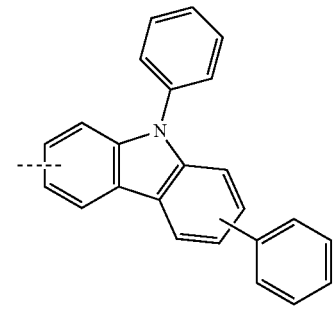
(A-29)
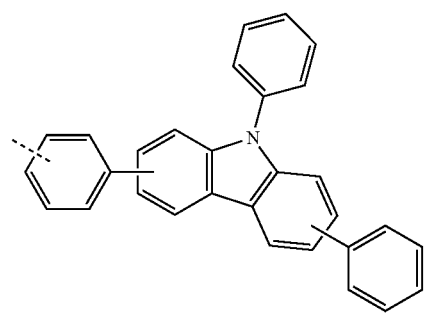
(A-30)
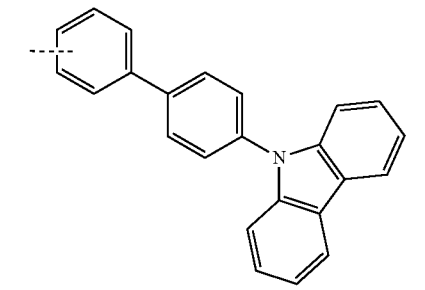
(A-31)
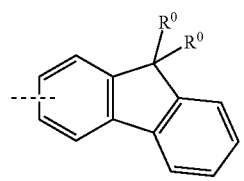
(A-32)
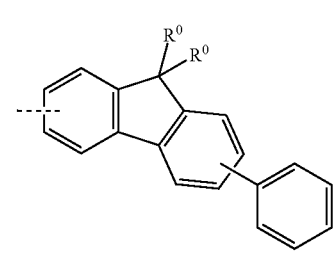

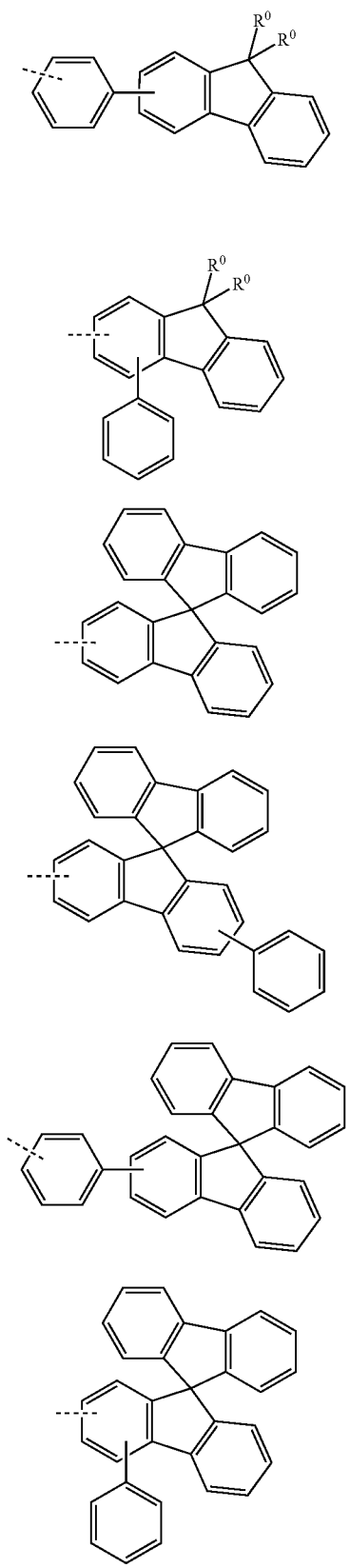
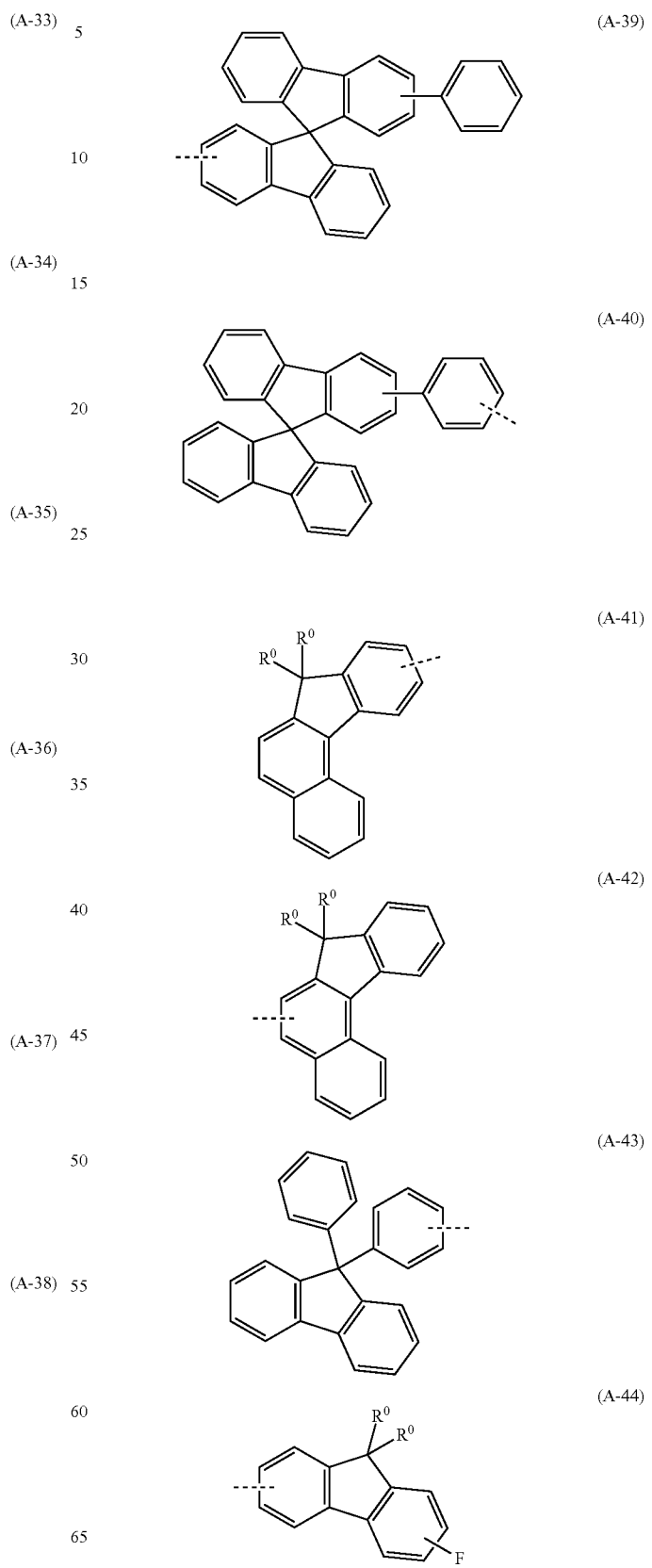

(A-45) 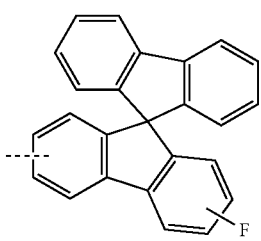

(A-46) 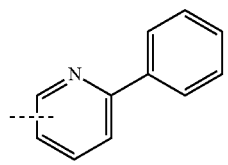

(A-47) 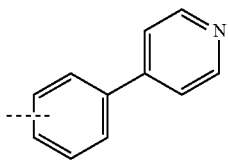

(A-48) 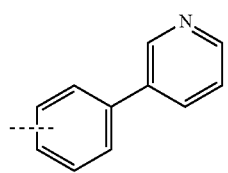

where the dashed bond indicates the bond to the nitrogen atom, where the groups of formulae (A-1) to (A-48) may further be substituted at each free position by a group $R^2$ as defined above, and where the group $R^0$, in formulae (A-31) to (A-34), (A-41), (A-42) and (A-44), is defined as above.

Suitable groups $Ar^1$ and $Ar^2$ in formulae (p-4), (p-5), (Int-1), (Int-1') and (1) are the groups of formulae (Ar-1) to (Ar-252), Ar-1 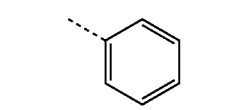

Ar-2 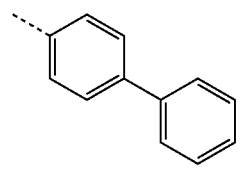

Ar-3 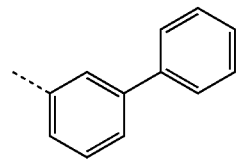

Ar-4 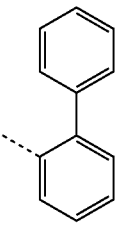

Ar-5 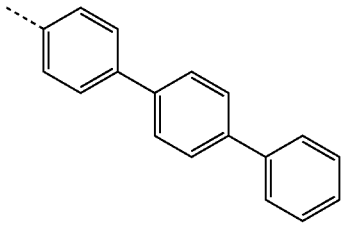

Ar-6 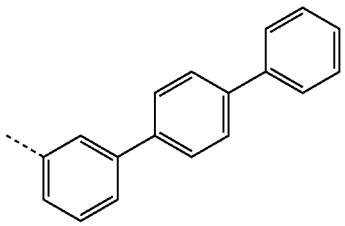

Ar-7 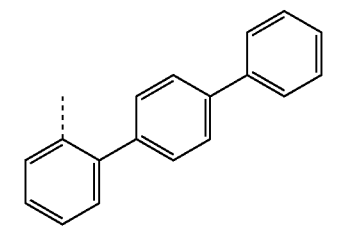

Ar-8 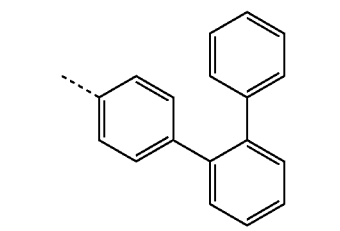

Ar-9 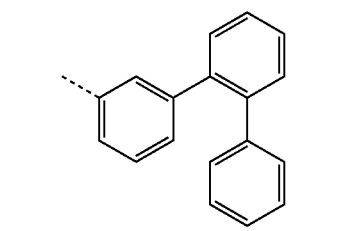

Ar-10 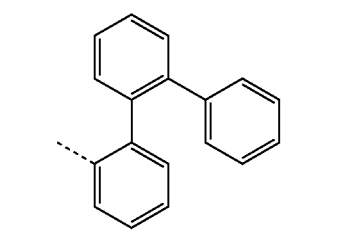

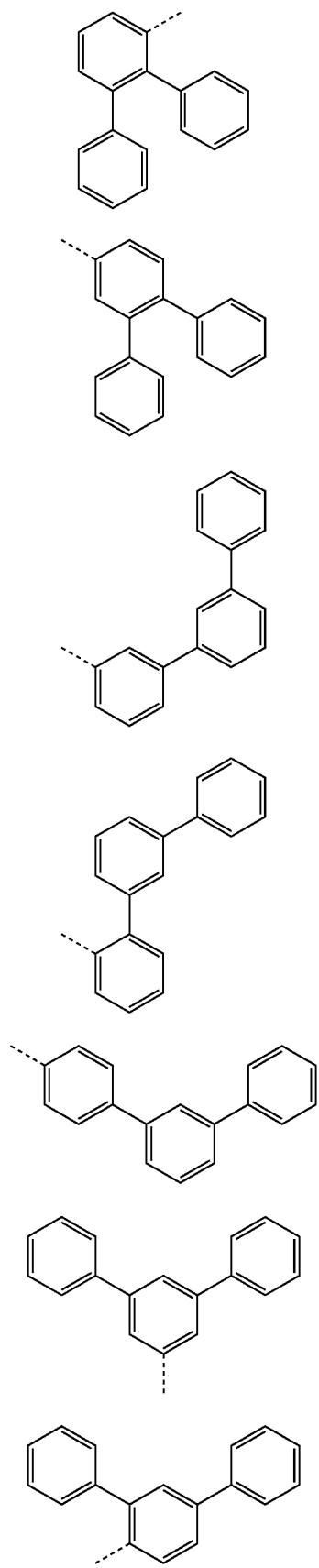
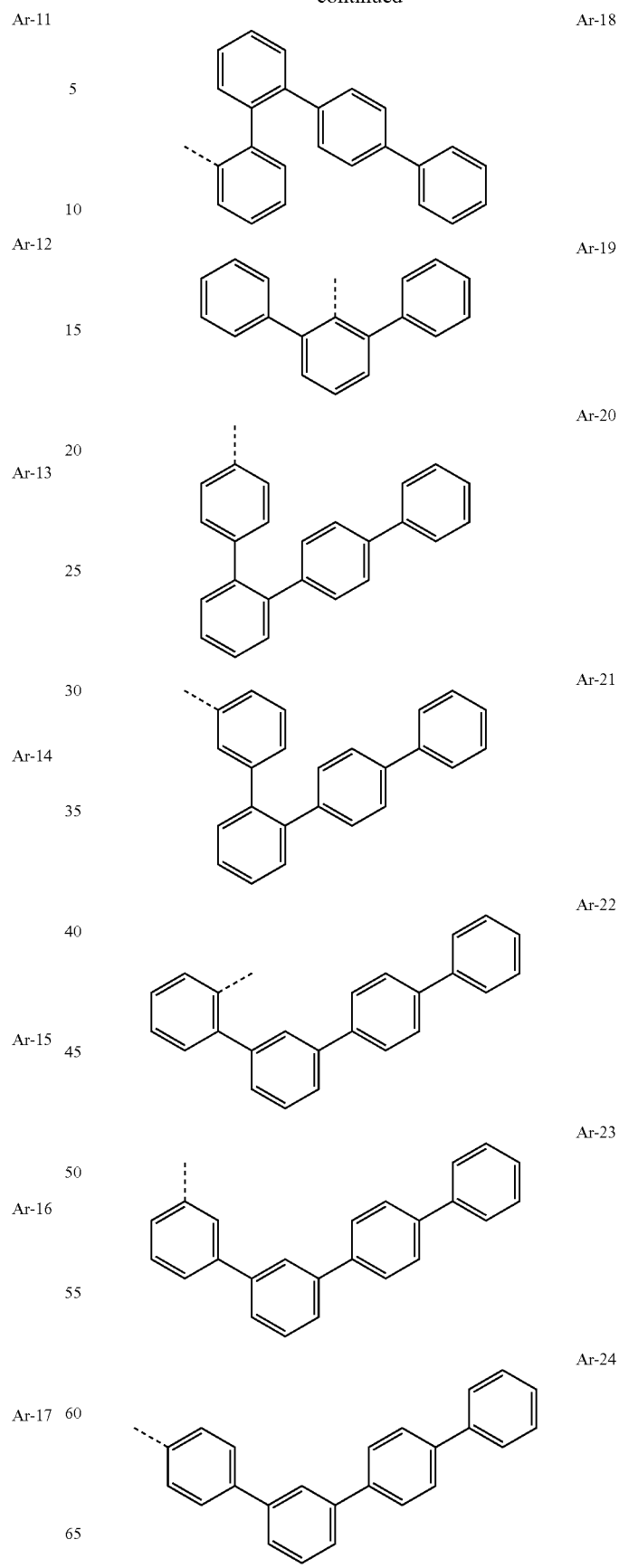

Ar-25
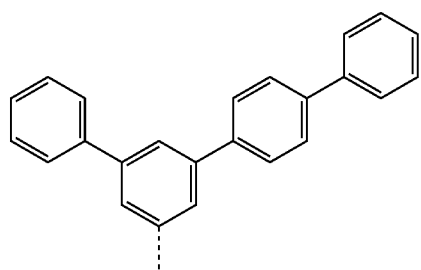
Ar-26
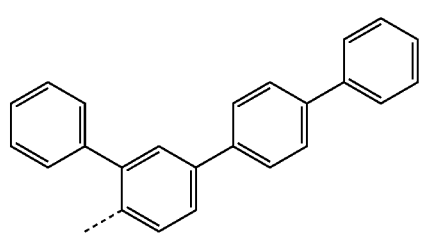
Ar-27
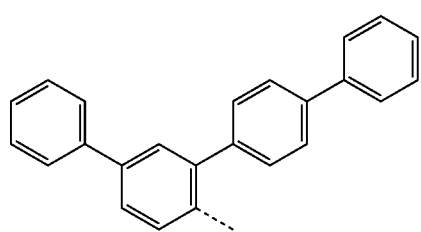
Ar-28
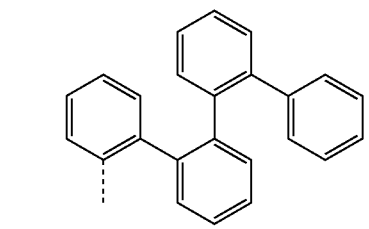
Ar-29
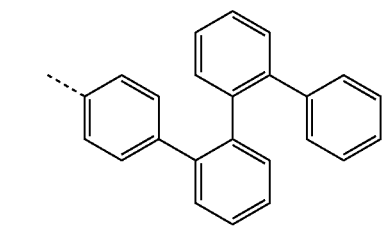
Ar-30
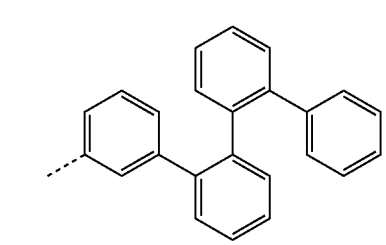
Ar-31
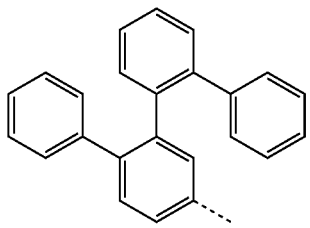
Ar-32
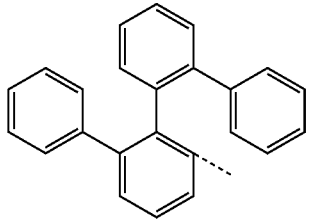
Ar-33
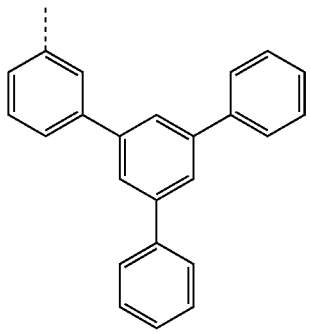
Ar-34
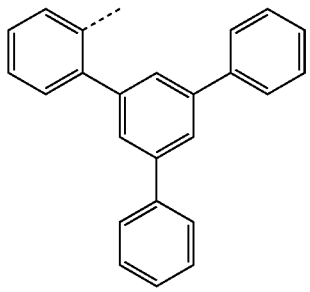
Ar-35
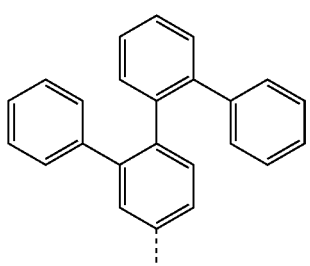
Ar-36
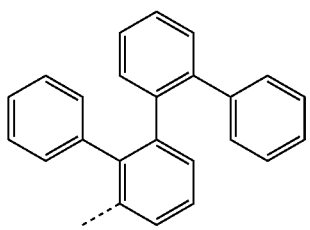

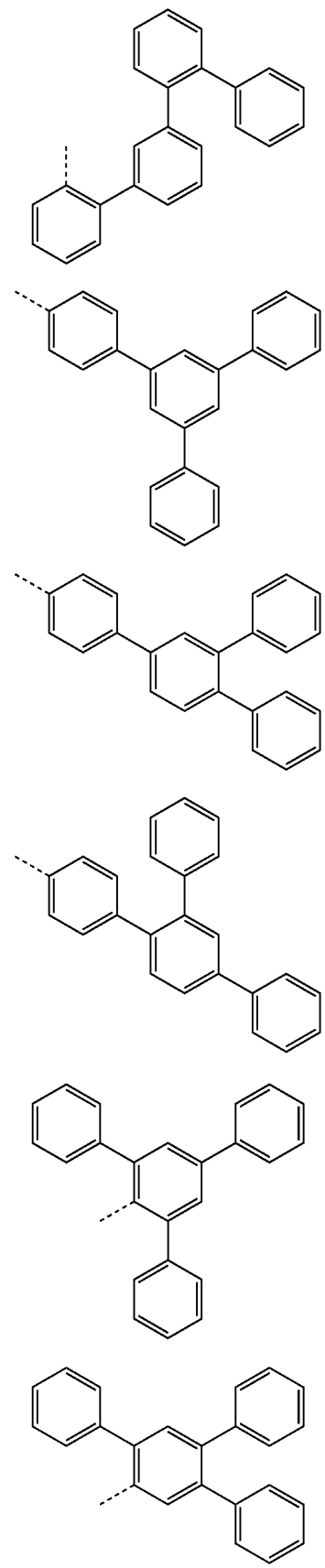
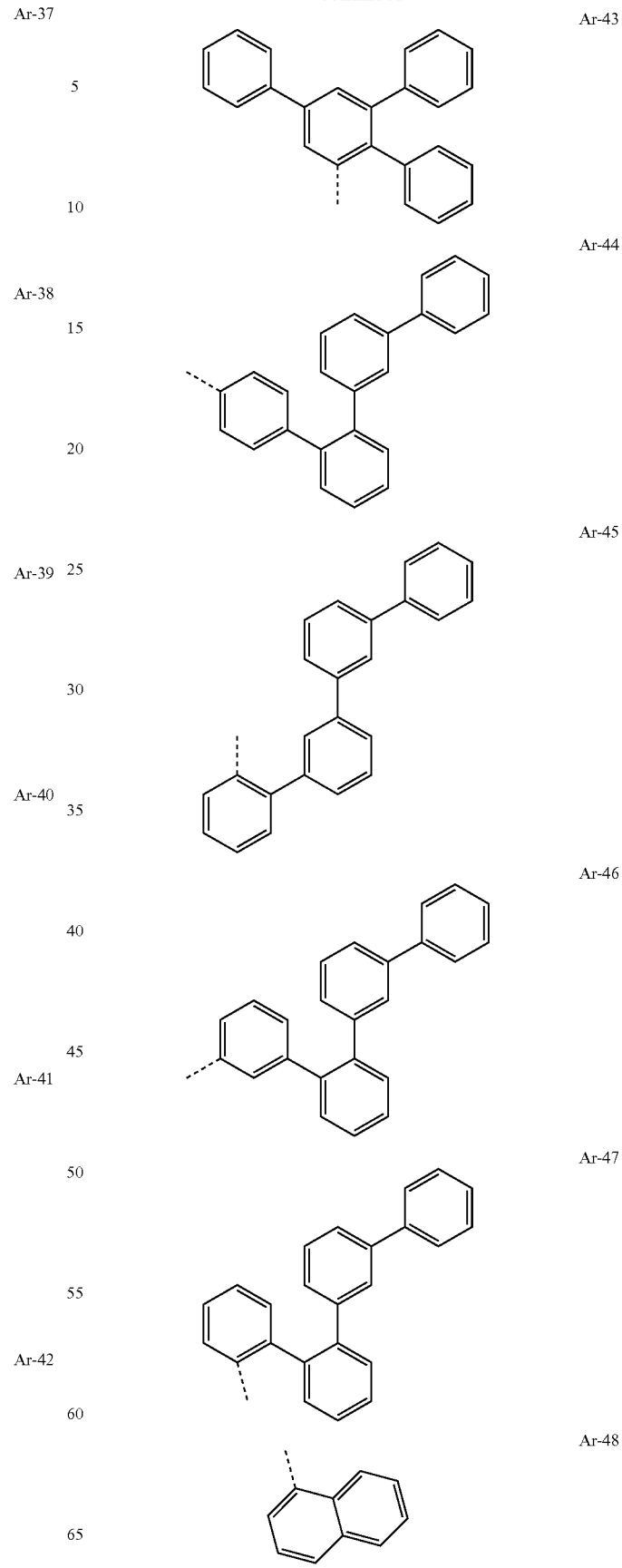

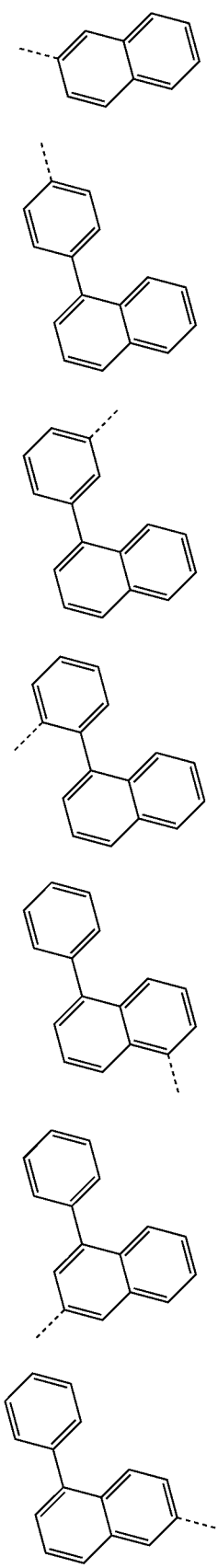
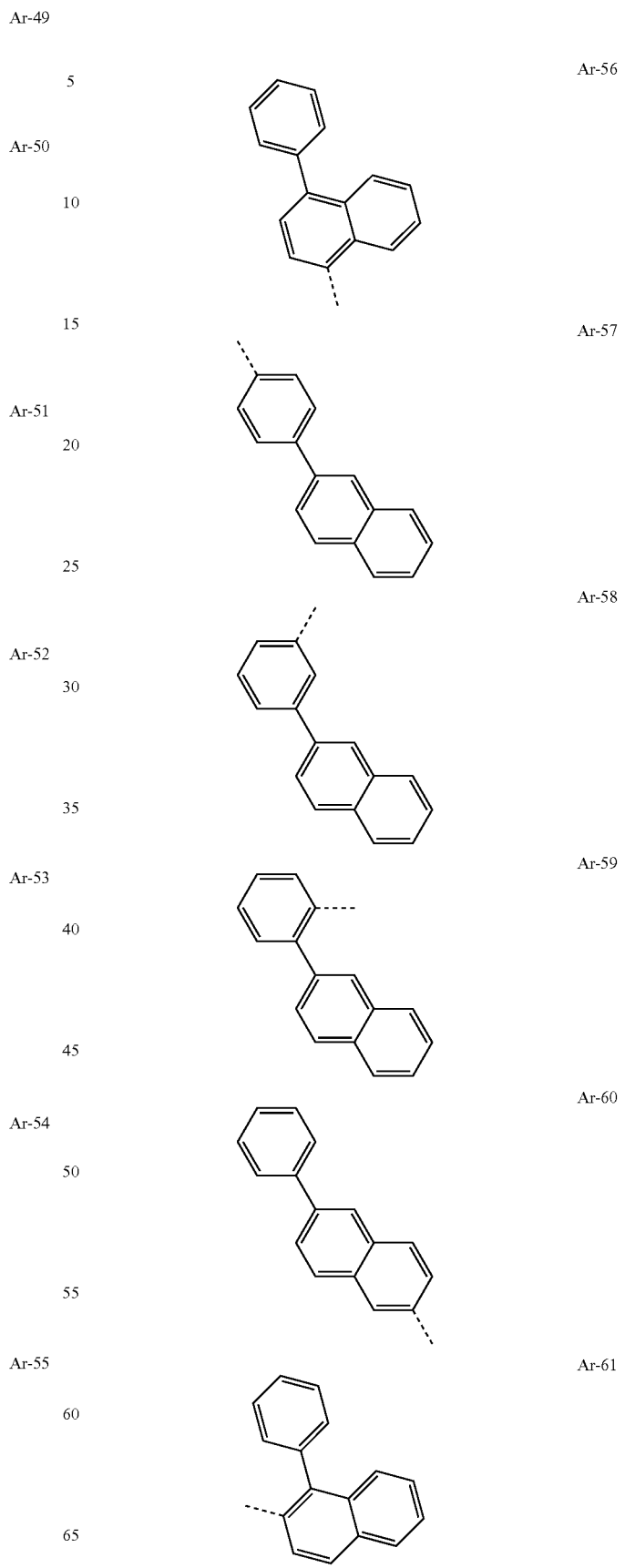

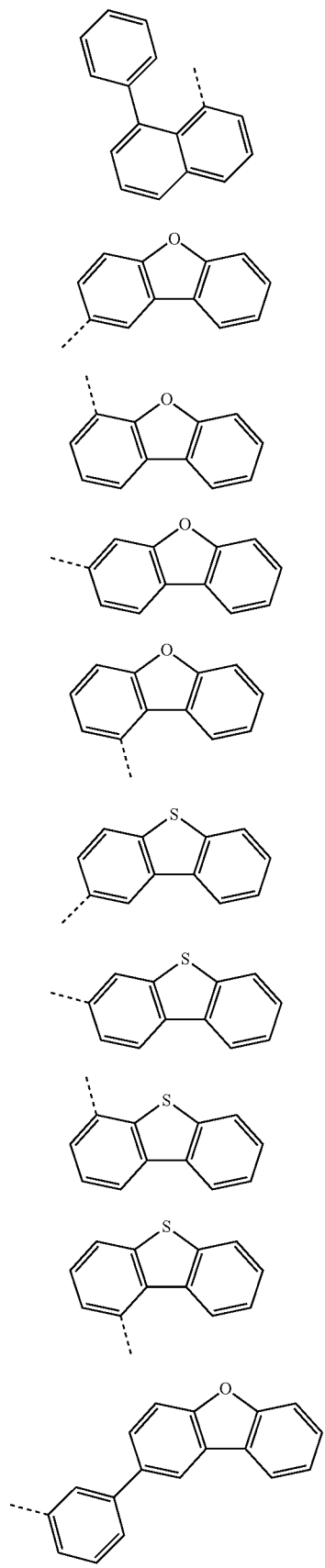
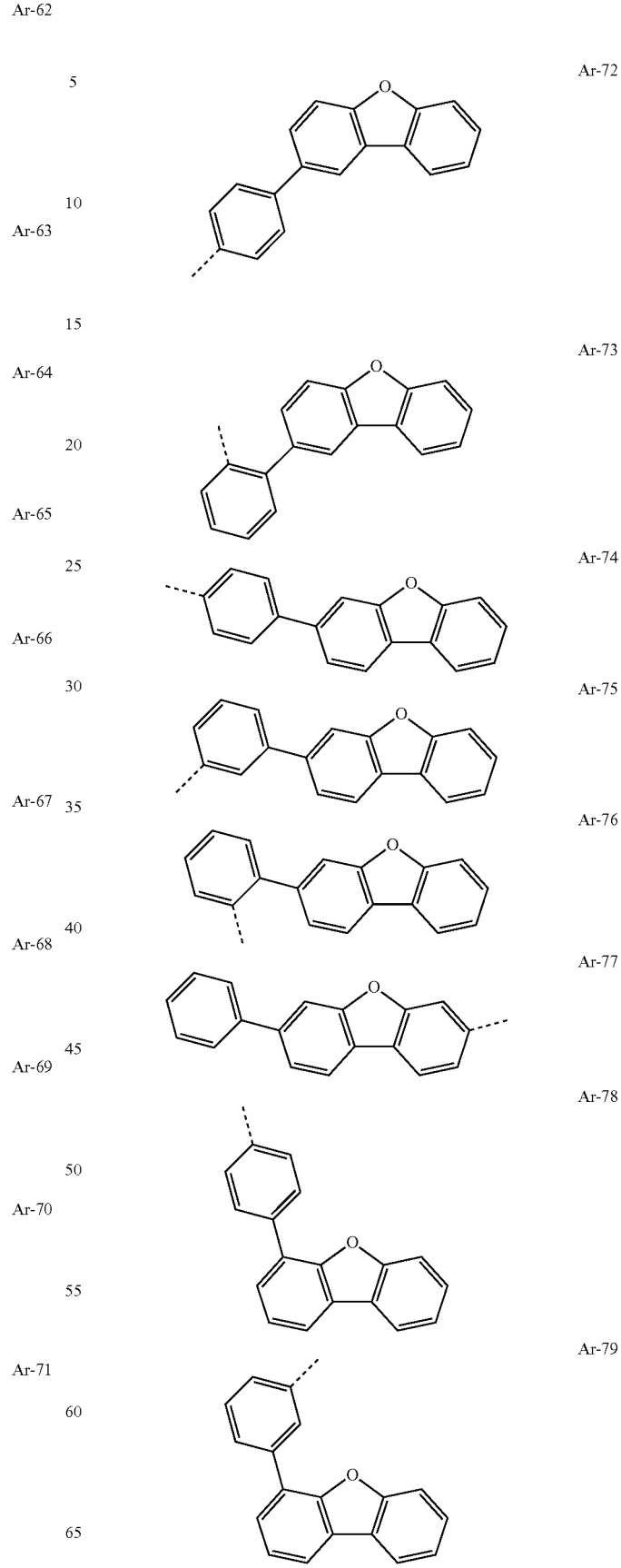
Ar-62
Ar-63
Ar-64
Ar-65
Ar-66
Ar-67
Ar-68
Ar-69
Ar-70
Ar-71
Ar-72
Ar-73
Ar-74
Ar-75
Ar-76
Ar-77
Ar-78
Ar-79

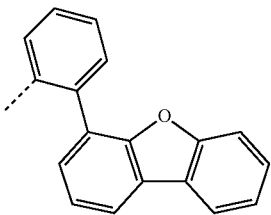 Ar-80
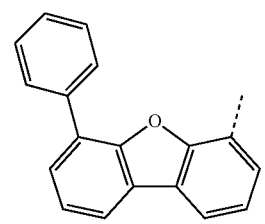 Ar-81
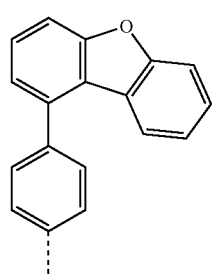 Ar-82
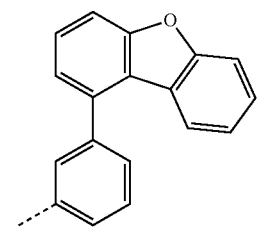 Ar-83
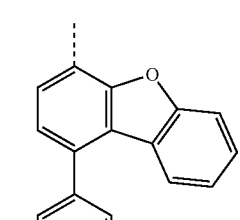 Ar-84
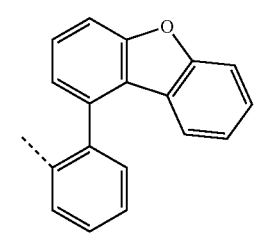 Ar-85
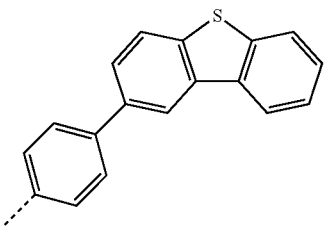 Ar-86
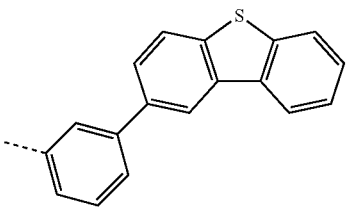 Ar-87
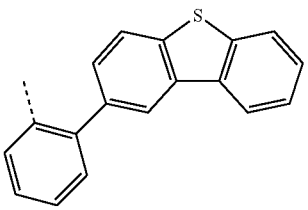 Ar-88
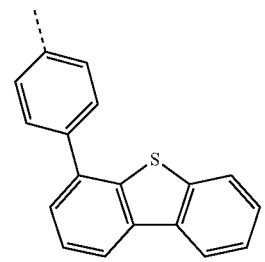 Ar-89
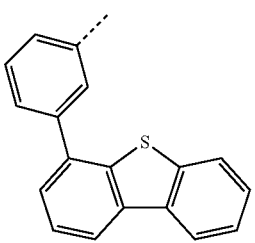 Ar-90
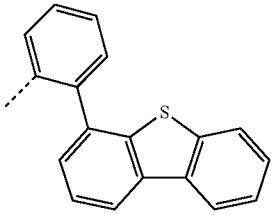 Ar-91
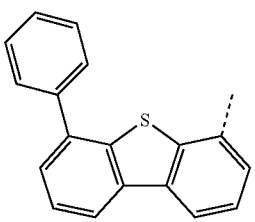 Ar-92

Ar-93 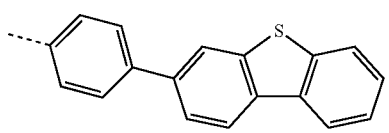
Ar-94 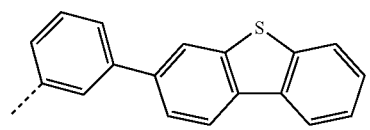
Ar-95 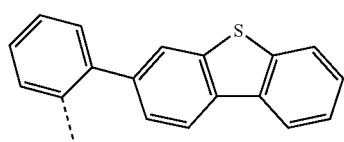
Ar-96 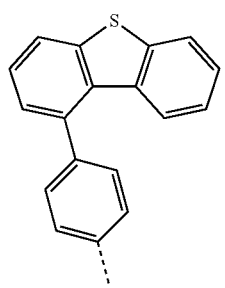
Ar-97 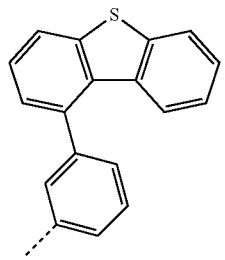
Ar-98 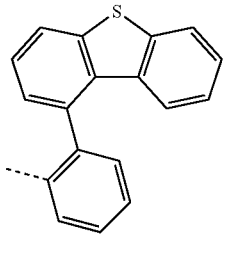
Ar-99 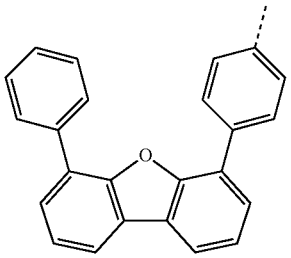
Ar-100 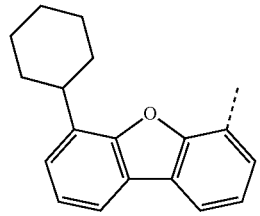
Ar-101 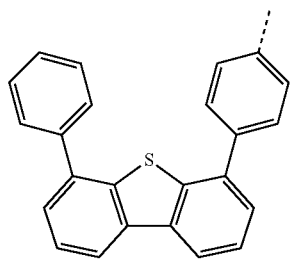
Ar-102 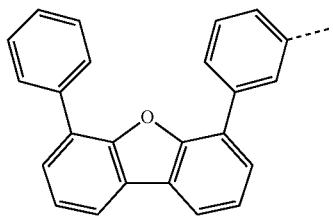
Ar-103 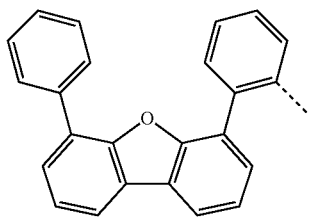
Ar-104 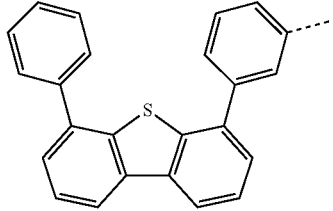
Ar-105 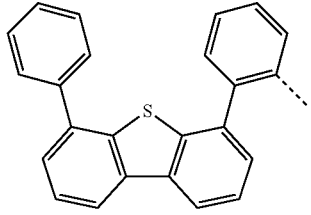
Ar-106 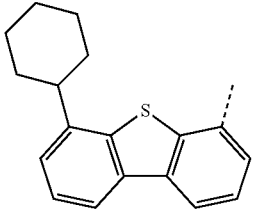

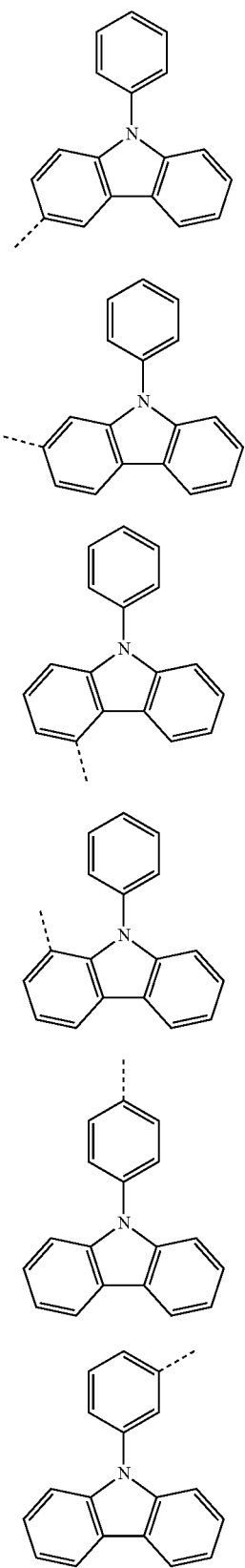
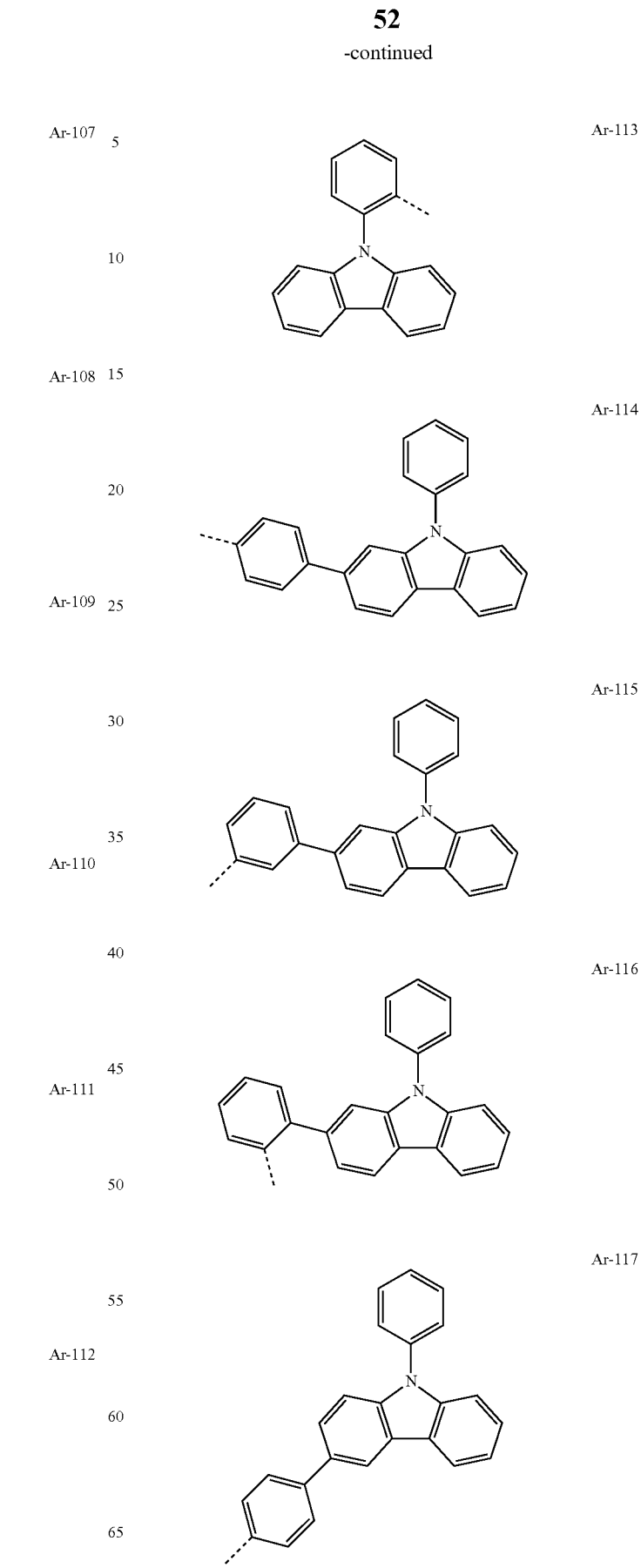

Ar-118
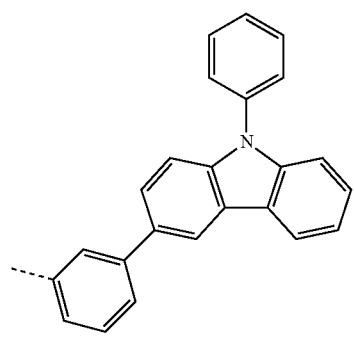
Ar-119
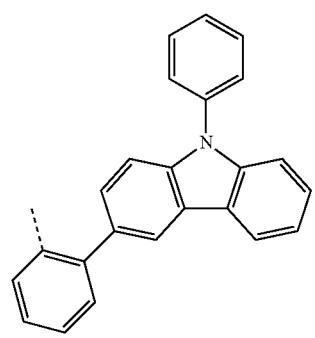
Ar-120
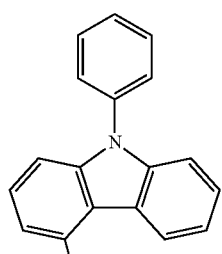
Ar-121
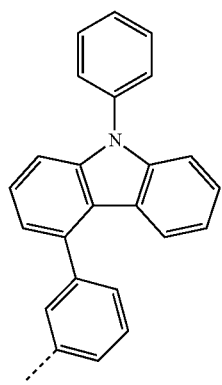
Ar-122
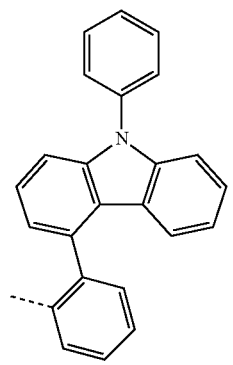
Ar-123
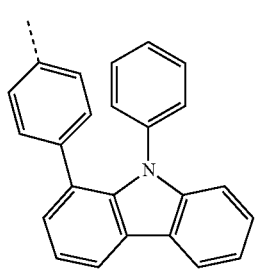
Ar-124
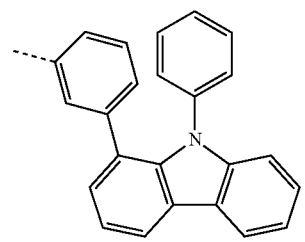
Ar-125
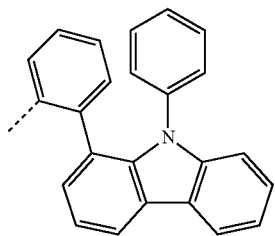
Ar-126
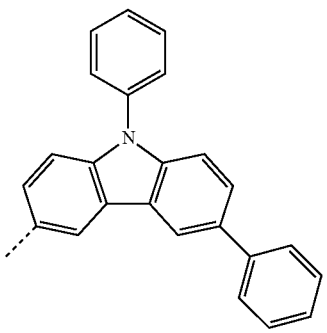

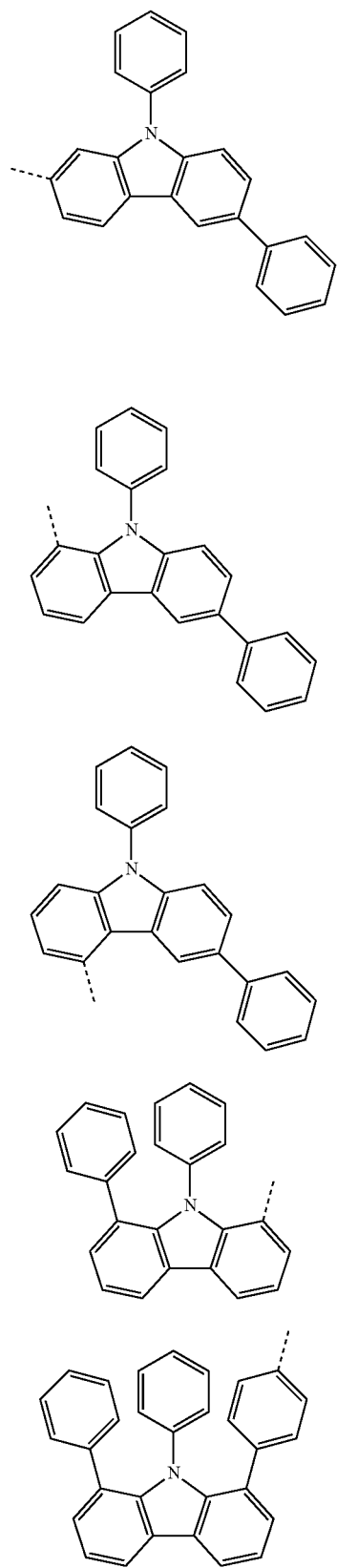
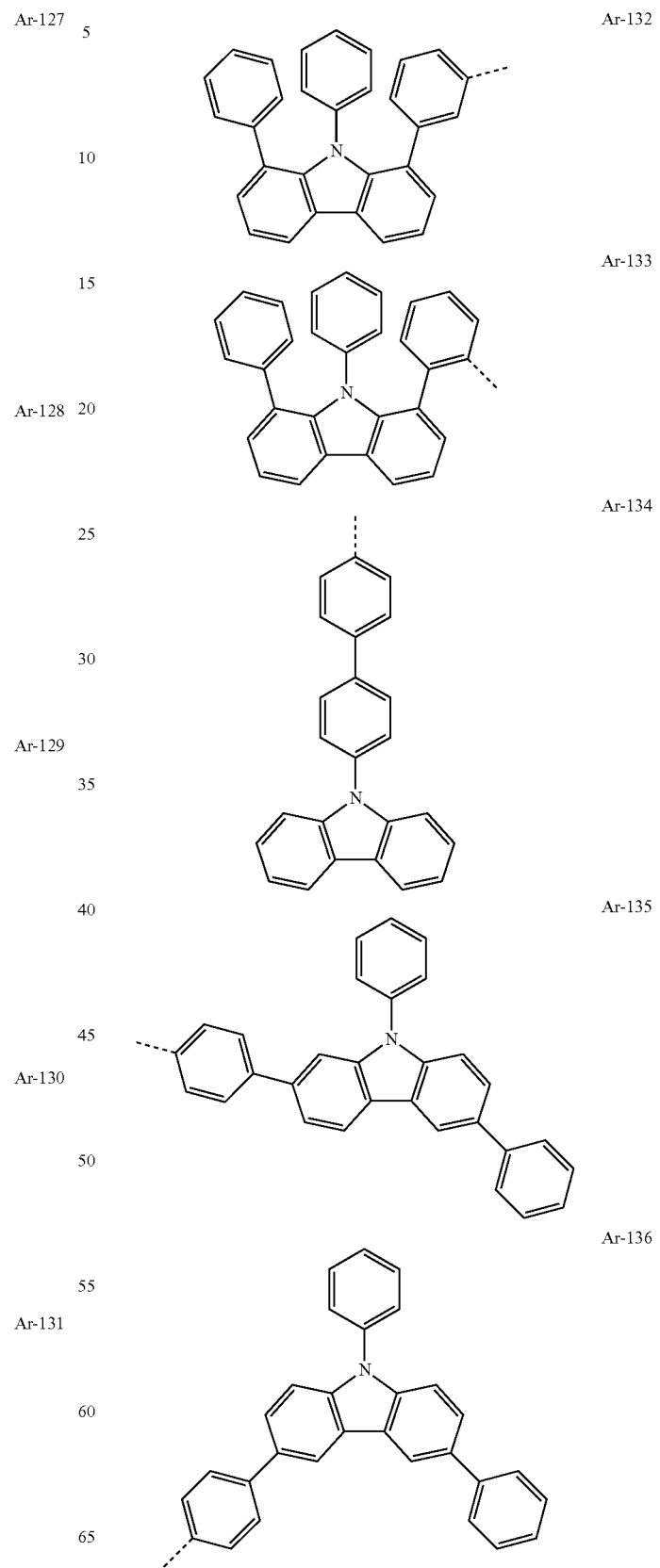

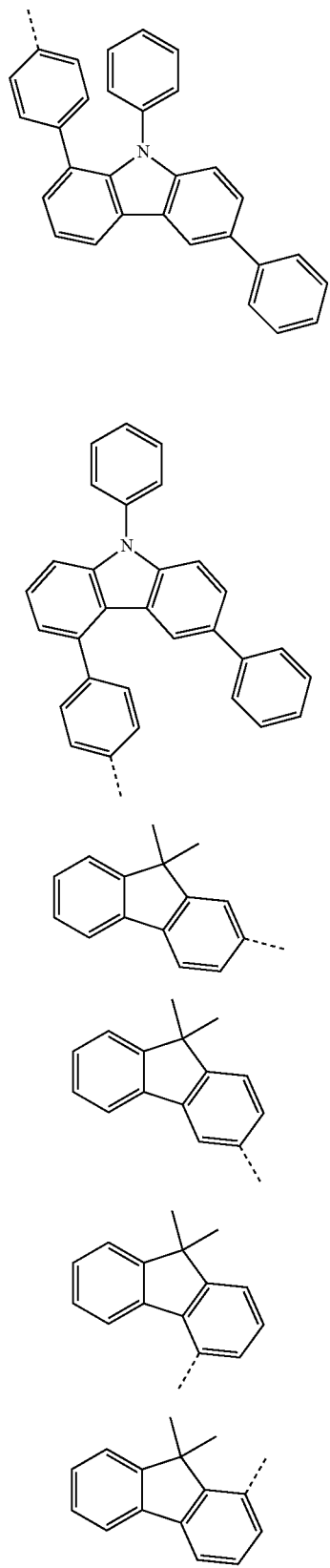
Ar-137
Ar-138
Ar-139
Ar-140
Ar-141
Ar-142
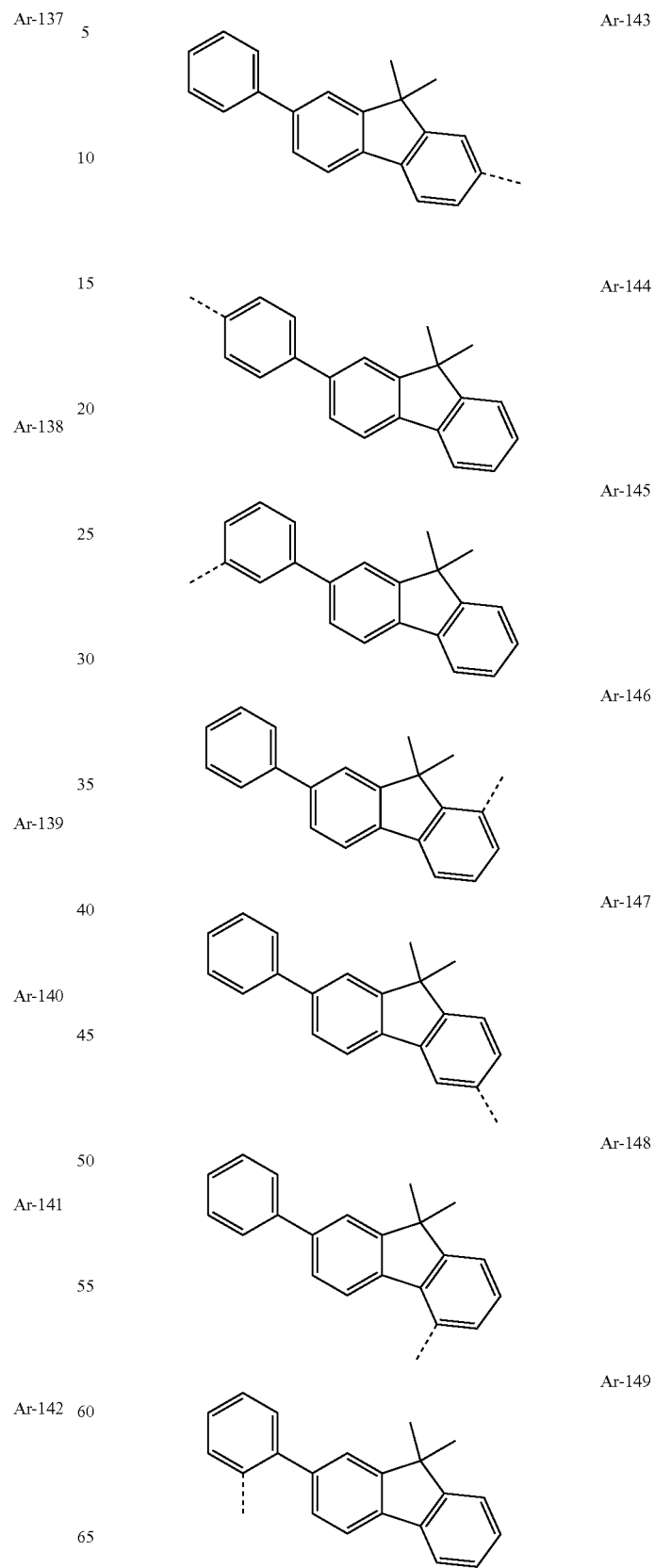
Ar-143
Ar-144
Ar-145
Ar-146
Ar-147
Ar-148
Ar-149

Ar-150
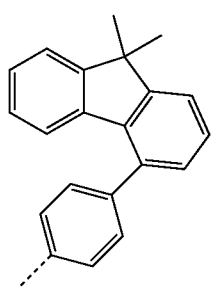
Ar-151
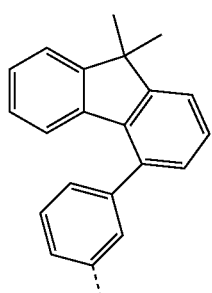
Ar-152
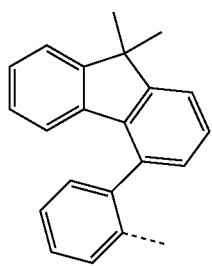
Ar-153
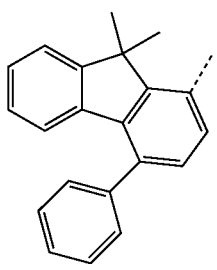
Ar-154
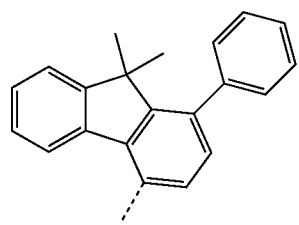
Ar-155
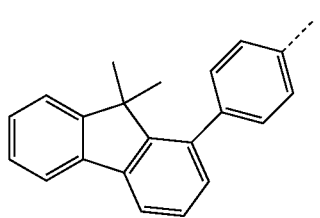
Ar-156
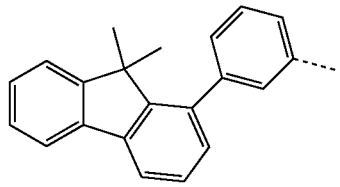
Ar-157
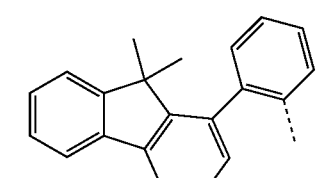
Ar-158
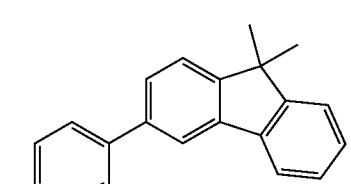
Ar-159
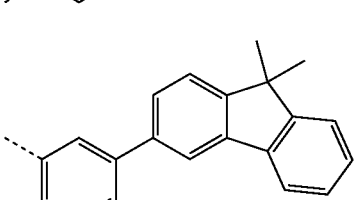
Ar-160
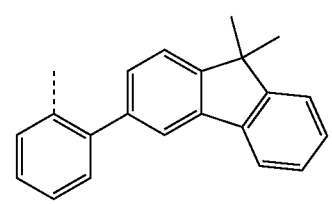
Ar-161
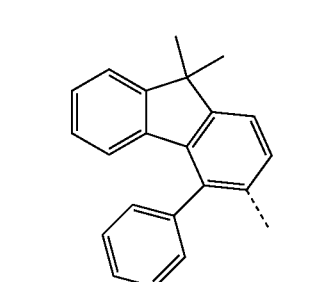
Ar-162
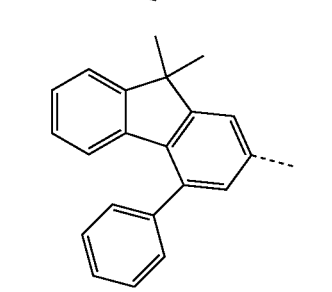

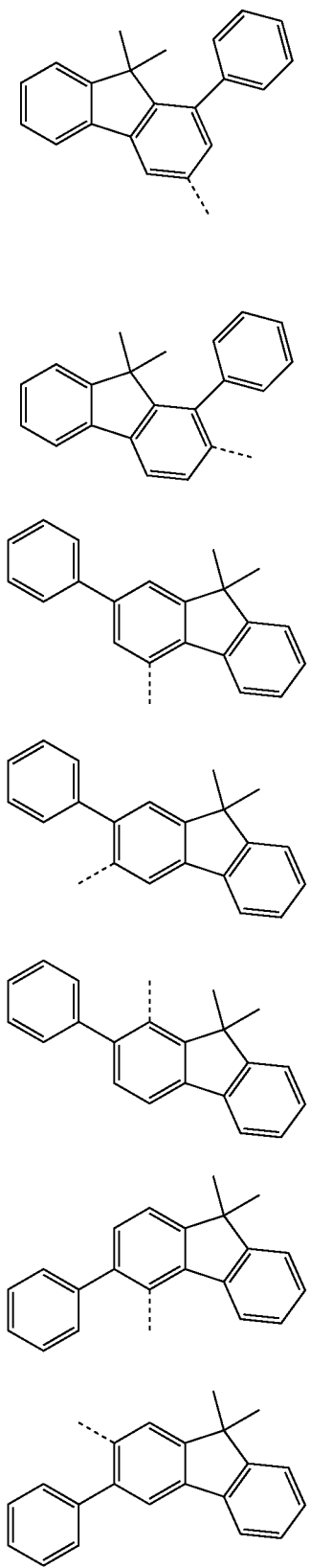
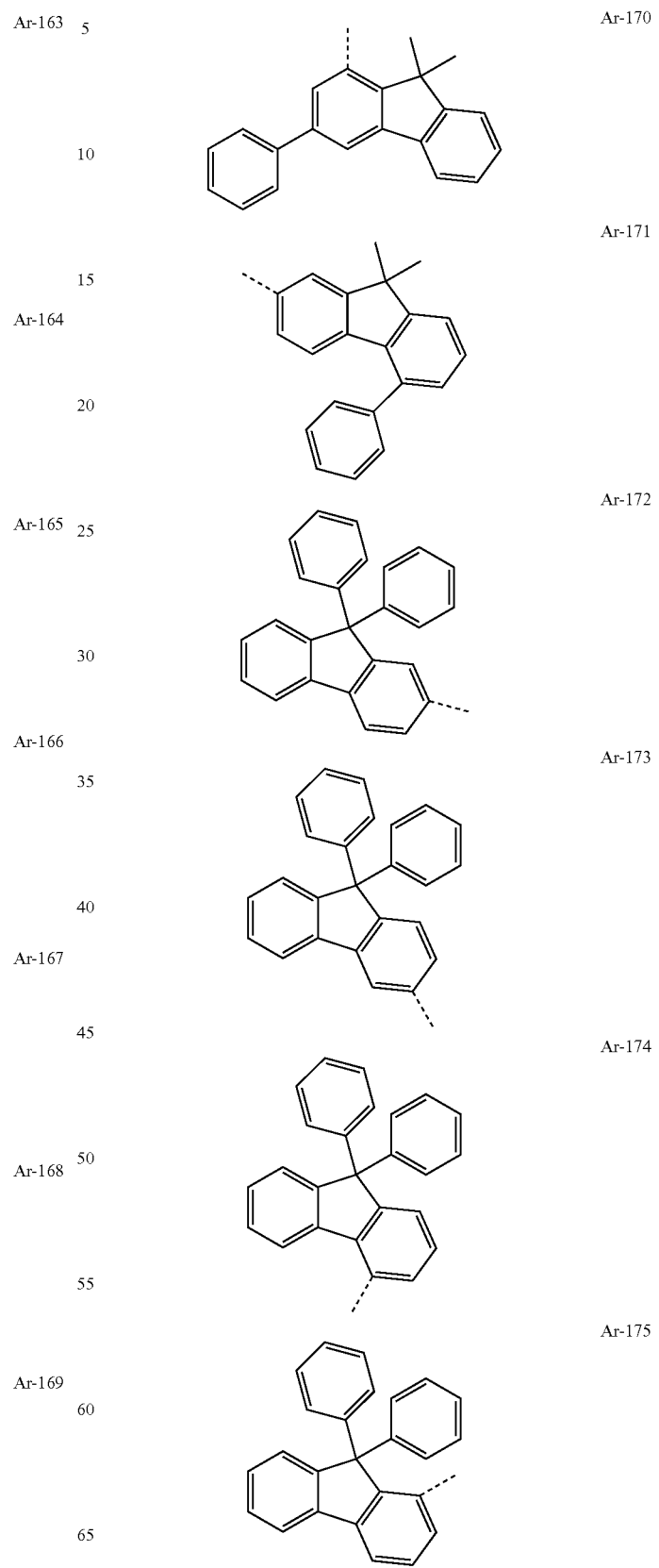

-continued
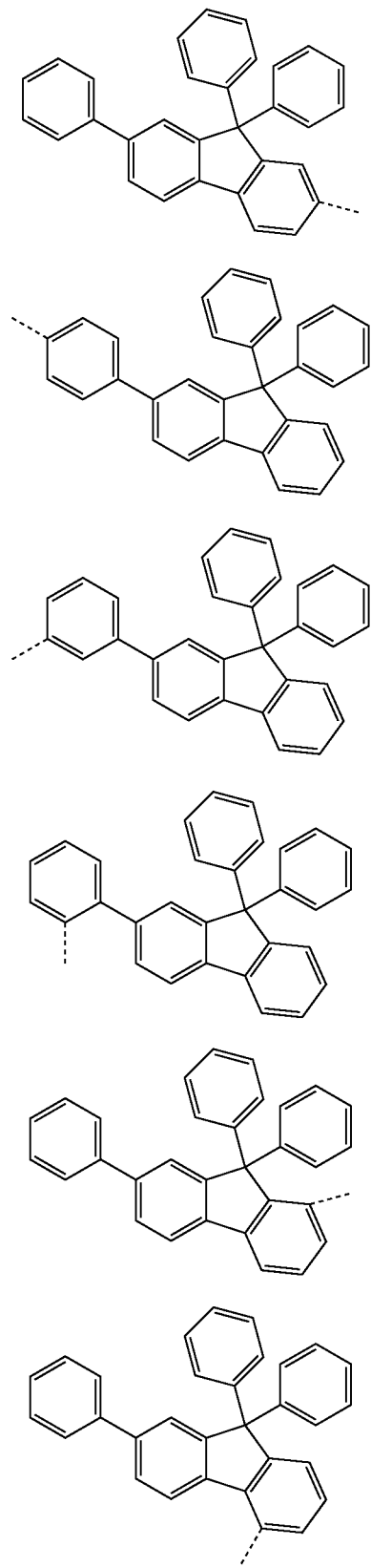
Ar-176
Ar-177
Ar-178
Ar-179
Ar-180
Ar-181
-continued
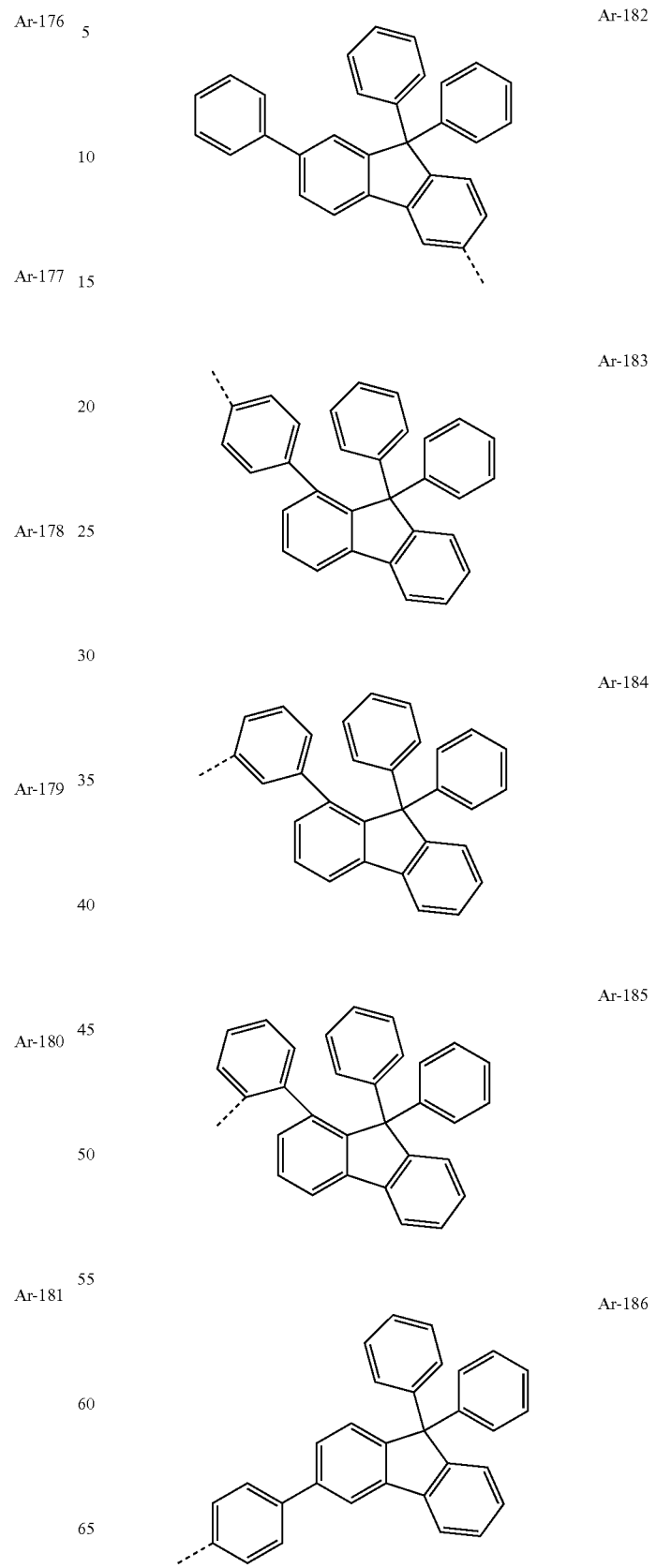
Ar-182
Ar-183
Ar-184
Ar-185
Ar-186

-continued
Ar-187
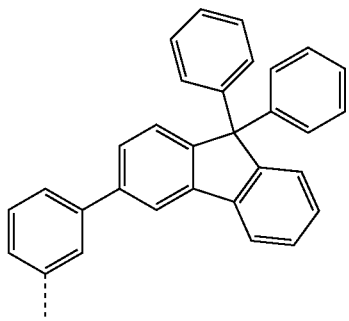
Ar-188
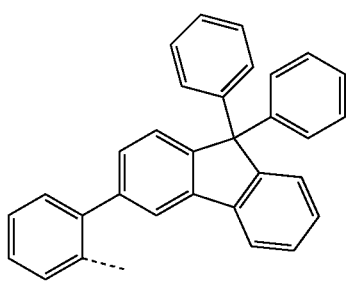
Ar-189
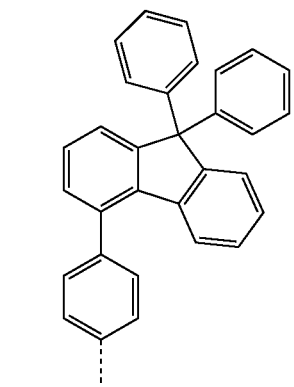
Ar-190
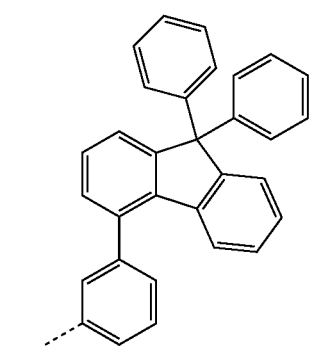
-continued
Ar-191
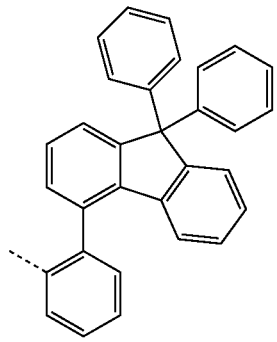
Ar-192
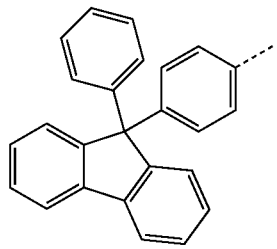
Ar-193
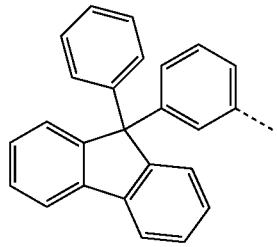
Ar-194
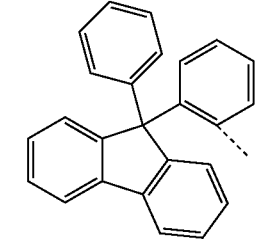
Ar-195
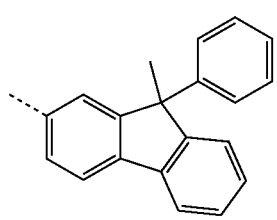
Ar-196
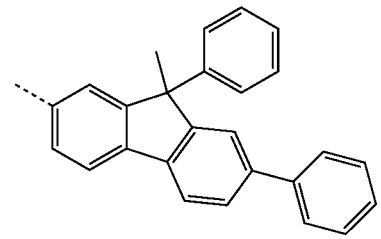

Ar-197 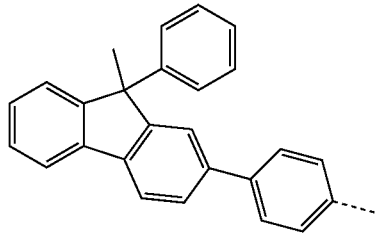
Ar-198 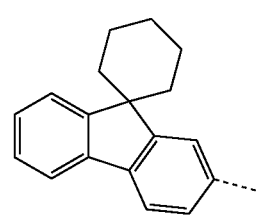
Ar-199 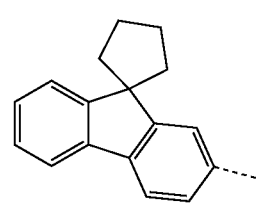
Ar-200 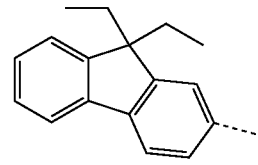
Ar-201 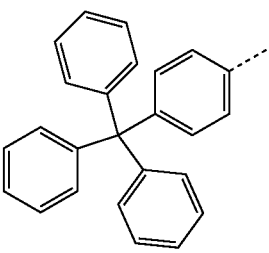
Ar-202 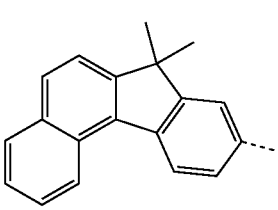
Ar-203 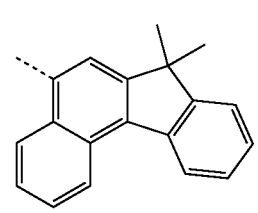
Ar-204 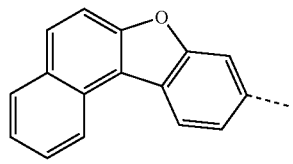
Ar-205 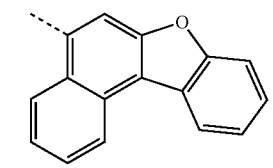
Ar-206 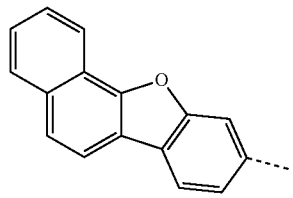
Ar-207 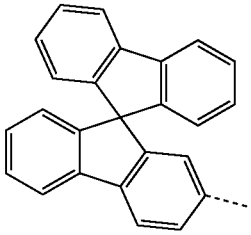
Ar-208 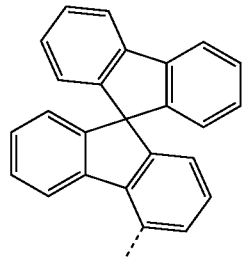
Ar-209 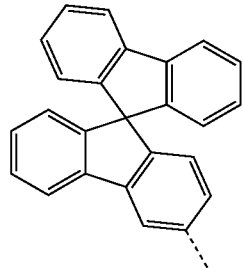
Ar-210 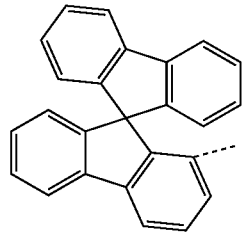

Ar-211 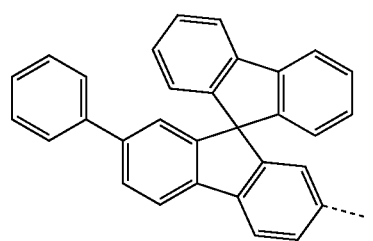
Ar-212 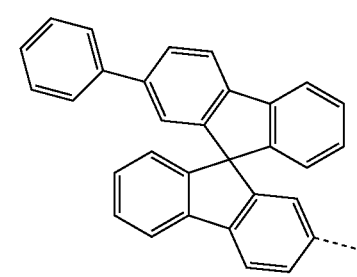
Ar-213 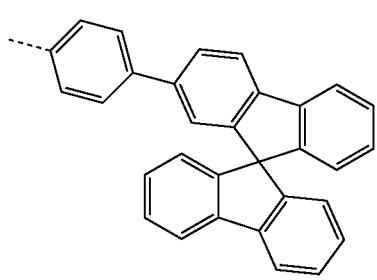
Ar-214 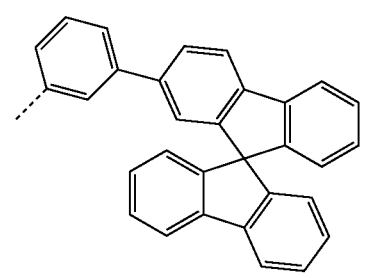
Ar-215 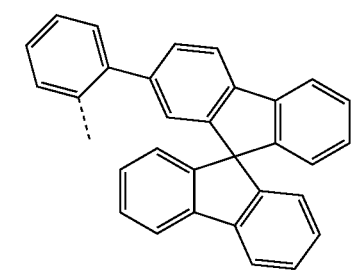
Ar-216 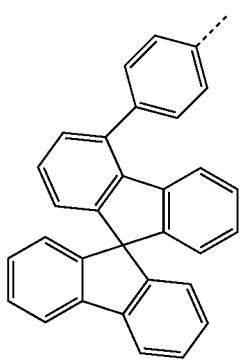
Ar-217 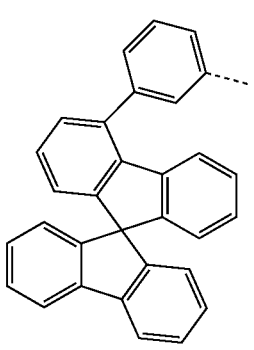
Ar-218 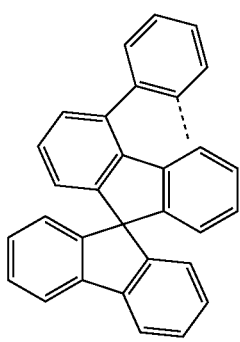
Ar-219 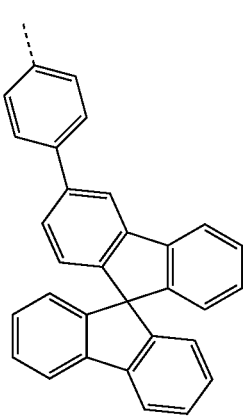

-continued
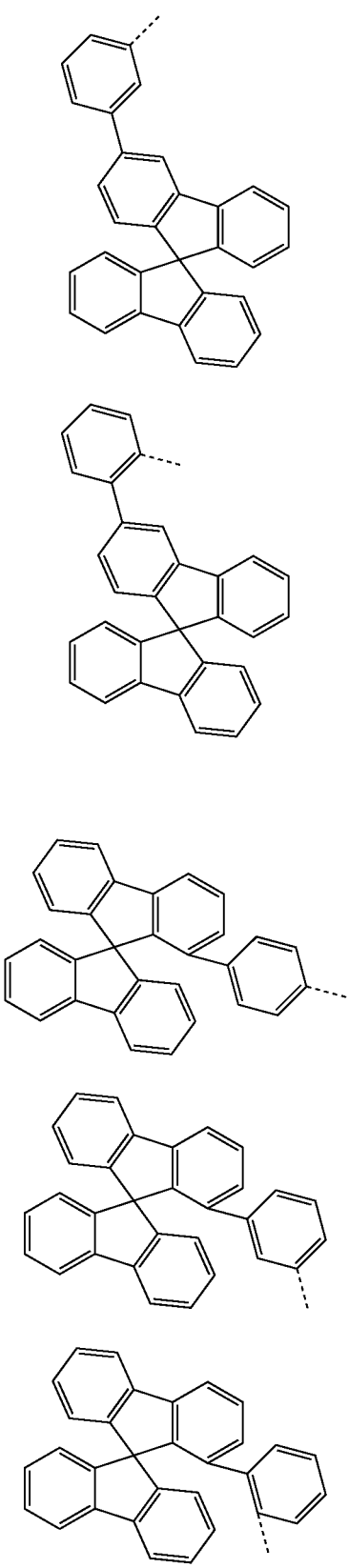
Ar-220
Ar-221
Ar-222
Ar-223
Ar-224
-continued
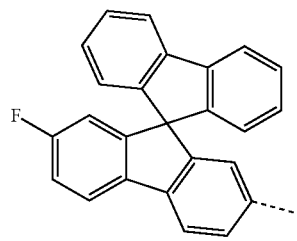
Ar-225
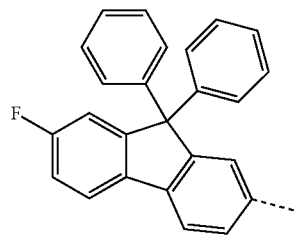
Ar-226
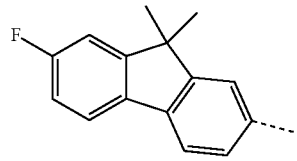
Ar-227
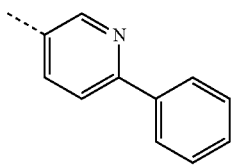
Ar-228
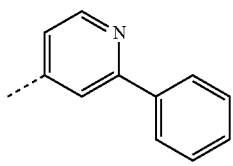
Ar-229
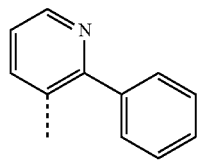
Ar-230
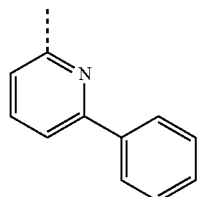
Ar-231
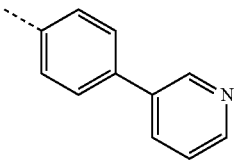
Ar-232

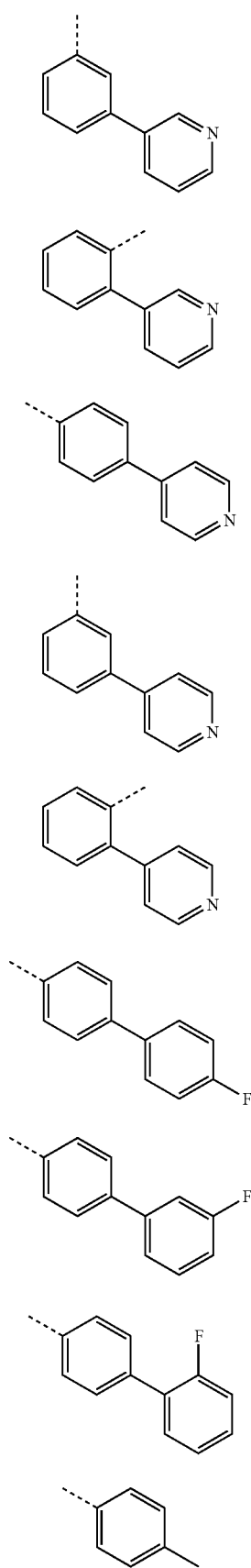
Ar-233
Ar-234
Ar-235
Ar-236
Ar-237
Ar-238
Ar-239
Ar-240
Ar-241
Ar-242
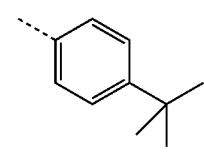
Ar-243
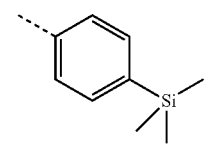
Ar-244
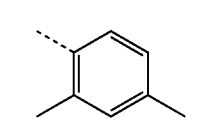
Ar-245
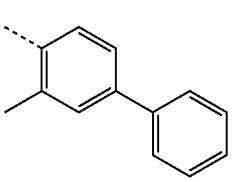
Ar-246
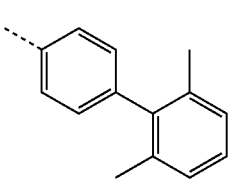
Ar-247
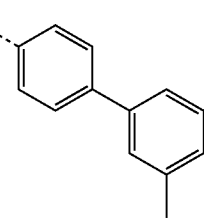
Ar-248
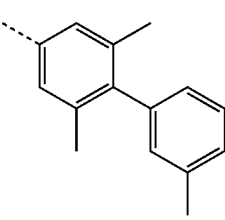
Ar-250
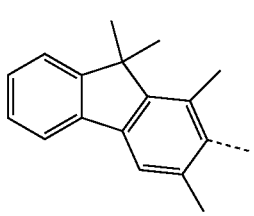
Ar-251
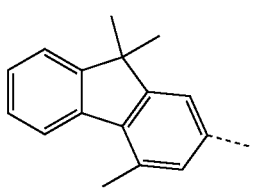

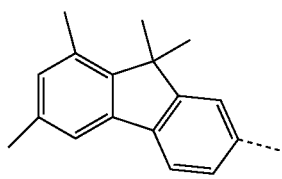

Ar-252 where the dashed bonds indicate the bonds to the nitrogen atom.

More preferably, the group Ar$^1$ and Ar$^2$ are selected from the groups (Ar-1), (Ar-2), (Ar-3), (Ar-4), (Ar-16), (Ar-63), (Ar-64), (Ar-67), (Ar-69), (Ar-78), (Ar-82), (Ar-89), (Ar-96), (Ar-99), (Ar-101), (Ar-107), (Ar-117), (Ar-134), (Ar-139), (Ar-141), (Ar-143), (Ar-150), (Ar-172), (Ar-174), (Ar-213), (Ar-216), (Ar-219) or (Ar-222).

Examples of suitable structures for compounds of formula (1) that can be obtained via the process according to the invention are the compounds of the formulae (S-1) to (S-50) as depicted below, where Ar$^L$ is selected from (Ar$^L$-25), (Ar$^L$-26), (Ar$^L$-27), (Ar$^L$-28), (Ar$^L$-29), (Ar$^L$-20), (Ar$^L$-33), (Ar$^L$-40), (Ar$^L$-43) or (Ar$^L$-101);

R is H, D, F, CN, a straight-chain alkyl having 1 to 5 C atoms or a branched or cyclic alkyl group having 3 to 6 C atoms, or an aryl or heteroaryl group having 5 to 18 aromatic ring atoms; and Ar$^1$, Ar$^2$ are selected from the groups (Ar-1), (Ar-2), (Ar-3), (Ar-4), (Ar-16), (Ar-63), (Ar-64), (Ar-67), (Ar-69), (Ar-78), (Ar-82), (Ar-89), (Ar-96), (Ar-99), (Ar-101), (Ar-107), (Ar-117), (Ar-134), (Ar-139), (Ar-141), (Ar-143), (Ar-150), (Ar-172), (Ar-174), (Ar-213), (Ar-216), (Ar-219) or (Ar-222).

S-1

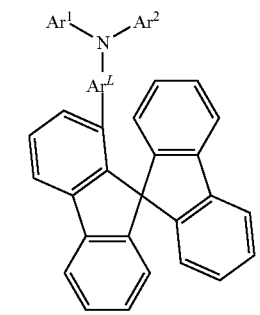

S-2

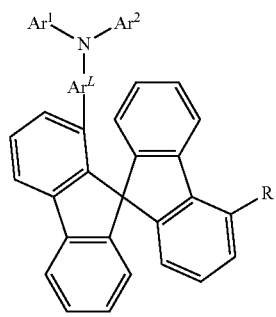

S-3

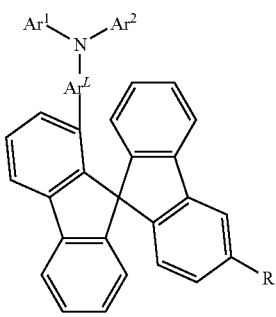

S-4

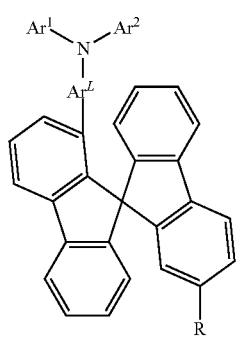

S-5

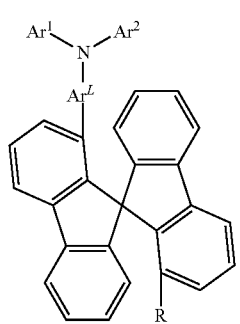

S-6

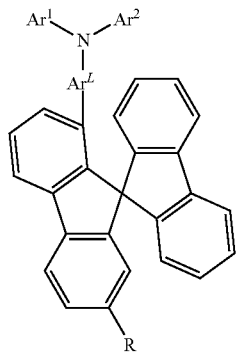

S-7

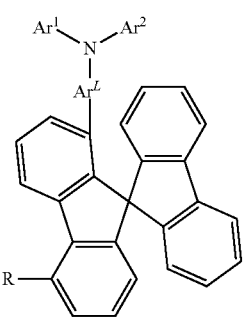

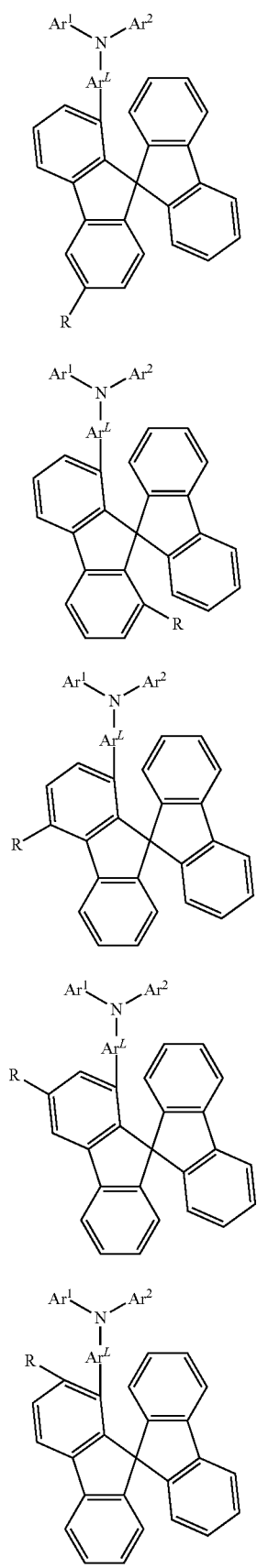
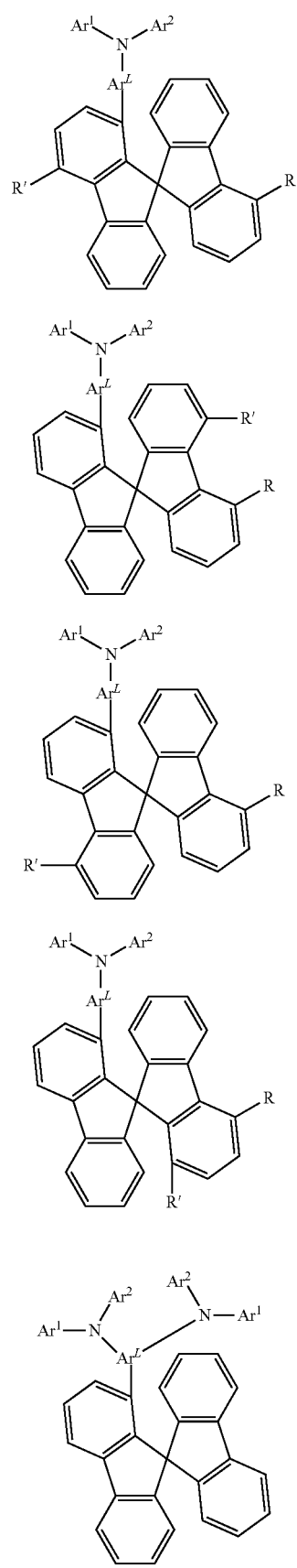

S-18
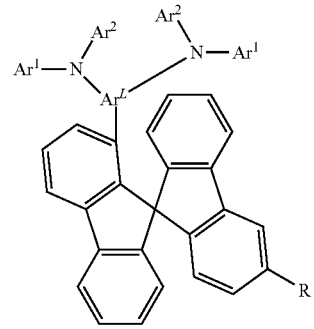
S-19
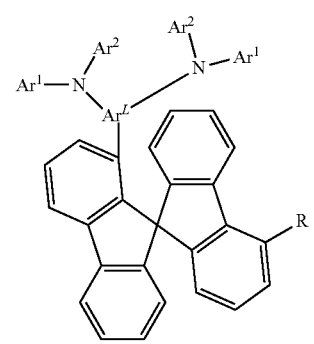
S-20
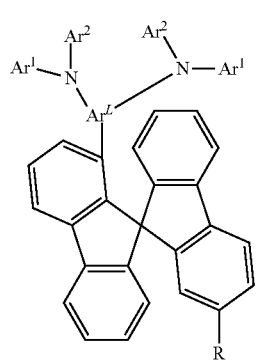
S-21
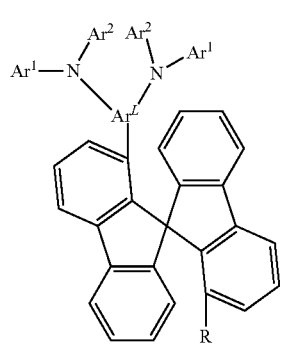
S-22
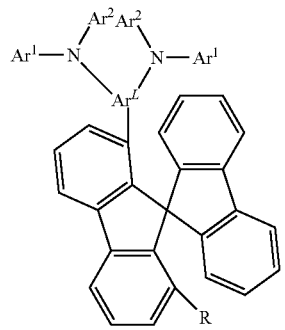
S-23
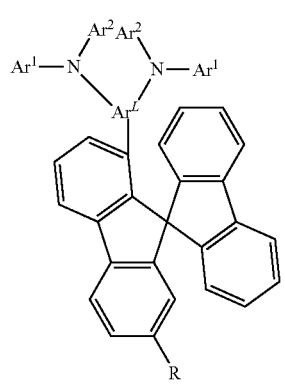
S-24
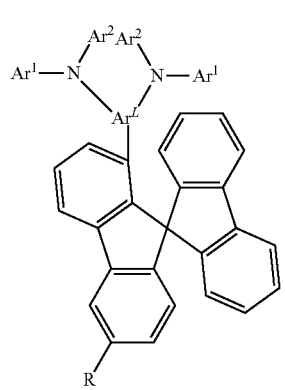
S-25
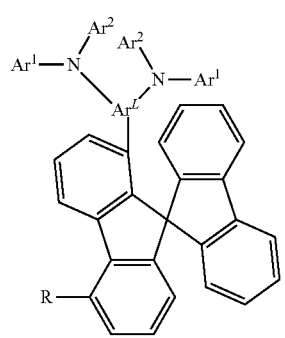

S-26
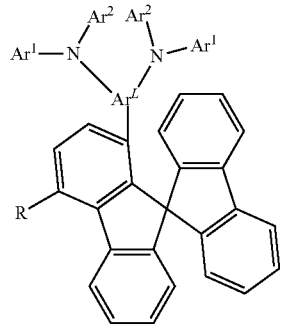
S-27
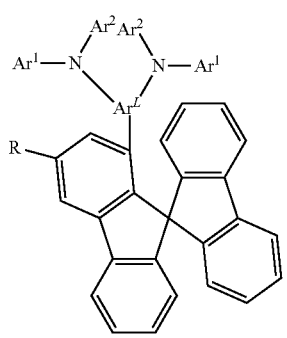
S-28
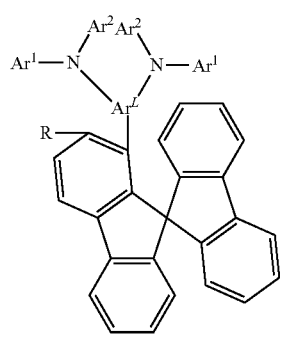
S-29
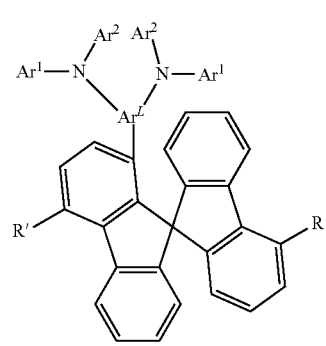
S-30
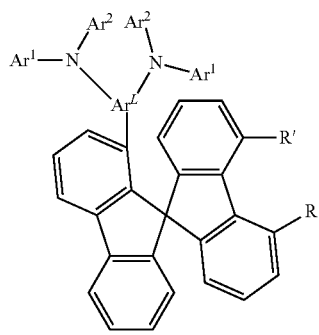
S-31
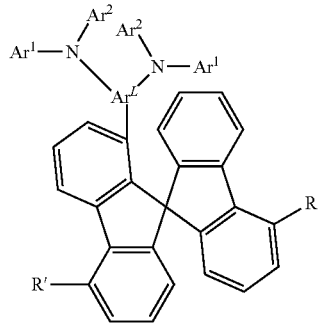
S-32
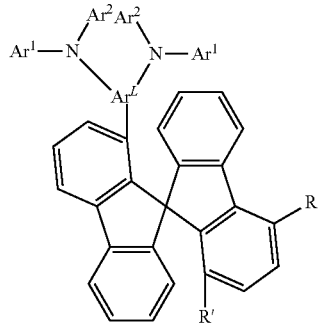
S-33
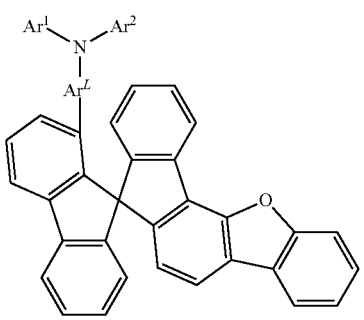
S-34
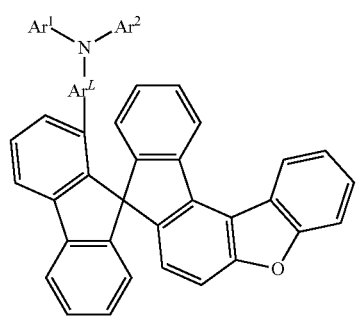

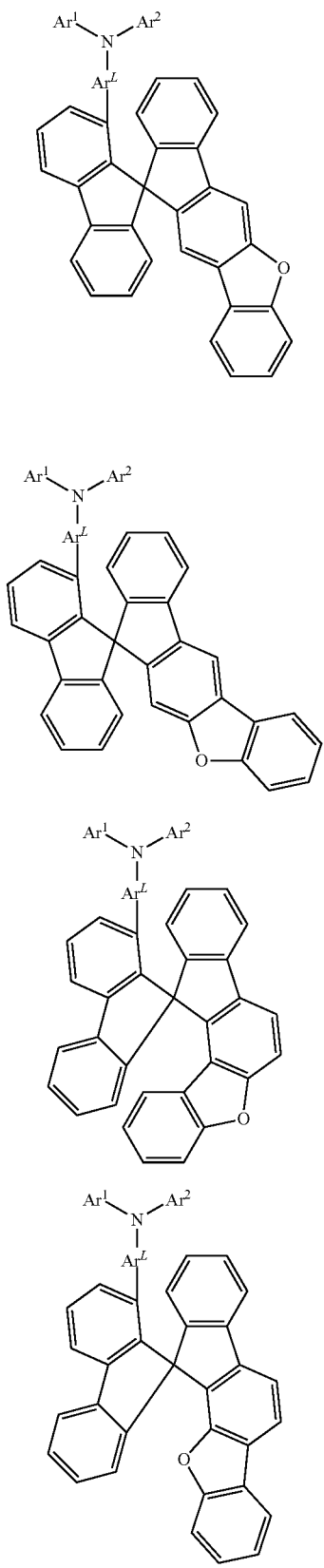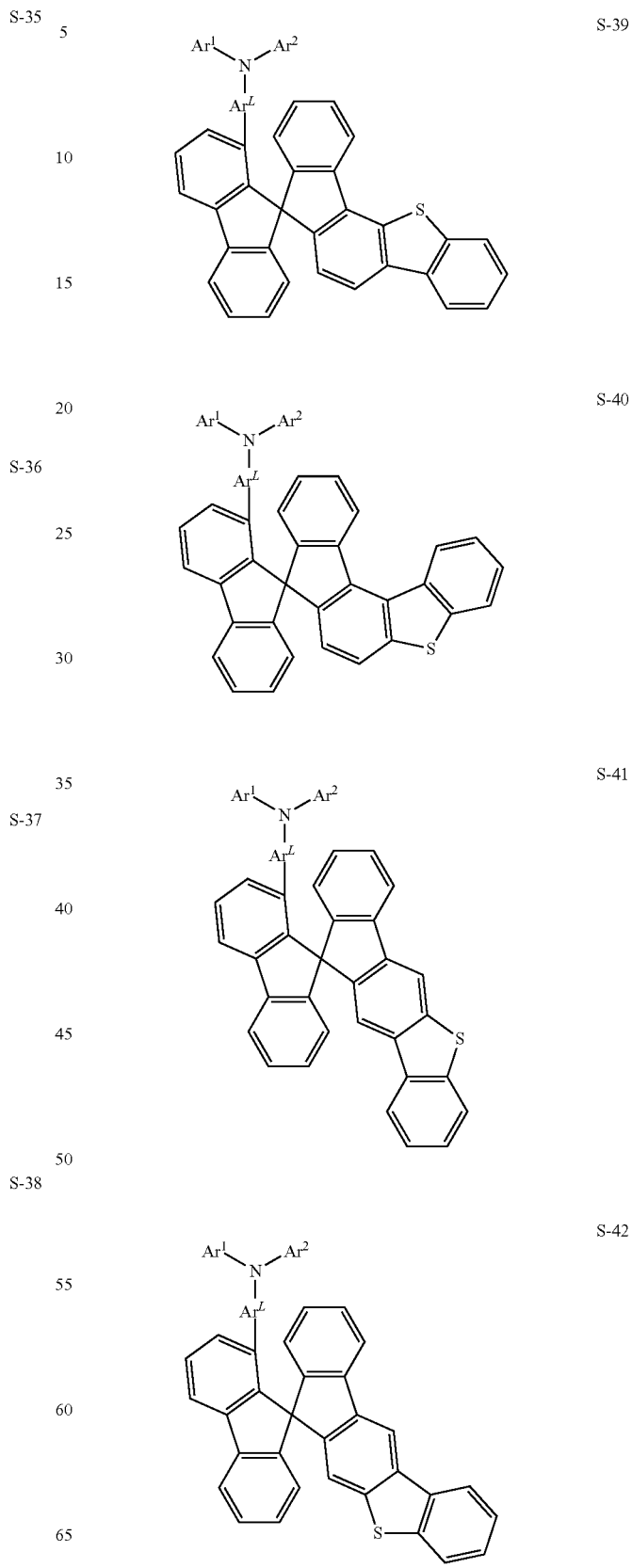

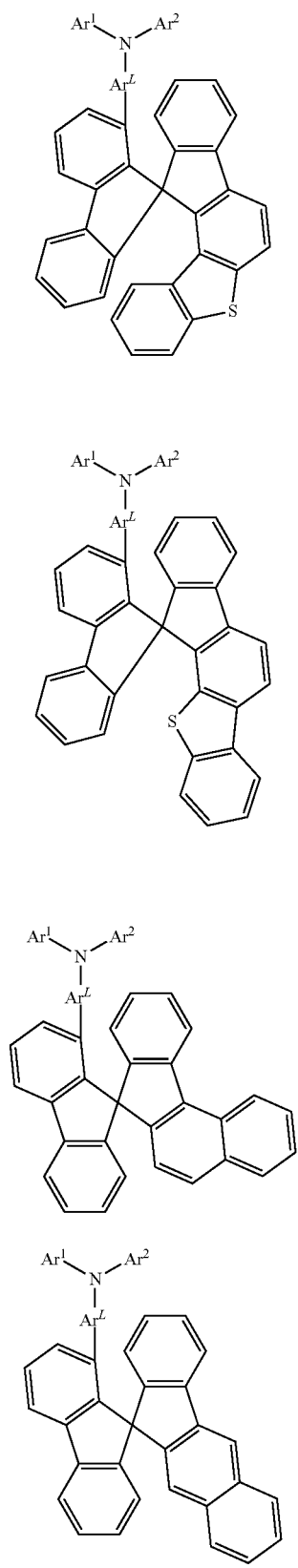
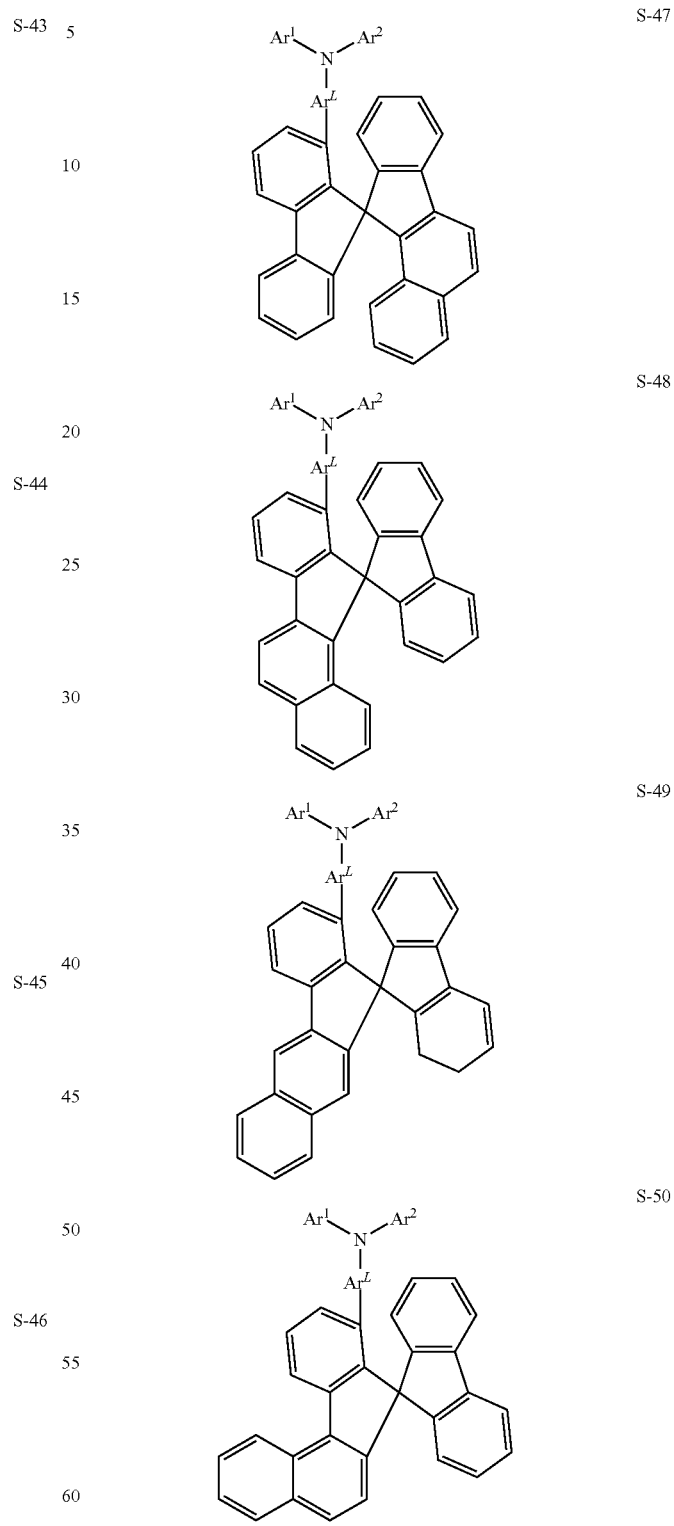
Among formulae (S-1) to (s-50), the formulae (S-10), (S-26), (S-33), (S-34), (S-39) and (S-40) are preferred.
Suitable compounds according to formula (1) are the compounds shown in the following table:

1
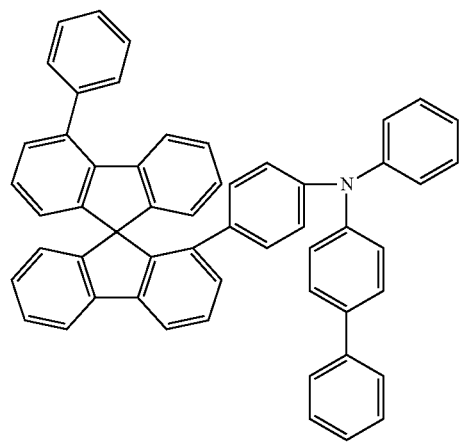 [SMILES: c1ccc(-c2ccc(N(c3ccccc3)c3ccc(-c4cccc5c4C4(c6ccccc6-5)c5ccccc5-c5c(-c6ccccc6)cccc54)cc3)cc2)cc1]
2
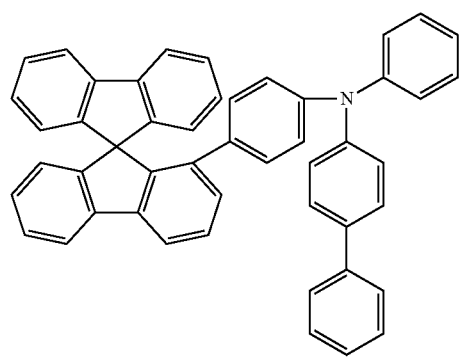 [SMILES: c1ccc(-c2ccc(N(c3ccccc3)c3ccc(-c4cccc5c4C4(c6ccccc6-c6ccccc64)c4ccccc4-5)cc3)cc2)cc1]
3
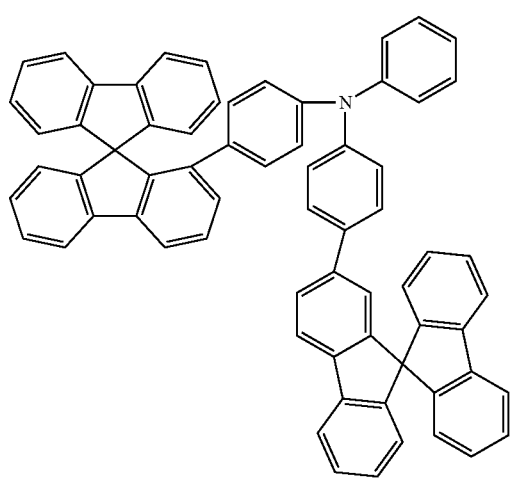 [SMILES: c1ccc(N(c2ccc(-c3ccc4c(c3)C3(c5ccccc5-c5ccccc53)c3ccccc3-4)cc2)c2ccc(-c3cccc4c3C3(c5ccccc5-c5ccccc53)c3ccccc3-4)cc2)cc1]

4
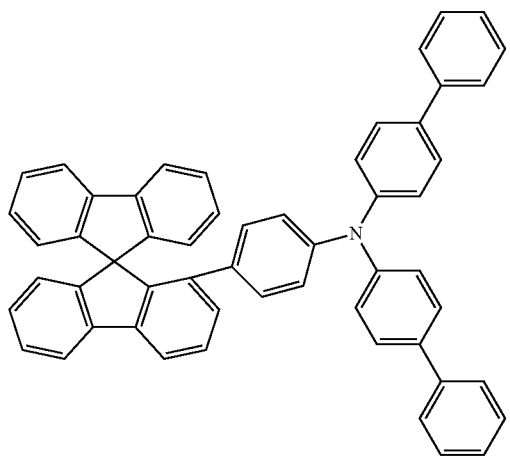 [SMILES: c1ccc(-c2ccc(N(c3ccc(-c4ccccc4)cc3)c3ccc(-c4cccc5c4C4(c6ccccc6-c6ccccc64)c4ccccc4-5)cc3)cc2)cc1]
5
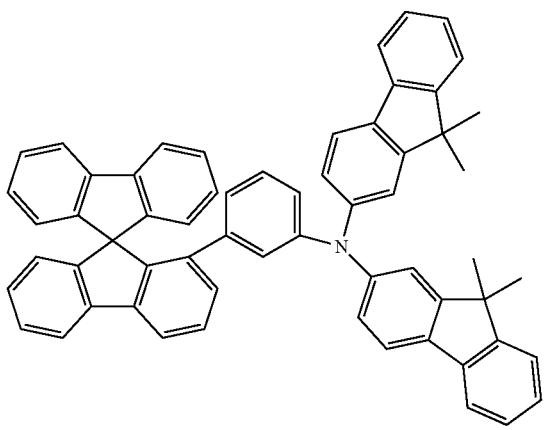 [SMILES: CC1(C)c2ccccc2-c2ccc(N(c3cccc(-c4cccc5c4C4(c6ccccc6-c6ccccc64)c4ccccc4-5)c3)c3ccc4c(c3)C(C)(C)c3ccccc3-4)cc21]
6
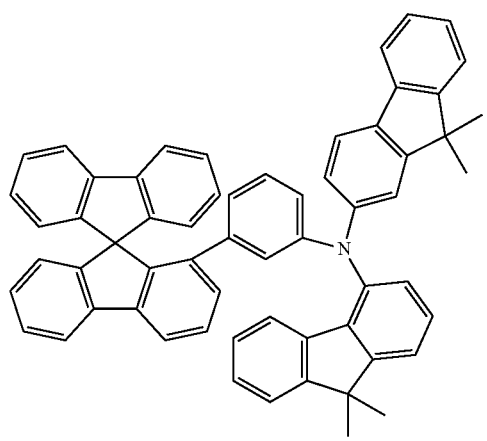 [SMILES: CC1(C)c2ccccc2-c2ccc(N(c3cccc(-c4cccc5c4C4(c6ccccc6-c6ccccc64)c4ccccc4-5)c3)c3cccc4c3-c3ccccc3C4(C)C)cc21]

-continued
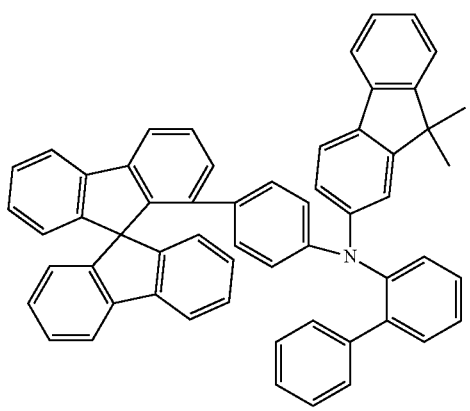 [SMILES: CC1(C)c2ccccc2-c2ccc(N(c3ccc(-c4cccc5c4C4(c6ccccc6-c6ccccc64)c4ccccc4-5)cc3)c3ccccc3-c3ccccc3)cc21]
7
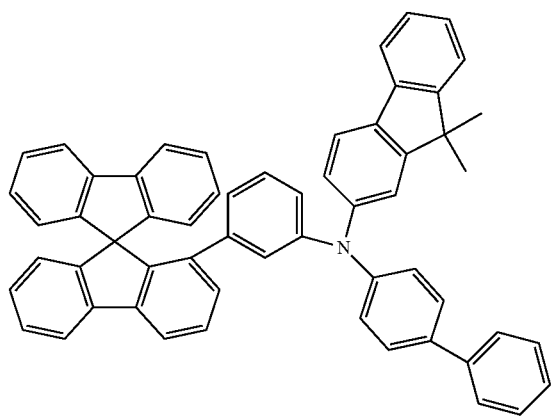 [SMILES: CC1(C)c2ccccc2-c2ccc(N(c3ccc(-c4ccccc4)cc3)c3cccc(-c4cccc5c4C4(c6ccccc6-c6ccccc64)c4ccccc4-5)c3)cc21]
8
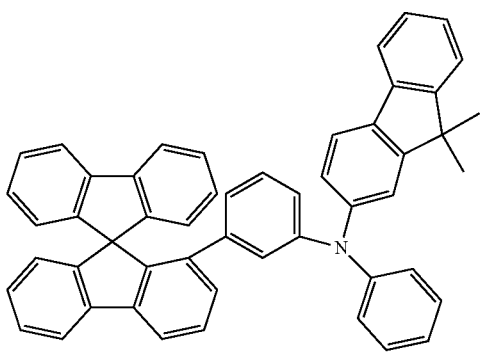 [SMILES: CC1(C)c2ccccc2-c2ccc(N(c3ccccc3)c3cccc(-c4cccc5c4C4(c6ccccc6-c6ccccc64)c4ccccc4-5)c3)cc21]
9
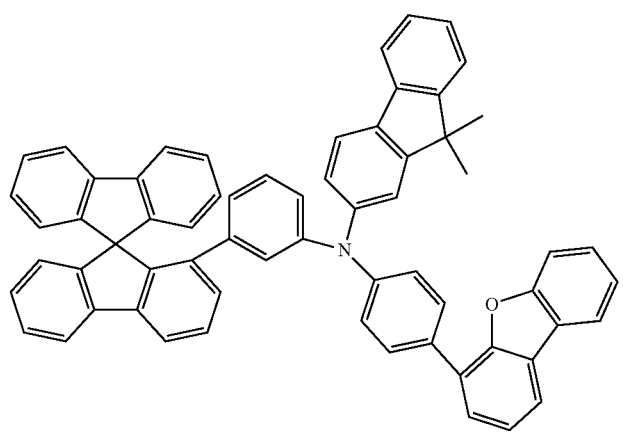 [SMILES: CC1(C)c2ccccc2-c2ccc(N(c3ccc(-c4cccc5c4oc4ccccc45)cc3)c3cccc(-c4cccc5c4C4(c6ccccc6-c6ccccc64)c4ccccc4-5)c3)cc21]
10

-continued
11
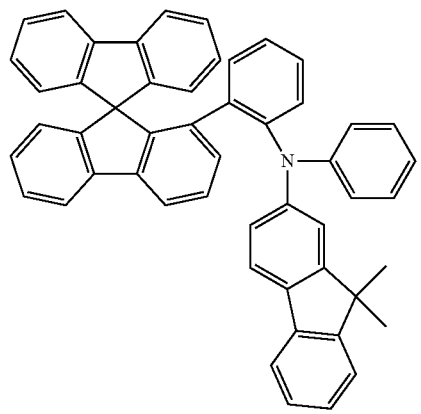 [SMILES: CC1(C)c2ccccc2-c2ccc(N(c3ccccc3)c3ccccc3-c3cccc4c3C3(c5ccccc5-c5ccccc53)c3ccccc3-4)cc21]
12
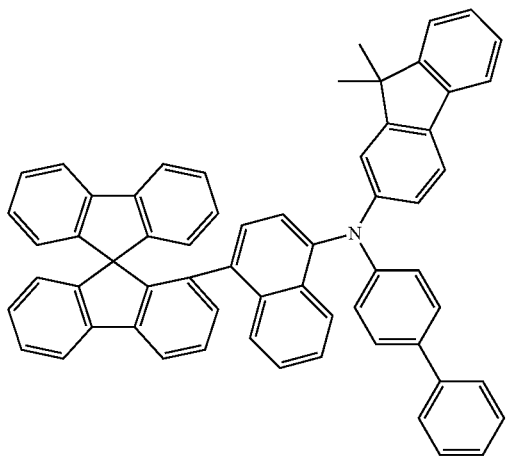 [SMILES: CC1(C)c2ccccc2-c2ccc(N(c3ccc(-c4ccccc4)cc3)c3ccc(-c4cccc5c4C4(c6ccccc6-c6ccccc64)c4ccccc4-5)c4ccccc34)cc21]
13
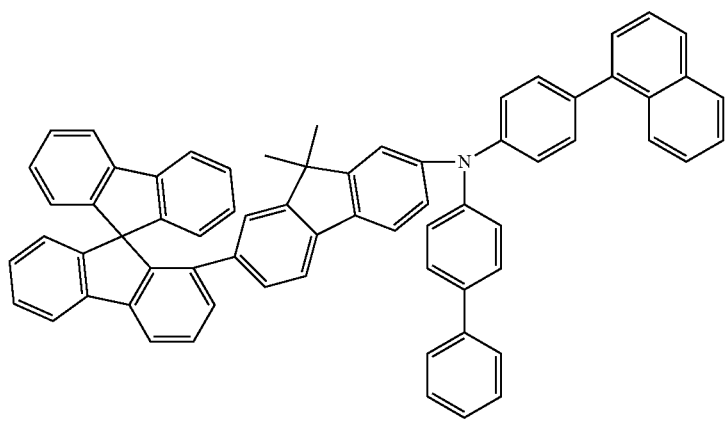 [SMILES: CC1(C)c2cc(-c3cccc4c3C3(c5ccccc5-c5ccccc53)c3ccccc3-4)ccc2-c2ccc(N(c3ccc(-c4ccccc4)cc3)c3ccc(-c4cccc5ccccc45)cc3)cc21]

-continued
14
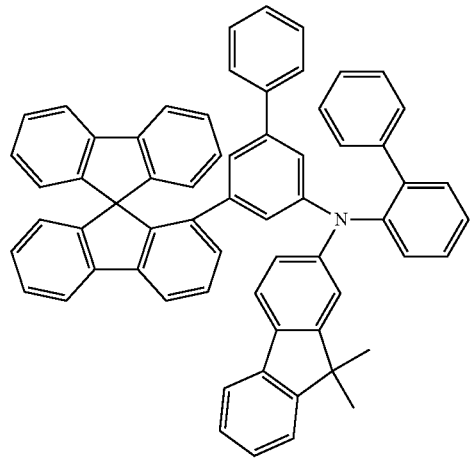 [SMILES: CC1(C)c2ccccc2-c2ccc(N(c3cc(-c4ccccc4)cc(-c4cccc5c4C4(c6ccccc6-c6ccccc64)c4ccccc4-5)c3)c3ccccc3-c3ccccc3)cc21]
15
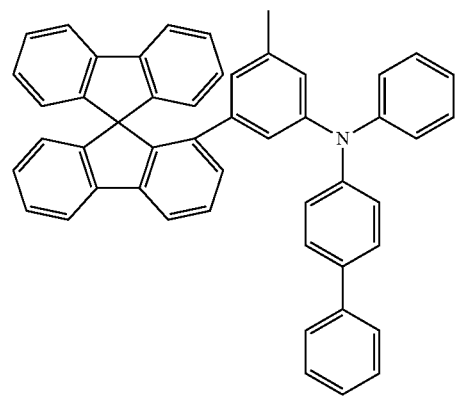 [SMILES: Cc1cc(-c2cccc3c2C2(c4ccccc4-c4ccccc42)c2ccccc2-3)cc(N(c2ccccc2)c2ccc(-c3ccccc3)cc2)c1]
16
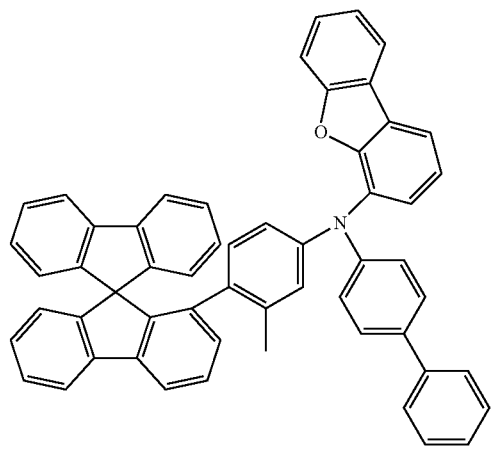 [SMILES: Cc1cc(N(c2ccc(-c3ccccc3)cc2)c2cccc3c2oc2ccccc23)ccc1-c1cccc2c1C1(c3ccccc3-c3ccccc31)c1ccccc1-2]

17
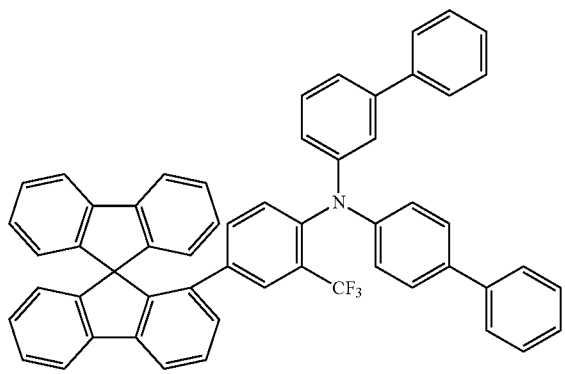 [SMILES: FC(F)(F)c1cc(-c2cccc3c2C2(c4ccccc4-c4ccccc42)c2ccccc2-3)ccc1N(c1ccc(-c2ccccc2)cc1)c1cccc(-c2ccccc2)c1]
18
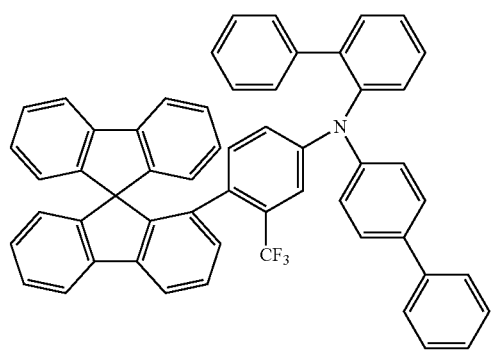 [SMILES: FC(F)(F)c1cc(N(c2ccc(-c3ccccc3)cc2)c2ccccc2-c2ccccc2)ccc1-c1cccc2c1C1(c3ccccc3-c3ccccc31)c1ccccc1-2]
19
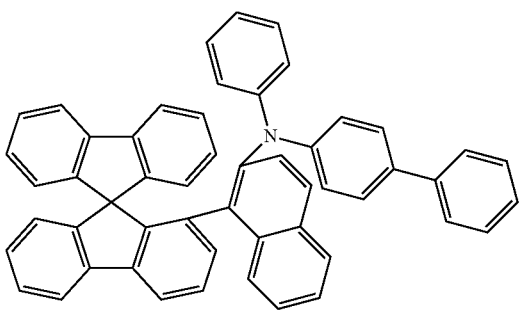 [SMILES: c1ccc(-c2ccc(N(c3ccccc3)c3ccc4ccccc4c3-c3cccc4c3C3(c5ccccc5-c5ccccc53)c3ccccc3-4)cc2)cc1]
20
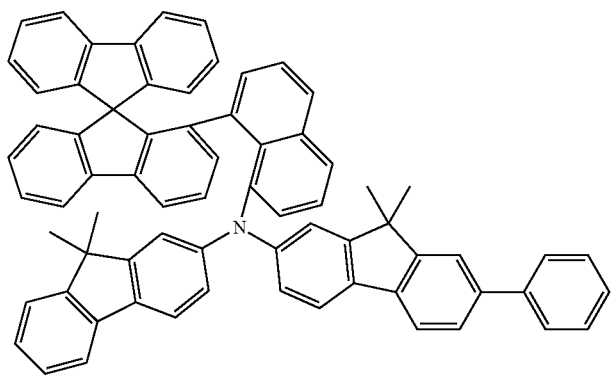 [SMILES: CC1(C)c2ccccc2-c2ccc(N(c3ccc4c(c3)C(C)(C)c3cc(-c5ccccc5)ccc3-4)c3cccc4cccc(-c5cccc6c5C5(c7ccccc7-c7ccccc75)c5ccccc5-6)c34)cc21]

-continued
21
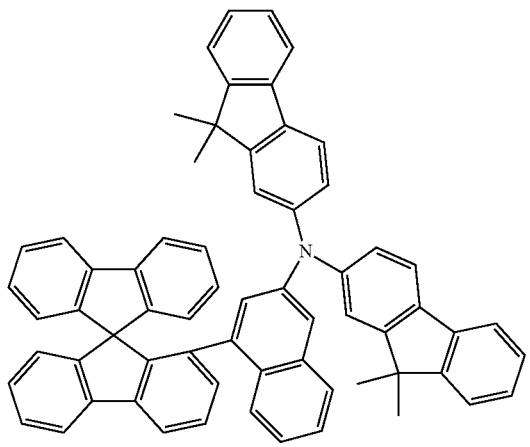 [SMILES: CC1(C)c2ccccc2-c2ccc(N(c3ccc4c(c3)C(C)(C)c3ccccc3-4)c3cc(-c4cccc5c4C4(c6ccccc6-c6ccccc64)c4ccccc4-5)c4ccccc4c3)cc21]
22
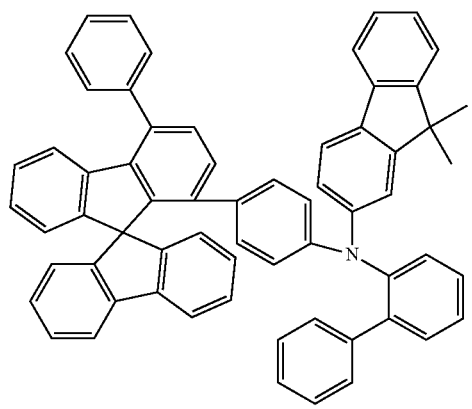 [SMILES: CC1(C)c2ccccc2-c2ccc(N(c3ccc(-c4ccc(-c5ccccc5)c5c4C4(c6ccccc6-c6ccccc64)c4ccccc4-5)cc3)c3ccccc3-c3ccccc3)cc21]
23
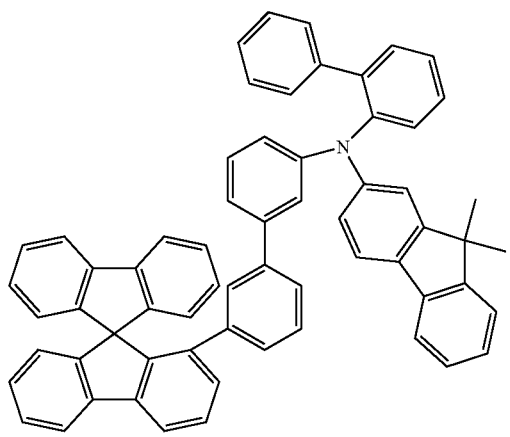 [SMILES: CC1(C)c2ccccc2-c2ccc(N(c3cccc(-c4cccc(-c5cccc6c5C5(c7ccccc7-c7ccccc75)c5ccccc5-6)c4)c3)c3ccccc3-c3ccccc3)cc21]

24
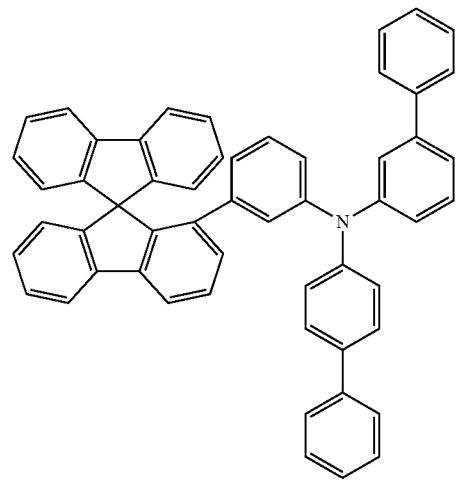 [SMILES: c1ccc(-c2ccc(N(c3cccc(-c4ccccc4)c3)c3cccc(-c4cccc5c4C4(c6ccccc6-c6ccccc64)c4ccccc4-5)c3)cc2)cc1]
25
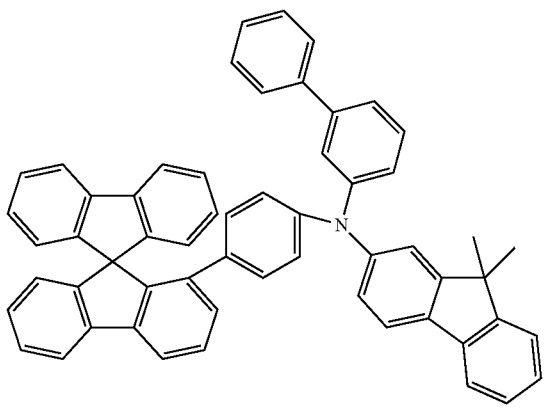 [SMILES: CC1(C)c2ccccc2-c2ccc(N(c3ccc(-c4cccc5c4C4(c6ccccc6-c6ccccc64)c4ccccc4-5)cc3)c3cccc(-c4ccccc4)c3)cc21]
26
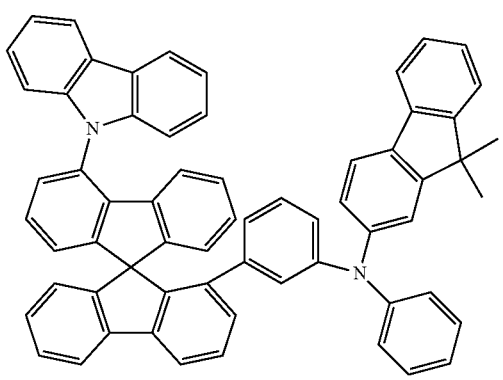 [SMILES: CC1(C)c2ccccc2-c2ccc(N(c3ccccc3)c3cccc(-c4cccc5c4C4(c6ccccc6-5)c5ccccc5-c5c(-n6c7ccccc7c7ccccc76)cccc54)c3)cc21]

27
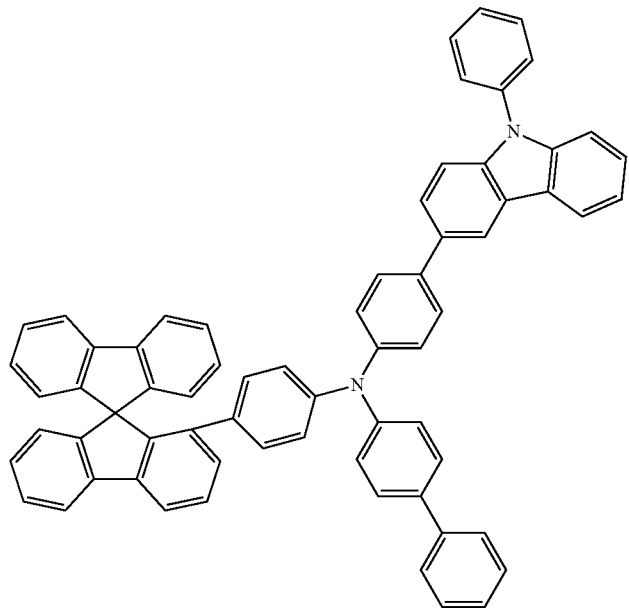 [SMILES: c1ccc(-c2ccc(N(c3ccc(-c4ccc5c(c4)c4ccccc4n5-c4ccccc4)cc3)c3ccc(-c4cccc5c4C4(c6ccccc6-c6ccccc64)c4ccccc4-5)cc3)cc2)cc1]
28
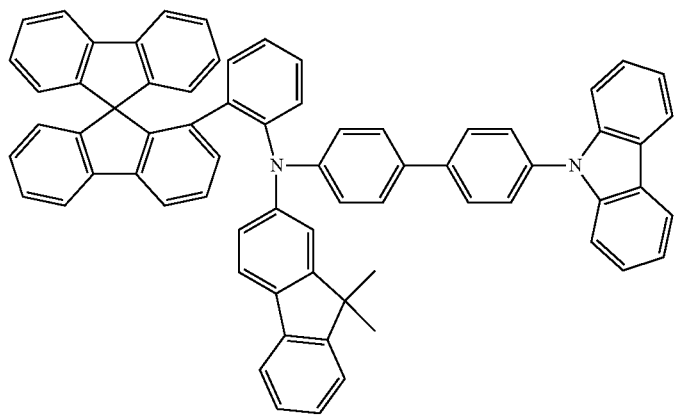 [SMILES: CC1(C)c2ccccc2-c2ccc(N(c3ccc(-c4ccc(-n5c6ccccc6c6ccccc65)cc4)cc3)c3ccccc3-c3cccc4c3C3(c5ccccc5-c5ccccc53)c3ccccc3-4)cc21]
29
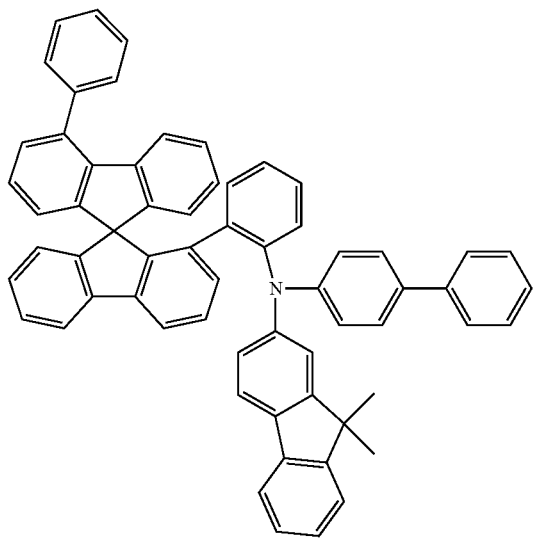 [SMILES: CC1(C)c2ccccc2-c2ccc(N(c3ccc(-c4ccccc4)cc3)c3ccccc3-c3cccc4c3C3(c5ccccc5-4)c4ccccc4-c4c(-c5ccccc5)cccc43)cc21]

-continued
30
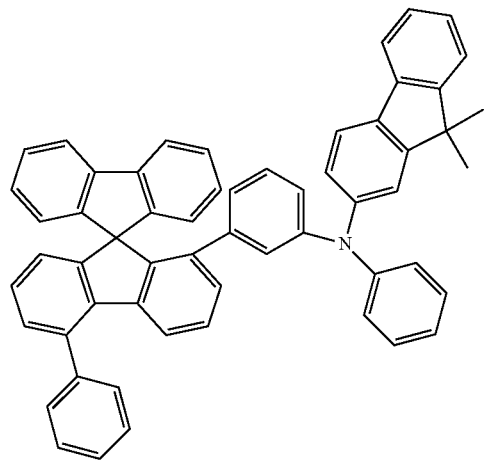 [SMILES: CC1(C)c2ccccc2-c2ccc(N(c3ccccc3)c3cccc(-c4cccc5c4C4(c6ccccc6-c6ccccc64)c4cccc(-c6ccccc6)c4-5)c3)cc21]
31
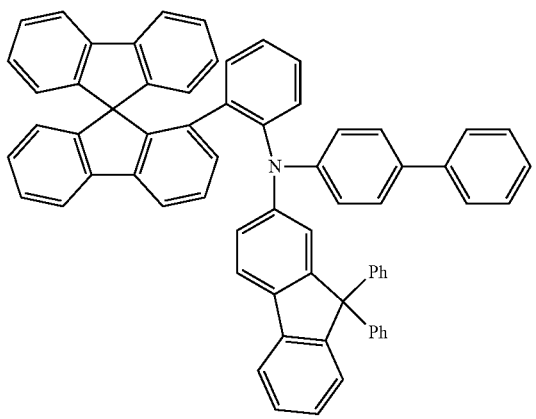 [SMILES: c1ccc(-c2ccc(N(c3ccc4c(c3)C(c3ccccc3)(c3ccccc3)c3ccccc3-4)c3ccccc3-c3cccc4c3C3(c5ccccc5-c5ccccc53)c3ccccc3-4)cc2)cc1]
32
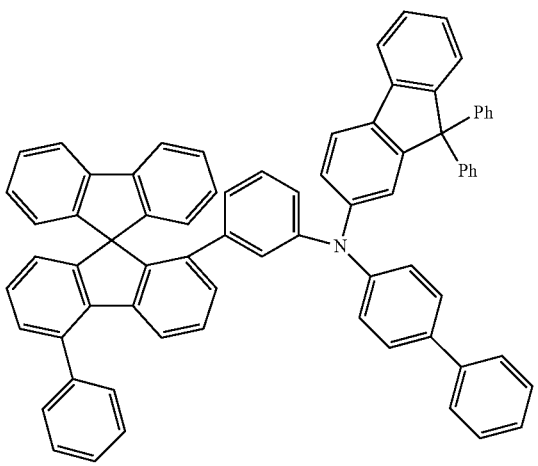 [SMILES: c1ccc(-c2ccc(N(c3cccc(-c4cccc5c4C4(c6ccccc6-c6ccccc64)c4cccc(-c6ccccc6)c4-5)c3)c3ccc4c(c3)C(c3ccccc3)(c3ccccc3)c3ccccc3-4)cc2)cc1]

-continued
33
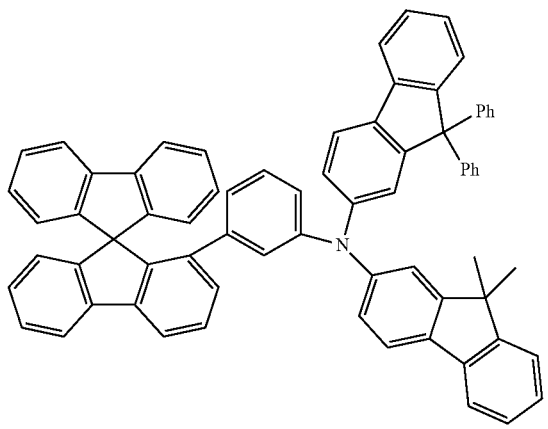 [SMILES: CC1(C)c2ccccc2-c2ccc(N(c3cccc(-c4cccc5c4C4(c6ccccc6-c6ccccc64)c4ccccc4-5)c3)c3ccc4c(c3)C(c3ccccc3)(c3ccccc3)c3ccccc3-4)cc21]
34
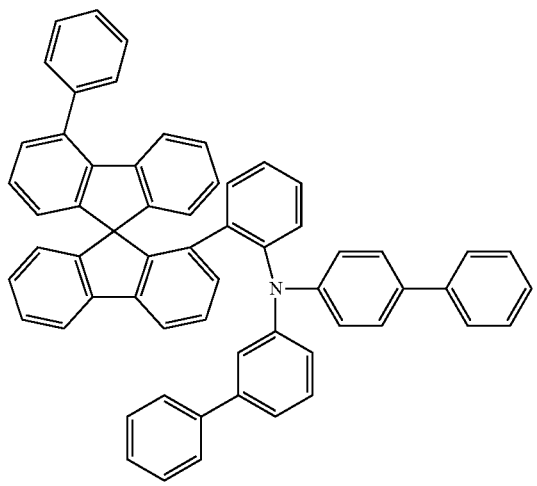 [SMILES: c1ccc(-c2ccc(N(c3cccc(-c4ccccc4)c3)c3ccccc3-c3cccc4c3C3(c5ccccc5-4)c4ccccc4-c4c(-c5ccccc5)cccc43)cc2)cc1]
35
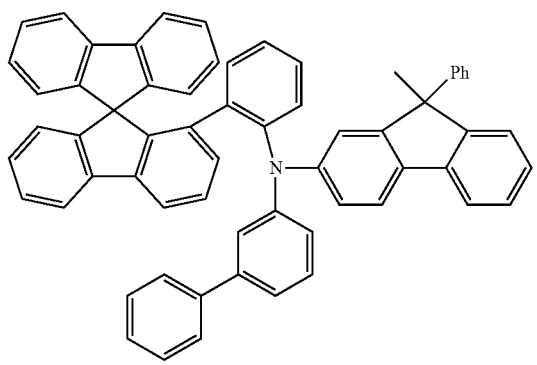 [SMILES: CC1(c2ccccc2)c2ccccc2-c2ccc(N(c3cccc(-c4ccccc4)c3)c3ccccc3-c3cccc4c3C3(c5ccccc5-c5ccccc53)c3ccccc3-4)cc21]

-continued
36
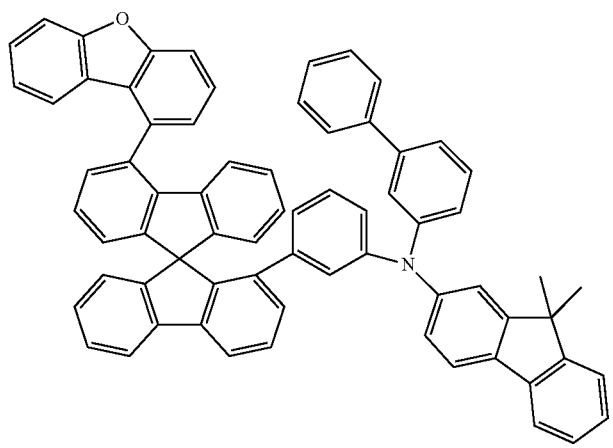 [SMILES: CC1(C)c2ccccc2-c2ccc(N(c3cccc(-c4ccccc4)c3)c3cccc(-c4cccc5c4C4(c6ccccc6-5)c5ccccc5-c5c(-c6cccc7oc8ccccc8c67)cccc54)c3)cc21]
37
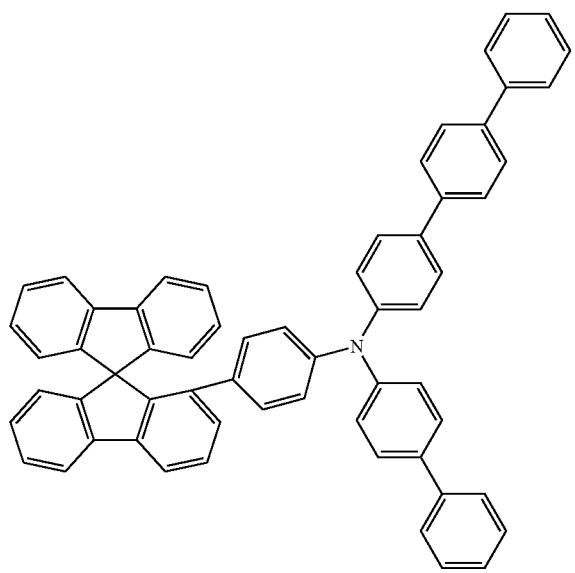 [SMILES: c1ccc(-c2ccc(-c3ccc(N(c4ccc(-c5ccccc5)cc4)c4ccc(-c5cccc6c5C5(c7ccccc7-c7ccccc75)c5ccccc5-6)cc4)cc3)cc2)cc1]
38
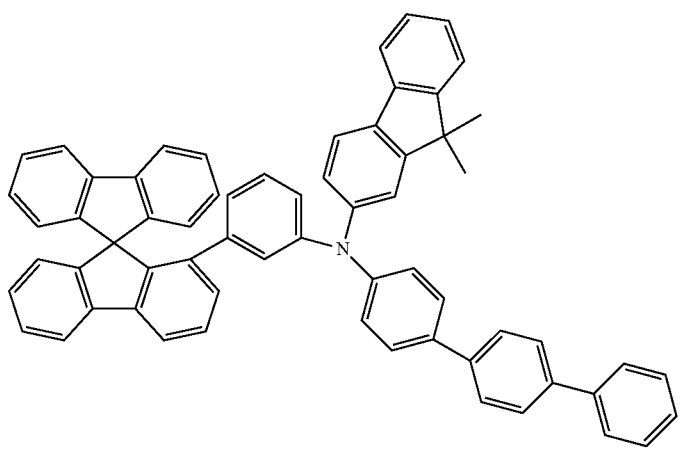 [SMILES: CC1(C)c2ccccc2-c2ccc(N(c3ccc(-c4ccc(-c5ccccc5)cc4)cc3)c3cccc(-c4cccc5c4C4(c6ccccc6-c6ccccc64)c4ccccc4-5)c3)cc21]

-continued
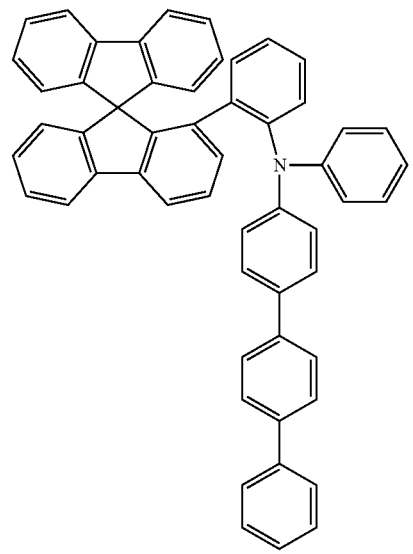 [SMILES: c1ccc(-c2ccc(-c3ccc(N(c4ccccc4)c4ccccc4-c4cccc5c4C4(c6ccccc6-c6ccccc64)c4ccccc4-5)cc3)cc2)cc1]
39
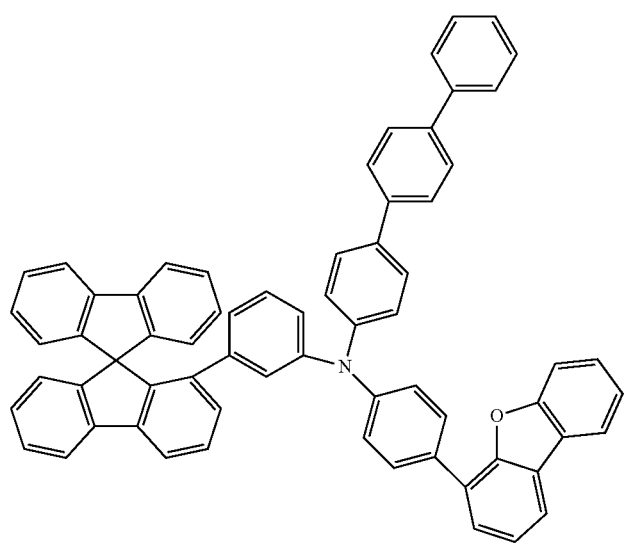 [SMILES: c1ccc(-c2ccc(-c3ccc(N(c4ccc(-c5cccc6c5oc5ccccc56)cc4)c4cccc(-c5cccc6c5C5(c7ccccc7-c7ccccc75)c5ccccc5-6)c4)cc3)cc2)cc1]
40
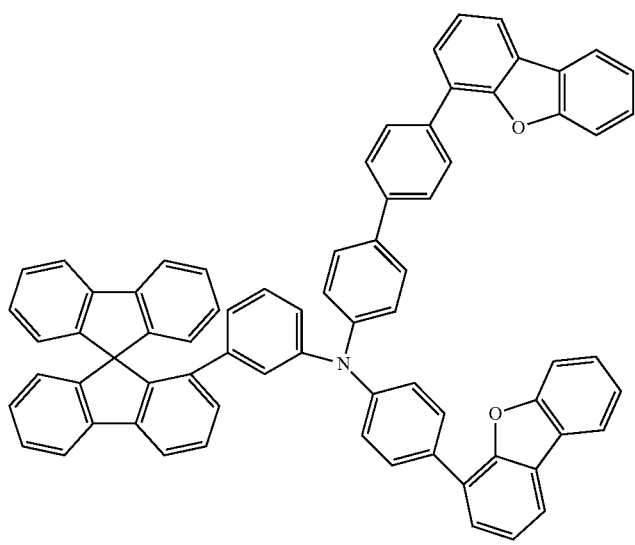 [SMILES: c1cc(-c2cccc3c2C2(c4ccccc4-c4ccccc42)c2ccccc2-3)cc(N(c2ccc(-c3ccc(-c4cccc5c4oc4ccccc45)cc3)cc2)c2ccc(-c3cccc4c3oc3ccccc34)cc2)c1]
41

-continued
42
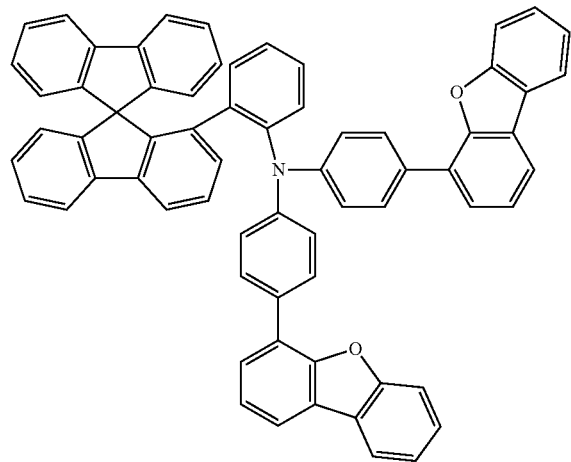 [SMILES: c1ccc(N(c2ccc(-c3cccc4c3oc3ccccc34)cc2)c2ccc(-c3cccc4c3oc3ccccc34)cc2)c(-c2cccc3c2C2(c4ccccc4-c4ccccc42)c2ccccc2-3)c1]
43
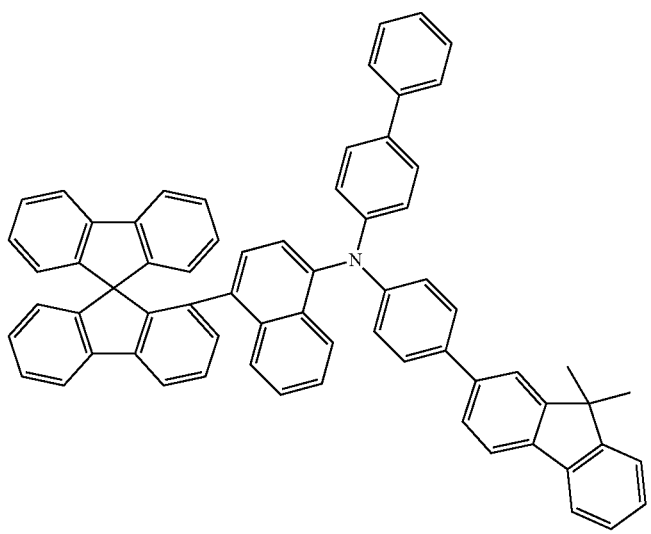 [SMILES: CC1(C)c2ccccc2-c2ccc(-c3ccc(N(c4ccc(-c5ccccc5)cc4)c4ccc(-c5cccc6c5C5(c7ccccc7-c7ccccc75)c5ccccc5-6)c5ccccc45)cc3)cc21]
44
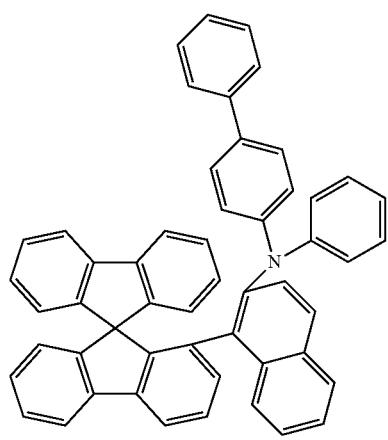 [SMILES: c1ccc(-c2ccc(N(c3ccccc3)c3ccc4ccccc4c3-c3cccc4c3C3(c5ccccc5-c5ccccc53)c3ccccc3-4)cc2)cc1]

45
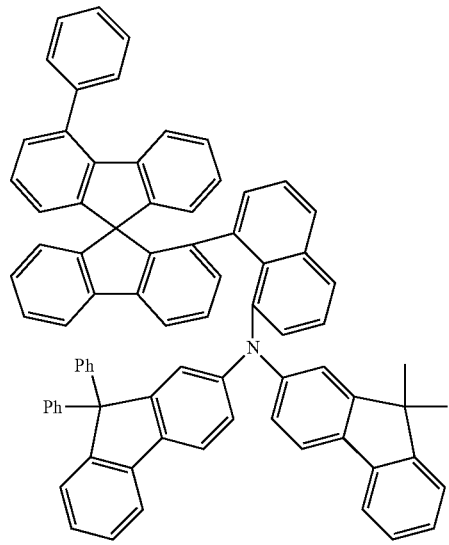 [SMILES: CC1(C)c2ccccc2-c2ccc(N(c3ccc4c(c3)C(c3ccccc3)(c3ccccc3)c3ccccc3-4)c3cccc4cccc(-c5cccc6c5C5(c7ccccc7-6)c6ccccc6-c6c(-c7ccccc7)cccc65)c34)cc21]
46
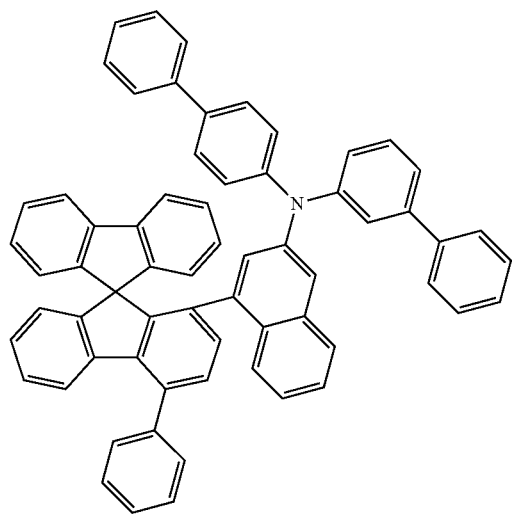 [SMILES: c1ccc(-c2ccc(N(c3cccc(-c4ccccc4)c3)c3cc(-c4ccc(-c5ccccc5)c5c4C4(c6ccccc6-c6ccccc64)c4ccccc4-5)c4ccccc4c3)cc2)cc1]
47
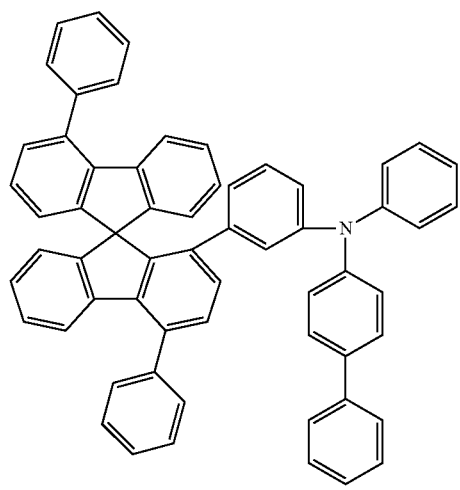 [SMILES: c1ccc(-c2ccc(N(c3ccccc3)c3cccc(-c4ccc(-c5ccccc5)c5c4C4(c6ccccc6-c6c(-c7ccccc7)cccc64)c4ccccc4-5)c3)cc2)cc1]

-continued
48
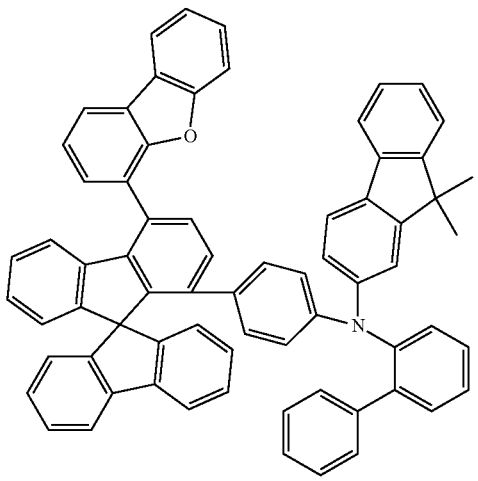 [SMILES: CC1(C)c2ccccc2-c2ccc(N(c3ccc(-c4ccc(-c5cccc6c5oc5ccccc56)c5c4C4(c6ccccc6-c6ccccc64)c4ccccc4-5)cc3)c3ccccc3-c3ccccc3)cc21]
49
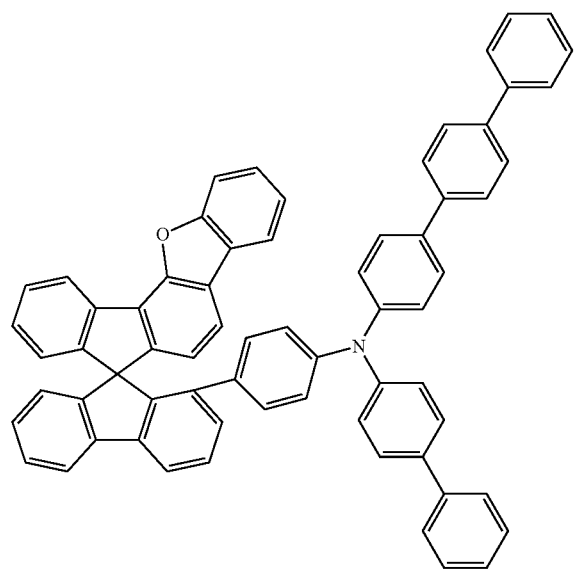 [SMILES: c1ccc(-c2ccc(-c3ccc(N(c4ccc(-c5ccccc5)cc4)c4ccc(-c5cccc6c5C5(c7ccccc7-6)c6ccccc6-c6c5ccc5c6oc6ccccc65)cc4)cc3)cc2)cc1]
50
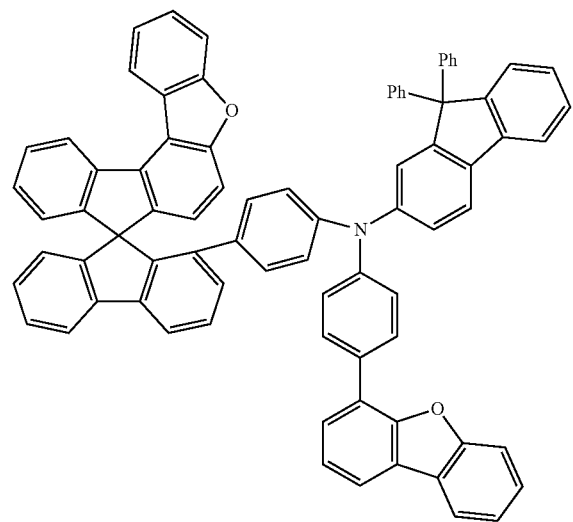 [SMILES: c1ccc(C2(c3ccccc3)c3ccccc3-c3ccc(N(c4ccc(-c5cccc6c5C5(c7ccccc7-6)c6ccccc6-c6c5ccc5oc7ccccc7c65)cc4)c4ccc(-c5cccc6c5oc5ccccc56)cc4)cc32)cc1]

-continued
51
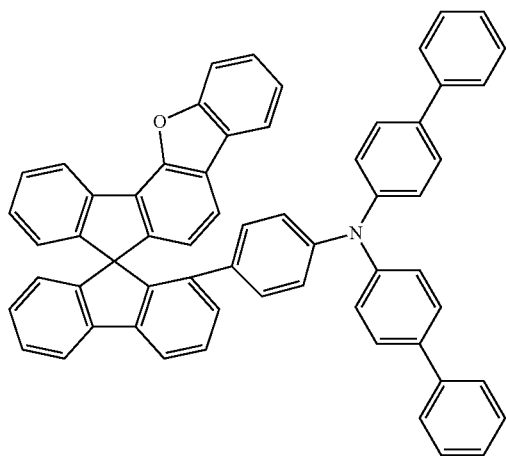 [SMILES: c1ccc(-c2ccc(N(c3ccc(-c4ccccc4)cc3)c3ccc(-c4cccc5c4C4(c6ccccc6-5)c5ccccc5-c5c4ccc4c5oc5ccccc54)cc3)cc2)cc1]
52
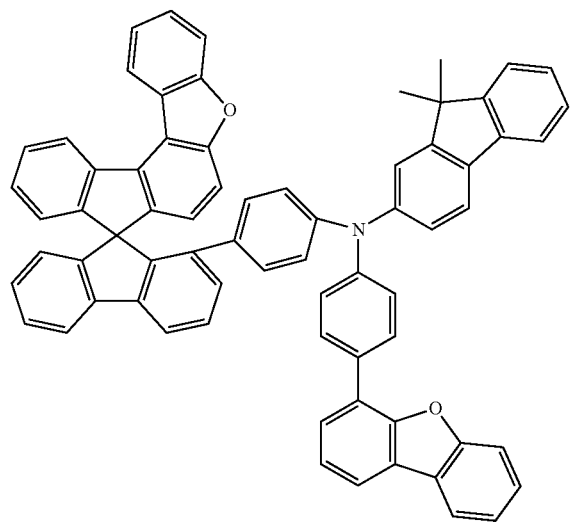 [SMILES: CC1(C)c2ccccc2-c2ccc(N(c3ccc(-c4cccc5c4C4(c6ccccc6-5)c5ccccc5-c5c4ccc4oc6ccccc6c54)cc3)c3ccc(-c4cccc5c4oc4ccccc45)cc3)cc21]
53
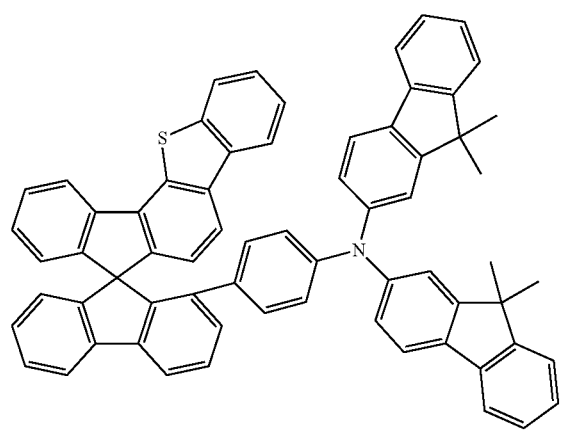 [SMILES: CC1(C)c2ccccc2-c2ccc(N(c3ccc(-c4cccc5c4C4(c6ccccc6-5)c5ccccc5-c5c4ccc4c5sc5ccccc54)cc3)c3ccc4c(c3)C(C)(C)c3ccccc3-4)cc21]

-continued
54
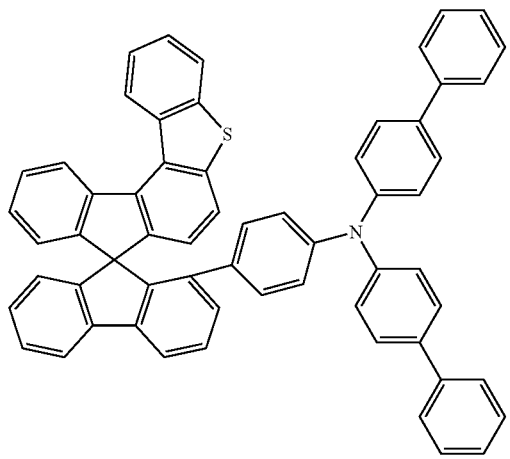 [SMILES: c1ccc(-c2ccc(N(c3ccc(-c4ccccc4)cc3)c3ccc(-c4cccc5c4C4(c6ccccc6-5)c5ccccc5-c5c4ccc4sc6ccccc6c54)cc3)cc2)cc1]
55
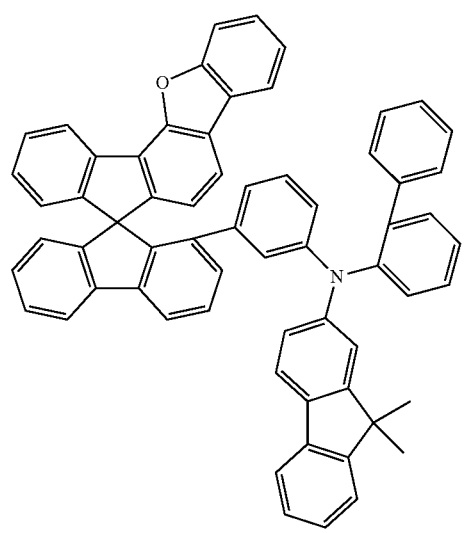 [SMILES: CC1(C)c2ccccc2-c2ccc(N(c3cccc(-c4cccc5c4C4(c6ccccc6-5)c5ccccc5-c5c4ccc4c5oc5ccccc54)c3)c3ccccc3-c3ccccc3)cc21]
56
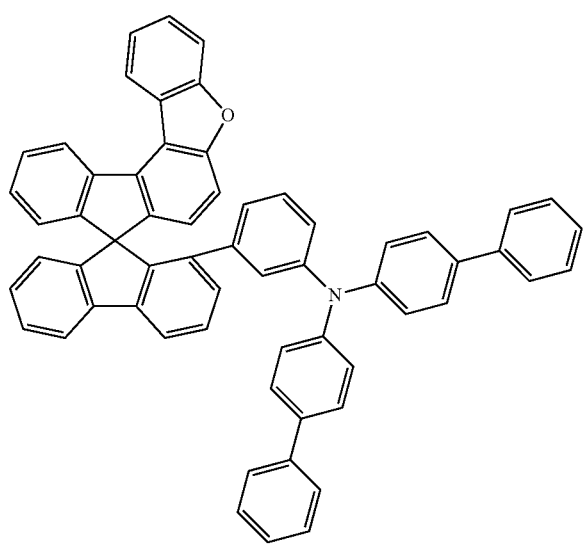 [SMILES: c1ccc(-c2ccc(N(c3ccc(-c4ccccc4)cc3)c3cccc(-c4cccc5c4C4(c6ccccc6-5)c5ccccc5-c5c4ccc4oc6ccccc6c54)c3)cc2)cc1]

-continued
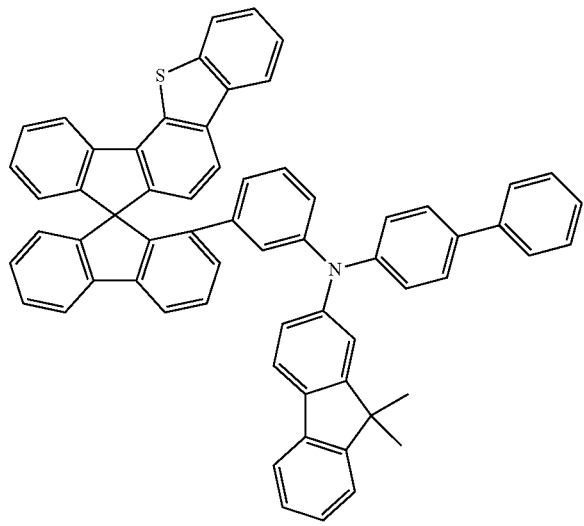 [SMILES: CC1(C)c2ccccc2-c2ccc(N(c3ccc(-c4ccccc4)cc3)c3cccc(-c4cccc5c4C4(c6ccccc6-5)c5ccccc5-c5c4ccc4c5sc5ccccc54)c3)cc21]
57
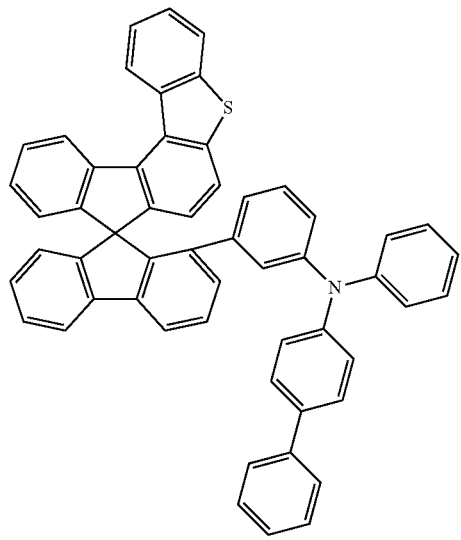 [SMILES: c1ccc(-c2ccc(N(c3ccccc3)c3cccc(-c4cccc5c4C4(c6ccccc6-5)c5ccccc5-c5c4ccc4sc6ccccc6c54)c3)cc2)cc1]
58
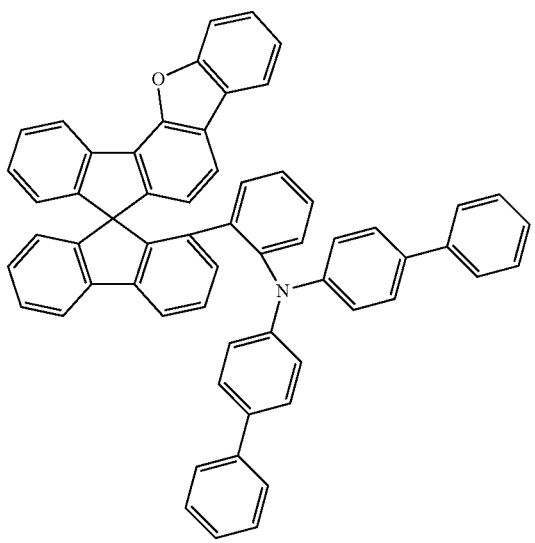 [SMILES: c1ccc(-c2ccc(N(c3ccc(-c4ccccc4)cc3)c3ccccc3-c3cccc4c3C3(c5ccccc5-4)c4ccccc4-c4c3ccc3c4oc4ccccc43)cc2)cc1]
59

-continued
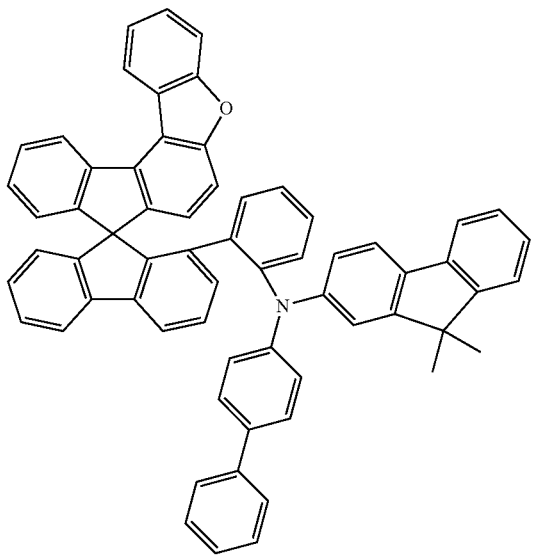 [SMILES: CC1(C)c2ccccc2-c2ccc(N(c3ccc(-c4ccccc4)cc3)c3ccccc3-c3cccc4c3C3(c5ccccc5-4)c4ccccc4-c4c3ccc3oc5ccccc5c43)cc21]
60
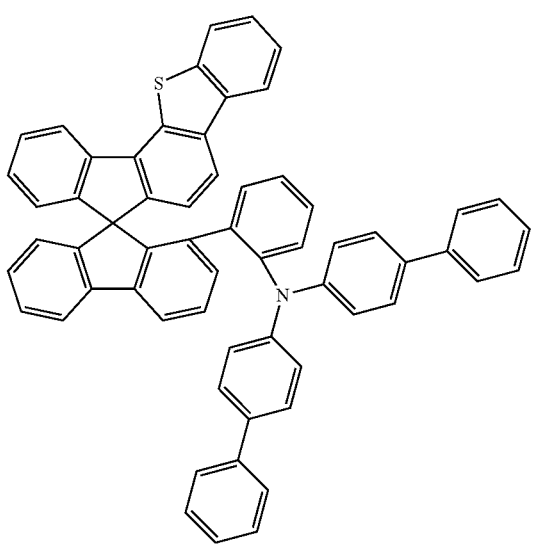
61
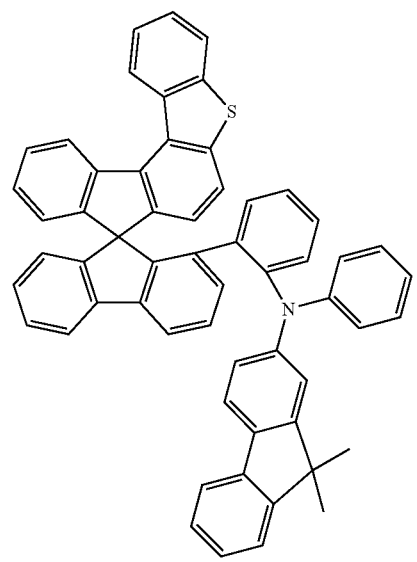 [SMILES: CC1(C)c2ccccc2-c2ccc(N(c3ccccc3)c3ccccc3-c3cccc4c3C3(c5ccccc5-4)c4ccccc4-c4c3ccc3sc5ccccc5c43)cc21]
62

-continued
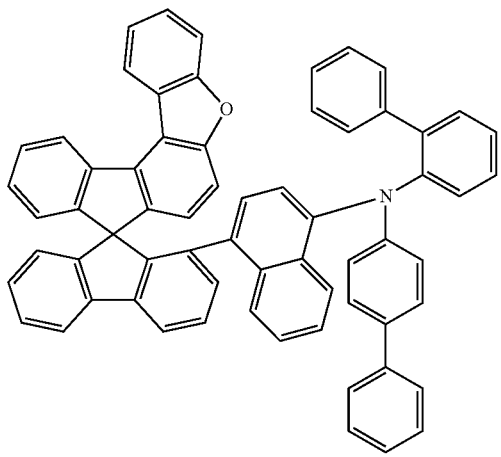 [SMILES: c1ccc(-c2ccc(N(c3ccccc3-c3ccccc3)c3ccc(-c4cccc5c4C4(c6ccccc6-5)c5ccccc5-c5c4ccc4oc6ccccc6c54)c4ccccc34)cc2)cc1]
63
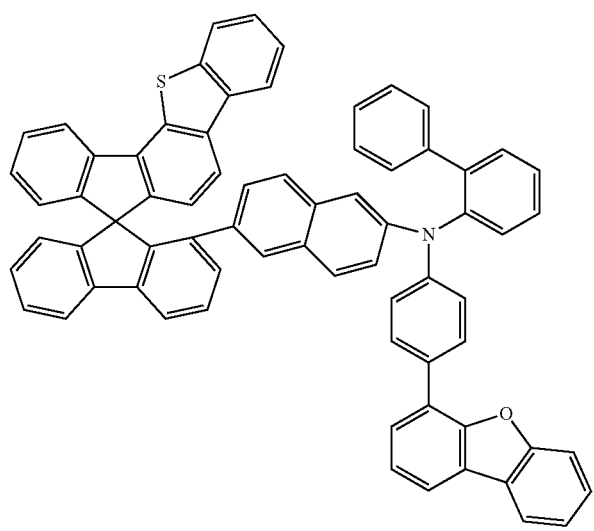 [SMILES: c1ccc(-c2ccccc2N(c2ccc(-c3cccc4c3oc3ccccc34)cc2)c2ccc3cc(-c4cccc5c4C4(c6ccccc6-5)c5ccccc5-c5c4ccc4c5sc5ccccc54)ccc3c2)cc1]
64
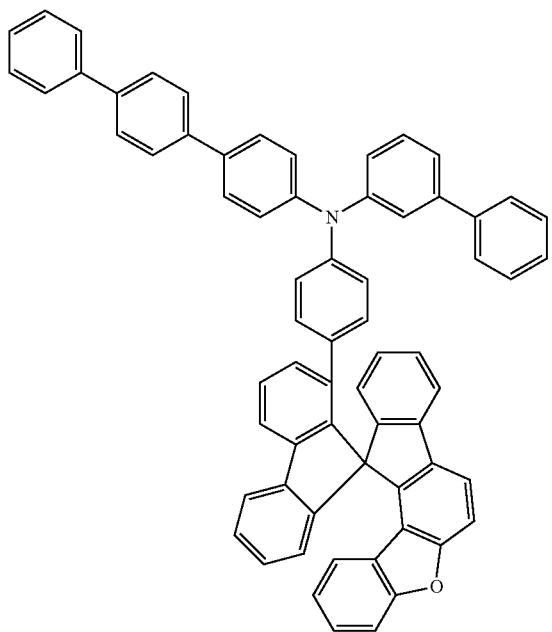 [SMILES: c1ccc(-c2ccc(-c3ccc(N(c4ccc(-c5cccc6c5C5(c7ccccc7-6)c6ccccc6-c6ccc7oc8ccccc8c7c65)cc4)c4cccc(-c5ccccc5)c4)cc3)cc2)cc1]
65

-continued
66
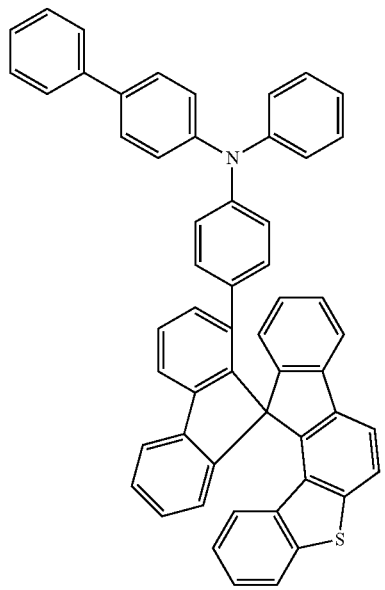 [SMILES: c1ccc(-c2ccc(N(c3ccccc3)c3ccc(-c4cccc5c4C4(c6ccccc6-5)c5ccccc5-c5ccc6sc7ccccc7c6c54)cc3)cc2)cc1]
67
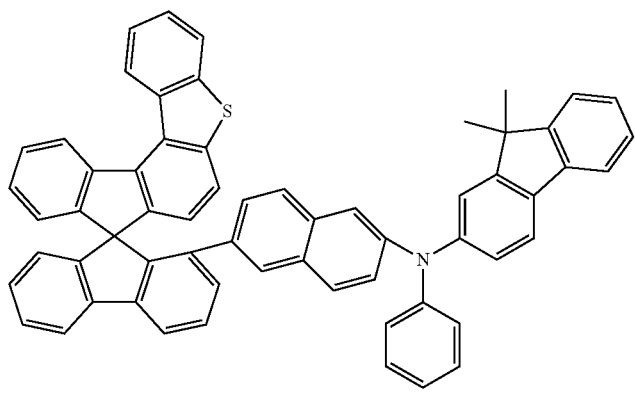 [SMILES: CC1(C)c2ccccc2-c2ccc(N(c3ccccc3)c3ccc4cc(-c5cccc6c5C5(c7ccccc7-6)c6ccccc6-c6c5ccc5sc7ccccc7c65)ccc4c3)cc21]
68
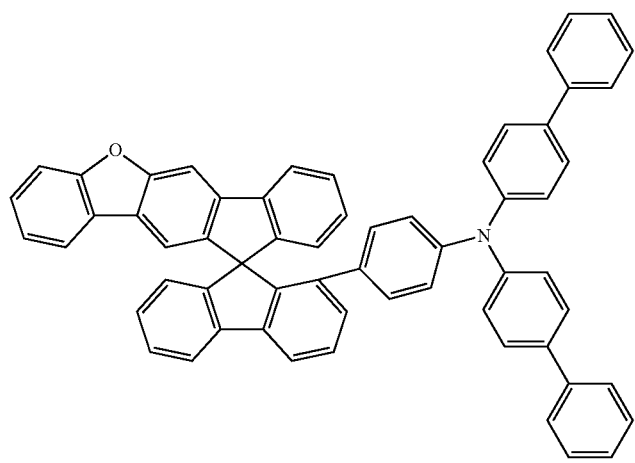 [SMILES: c1ccc(-c2ccc(N(c3ccc(-c4ccccc4)cc3)c3ccc(-c4cccc5c4C4(c6ccccc6-c6cc7oc8ccccc8c7cc64)c4ccccc4-5)cc3)cc2)cc1]

-continued
69
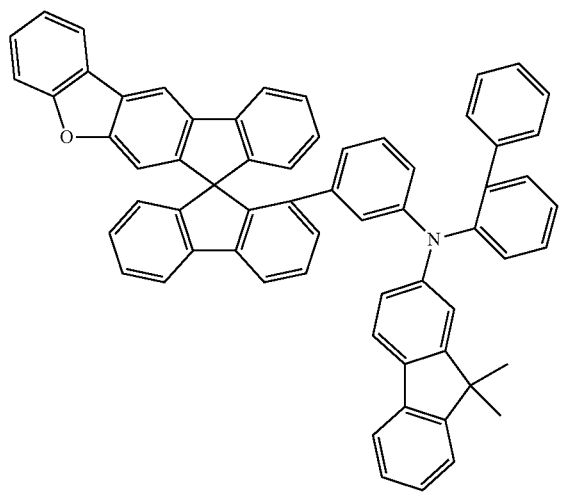 [SMILES: CC1(C)c2ccccc2-c2ccc(N(c3cccc(-c4cccc5c4C4(c6ccccc6-c6cc7c(cc64)oc4ccccc47)c4ccccc4-5)c3)c3ccccc3-c3ccccc3)cc21]
70
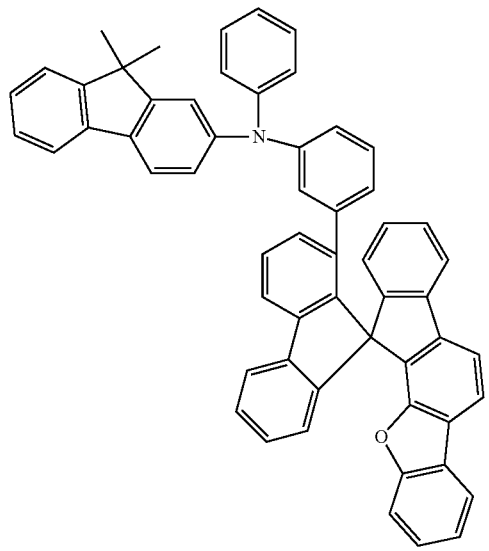 [SMILES: CC1(C)c2ccccc2-c2ccc(N(c3ccccc3)c3cccc(-c4cccc5c4C4(c6ccccc6-5)c5ccccc5-c5ccc6c(oc7ccccc76)c54)c3)cc21]
71
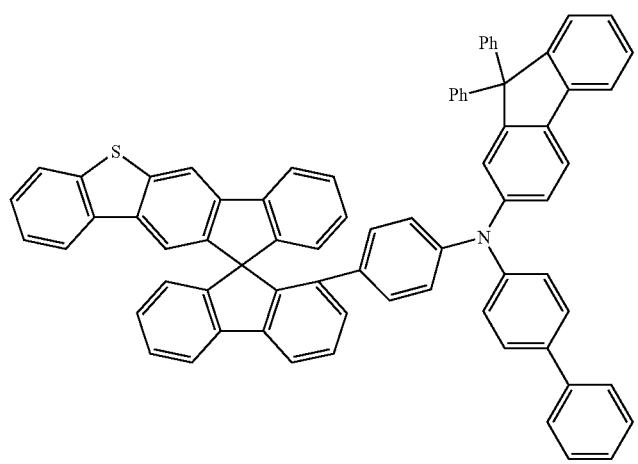 [SMILES: c1ccc(-c2ccc(N(c3ccc(-c4cccc5c4C4(c6ccccc6-c6cc7sc8ccccc8c7cc64)c4ccccc4-5)cc3)c3ccc4c(c3)C(c3ccccc3)(c3ccccc3)c3ccccc3-4)cc2)cc1]

-continued
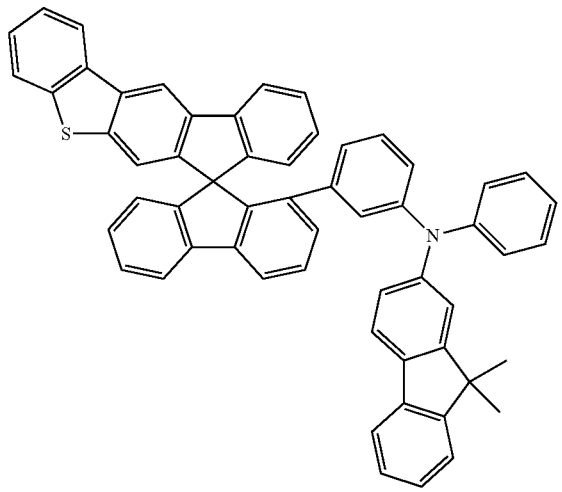 [SMILES: CC1(C)c2ccccc2-c2ccc(N(c3ccccc3)c3cccc(-c4cccc5c4C4(c6ccccc6-c6cc7c(cc64)sc4ccccc47)c4ccccc4-5)c3)cc21]
72
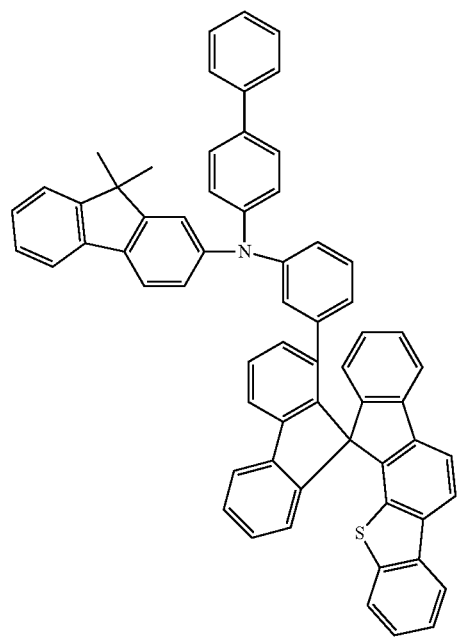 [SMILES: CC1(C)c2ccccc2-c2ccc(N(c3ccc(-c4ccccc4)cc3)c3cccc(-c4cccc5c4C4(c6ccccc6-5)c5ccccc5-c5ccc6c(sc7ccccc76)c54)c3)cc21]
73
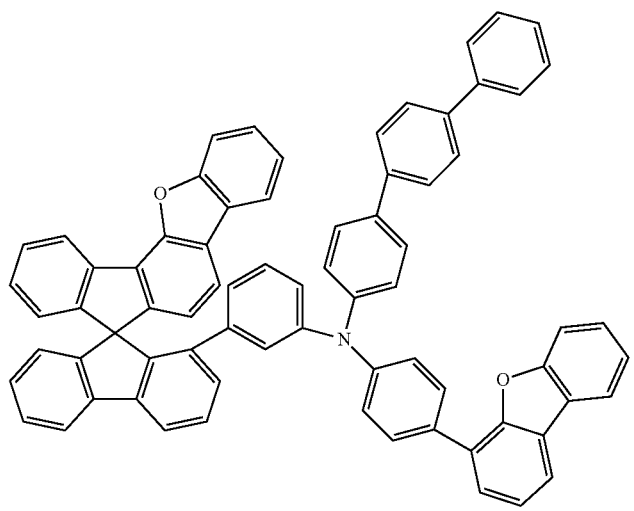 [SMILES: c1ccc(-c2ccc(-c3ccc(N(c4ccc(-c5cccc6c5oc5ccccc56)cc4)c4cccc(-c5cccc6c5C5(c7ccccc7-6)c6ccccc6-c6c5ccc5c6oc6ccccc65)c4)cc3)cc2)cc1]
74

75
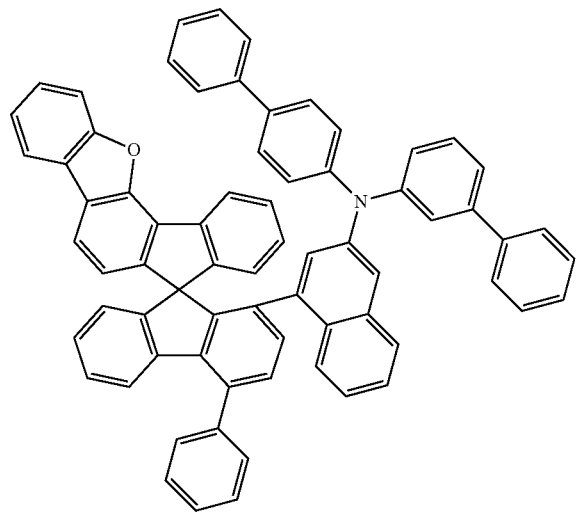 [SMILES: c1ccc(-c2ccc(N(c3cccc(-c4ccccc4)c3)c3cc(-c4ccc(-c5ccccc5)c5c4C4(c6ccccc6-5)c5ccccc5-c5c4ccc4c5oc5ccccc54)c4ccccc4c3)cc2)cc1]
76
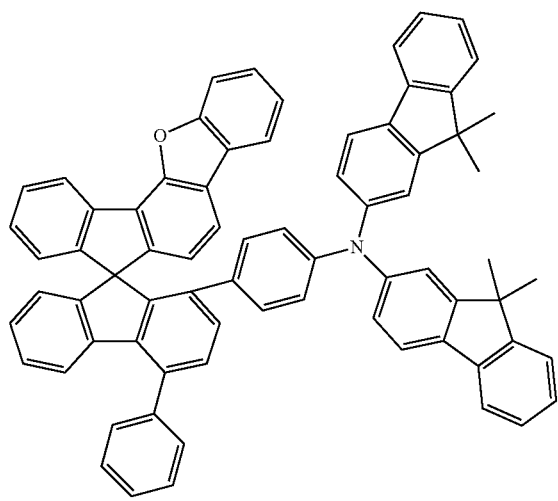 [SMILES: CC1(C)c2ccccc2-c2ccc(N(c3ccc(-c4ccc(-c5ccccc5)c5c4C4(c6ccccc6-5)c5ccccc5-c5c4ccc4c5oc5ccccc54)cc3)c3ccc4c(c3)C(C)(C)c3ccccc3-4)cc21]
77
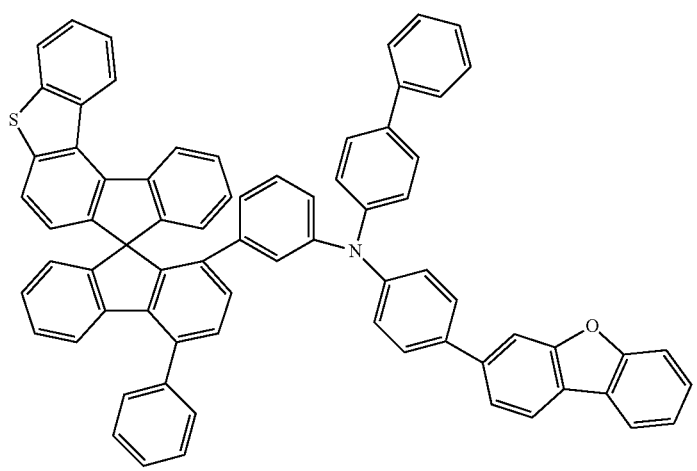 [SMILES: c1ccc(-c2ccc(N(c3ccc(-c4ccc5c(c4)oc4ccccc45)cc3)c3cccc(-c4ccc(-c5ccccc5)c5c4C4(c6ccccc6-5)c5ccccc5-c5c4ccc4sc6ccccc6c54)c3)cc2)cc1]

78
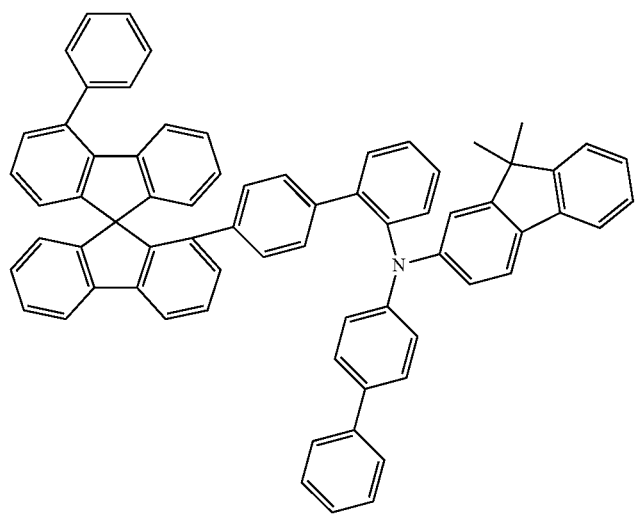 [SMILES: CC1(C)c2ccccc2-c2ccc(N(c3ccc(-c4ccccc4)cc3)c3ccccc3-c3ccc(-c4cccc5c4C4(c6ccccc6-5)c5ccccc5-c5c(-c6ccccc6)cccc54)cc3)cc21]
79
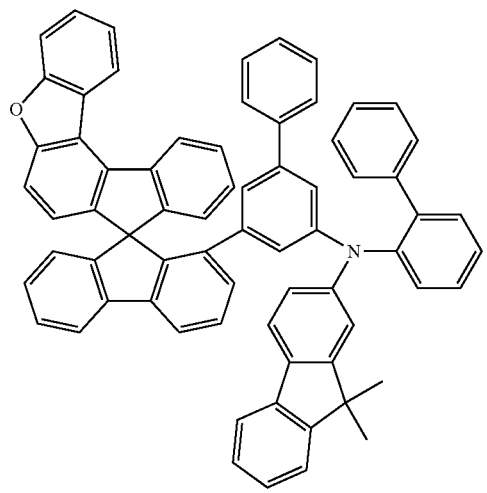 [SMILES: CC1(C)c2ccccc2-c2ccc(N(c3cc(-c4ccccc4)cc(-c4cccc5c4C4(c6ccccc6-5)c5ccccc5-c5c4ccc4oc6ccccc6c54)c3)c3ccccc3-c3ccccc3)cc21]
80
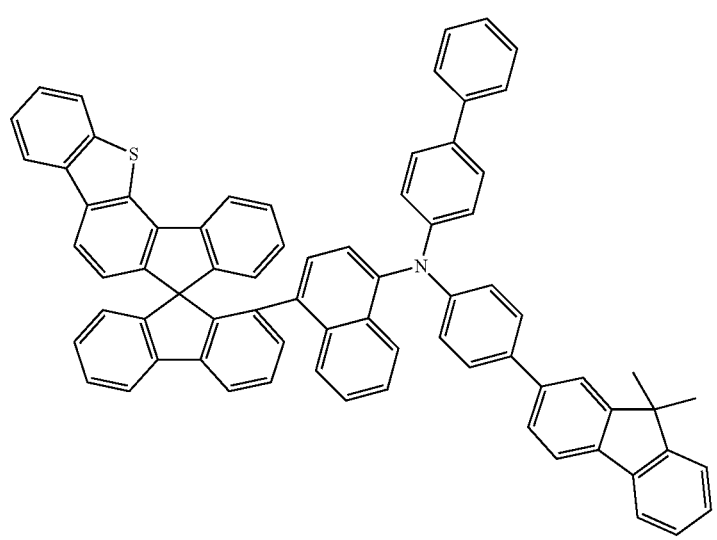 [SMILES: CC1(C)c2ccccc2-c2ccc(-c3ccc(N(c4ccc(-c5ccccc5)cc4)c4ccc(-c5cccc6c5C5(c7ccccc7-6)c6ccccc6-c6c5ccc5c6sc6ccccc65)c5ccccc45)cc3)cc21]

81
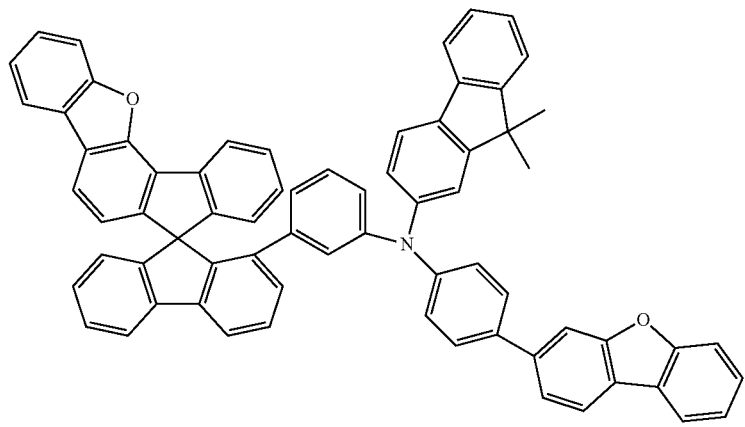 [SMILES: CC1(C)c2ccccc2-c2ccc(N(c3ccc(-c4ccc5c(c4)oc4ccccc45)cc3)c3cccc(-c4cccc5c4C4(c6ccccc6-5)c5ccccc5-c5c4ccc4c5oc5ccccc54)c3)cc21]
82
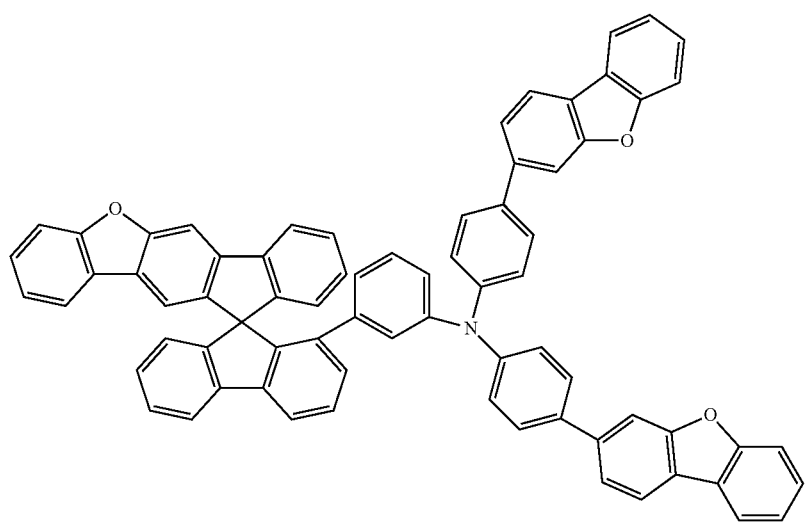 [SMILES: c1cc(-c2cccc3c2C2(c4ccccc4-c4cc5oc6ccccc6c5cc42)c2ccccc2-3)cc(N(c2ccc(-c3ccc4c(c3)oc3ccccc34)cc2)c2ccc(-c3ccc4c(c3)oc3ccccc34)cc2)c1]
83
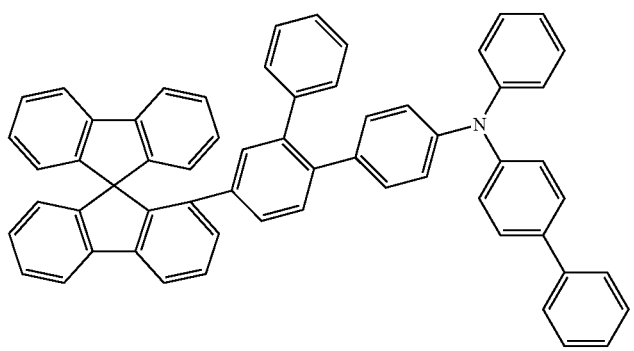 [SMILES: c1ccc(-c2ccc(N(c3ccccc3)c3ccc(-c4ccc(-c5cccc6c5C5(c7ccccc7-c7ccccc75)c5ccccc5-6)cc4-c4ccccc4)cc3)cc2)cc1]

84
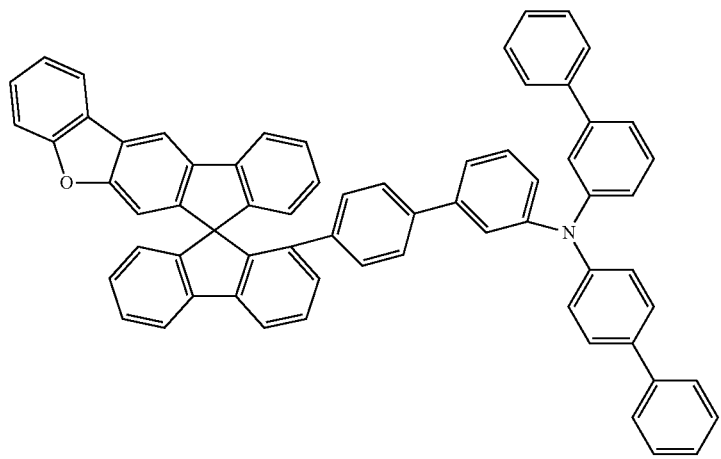 [SMILES: c1ccc(-c2ccc(N(c3cccc(-c4ccccc4)c3)c3cccc(-c4ccc(-c5cccc6c5C5(c7ccccc7-c7cc8c(cc75)oc5ccccc58)c5ccccc5-6)cc4)c3)cc2)cc1]
85
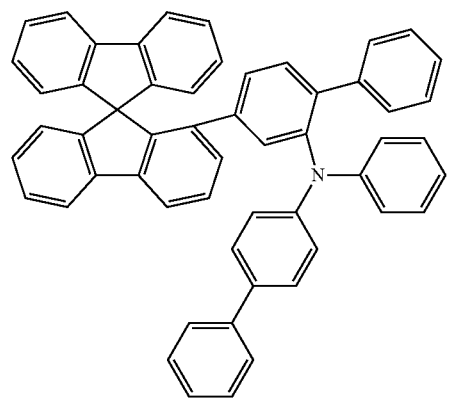 [SMILES: c1ccc(-c2ccc(N(c3ccccc3)c3cc(-c4cccc5c4C4(c6ccccc6-c6ccccc64)c4ccccc4-5)ccc3-c3ccccc3)cc2)cc1]
86
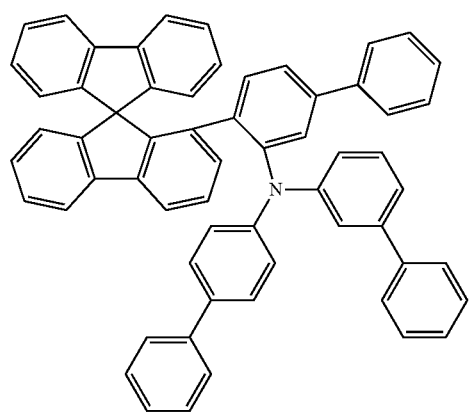 [SMILES: c1ccc(-c2ccc(N(c3cccc(-c4ccccc4)c3)c3cc(-c4ccccc4)ccc3-c3cccc4c3C3(c5ccccc5-c5ccccc53)c3ccccc3-4)cc2)cc1]

87
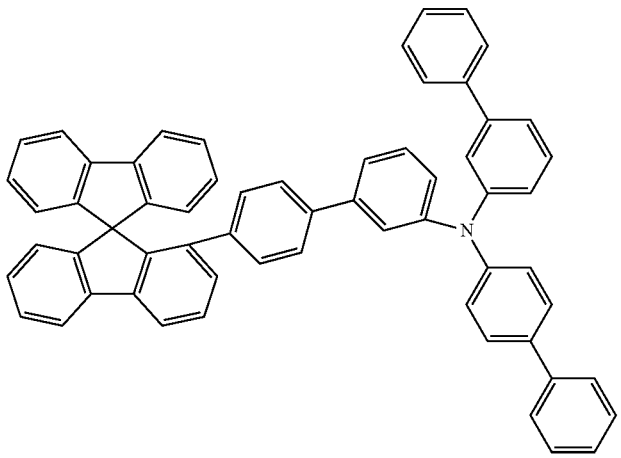 [SMILES: c1ccc(-c2ccc(N(c3cccc(-c4ccccc4)c3)c3cccc(-c4ccc(-c5cccc6c5C5(c7ccccc7-c7ccccc75)c5ccccc5-6)cc4)c3)cc2)cc1]
88
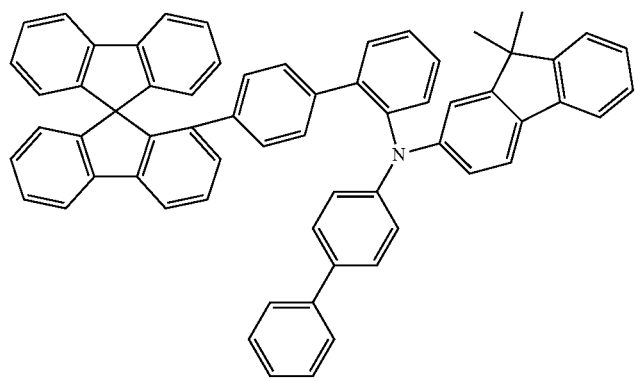 [SMILES: CC1(C)c2ccccc2-c2ccc(N(c3ccc(-c4ccccc4)cc3)c3ccccc3-c3ccc(-c4cccc5c4C4(c6ccccc6-c6ccccc64)c4ccccc4-5)cc3)cc21]
89
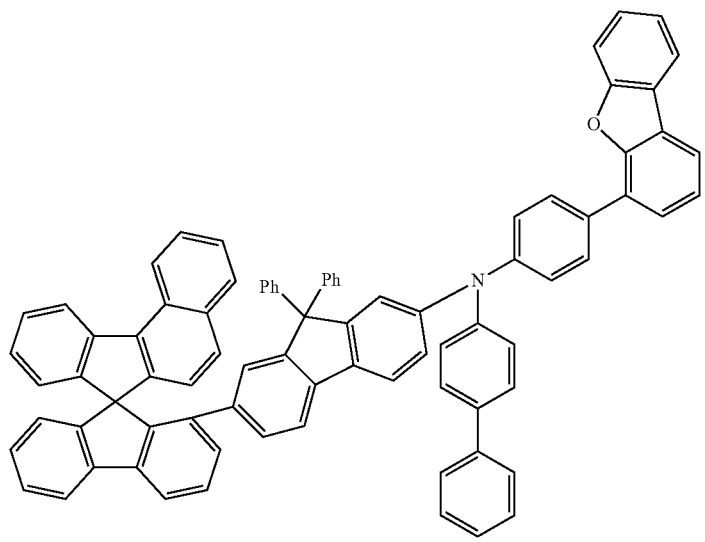 [SMILES: c1ccc(-c2ccc(N(c3ccc(-c4cccc5c4oc4ccccc45)cc3)c3ccc4c(c3)C(c3ccccc3)(c3ccccc3)c3cc(-c5cccc6c5C5(c7ccccc7-6)c6ccccc6-c6c5ccc5ccccc65)ccc3-4)cc2)cc1]

90
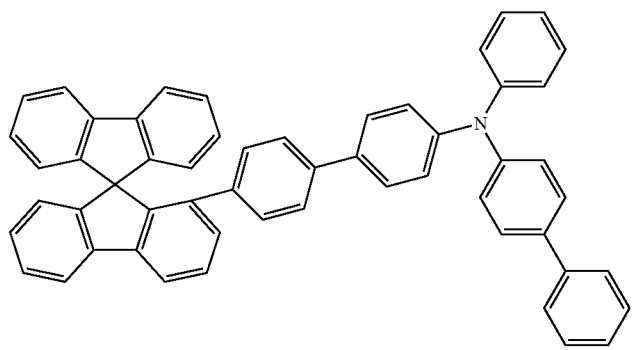 [SMILES: c1ccc(-c2ccc(N(c3ccccc3)c3ccc(-c4ccc(-c5cccc6c5C5(c7ccccc7-c7ccccc75)c5ccccc5-6)cc4)cc3)cc2)cc1]
91
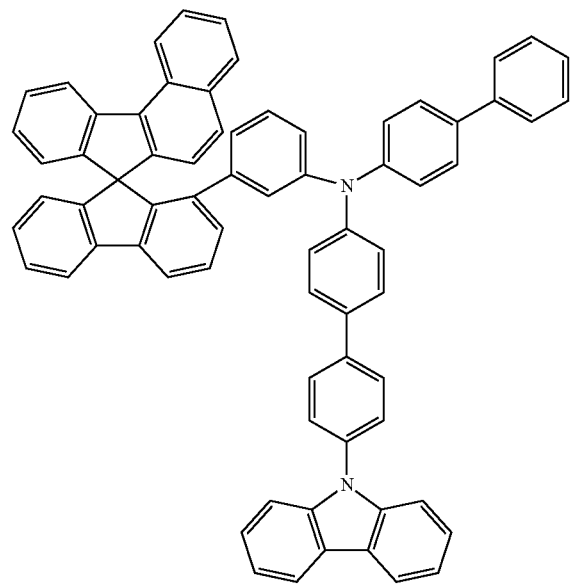 [SMILES: c1ccc(-c2ccc(N(c3ccc(-c4ccc(-n5c6ccccc6c6ccccc65)cc4)cc3)c3cccc(-c4cccc5c4C4(c6ccccc6-5)c5ccccc5-c5c4ccc4ccccc54)c3)cc2)cc1]
92
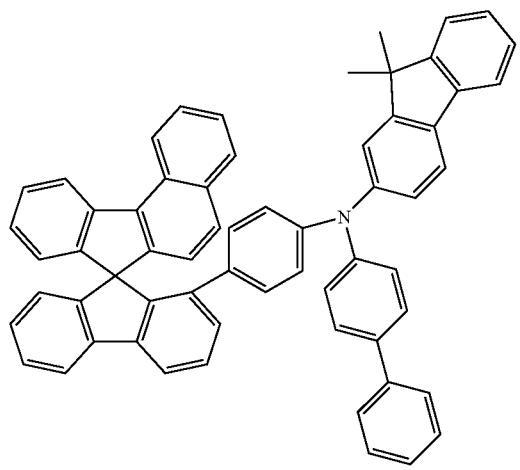 [SMILES: CC1(C)c2ccccc2-c2ccc(N(c3ccc(-c4ccccc4)cc3)c3ccc(-c4cccc5c4C4(c6ccccc6-5)c5ccccc5-c5c4ccc4ccccc54)cc3)cc21]

-continued
93
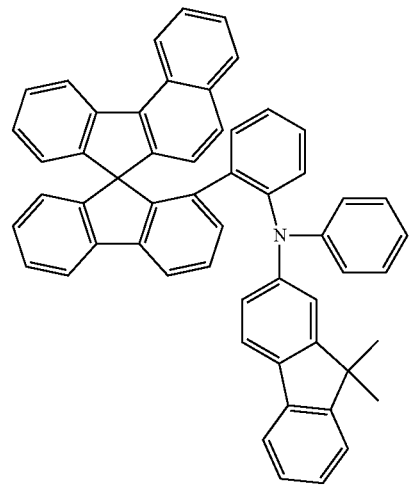 [SMILES: CC1(C)c2ccccc2-c2ccc(N(c3ccccc3)c3ccccc3-c3cccc4c3C3(c5ccccc5-4)c4ccccc4-c4c3ccc3ccccc43)cc21]
94
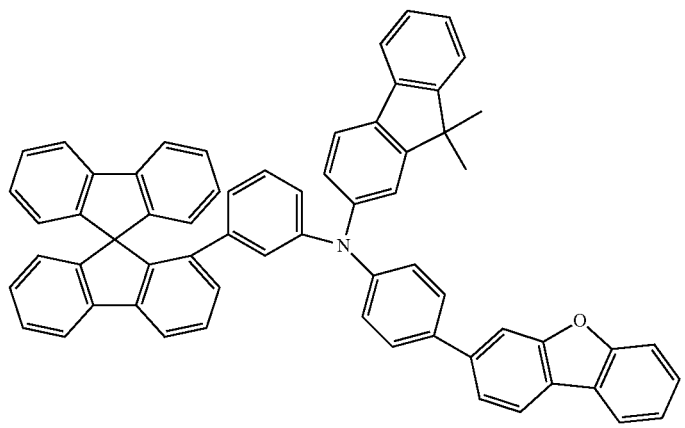 [SMILES: CC1(C)c2ccccc2-c2ccc(N(c3ccc(-c4ccc5c(c4)oc4ccccc45)cc3)c3cccc(-c4cccc5c4C4(c6ccccc6-c6ccccc64)c4ccccc4-5)c3)cc21]
95
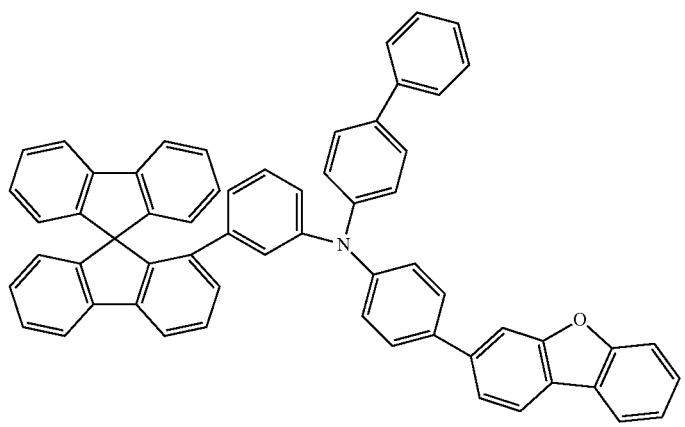 [SMILES: c1ccc(-c2ccc(N(c3ccc(-c4ccc5c(c4)oc4ccccc45)cc3)c3cccc(-c4cccc5c4C4(c6ccccc6-c6ccccc64)c4ccccc4-5)c3)cc2)cc1]

96
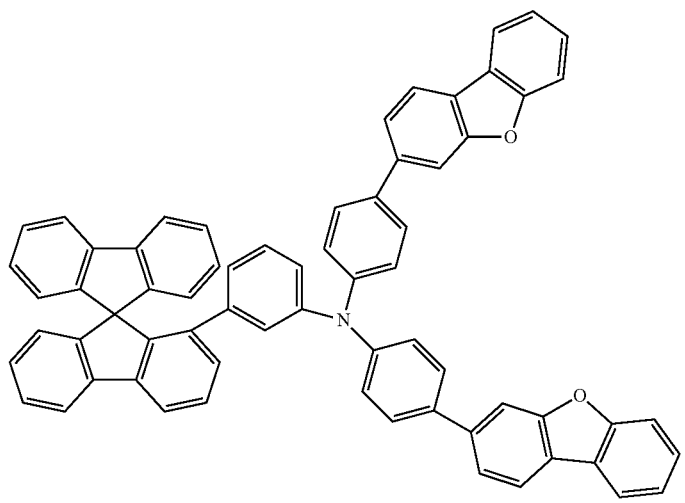 [SMILES: c1cc(-c2cccc3c2C2(c4ccccc4-c4ccccc42)c2ccccc2-3)cc(N(c2ccc(-c3ccc4c(c3)oc3ccccc34)cc2)c2ccc(-c3ccc4c(c3)oc3ccccc34)cc2)c1]
97
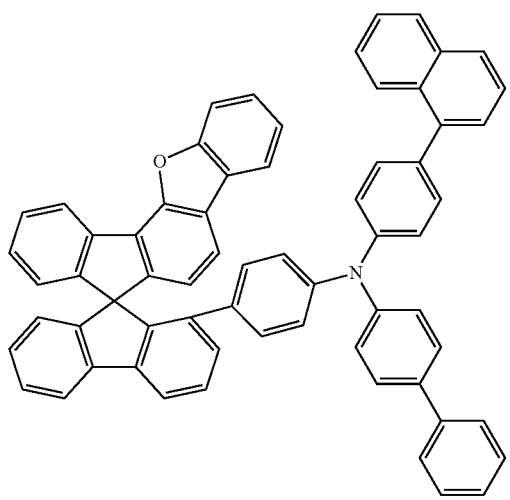 [SMILES: c1ccc(-c2ccc(N(c3ccc(-c4cccc5c4C4(c6ccccc6-5)c5ccccc5-c5c4ccc4c5oc5ccccc54)cc3)c3ccc(-c4cccc5ccccc45)cc3)cc2)cc1]
98
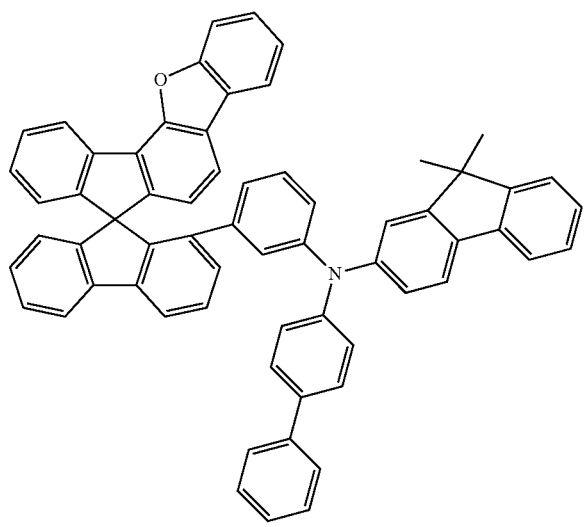 [SMILES: CC1(C)c2ccccc2-c2ccc(N(c3ccc(-c4ccccc4)cc3)c3cccc(-c4cccc5c4C4(c6ccccc6-5)c5ccccc5-c5c4ccc4c5oc5ccccc54)c3)cc21]

-continued
99
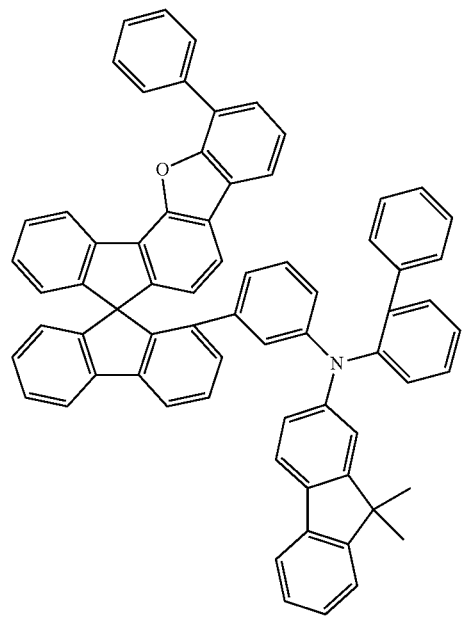 [SMILES: CC1(C)c2ccccc2-c2ccc(N(c3cccc(-c4cccc5c4C4(c6ccccc6-5)c5ccccc5-c5c4ccc4c5oc5c(-c6ccccc6)cccc54)c3)c3ccccc3-c3ccccc3)cc21]
100
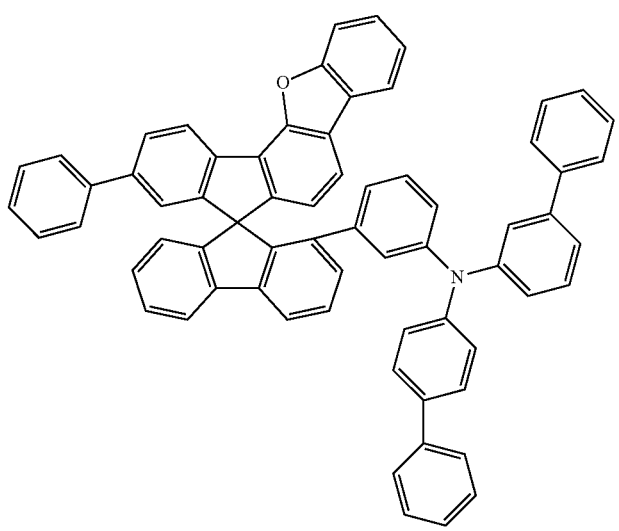 [SMILES: c1ccc(-c2ccc(N(c3cccc(-c4ccccc4)c3)c3cccc(-c4cccc5c4C4(c6ccccc6-5)c5cc(-c6ccccc6)ccc5-c5c4ccc4c5oc5ccccc54)c3)cc2)cc1]
101
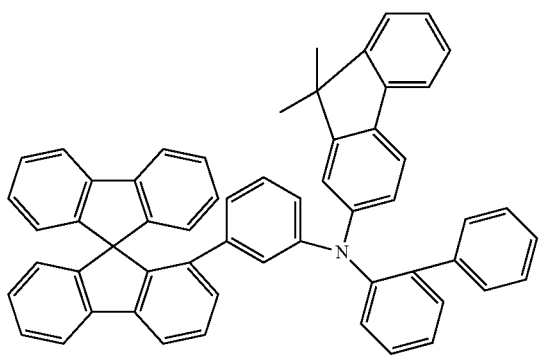 [SMILES: CC1(C)c2ccccc2-c2ccc(N(c3cccc(-c4cccc5c4C4(c6ccccc6-c6ccccc64)c4ccccc4-5)c3)c3ccccc3-c3ccccc3)cc21]

-continued
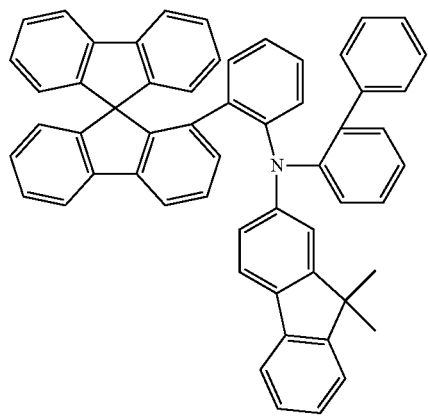 [SMILES: CC1(C)c2ccccc2-c2ccc(N(c3ccccc3-c3ccccc3)c3ccccc3-c3cccc4c3C3(c5ccccc5-c5ccccc53)c3ccccc3-4)cc21]
102
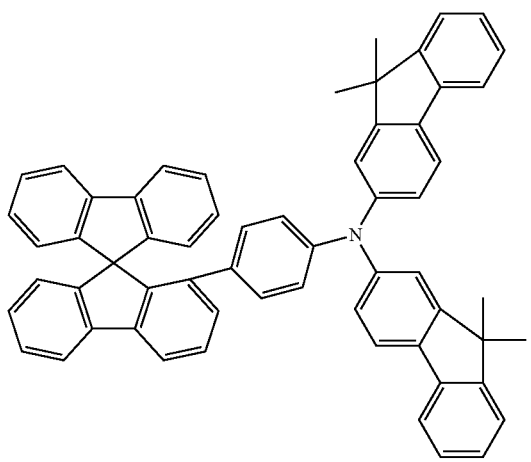 [SMILES: CC1(C)c2ccccc2-c2ccc(N(c3ccc(-c4cccc5c4C4(c6ccccc6-c6ccccc64)c4ccccc4-5)cc3)c3ccc4c(c3)C(C)(C)c3ccccc3-4)cc21]
103
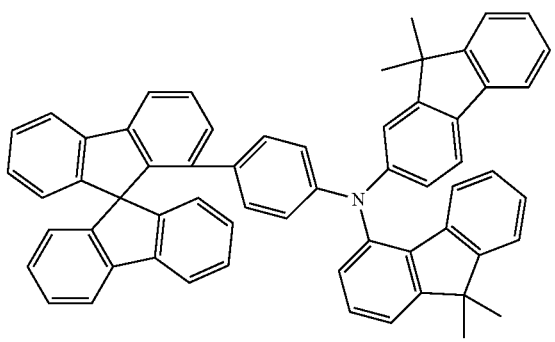 [SMILES: CC1(C)c2ccccc2-c2ccc(N(c3ccc(-c4cccc5c4C4(c6ccccc6-c6ccccc64)c4ccccc4-5)cc3)c3cccc4c3-c3ccccc3C4(C)C)cc21]
104
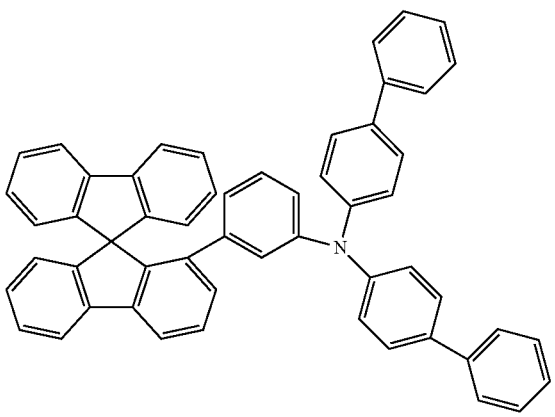 [SMILES: c1ccc(-c2ccc(N(c3ccc(-c4ccccc4)cc3)c3cccc(-c4cccc5c4C4(c6ccccc6-c6ccccc64)c4ccccc4-5)c3)cc2)cc1]
105

-continued
106
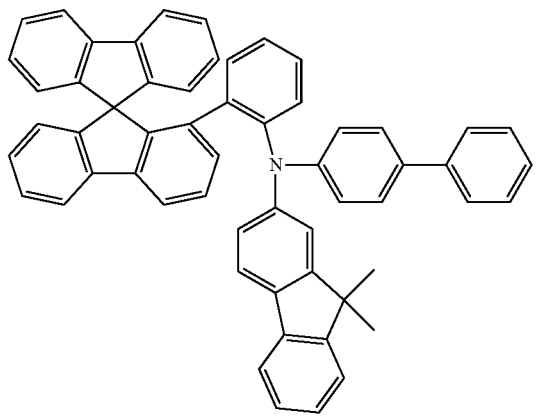 [SMILES: CC1(C)c2ccccc2-c2ccc(N(c3ccc(-c4ccccc4)cc3)c3ccccc3-c3cccc4c3C3(c5ccccc5-c5ccccc53)c3ccccc3-4)cc21]
107
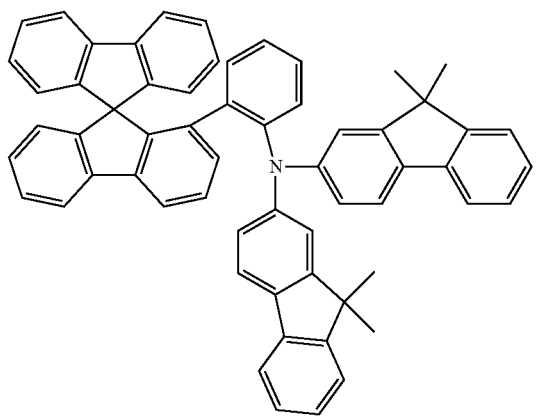 [SMILES: CC1(C)c2ccccc2-c2ccc(N(c3ccc4c(c3)C(C)(C)c3ccccc3-4)c3ccccc3-c3cccc4c3C3(c5ccccc5-c5ccccc53)c3ccccc3-4)cc21]
108
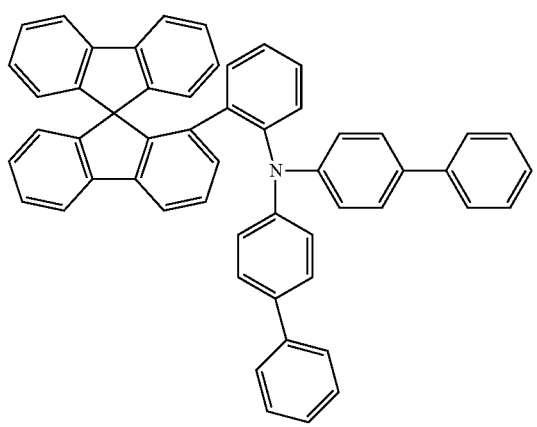 [SMILES: c1ccc(-c2ccc(N(c3ccc(-c4ccccc4)cc3)c3ccccc3-c3cccc4c3C3(c5ccccc5-c5ccccc53)c3ccccc3-4)cc2)cc1]

109
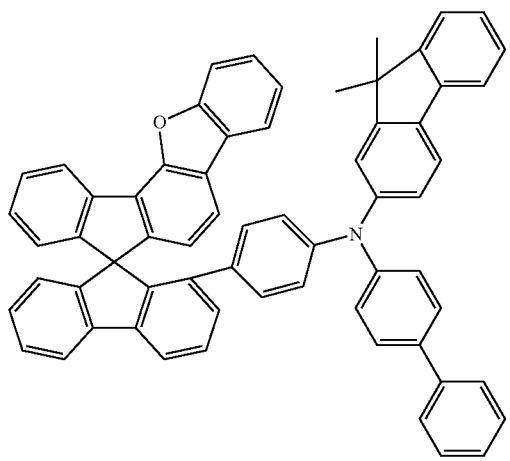 [SMILES: CC1(C)c2ccccc2-c2ccc(N(c3ccc(-c4ccccc4)cc3)c3ccc(-c4cccc5c4C4(c6ccccc6-5)c5ccccc5-c5c4ccc4c5oc5ccccc54)cc3)cc21]
110
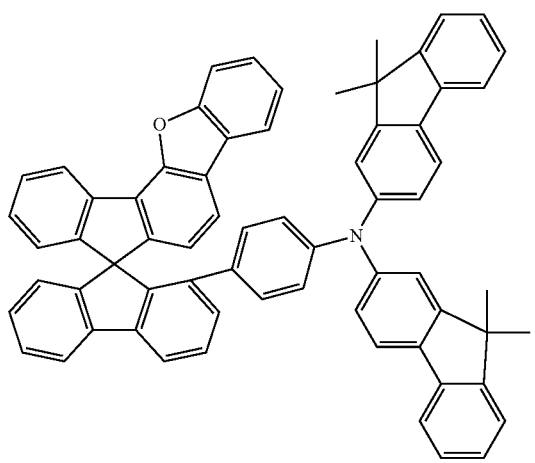 [SMILES: CC1(C)c2ccccc2-c2ccc(N(c3ccc(-c4cccc5c4C4(c6ccccc6-5)c5ccccc5-c5c4ccc4c5oc5ccccc54)cc3)c3ccc4c(c3)C(C)(C)c3ccccc3-4)cc21]
111
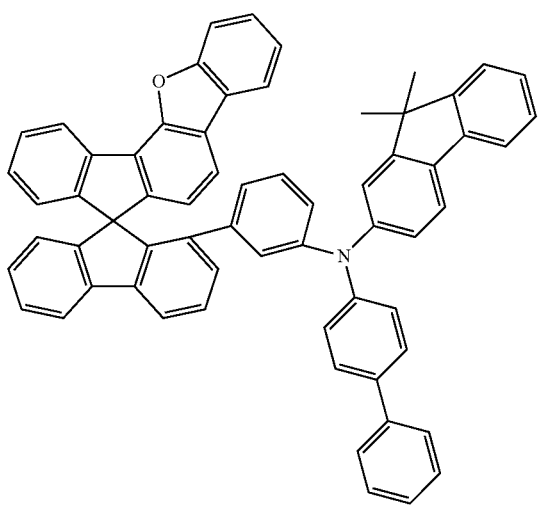 [SMILES: CC1(C)c2ccccc2-c2ccc(N(c3ccc(-c4ccccc4)cc3)c3cccc(-c4cccc5c4C4(c6ccccc6-5)c5ccccc5-c5c4ccc4c5oc5ccccc54)c3)cc21]

-continued
112
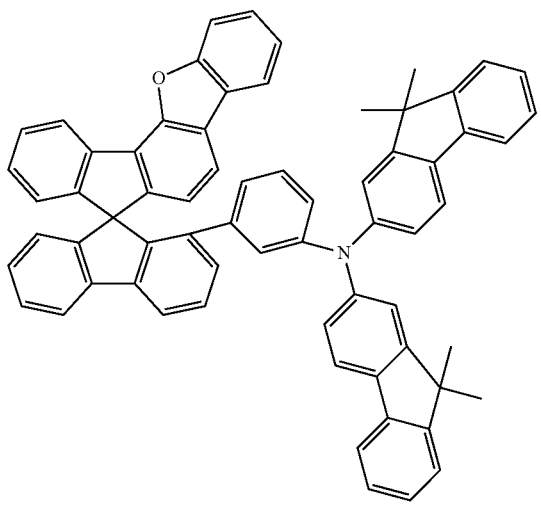 [SMILES: CC1(C)c2ccccc2-c2ccc(N(c3cccc(-c4cccc5c4C4(c6ccccc6-5)c5ccccc5-c5c4ccc4c5oc5ccccc54)c3)c3ccc4c(c3)C(C)(C)c3ccccc3-4)cc21]
113
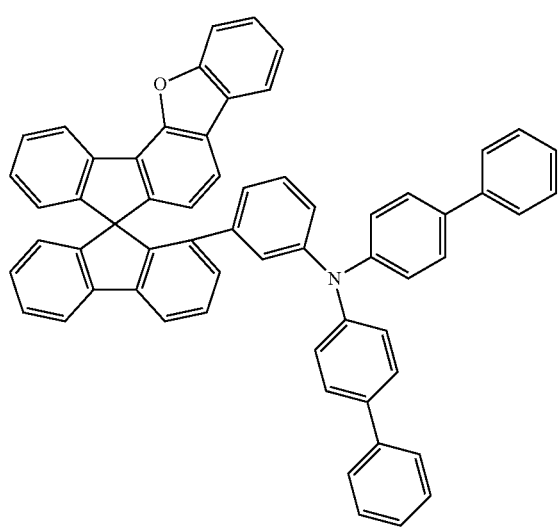 [SMILES: c1ccc(-c2ccc(N(c3ccc(-c4ccccc4)cc3)c3cccc(-c4cccc5c4C4(c6ccccc6-5)c5ccccc5-c5c4ccc4c5oc5ccccc54)c3)cc2)cc1]
114
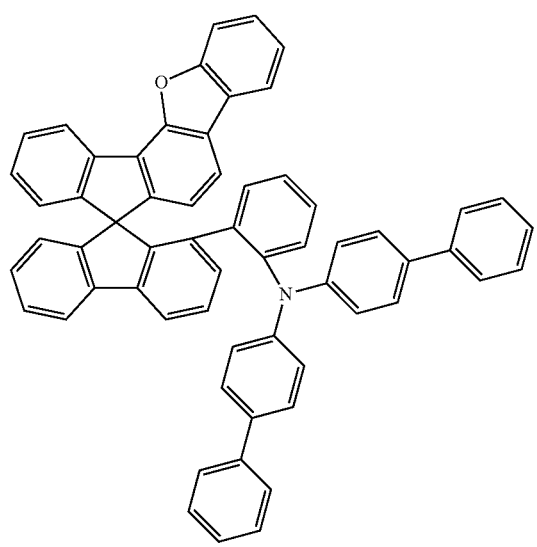

115
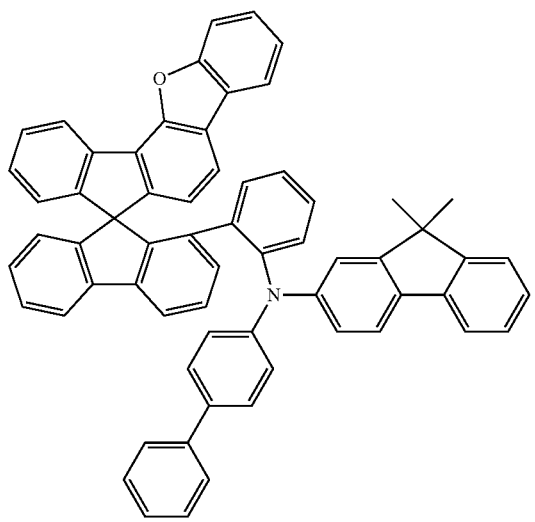 [SMILES: CC1(C)c2ccccc2-c2ccc(N(c3ccc(-c4ccccc4)cc3)c3ccccc3-c3cccc4c3C3(c5ccccc5-4)c4ccccc4-c4c3ccc3c4oc4ccccc43)cc21]
116
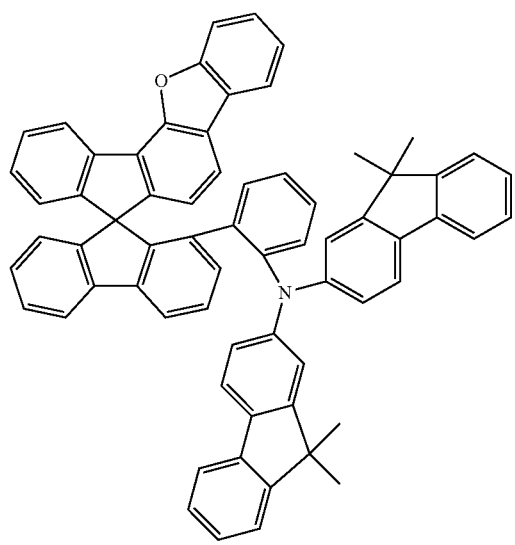 [SMILES: CC1(C)c2ccccc2-c2ccc(N(c3ccc4c(c3)C(C)(C)c3ccccc3-4)c3ccccc3-c3cccc4c3C3(c5ccccc5-4)c4ccccc4-c4c3ccc3c4oc4ccccc43)cc21]
117
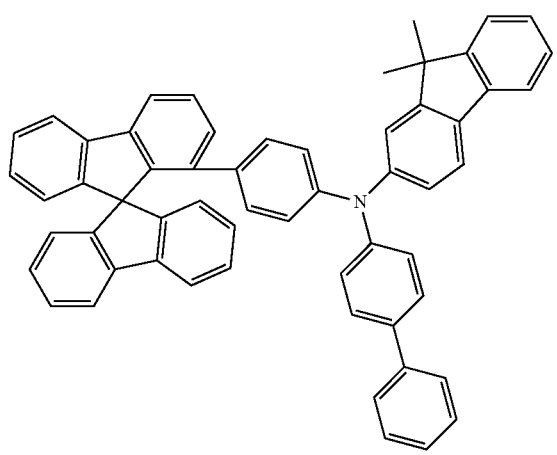 [SMILES: CC1(C)c2ccccc2-c2ccc(N(c3ccc(-c4ccccc4)cc3)c3ccc(-c4cccc5c4C4(c6ccccc6-c6ccccc64)c4ccccc4-5)cc3)cc21]

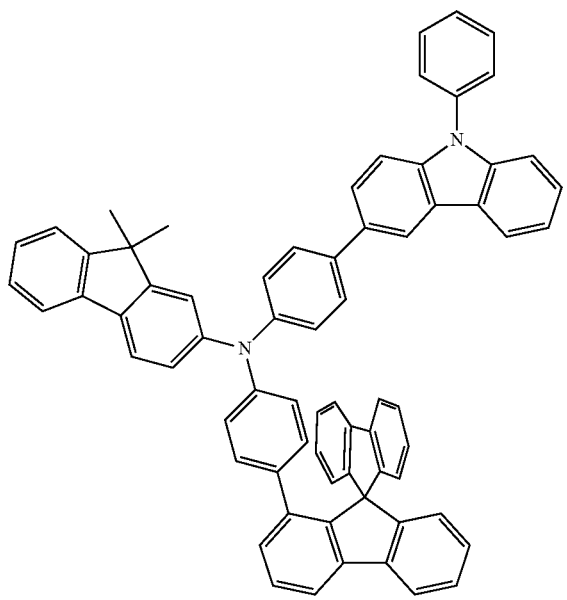 [SMILES: CC1(C)c2ccccc2-c2ccc(N(c3ccc(-c4ccc5c(c4)c4ccccc4n5-c4ccccc4)cc3)c3ccc(-c4cccc5c4C4(c6ccccc6-c6ccccc64)c4ccccc4-5)cc3)cc21]

The present invention also relates to the intermediate compound of formula (Int-1),

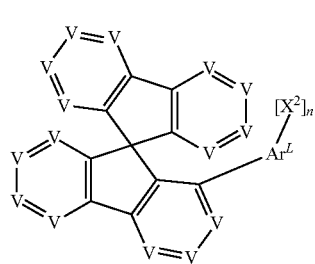

formula (Int-1)

where the symbols V, $Ar^L$, $X^2$ and the index n as well as the preferred embodiments for these symbols and indices are as defined above.

Furthermore, it is preferred that the intermediate compound of formula (Int-1) is selected from the compounds of the following formulae (Int-2) to (Int-9),

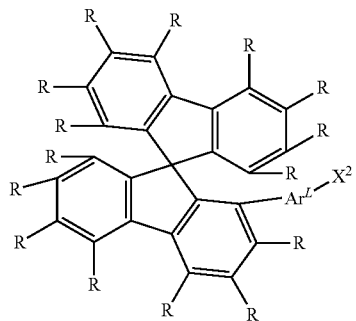

formula (Int-2)

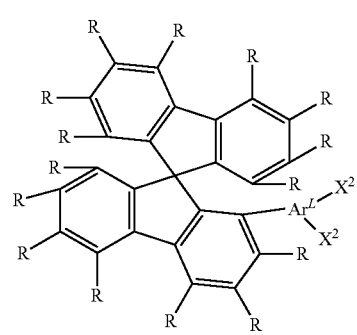

formula (Int-3)

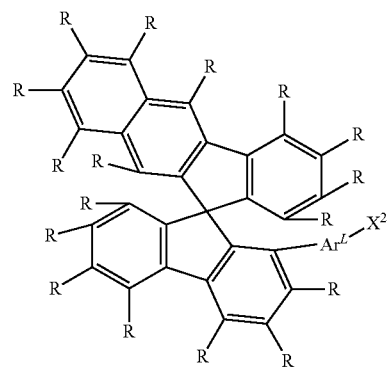

formula (Int-4)

formula (Int-5)
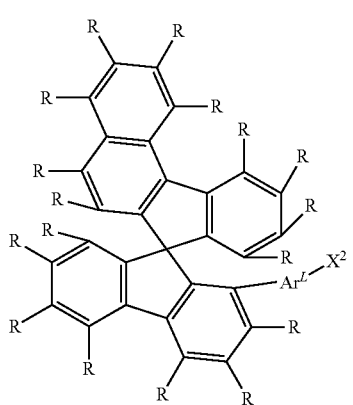
formula (Int-6)
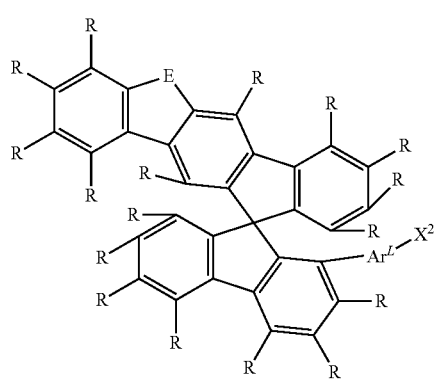
formula (Int-7)
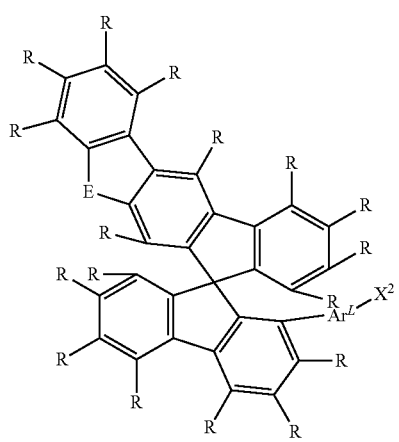
formula (Int-8)
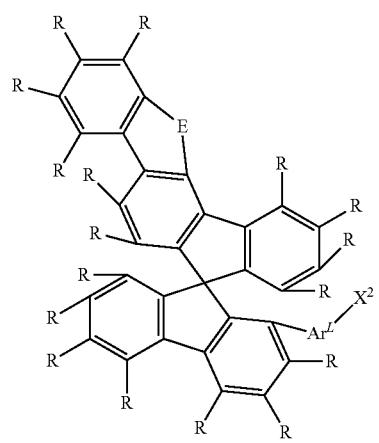
formula (Int-9)
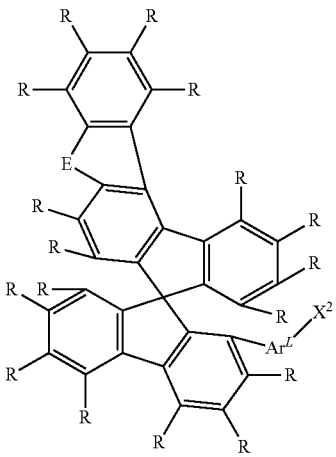
where the symbols have the same meaning as defined above.
It is even more preferred that the intermediate compound of formula (Int-1) is selected from the compounds of the following formulae (Int-2-1) to (Int-2-8),
formula (Int-2-1)
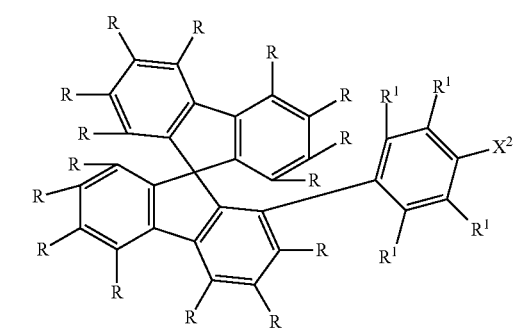
formula (Int-2-2)
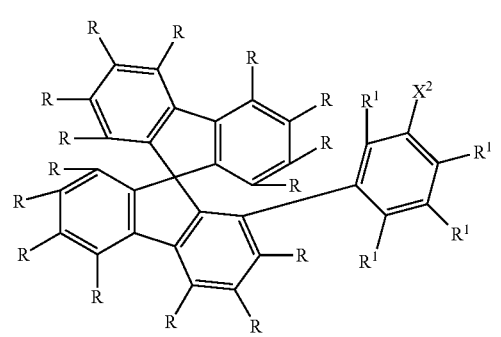

formula (Int-2-3)
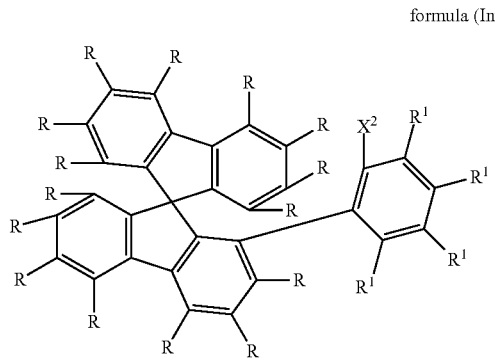
formula (Int-2-4)
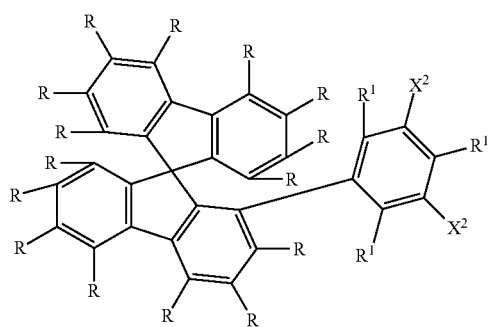
formula (Int-2-5)
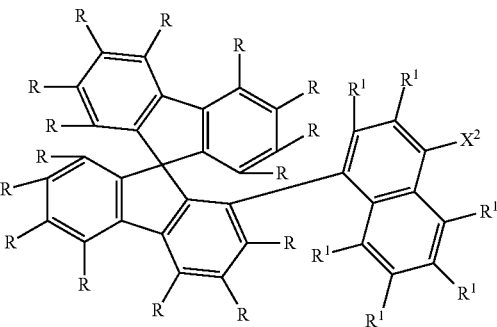
formula (Int-2-6)
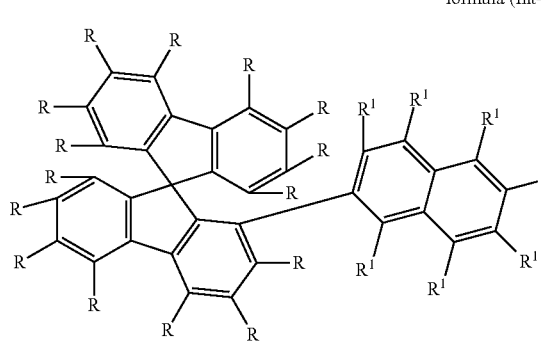
formula (Int-2-7)
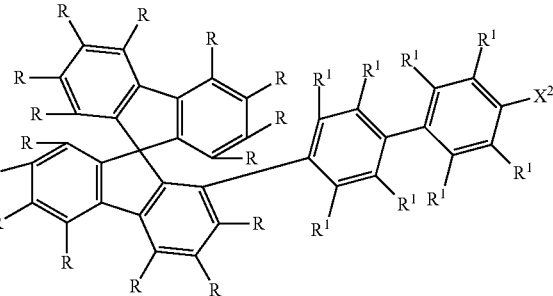
formula (Int-2-8)
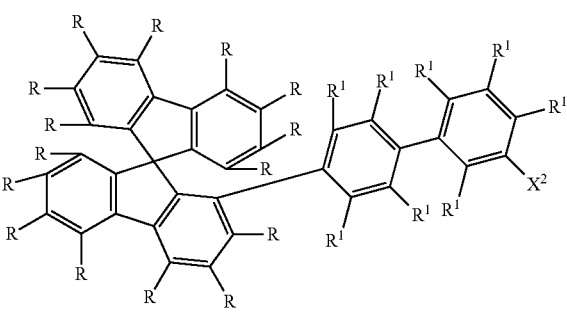
where the symbols have the same meaning as defined as above.
Among the intermediate compounds of formulae (Int-2) to (Int-8), the compounds of the following formulae (Int-2-1-1) to (Int-2-8-1) are preferred,
formula (Int-2-1-1)
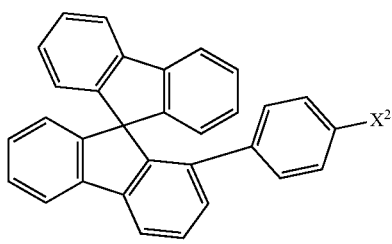
formula (Int-2-2-1)
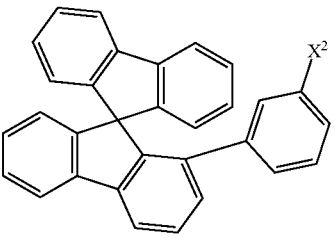
formula (Int-2-3-1)
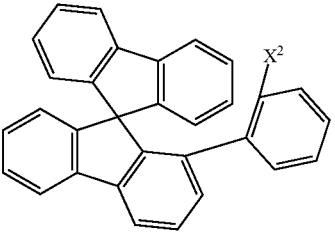

169
-continued formula (Int-2-4-1)
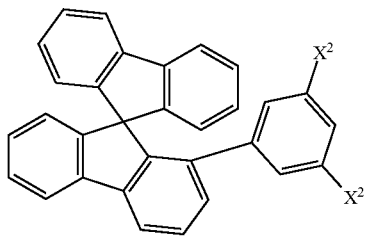

formula (Int-2-5-1)
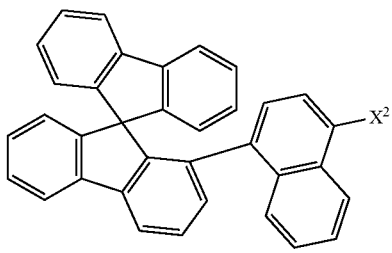

formula (Int-2-6-1)
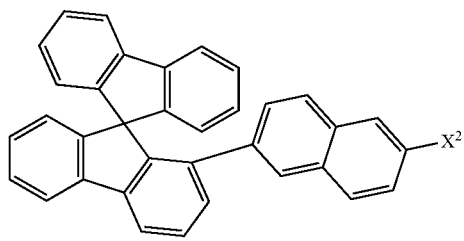

formula (Int-2-7-1)
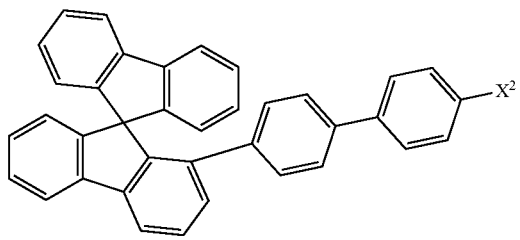

formula (Int-2-8-1)
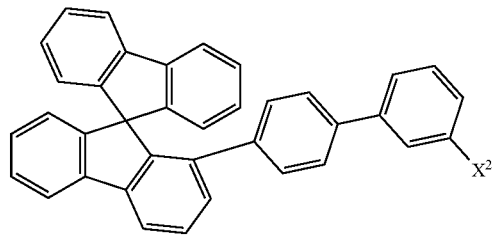

where $X^2$ has the same meaning as above.

Examples of suitable structures for compounds of formula (Int-1) are the compounds of the formulae (Int-8) to (Int-58) as depicted below, where $Ar^L$ is selected from ($Ar^L$-25), ($Ar^L$-26), ($Ar^L$-27), ($Ar^L$-28), ($Ar^L$-29), ($Ar^L$-20), ($Ar^L$-33), ($Ar^L$-40), ($Ar^L$-43) or ($Ar^L$-101);

$X^2$ is Cl, Br or I; and

R is H, D, F, CN, a straight-chain alkyl having 1 to 5 C atoms or a branched or cyclic alkyl group having 3 to 6 C atoms, or an aryl or heteroaryl group having 5 to 18 aromatic ring atoms.

170

Int-8
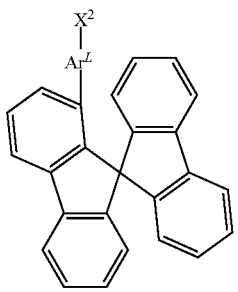

Int-9
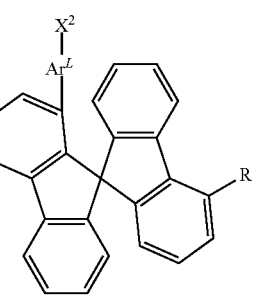

Int-10
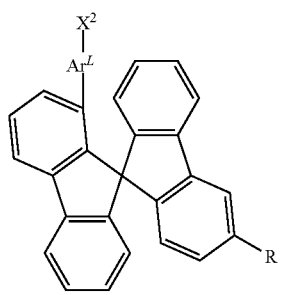

Int-11
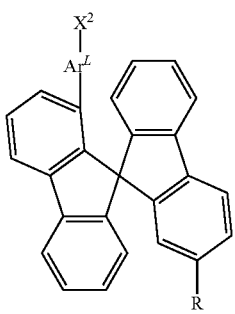

Int-12
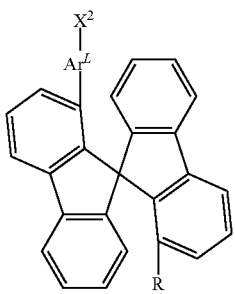

-continued
Int-13
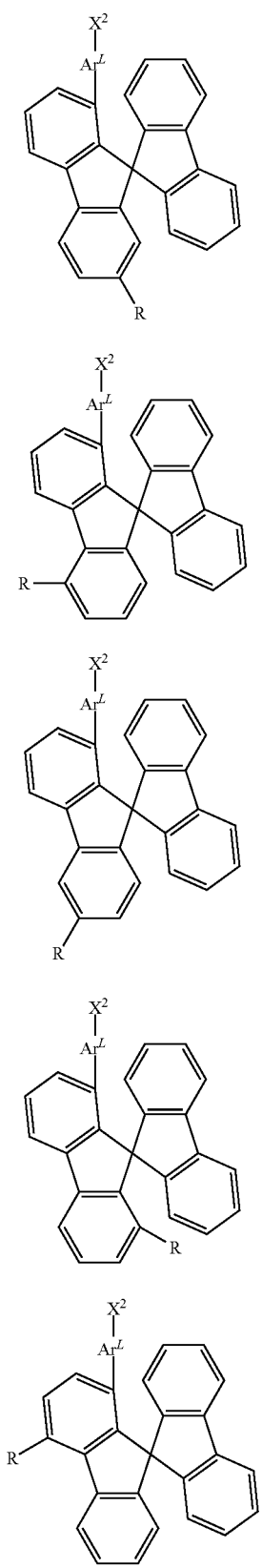
Int-14
Int-15
Int-16
Int-17
-continued
Int-18
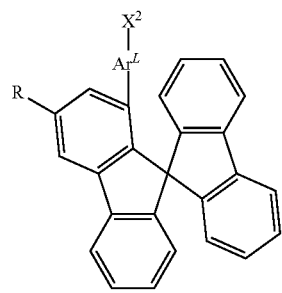
Int-19
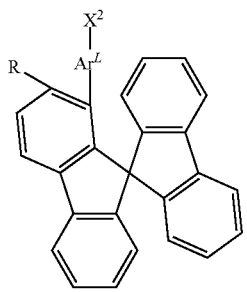
Int-20
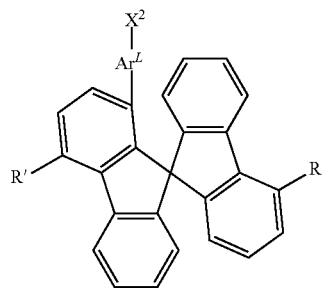
Int-21
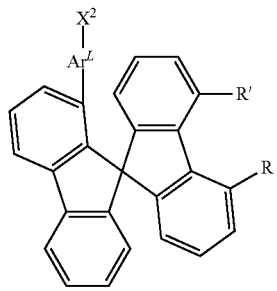
Int-22
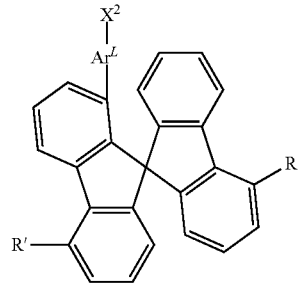

Int-23
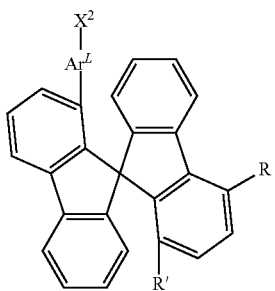
Int-24
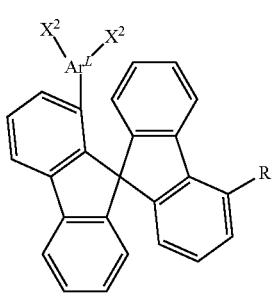
Int-25
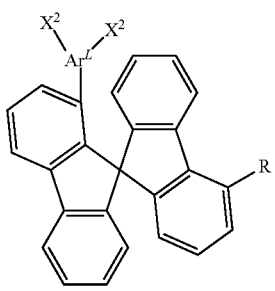
Int-26
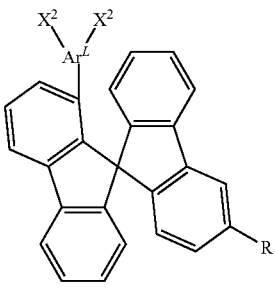
Int-27
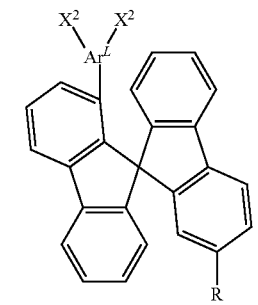
Int-28
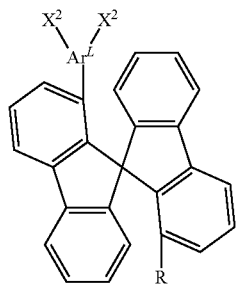
Int-29
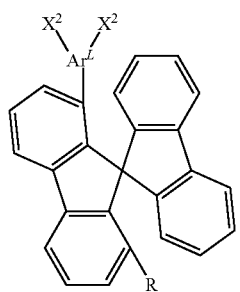
Int-30
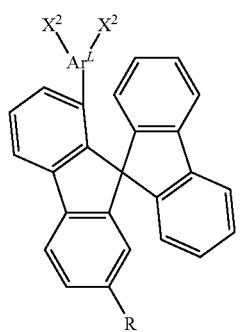
Int-31
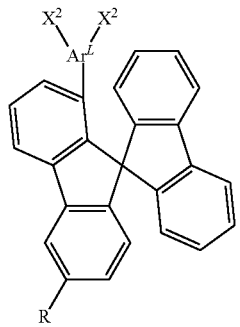
Int-32
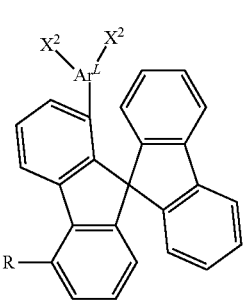

Int-33
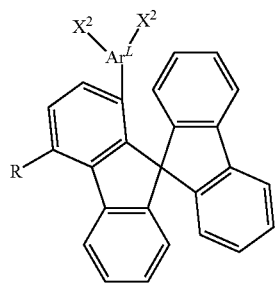
Int-34
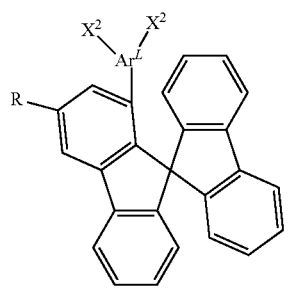
Int-35
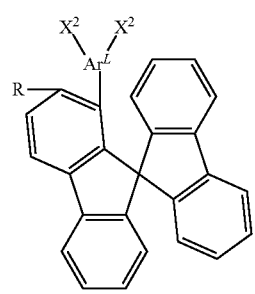
Int-36
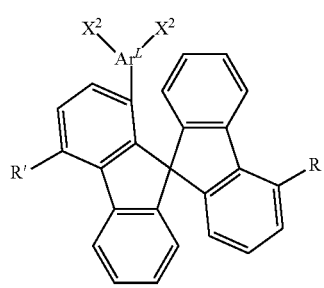
Int-37
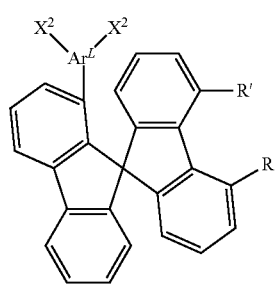
Int-38
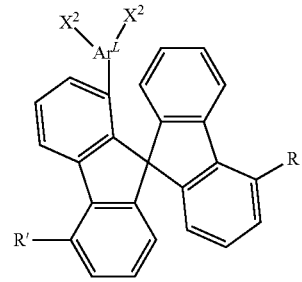
Int-39
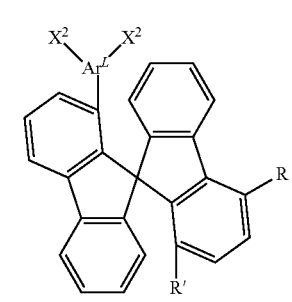
Int-40
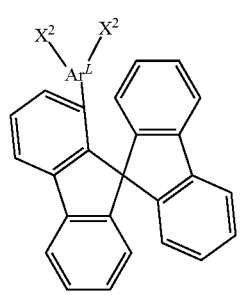
Int-41
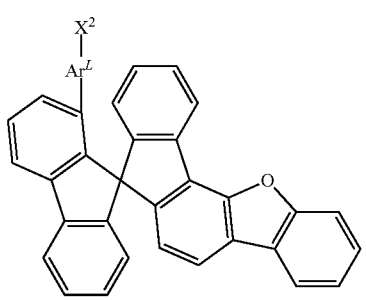
Int-42
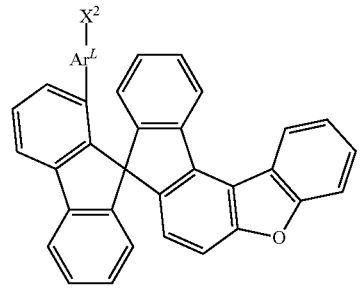

-continued
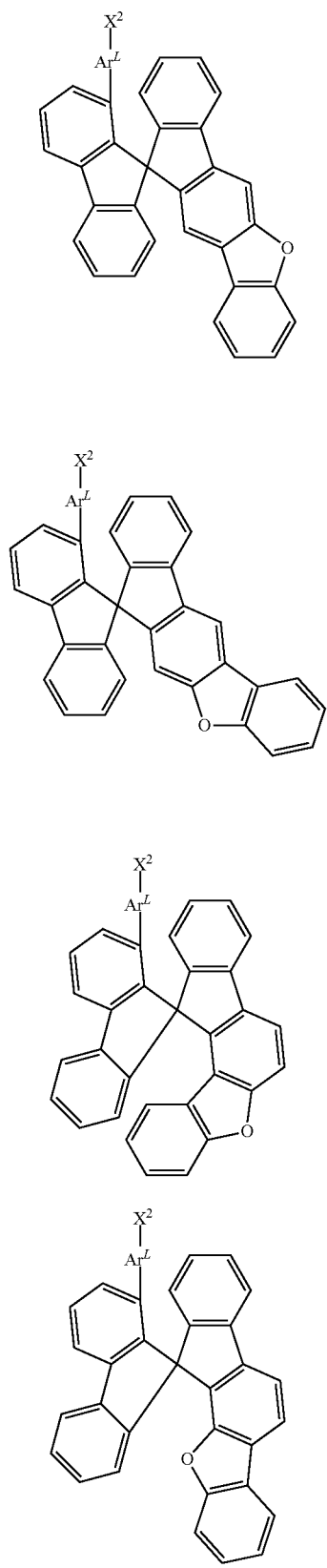
Int-43
Int-44
Int-45
Int-46
-continued
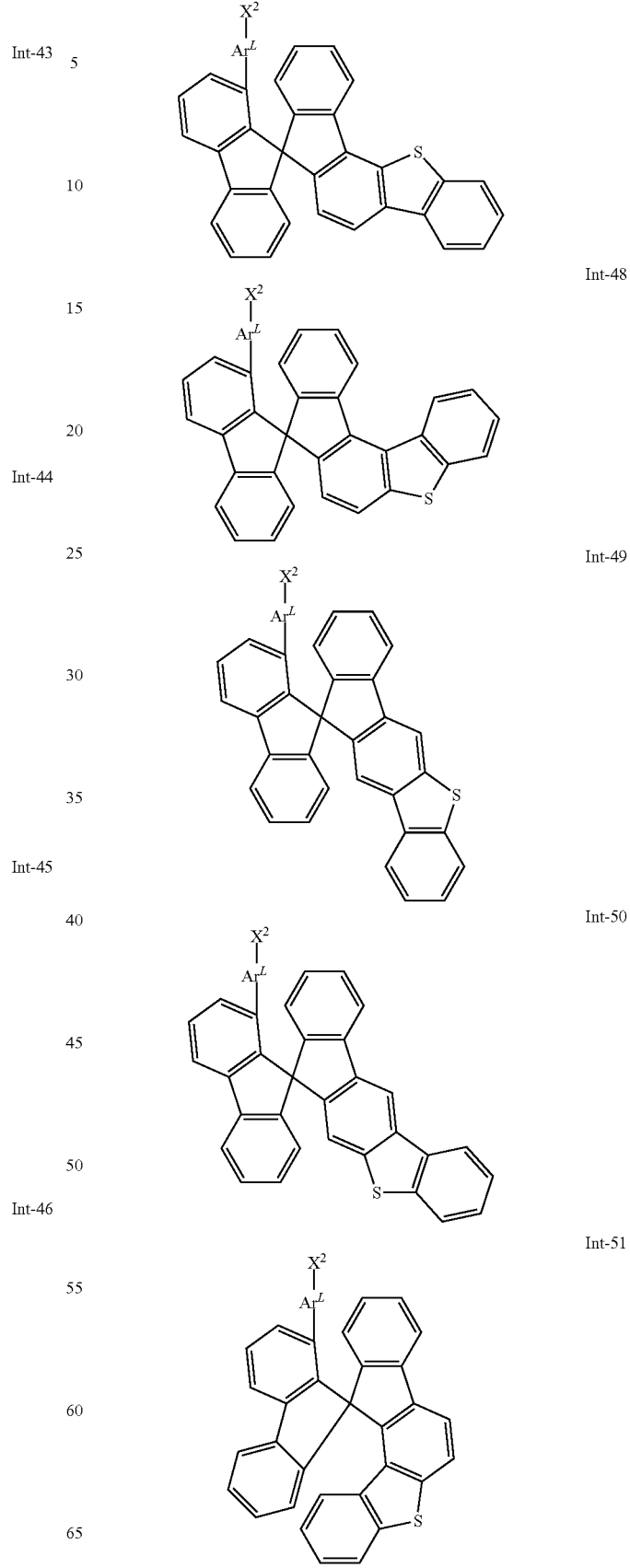
Int-47
Int-48
Int-49
Int-50
Int-51

Int-52
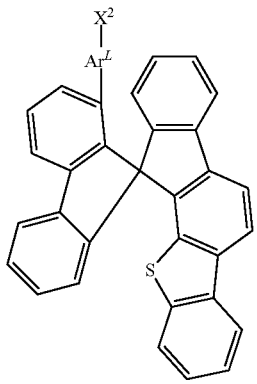

Int-53
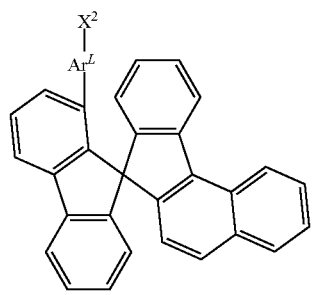

Int-54
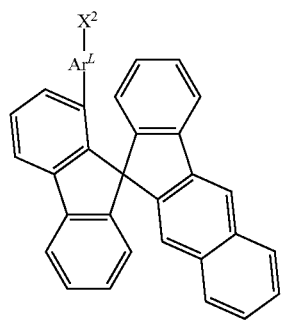

Int-55
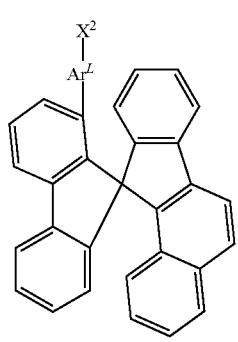

Int-56
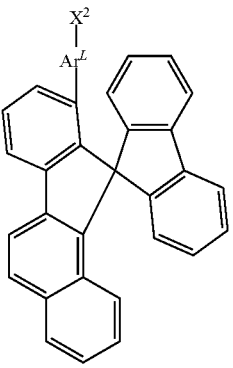

Int-57
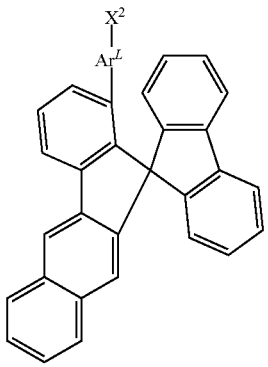

Int-58
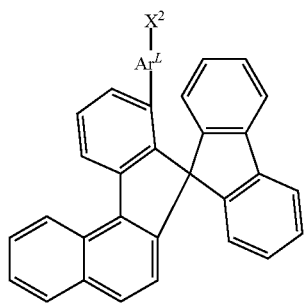

Examples of suitable compounds according to formula (Int-1) are:

the compounds of formulae (Int-9), (Int-17), (Int-33), (Int-41), (Int-42), (Int-47), (Int-48), (Int-53) or (Int-58); where $X^2$ is Cl, Br or I;

$Ar^L$ is a group of formula ($Ar^L$-25), ($Ar^L$-26), ($Ar^L$-27), ($Ar^L$-33), ($Ar^L$-36), ($Ar^L$-40), ($Ar^L$-41), ($Ar^L$-42), ($Ar^L$-43), ($Ar^L$-60), ($Ar^L$-96), ($Ar^L$-97); and where R is H, phenyl or a group of formula (R-1);

(R-1)
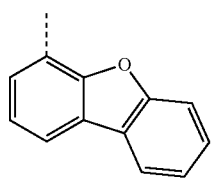

and where R, $Ar^L$ and $X^2$ are combined as listed in the table below:

| Int | R | Ar^L | X^2 | Int | R | Ar^L | X^2 |
|---|---|---|---|---|---|---|---|
| Int-9 | H | Ar^L-25 | Br | Int-9 | H | Ar^L-25 | Cl |
| Int-17 | H | Ar^L-25 | Br | Int-17 | H | Ar^L-25 | Cl |
| Int-33 | H | Ar^L-25 | Br | Int-33 | H | Ar^L-25 | Cl |
| Int-41 | — | Ar^L-25 | Br | Int-41 | — | Ar^L-25 | Cl |
| Int-42 | — | Ar^L-25 | Br | Int-42 | — | Ar^L-25 | Cl |
| Int-47 | — | Ar^L-25 | Br | Int-47 | — | Ar^L-25 | Cl |
| Int-48 | — | Ar^L-25 | Br | Int-48 | — | Ar^L-25 | Cl |
| Int-53 | — | Ar^L-25 | Br | Int-53 | — | Ar^L-25 | Cl |
| Int-58 | — | Ar^L-25 | Br | Int-58 | — | Ar^L-25 | Cl |
| Int-9 | phenyl | Ar^L-25 | Br | Int-9 | phenyl | Ar^L-25 | Cl |
| Int-17 | phenyl | Ar^L-25 | Br | Int-17 | phenyl | Ar^L-25 | Cl |
| Int-33 | phenyl | Ar^L-25 | Br | Int-33 | phenyl | Ar^L-25 | Cl |
| Int-9 | (R-1) | Ar^L-25 | Br | Int-9 | (R-1) | Ar^L-25 | Cl |
| Int-17 | (R-1) | Ar^L-25 | Br | Int-17 | (R-1) | Ar^L-25 | Cl |
| Int-33 | (R-1) | Ar^L-25 | Br | Int-33 | (R-1) | Ar^L-25 | Cl |
| Int-9 | H | Ar^L-26 | Br | Int-9 | H | Ar^L-26 | Cl |
| Int-17 | H | Ar^L-26 | Br | Int-17 | H | Ar^L-26 | Cl |
| Int-33 | H | Ar^L-26 | Br | Int-33 | H | Ar^L-26 | Cl |
| Int-41 | — | Ar^L-26 | Br | Int-41 | — | Ar^L-26 | Cl |
| Int-42 | — | Ar^L-26 | Br | Int-42 | — | Ar^L-26 | Cl |
| Int-47 | — | Ar^L-26 | Br | Int-47 | — | Ar^L-26 | Cl |
| Int-48 | — | Ar^L-26 | Br | Int-48 | — | Ar^L-26 | Cl |
| Int-53 | — | Ar^L-26 | Br | Int-53 | — | Ar^L-26 | Cl |
| Int-58 | — | Ar^L-26 | Br | Int-58 | — | Ar^L-26 | Cl |
| Int-9 | phenyl | Ar^L-26 | Br | Int-9 | phenyl | Ar^L-26 | Cl |
| Int-17 | phenyl | Ar^L-26 | Br | Int-17 | phenyl | Ar^L-26 | Cl |
| Int-33 | phenyl | Ar^L-26 | Br | Int-33 | phenyl | Ar^L-26 | Cl |
| Int-9 | (R-1) | Ar^L-26 | Br | Int-9 | (R-1) | Ar^L-26 | Cl |
| Int-17 | (R-1) | Ar^L-26 | Br | Int-17 | (R-1) | Ar^L-26 | Cl |
| Int-33 | (R-1) | Ar^L-26 | Br | Int-33 | (R-1) | Ar^L-26 | Cl |
| Int-9 | H | Ar^L-27 | Br | Int-9 | H | Ar^L-27 | Cl |
| Int-17 | H | Ar^L-27 | Br | Int-17 | H | Ar^L-27 | Cl |
| Int-33 | H | Ar^L-27 | Br | Int-33 | H | Ar^L-27 | Cl |
| Int-41 | — | Ar^L-27 | Br | Int-41 | — | Ar^L-27 | Cl |
| Int-42 | — | Ar^L-27 | Br | Int-42 | — | Ar^L-27 | Cl |
| Int-47 | — | Ar^L-27 | Br | Int-47 | — | Ar^L-27 | Cl |
| Int-48 | — | Ar^L-27 | Br | Int-48 | — | Ar^L-27 | Cl |
| Int-53 | — | Ar^L-27 | Br | Int-53 | — | Ar^L-27 | Cl |
| Int-58 | — | Ar^L-27 | Br | Int-58 | — | Ar^L-27 | Cl |
| Int-9 | phenyl | Ar^L-27 | Br | Int-9 | phenyl | Ar^L-27 | Cl |
| Int-17 | phenyl | Ar^L-27 | Br | Int-17 | phenyl | Ar^L-27 | Cl |
| Int-33 | phenyl | Ar^L-27 | Br | Int-33 | phenyl | Ar^L-27 | Cl |
| Int-9 | (R-1) | Ar^L-27 | Br | Int-9 | (R-1) | Ar^L-27 | Cl |
| Int-17 | (R-1) | Ar^L-27 | Br | Int-17 | (R-1) | Ar^L-27 | Cl |
| Int-33 | (R-1) | Ar^L-27 | Br | Int-33 | (R-1) | Ar^L-27 | Cl |
| Int-9 | H | Ar^L-33 | Br | Int-9 | H | Ar^L-33 | Cl |
| Int-17 | H | Ar^L-33 | Br | Int-17 | H | Ar^L-33 | Cl |
| Int-33 | H | Ar^L-33 | Br | Int-33 | H | Ar^L-33 | Cl |
| Int-41 | — | Ar^L-33 | Br | Int-41 | — | Ar^L-33 | Cl |
| Int-42 | — | Ar^L-33 | Br | Int-42 | — | Ar^L-33 | Cl |
| Int-47 | — | Ar^L-33 | Br | Int-47 | — | Ar^L-33 | Cl |
| Int-48 | — | Ar^L-33 | Br | Int-48 | — | Ar^L-33 | Cl |
| Int-53 | — | Ar^L-33 | Br | Int-53 | — | Ar^L-33 | Cl |
| Int-58 | — | Ar^L-33 | Br | Int-58 | — | Ar^L-33 | Cl |
| Int-9 | phenyl | Ar^L-33 | Br | Int-9 | phenyl | Ar^L-33 | Cl |
| Int-17 | phenyl | Ar^L-33 | Br | Int-17 | phenyl | Ar^L-33 | Cl |
| Int-33 | phenyl | Ar^L-33 | Br | Int-33 | phenyl | Ar^L-33 | Cl |
| Int-9 | (R-1) | Ar^L-33 | Br | Int-9 | (R-1) | Ar^L-33 | Cl |
| Int-17 | (R-1) | Ar^L-33 | Br | Int-17 | (R-1) | Ar^L-33 | Cl |
| Int-33 | (R-1) | Ar^L-33 | Br | Int-33 | (R-1) | Ar^L-33 | Cl |
| Int-9 | H | Ar^L-36 | Br | Int-9 | H | Ar^L-36 | Cl |
| Int-17 | H | Ar^L-36 | Br | Int-17 | H | Ar^L-36 | Cl |
| Int-33 | H | Ar^L-36 | Br | Int-33 | H | Ar^L-36 | Cl |
| Int-41 | — | Ar^L-36 | Br | Int-41 | — | Ar^L-36 | Cl |
| Int-42 | — | Ar^L-36 | Br | Int-42 | — | Ar^L-36 | Cl |
| Int-47 | — | Ar^L-36 | Br | Int-47 | — | Ar^L-36 | Cl |
| Int-48 | — | Ar-36 | Br | Int-48 | — | Ar-36 | Cl |
| Int-53 | — | Ar^L-36 | Br | Int-53 | — | Ar^L-36 | Cl |
| Int-58 | — | Ar^L-36 | Br | Int-58 | — | Ar^L-36 | Cl |
| Int-9 | phenyl | Ar^L-36 | Br | Int-9 | phenyl | Ar^L-36 | Cl |
| Int-17 | phenyl | Ar^L-36 | Br | Int-17 | phenyl | Ar^L-36 | Cl |
| Int-33 | phenyl | Ar^L-36 | Br | Int-33 | phenyl | Ar^L-36 | Cl |
| Int-9 | (R-1) | Ar^L-36 | Br | Int-9 | (R-1) | Ar^L-36 | Cl |
| Int-17 | (R-1) | Ar^L-36 | Br | Int-17 | (R-1) | Ar^L-36 | Cl |
| Int-33 | (R-1) | Ar^L-36 | Br | Int-33 | (R-1) | Ar^L-36 | Cl |
| Int-9 | H | Ar^L-40 | Br | Int-9 | H | Ar^L-40 | Cl |
| Int-17 | H | Ar^L-40 | Br | Int-17 | H | Ar^L-40 | Cl |
| Int-33 | H | Ar^L-40 | Br | Int-33 | H | Ar^L-40 | Cl |
| Int-41 | — | Ar^L-40 | Br | Int-41 | — | Ar^L-40 | Cl |
| Int-42 | — | Ar^L-40 | Br | Int-42 | — | Ar^L-40 | Cl |
| Int-47 | — | Ar^L-40 | Br | Int-47 | — | Ar^L-40 | Cl |
| Int-48 | — | Ar^L-40 | Br | Int-48 | — | Ar^L-40 | Cl |
| Int-53 | — | Ar^L-40 | Br | Int-53 | — | Ar^L-40 | Cl |
| Int-58 | — | Ar^L-40 | Br | Int-58 | — | Ar^L-40 | Cl |
| Int-9 | phenyl | Ar^L-40 | Br | Int-9 | phenyl | Ar^L-40 | Cl |
| Int-17 | phenyl | Ar^L-40 | Br | Int-17 | phenyl | Ar^L-40 | Cl |
| Int-33 | phenyl | Ar^L-40 | Br | Int-33 | phenyl | Ar^L-40 | Cl |
| Int-9 | (R-1) | Ar^L-40 | Br | Int-9 | (R-1) | Ar^L-40 | Cl |
| Int-17 | (R-1) | Ar^L-40 | Br | Int-17 | (R-1) | Ar^L-40 | Cl |
| Int-33 | (R-1) | Ar^L-40 | Br | Int-33 | (R-1) | Ar^L-40 | Cl |
| Int-9 | H | Ar^L-41 | Br | Int-9 | H | Ar^L-41 | Cl |
| Int-17 | H | Ar^L-41 | Br | Int-17 | H | Ar^L-41 | Cl |
| Int-33 | H | Ar^L-41 | Br | Int-33 | H | Ar^L-41 | Cl |
| Int-41 | — | Ar^L-41 | Br | Int-41 | — | Ar^L-41 | Cl |
| Int-42 | — | Ar^L-41 | Br | Int-42 | — | Ar^L-41 | Cl |
| Int-47 | — | Ar^L-41 | Br | Int-47 | — | Ar^L-41 | Cl |
| Int-48 | — | Ar^L-41 | Br | Int-48 | — | Ar^L-41 | Cl |
| Int-53 | — | Ar^L-41 | Br | Int-53 | — | Ar^L-41 | Cl |
| Int-58 | — | Ar^L-41 | Br | Int-58 | — | Ar^L-41 | Cl |
| Int-9 | phenyl | Ar^L-41 | Br | Int-9 | phenyl | Ar^L-41 | Cl |
| Int-17 | phenyl | Ar^L-41 | Br | Int-17 | phenyl | Ar^L-41 | Cl |
| Int-33 | phenyl | Ar^L-41 | Br | Int-33 | phenyl | Ar^L-41 | Cl |
| Int-9 | (R-1) | Ar^L-41 | Br | Int-9 | (R-1) | Ar^L-41 | Cl |
| Int-17 | (R-1) | Ar^L-41 | Br | Int-17 | (R-1) | Ar^L-41 | Cl |
| Int-33 | (R-1) | Ar^L-41 | Br | Int-33 | (R-1) | Ar^L-41 | Cl |
| Int-9 | H | Ar^L-42 | Br | Int-9 | H | Ar^L-42 | Cl |
| Int-17 | H | Ar^L-42 | Br | Int-17 | H | Ar^L-42 | Cl |
| Int-33 | H | Ar^L-42 | Br | Int-33 | H | Ar^L-42 | Cl |
| Int-41 | — | Ar^L-42 | Br | Int-41 | — | Ar^L-42 | Cl |
| Int-42 | — | Ar^L-42 | Br | Int-42 | — | Ar^L-42 | Cl |
| Int-47 | — | Ar^L-42 | Br | Int-47 | — | Ar^L-42 | Cl |
| Int-48 | — | Ar^L-42 | Br | Int-48 | — | Ar^L-42 | Cl |
| Int-53 | — | Ar^L-42 | Br | Int-53 | — | Ar^L-42 | Cl |
| Int-58 | — | Ar^L-42 | Br | Int-58 | — | Ar^L-42 | Cl |
| Int-9 | phenyl | Ar^L-42 | Br | Int-9 | phenyl | Ar^L-42 | Cl |
| Int-17 | phenyl | Ar^L-42 | Br | Int-17 | phenyl | Ar^L-42 | Cl |
| Int-33 | phenyl | Ar^L-42 | Br | Int-33 | phenyl | Ar^L-42 | Cl |
| Int-9 | (R-1) | Ar^L-42 | Br | Int-9 | (R-1) | Ar^L-42 | Cl |
| Int-17 | (R-1) | Ar^L-42 | Br | Int-17 | (R-1) | Ar^L-42 | Cl |
| Int-33 | (R-1) | Ar^L-42 | Br | Int-33 | (R-1) | Ar^L-42 | Cl |
| Int-9 | H | Ar^L-43 | Br | Int-9 | H | Ar^L-43 | Cl |
| Int-17 | H | Ar^L-43 | Br | Int-17 | H | Ar^L-43 | Cl |
| Int-33 | H | Ar^L-43 | Br | Int-33 | H | Ar^L-43 | Cl |
| Int-41 | — | Ar^L-43 | Br | Int-41 | — | Ar^L-43 | Cl |
| Int-42 | — | Ar^L-43 | Br | Int-42 | — | Ar^L-43 | Cl |
| Int-47 | — | Ar^L-43 | Br | Int-47 | — | Ar^L-43 | Cl |
| Int-48 | — | Ar^L-43 | Br | Int-48 | — | Ar^L-43 | Cl |
| Int-53 | — | Ar^L-43 | Br | Int-53 | — | Ar^L-43 | Cl |
| Int-58 | — | Ar^L-43 | Br | Int-58 | — | Ar^L-43 | Cl |
| Int-9 | phenyl | Ar^L-43 | Br | Int-9 | phenyl | Ar^L-43 | Cl |
| Int-17 | phenyl | Ar^L-43 | Br | Int-17 | phenyl | Ar^L-43 | Cl |
| Int-33 | phenyl | Ar^L-43 | Br | Int-33 | phenyl | Ar^L-43 | Cl |
| Int-9 | (R-1) | Ar^L-43 | Br | Int-9 | (R-1) | Ar^L-43 | Cl |
| Int-17 | (R-1) | Ar^L-43 | Br | Int-17 | (R-1) | Ar^L-43 | Cl |
| Int-33 | (R-1) | Ar^L-43 | Br | Int-33 | (R-1) | Ar^L-43 | Cl |
| Int-9 | H | Ar^L-60 | Br | Int-9 | H | Ar^L-60 | Cl |
| Int-17 | H | Ar^L-60 | Br | Int-17 | H | Ar^L-60 | Cl |
| Int-33 | H | Ar^L-60 | Br | Int-33 | H | Ar^L-60 | Cl |
| Int-41 | — | Ar^L-60 | Br | Int-41 | — | Ar^L-60 | Cl |
| Int-42 | — | Ar^L-60 | Br | Int-42 | — | Ar^L-60 | Cl |
| Int-47 | — | Ar^L-60 | Br | Int-47 | — | Ar^L-60 | Cl |
| Int-48 | — | Ar^L-60 | Br | Int-48 | — | Ar^L-60 | Cl |
| Int-53 | — | Ar^L-60 | Br | Int-53 | — | Ar^L-60 | Cl |
| Int-58 | — | Ar^L-60 | Br | Int-58 | — | Ar^L-60 | Cl |
| Int-9 | phenyl | Ar^L-60 | Br | Int-9 | phenyl | Ar^L-60 | Cl |
| Int-17 | phenyl | Ar^L-60 | Br | Int-17 | phenyl | Ar^L-60 | Cl |
| Int-33 | phenyl | Ar^L-60 | Br | Int-33 | phenyl | Ar^L-60 | Cl |
| Int-9 | (R-1) | Ar^L-60 | Br | Int-9 | (R-1) | Ar^L-60 | Cl |
| Int-17 | (R-1) | Ar^L-60 | Br | Int-17 | (R-1) | Ar^L-60 | Cl |
| Int-33 | (R-1) | Ar^L-60 | Br | Int-33 | (R-1) | Ar^L-60 | Cl |
| Int-9 | H | Ar^L-96 | Br | Int-9 | H | Ar^L-96 | Cl |
| Int-17 | H | Ar^L-96 | Br | Int-17 | H | Ar^L-96 | Cl |
| Int-33 | H | Ar^L-96 | Br | Int-33 | H | Ar^L-96 | Cl |
| Int-41 | — | Ar^L-96 | Br | Int-41 | — | Ar^L-96 | Cl |
| Int-42 | — | Ar^L-96 | Br | Int-42 | — | Ar^L-96 | Cl |
| Int-47 | — | Ar^L-96 | Br | Int-47 | — | Ar^L-96 | Cl |

-continued

| Int | R | $Ar^L$ | $X^2$ | Int | R | $Ar^L$ | $X^2$ |
|---|---|---|---|---|---|---|---|
| Int-48 | — | $Ar^L$-96 | Br | Int-48 | — | $Ar^L$-96 | Cl |
| Int-53 | — | $Ar^L$-96 | Br | Int-53 | — | $Ar^L$-96 | Cl |
| Int-58 | — | $Ar^L$-96 | Br | Int-58 | — | $Ar^L$-96 | Cl |
| Int-9 | phenyl | $Ar^L$-96 | Br | Int-9 | phenyl | $Ar^L$-96 | Cl |
| Int-17 | phenyl | $Ar^L$-96 | Br | Int-17 | phenyl | $Ar^L$-96 | Cl |
| Int-33 | phenyl | $Ar^L$-96 | Br | Int-33 | phenyl | $Ar^L$-96 | Cl |
| Int-9 | (R-1) | $Ar^L$-96 | Br | Int-9 | (R-1) | $Ar^L$-96 | Cl |
| Int-17 | (R-1) | $Ar^L$-96 | Br | Int-17 | (R-1) | $Ar^L$-96 | Cl |
| Int-33 | (R-1) | $Ar^L$-96 | Br | Int-33 | (R-1) | $Ar^L$-96 | Cl |
| Int-9 | H | $Ar^L$-97 | Br | Int-9 | H | $Ar^L$-97 | Cl |
| Int-17 | H | $Ar^L$-97 | Br | Int-17 | H | $Ar^L$-97 | Cl |
| Int-33 | H | $Ar^L$-97 | Br | Int-33 | H | $Ar^L$-97 | Cl |
| Int-41 | — | $Ar^L$-97 | Br | Int-41 | — | $Ar^L$-97 | Cl |
| Int-42 | — | $Ar^L$-97 | Br | Int-42 | — | $Ar^L$-97 | Cl |
| Int-47 | — | $Ar^L$-97 | Br | Int-47 | — | $Ar^L$-97 | Cl |
| Int-48 | — | $Ar^L$-97 | Br | Int-48 | — | $Ar^L$-97 | Cl |
| Int-53 | — | $Ar^L$-97 | Br | Int-53 | — | $Ar^L$-97 | Cl |
| Int-58 | — | $Ar^L$-97 | Br | Int-58 | — | $Ar^L$-97 | Cl |
| Int-9 | phenyl | $Ar^L$-97 | Br | Int-9 | phenyl | $Ar^L$-97 | Cl |
| Int-17 | phenyl | $Ar^L$-97 | Br | Int-17 | phenyl | $Ar^L$-97 | Cl |
| Int-33 | phenyl | $Ar^L$-97 | Br | Int-33 | phenyl | $Ar^L$-97 | Cl |
| Int-9 | (R-1) | $Ar^L$-97 | Br | Int-9 | (R-1) | $Ar^L$-97 | Cl |
| Int-17 | (R-1) | $Ar^L$-97 | Br | Int-17 | (R-1) | $Ar^L$-97 | Cl |
| Int-33 | (R-1) | $Ar^L$-97 | Br | Int-33 | (R-1) | $Ar^L$-97 | Cl |
| Int-9 | H | $Ar^L$-25 | I | Int-9 | H | $Ar^L$-41 | I |
| Int-17 | H | $Ar^L$-25 | I | Int-17 | H | $Ar^L$-41 | I |
| Int-33 | H | $Ar^L$-25 | I | Int-33 | H | $Ar^L$-41 | I |
| Int-41 | — | $Ar^L$-25 | I | Int-41 | — | $Ar^L$-41 | I |
| Int-42 | — | $Ar^L$-25 | I | Int-42 | — | $Ar^L$-41 | I |
| Int-47 | — | $Ar^L$-25 | I | Int-47 | — | $Ar^L$-41 | I |
| Int-48 | — | $Ar^L$-25 | I | Int-48 | — | $Ar^L$-41 | I |
| Int-53 | — | $Ar^L$-25 | I | Int-53 | — | $Ar^L$-41 | I |
| Int-58 | — | $Ar^L$-25 | I | Int-58 | — | $Ar^L$-41 | I |
| Int-9 | phenyl | $Ar^L$-25 | I | Int-9 | phenyl | $Ar^L$-41 | I |
| Int-17 | phenyl | $Ar^L$-25 | I | Int-17 | phenyl | $Ar^L$-41 | I |
| Int-33 | phenyl | $Ar^L$-25 | I | Int-33 | phenyl | $Ar^L$-41 | I |
| Int-9 | (R-1) | $Ar^L$-25 | I | Int-9 | (R-1) | $Ar^L$-41 | I |
| Int-17 | (R-1) | $Ar^L$-25 | I | Int-17 | (R-1) | $Ar^L$-41 | I |
| Int-33 | (R-1) | $Ar^L$-25 | I | Int-33 | (R-1) | $Ar^L$-41 | I |
| Int-9 | H | $Ar^L$-26 | I | Int-9 | H | $Ar^L$-42 | I |
| Int-17 | H | $Ar^L$-26 | I | Int-17 | H | $Ar^L$-42 | I |
| Int-33 | H | $Ar^L$-26 | I | Int-33 | H | $Ar^L$-42 | I |
| Int-41 | — | $Ar^L$-26 | I | Int-41 | — | $Ar^L$-42 | I |
| Int-42 | — | $Ar^L$-26 | I | Int-42 | — | $Ar^L$-42 | I |
| Int-47 | — | $Ar^L$-26 | I | Int-47 | — | $Ar^L$-42 | I |
| Int-48 | — | $Ar^L$-26 | I | Int-48 | — | $Ar^L$-42 | I |
| Int-53 | — | $Ar^L$-26 | I | Int-53 | — | $Ar^L$-42 | I |
| Int-58 | — | $Ar^L$-26 | I | Int-58 | — | $Ar^L$-42 | I |
| Int-9 | phenyl | $Ar^L$-26 | I | Int-9 | phenyl | $Ar^L$-42 | I |
| Int-17 | phenyl | $Ar^L$-26 | I | Int-17 | phenyl | $Ar^L$-42 | I |
| Int-33 | phenyl | $Ar^L$-26 | I | Int-33 | phenyl | $Ar^L$-42 | I |
| Int-9 | (R-1) | $Ar^L$-26 | I | Int-9 | (R-1) | $Ar^L$-42 | I |
| Int-17 | (R-1) | $Ar^L$-26 | I | Int-17 | (R-1) | $Ar^L$-42 | I |
| Int-33 | (R-1) | $Ar^L$-26 | I | Int-33 | (R-1) | $Ar^L$-42 | I |
| Int-9 | H | $Ar^L$-27 | I | Int-9 | H | $Ar^L$-43 | I |
| Int-17 | H | $Ar^L$-27 | I | Int-17 | H | $Ar^L$-43 | I |
| Int-33 | H | $Ar^L$-27 | I | Int-33 | H | $Ar^L$-43 | I |
| Int-41 | — | $Ar^L$-27 | I | Int-41 | — | $Ar^L$-43 | I |
| Int-42 | — | $Ar^L$-27 | I | Int-42 | — | $Ar^L$-43 | I |
| Int-47 | — | $Ar^L$-27 | I | Int-47 | — | $Ar^L$-43 | I |
| Int-48 | — | $Ar^L$-27 | I | Int-48 | — | $Ar^L$-43 | I |
| Int-53 | — | $Ar^L$-27 | I | Int-53 | — | $Ar^L$-43 | I |
| Int-58 | — | $Ar^L$-27 | I | Int-58 | — | $Ar^L$-43 | I |
| Int-9 | phenyl | $Ar^L$-27 | I | Int-9 | phenyl | $Ar^L$-43 | I |
| Int-17 | phenyl | $Ar^L$-27 | I | Int-17 | phenyl | $Ar^L$-43 | I |
| Int-33 | phenyl | Ar-27 | I | Int-33 | phenyl | Ar-43 | I |
| Int-9 | (R-1) | $Ar^L$-27 | I | Int-9 | (R-1) | $Ar^L$-43 | I |
| Int-17 | (R-1) | $Ar^L$-27 | I | Int-17 | (R-1) | $Ar^L$-43 | I |
| Int-33 | (R-1) | $Ar^L$-27 | I | Int-33 | (R-1) | $Ar^L$-43 | I |
| Int-9 | H | $Ar^L$-33 | I | Int-9 | H | $Ar^L$-60 | I |
| Int-17 | H | $Ar^L$-33 | I | Int-17 | H | $Ar^L$-60 | I |
| Int-33 | H | $Ar^L$-33 | I | Int-33 | H | $Ar^L$-60 | I |
| Int-41 | — | $Ar^L$-33 | I | Int-41 | — | $Ar^L$-60 | I |
| Int-42 | — | $Ar^L$-33 | I | Int-42 | — | $Ar^L$-60 | I |
| Int-47 | — | $Ar^L$-33 | I | Int-47 | — | $Ar^L$-60 | I |
| Int-48 | — | $Ar^L$-33 | I | Int-48 | — | $Ar^L$-60 | I |
| Int-53 | — | $Ar^L$-33 | I | Int-53 | — | $Ar^L$-60 | I |
| Int-58 | — | $Ar^L$-33 | I | Int-58 | — | $Ar^L$-60 | I |
| Int-9 | phenyl | $Ar^L$-33 | I | Int-9 | phenyl | $Ar^L$-60 | I |
| Int-17 | phenyl | $Ar^L$-33 | I | Int-17 | phenyl | $Ar^L$-60 | I |
| Int-33 | phenyl | $Ar^L$-33 | I | Int-33 | phenyl | $Ar^L$-60 | I |
| Int-9 | (R-1) | $Ar^L$-33 | I | Int-9 | (R-1) | $Ar^L$-60 | I |
| Int-17 | (R-1) | $Ar^L$-33 | I | Int-17 | (R-1) | $Ar^L$-60 | I |
| Int-33 | (R-1) | $Ar^L$-33 | I | Int-33 | (R-1) | $Ar^L$-60 | I |
| Int-9 | H | $Ar^L$-36 | I | Int-9 | H | $Ar^L$-96 | I |
| Int-17 | H | $Ar^L$-36 | I | Int-17 | H | $Ar^L$-96 | I |
| Int-33 | H | $Ar^L$-36 | I | Int-33 | H | $Ar^L$-96 | I |
| Int-41 | — | $Ar^L$-36 | I | Int-41 | — | $Ar^L$-96 | I |
| Int-42 | — | $Ar^L$-36 | I | Int-42 | — | $Ar^L$-96 | I |
| Int-47 | — | $Ar^L$-36 | I | Int-47 | — | $Ar^L$-96 | I |
| Int-48 | — | $Ar^L$-36 | I | Int-48 | — | $Ar^L$-96 | I |
| Int-53 | — | $Ar^L$-36 | I | Int-53 | — | $Ar^L$-96 | I |
| Int-58 | — | $Ar^L$-36 | I | Int-58 | — | $Ar^L$-96 | I |
| Int-9 | phenyl | $Ar^L$-36 | I | Int-9 | phenyl | $Ar^L$-96 | I |
| Int-17 | phenyl | $Ar^L$-36 | I | Int-17 | phenyl | $Ar^L$-96 | I |
| Int-33 | phenyl | $Ar^L$-36 | I | Int-33 | phenyl | $Ar^L$-96 | I |
| Int-9 | (R-1) | $Ar^L$-36 | I | Int-9 | (R-1) | $Ar^L$-96 | I |
| Int-17 | (R-1) | $Ar^L$-36 | I | Int-17 | (R-1) | $Ar^L$-96 | I |
| Int-33 | (R-1) | $Ar^L$-36 | I | Int-33 | (R-1) | $Ar^L$-96 | I |
| Int-9 | H | $Ar^L$-40 | I | Int-9 | H | $Ar^L$-97 | I |
| Int-17 | H | $Ar^L$-40 | I | Int-17 | H | $Ar^L$-97 | I |
| Int-33 | H | $Ar^L$-40 | I | Int-33 | H | $Ar^L$-97 | I |
| Int-41 | — | $Ar^L$-40 | I | Int-41 | — | $Ar^L$-97 | I |
| Int-42 | — | $Ar^L$-40 | I | Int-42 | — | $Ar^L$-97 | I |
| Int-47 | — | $Ar^L$-40 | I | Int-47 | — | $Ar^L$-97 | I |
| Int-48 | — | $Ar^L$-40 | I | Int-48 | — | $Ar^L$-97 | I |
| Int-53 | — | $Ar^L$-40 | I | Int-53 | — | $Ar^L$-97 | I |
| Int-58 | — | $Ar^L$-40 | I | Int-58 | — | $Ar^L$-97 | I |
| Int-9 | phenyl | $Ar^L$-40 | I | Int-9 | phenyl | $Ar^L$-97 | I |
| Int-17 | phenyl | $Ar^L$-40 | I | Int-17 | phenyl | $Ar^L$-97 | I |
| Int-33 | phenyl | $Ar^L$-40 | I | Int-33 | phenyl | $Ar^L$-97 | I |
| Int-9 | (R-1) | $Ar^L$-40 | I | Int-9 | (R-1) | $Ar^L$-97 | I |
| Int-17 | (R-1) | $Ar^L$-40 | I | Int-17 | (R-1) | $Ar^L$-97 | I |
| Int-33 | (R-1) | $Ar^L$-40 | I | Int-33 | (R-1) | $Ar^L$-97 | I |

Examples of particularly preferred suitable compounds according to formula (Int-1) are the compounds in the table above where the compounds are of formula (Int-9), (Int-17), (Int-41) or (Int-42), where $X^2$ is Cl, and where $Ar^L$ is a group of formula ($Ar^L$-25), ($Ar^L$-26), ($Ar^L$-27), ($Ar^L$-36), ($Ar^L$-40), ($Ar^L$-41) or ($Ar^L$-42) and where R is H, phenyl or a group of formula (R-1);

(R-1)

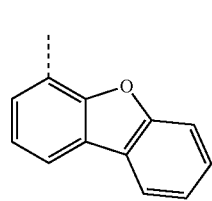

The present invention furthermore relates to compounds of formula (1-1) and (1-2) as depicted below. These compounds may be prepared with the process of the invention. The compounds of formula (1-1) to (1-2) are as follows:

formula (1-1)

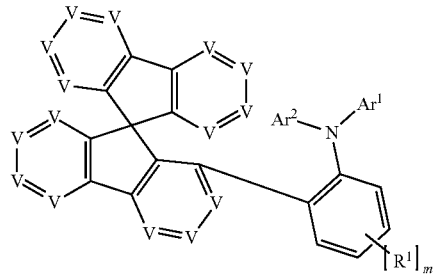

formula (1-2)

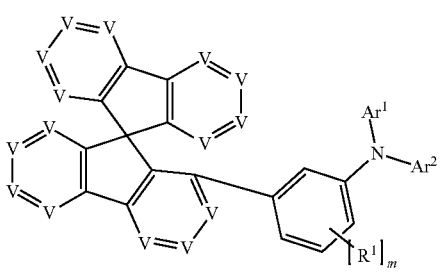

where the symbols V, Ar¹, Ar² and R¹ as well as the preferred embodiments for these symbols are as defined above and where the index m is 0, 1, 2, 3 or 4.

In accordance with a preferred embodiment of the invention, the compounds of formulae (1-1) and (1-2) are selected from the following compounds of formulae (1-1-1) to (1-1-7) and (1-2-1) to (1-2-7), (formula 1-1-1)

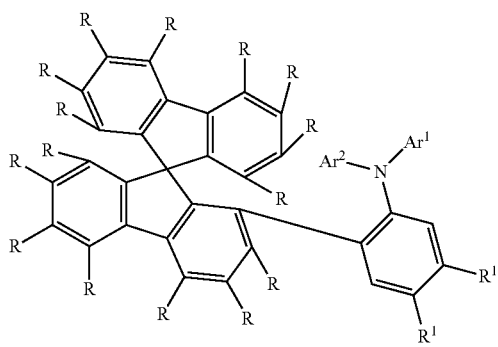

(formula 1-2-1)

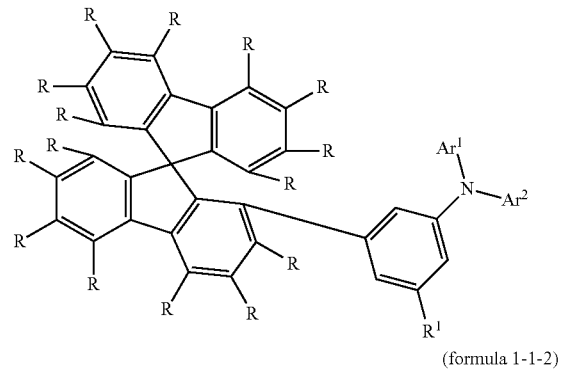

(formula 1-1-2)

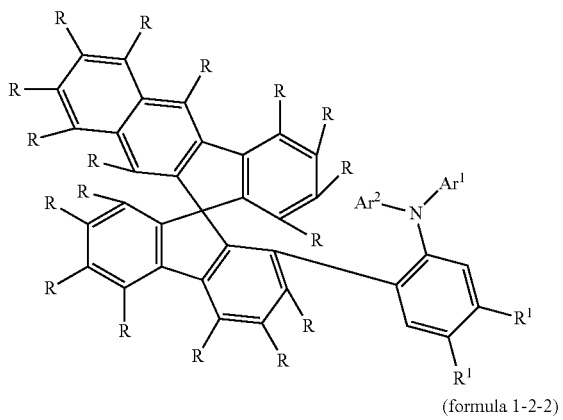

(formula 1-2-2)

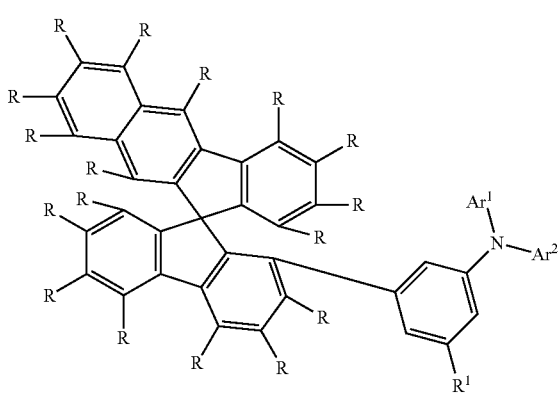

formula (1-1-3)

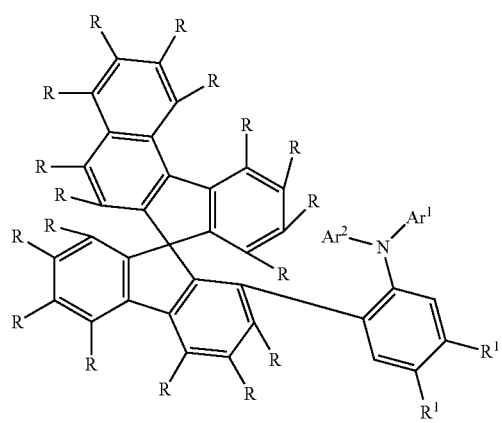

formula (1-2-3)
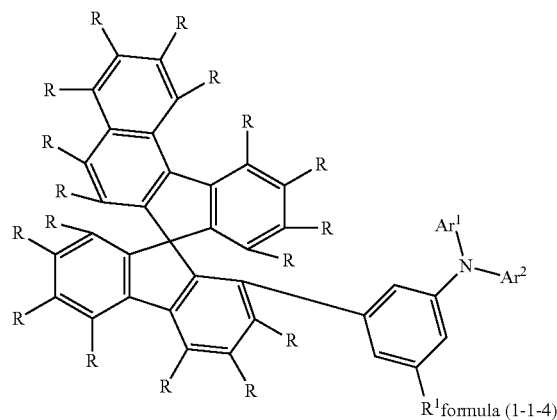
formula (1-1-4)
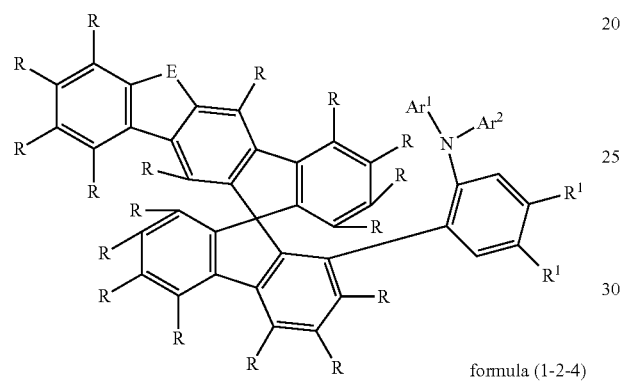
formula (1-2-4)
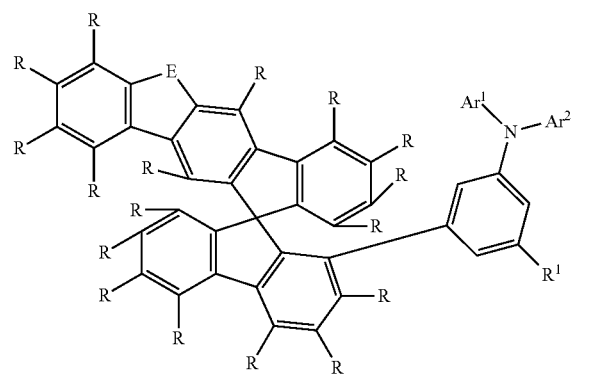
formula (1-1-5)
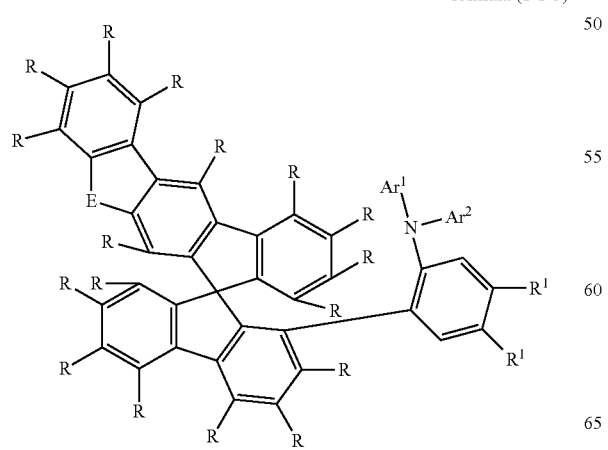
formula (1-2-5)
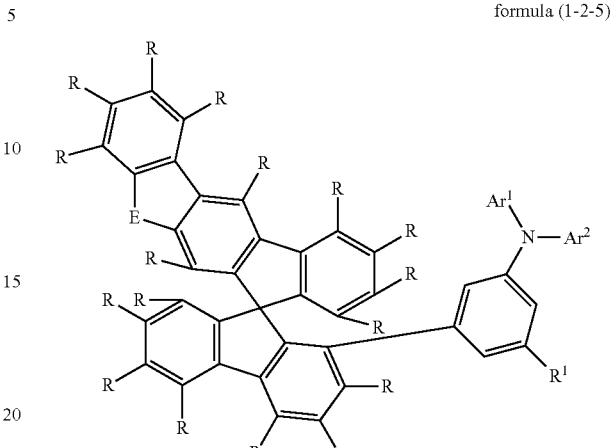
formula (1-1-6)
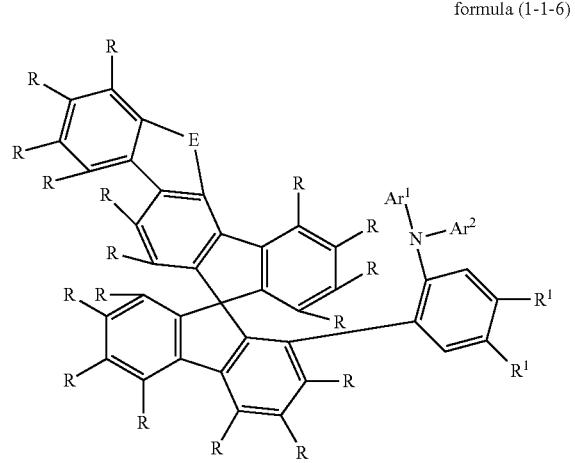
formula (1-2-6)
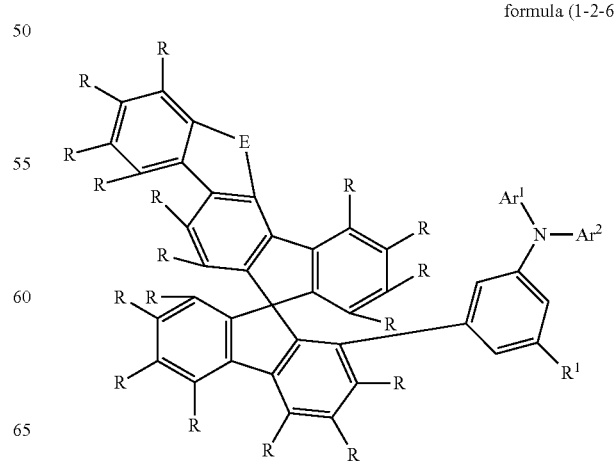

formula (1-1-7)

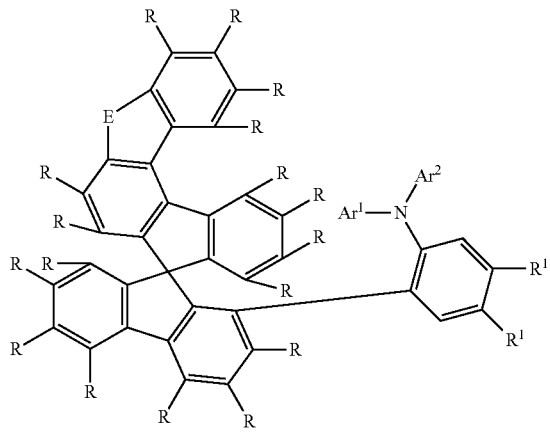

formula (1-2-7)

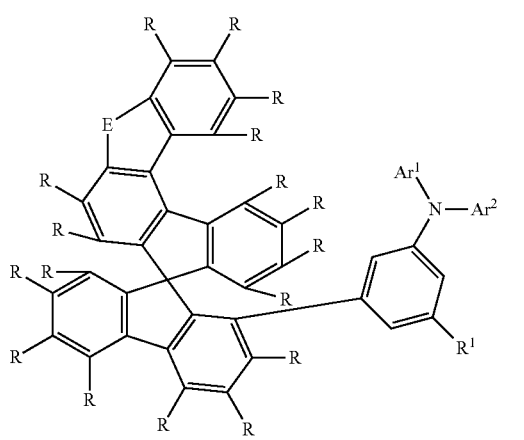

where E, R, R¹, Ar¹ and Ar² have the same meaning as defined above.

More preferably, the compounds of formulae (1-1-1) and (1-2-1) are selected from the compounds of formulae (1-1-1a) and (1-2-1a), formula (1-1-1a)

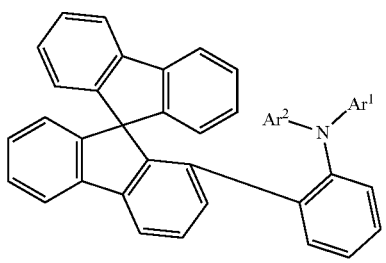

formula (1-2-1a)

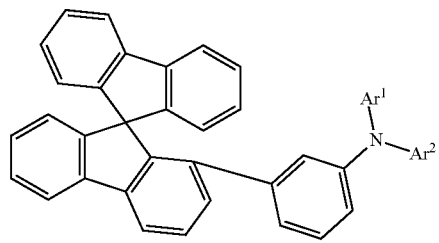

where the symbols Ar¹ and Ar² have the same meaning as defined above.

Examples of suitable structures for compounds of formulae (1-1) and (1-2) are the compounds of the formulae (S-10-1), (S-10-2), (S-33-1), (S-33-2), (S-34-1), (S-34-2), (S-39-1), (S-39-2), (S-40-1) et (S-40-2) as depicted below, where R is H, D, F, CN, a straight-chain alkyl having 1 to 5 C atoms or a branched or cyclic alkyl group having 3 to 6 C atoms, or an aryl or heteroaryl group having 5 to 18 aromatic ring atoms; and Ar¹, Ar² are selected from the groups (Ar-1), (Ar-2), (Ar-3), (Ar-4), (Ar-16), (Ar-63), (Ar-64), (Ar-66), (Ar-67), (Ar-69), (Ar-74), (Ar-78), (Ar-82), (Ar-89), (Ar-96), (Ar-99), (Ar-101), (Ar-107), (Ar-117), (Ar-134), (Ar-139), (Ar-141), (Ar-143), (Ar-150), (Ar-155), (Ar-172), (Ar-174), (Ar-177), (Ar-213), (Ar-216), (Ar-219), (Ar-222) or (Ar-247).

S-10-1

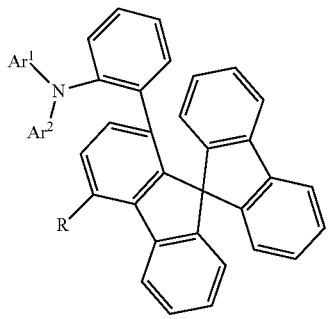

S-10-2

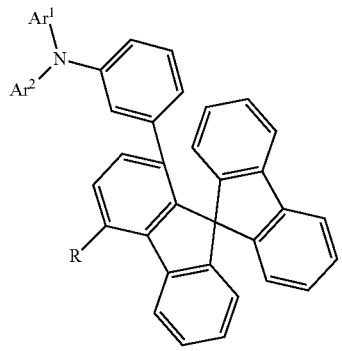

S-33-1

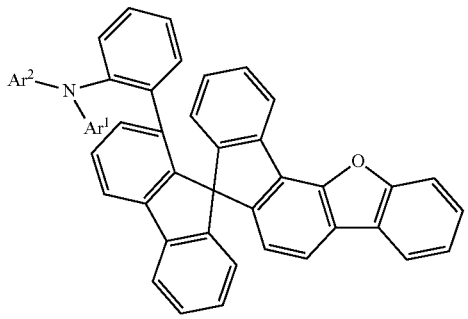

S-33-2
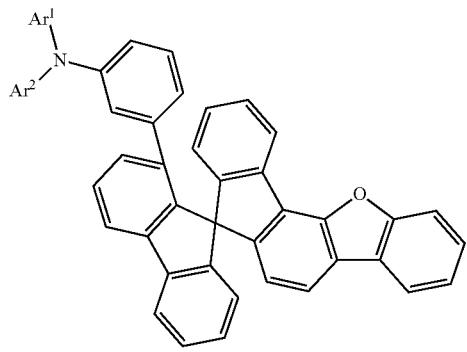
S-34-1
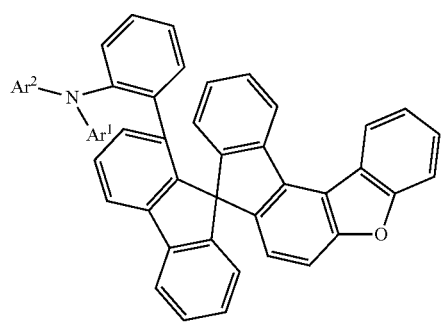
S-34-2
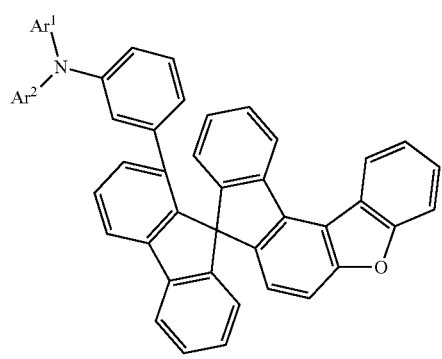
S-39-1
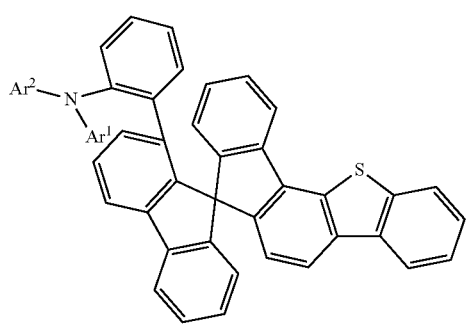
S-39-2
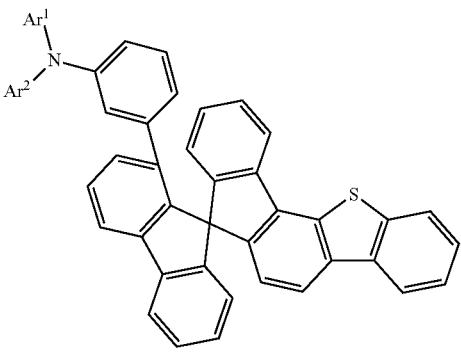
S-40-1
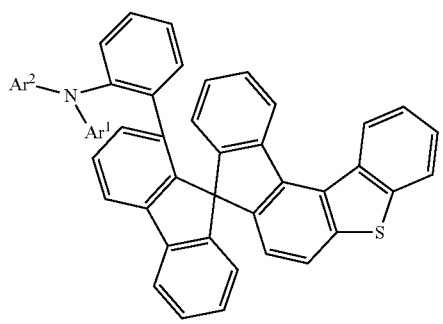
S-41-2
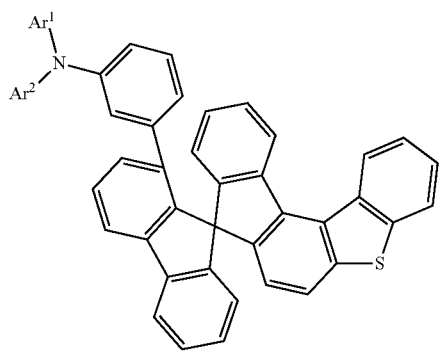
Particularly preferred examples of suitable compounds according to formulae (1-1) and (1-2) are the compounds of: formulae (S-10-1) and (S-10-2); where R is H, phenyl or a group of formula (R-1):
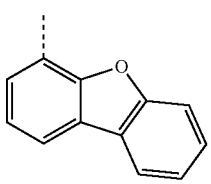
(R-1)
and where the groups R, Ar¹ and Ar² in formulae (S-10-1) and (S-10-2) are combined as listed in the table below:
| R | Ar¹ | Ar² | R | Ar¹ | Ar² |
|---|-----|-----|---|-----|-----|
| H | Ar-1 | Ar-2 | Phenyl | Ar-1 | Ar-2 |
| H | Ar-1 | Ar-3 | Phenyl | Ar-1 | Ar-3 |
| H | Ar-1 | Ar-4 | Phenyl | Ar-1 | Ar-4 |
| H | Ar-1 | Ar-16 | Phenyl | Ar-1 | Ar-16 |

| R | Ar¹ | Ar² | R | Ar¹ | Ar² |
|---|---|---|---|---|---|
| H | Ar-1 | Ar-64 | Phenyl | Ar-1 | Ar-64 |
| H | Ar-1 | Ar-66 | Phenyl | Ar-1 | Ar-66 |
| H | Ar-1 | Ar-69 | Phenyl | Ar-1 | Ar-69 |
| H | Ar-1 | Ar-74 | Phenyl | Ar-1 | Ar-74 |
| H | Ar-1 | Ar-78 | Phenyl | Ar-1 | Ar-78 |
| H | Ar-1 | Ar-82 | Phenyl | Ar-1 | Ar-82 |
| H | Ar-1 | Ar-89 | Phenyl | Ar-1 | Ar-89 |
| H | Ar-1 | Ar-99 | Phenyl | Ar-1 | Ar-99 |
| H | Ar-1 | Ar-117 | Phenyl | Ar-1 | Ar-117 |
| H | Ar-1 | Ar-134 | Phenyl | Ar-1 | Ar-134 |
| H | Ar-1 | Ar-139 | Phenyl | Ar-1 | Ar-139 |
| H | Ar-1 | Ar-141 | Phenyl | Ar-1 | Ar-141 |
| H | Ar-1 | Ar-143 | Phenyl | Ar-1 | Ar-143 |
| H | Ar-1 | Ar-150 | Phenyl | Ar-1 | Ar-150 |
| H | Ar-1 | Ar-155 | Phenyl | Ar-1 | Ar-155 |
| H | Ar-1 | Ar-172 | Phenyl | Ar-1 | Ar-172 |
| H | Ar-1 | Ar-177 | Phenyl | Ar-1 | Ar-177 |
| H | Ar-1 | Ar-213 | Phenyl | Ar-1 | Ar-213 |
| H | Ar-1 | Ar-216 | Phenyl | Ar-1 | Ar-216 |
| H | Ar-1 | Ar-222 | Phenyl | Ar-1 | Ar-222 |
| H | Ar-1 | Ar-247 | Phenyl | Ar-1 | Ar-247 |
| H | Ar-2 | Ar-2 | Phenyl | Ar-2 | Ar-2 |
| H | Ar-2 | Ar-3 | Phenyl | Ar-2 | Ar-3 |
| H | Ar-2 | Ar-4 | Phenyl | Ar-2 | Ar-4 |
| H | Ar-2 | Ar-16 | Phenyl | Ar-2 | Ar-16 |
| H | Ar-2 | Ar-64 | Phenyl | Ar-2 | Ar-64 |
| H | Ar-2 | Ar-66 | Phenyl | Ar-2 | Ar-66 |
| H | Ar-2 | Ar-69 | Phenyl | Ar-2 | Ar-69 |
| H | Ar-2 | Ar-74 | Phenyl | Ar-2 | Ar-74 |
| H | Ar-2 | Ar-78 | Phenyl | Ar-2 | Ar-78 |
| H | Ar-2 | Ar-82 | Phenyl | Ar-2 | Ar-82 |
| H | Ar-2 | Ar-89 | Phenyl | Ar-2 | Ar-89 |
| H | Ar-2 | Ar-99 | Phenyl | Ar-2 | Ar-99 |
| H | Ar-2 | Ar-117 | Phenyl | Ar-2 | Ar-117 |
| H | Ar-2 | Ar-134 | Phenyl | Ar-2 | Ar-134 |
| H | Ar-2 | Ar-139 | Phenyl | Ar-2 | Ar-139 |
| H | Ar-2 | Ar-141 | Phenyl | Ar-2 | Ar-141 |
| H | Ar-2 | Ar-143 | Phenyl | Ar-2 | Ar-143 |
| H | Ar-2 | Ar-150 | Phenyl | Ar-2 | Ar-150 |
| H | Ar-2 | Ar-155 | Phenyl | Ar-2 | Ar-155 |
| H | Ar-2 | Ar-172 | Phenyl | Ar-2 | Ar-172 |
| H | Ar-2 | Ar-177 | Phenyl | Ar-2 | Ar-177 |
| H | Ar-2 | Ar-213 | Phenyl | Ar-2 | Ar-213 |
| H | Ar-2 | Ar-216 | Phenyl | Ar-2 | Ar-216 |
| H | Ar-2 | Ar-222 | Phenyl | Ar-2 | Ar-222 |
| H | Ar-2 | Ar-247 | Phenyl | Ar-2 | Ar-247 |
| H | Ar-3 | Ar-2 | Phenyl | Ar-3 | Ar-2 |
| H | Ar-3 | Ar-3 | Phenyl | Ar-3 | Ar-3 |
| H | Ar-3 | Ar-4 | Phenyl | Ar-3 | Ar-4 |
| H | Ar-3 | Ar-16 | Phenyl | Ar-3 | Ar-16 |
| H | Ar-3 | Ar-64 | Phenyl | Ar-3 | Ar-64 |
| H | Ar-3 | Ar-66 | Phenyl | Ar-3 | Ar-66 |
| H | Ar-3 | Ar-69 | Phenyl | Ar-3 | Ar-69 |
| H | Ar-3 | Ar-74 | Phenyl | Ar-3 | Ar-74 |
| H | Ar-3 | Ar-78 | Phenyl | Ar-3 | Ar-78 |
| H | Ar-3 | Ar-82 | Phenyl | Ar-3 | Ar-82 |
| H | Ar-3 | Ar-89 | Phenyl | Ar-3 | Ar-89 |
| H | Ar-3 | Ar-99 | Phenyl | Ar-3 | Ar-99 |
| H | Ar-3 | Ar-117 | Phenyl | Ar-3 | Ar-117 |
| H | Ar-3 | Ar-134 | Phenyl | Ar-3 | Ar-134 |
| H | Ar-3 | Ar-139 | Phenyl | Ar-3 | Ar-139 |
| H | Ar-3 | Ar-141 | Phenyl | Ar-3 | Ar-141 |
| H | Ar-3 | Ar-143 | Phenyl | Ar-3 | Ar-143 |
| H | Ar-3 | Ar-150 | Phenyl | Ar-3 | Ar-150 |
| H | Ar-3 | Ar-155 | Phenyl | Ar-3 | Ar-155 |
| H | Ar-3 | Ar-172 | Phenyl | Ar-3 | Ar-172 |
| H | Ar-3 | Ar-177 | Phenyl | Ar-3 | Ar-177 |
| H | Ar-3 | Ar-213 | Phenyl | Ar-3 | Ar-213 |
| H | Ar-3 | Ar-216 | Phenyl | Ar-3 | Ar-216 |
| H | Ar-3 | Ar-222 | Phenyl | Ar-3 | Ar-222 |
| H | Ar-3 | Ar-247 | Phenyl | Ar-3 | Ar-247 |
| H | Ar-4 | Ar-2 | Phenyl | Ar-4 | Ar-2 |
| H | Ar-4 | Ar-3 | Phenyl | Ar-4 | Ar-3 |
| H | Ar-4 | Ar-4 | Phenyl | Ar-4 | Ar-4 |
| H | Ar-4 | Ar-16 | Phenyl | Ar-4 | Ar-16 |
| H | Ar-4 | Ar-64 | Phenyl | Ar-4 | Ar-64 |
| H | Ar-4 | Ar-66 | Phenyl | Ar-4 | Ar-66 |
| H | Ar-4 | Ar-69 | Phenyl | Ar-4 | Ar-69 |
| H | Ar-4 | Ar-74 | Phenyl | Ar-4 | Ar-74 |
| H | Ar-4 | Ar-78 | Phenyl | Ar-4 | Ar-78 |
| H | Ar-4 | Ar-82 | Phenyl | Ar-4 | Ar-82 |
| H | Ar-4 | Ar-89 | Phenyl | Ar-4 | Ar-89 |
| H | Ar-4 | Ar-99 | Phenyl | Ar-4 | Ar-99 |
| H | Ar-4 | Ar-117 | Phenyl | Ar-4 | Ar-117 |
| H | Ar-4 | Ar-134 | Phenyl | Ar-4 | Ar-134 |
| H | Ar-4 | Ar-139 | Phenyl | Ar-4 | Ar-139 |
| H | Ar-4 | Ar-141 | Phenyl | Ar-4 | Ar-141 |
| H | Ar-4 | Ar-143 | Phenyl | Ar-4 | Ar-143 |
| H | Ar-4 | Ar-150 | Phenyl | Ar-4 | Ar-150 |
| H | Ar-4 | Ar-155 | Phenyl | Ar-4 | Ar-155 |
| H | Ar-4 | Ar-172 | Phenyl | Ar-4 | Ar-172 |
| H | Ar-4 | Ar-177 | Phenyl | Ar-4 | Ar-177 |
| H | Ar-4 | Ar-213 | Phenyl | Ar-4 | Ar-213 |
| H | Ar-4 | Ar-216 | Phenyl | Ar-4 | Ar-216 |
| H | Ar-4 | Ar-222 | Phenyl | Ar-4 | Ar-222 |
| H | Ar-4 | Ar-247 | Phenyl | Ar-4 | Ar-247 |
| H | Ar-78 | Ar-2 | Phenyl | Ar-78 | Ar-2 |
| H | Ar-78 | Ar-3 | Phenyl | Ar-78 | Ar-3 |
| H | Ar-78 | Ar-4 | Phenyl | Ar-78 | Ar-4 |
| H | Ar-78 | Ar-16 | Phenyl | Ar-78 | Ar-16 |
| H | Ar-78 | Ar-64 | Phenyl | Ar-78 | Ar-64 |
| H | Ar-78 | Ar-66 | Phenyl | Ar-78 | Ar-66 |
| H | Ar-78 | Ar-69 | Phenyl | Ar-78 | Ar-69 |
| H | Ar-78 | Ar-74 | Phenyl | Ar-78 | Ar-74 |
| H | Ar-78 | Ar-78 | Phenyl | Ar-78 | Ar-78 |
| H | Ar-78 | Ar-82 | Phenyl | Ar-78 | Ar-82 |
| H | Ar-78 | Ar-89 | Phenyl | Ar-78 | Ar-89 |
| H | Ar-78 | Ar-99 | Phenyl | Ar-78 | Ar-99 |
| H | Ar-78 | Ar-117 | Phenyl | Ar-78 | Ar-117 |
| H | Ar-78 | Ar-134 | Phenyl | Ar-78 | Ar-134 |
| H | Ar-78 | Ar-139 | Phenyl | Ar-78 | Ar-139 |
| H | Ar-78 | Ar-141 | Phenyl | Ar-78 | Ar-141 |
| H | Ar-78 | Ar-143 | Phenyl | Ar-78 | Ar-143 |
| H | Ar-78 | Ar-150 | Phenyl | Ar-78 | Ar-150 |
| H | Ar-78 | Ar-155 | Phenyl | Ar-78 | Ar-155 |
| H | Ar-78 | Ar-172 | Phenyl | Ar-78 | Ar-172 |
| H | Ar-78 | Ar-177 | Phenyl | Ar-78 | Ar-177 |
| H | Ar-78 | Ar-213 | Phenyl | Ar-78 | Ar-213 |
| H | Ar-78 | Ar-216 | Phenyl | Ar-78 | Ar-216 |
| H | Ar-78 | Ar-222 | Phenyl | Ar-78 | Ar-222 |
| H | Ar-78 | Ar-247 | Phenyl | Ar-78 | Ar-247 |
| H | Ar-139 | Ar-2 | Phenyl | Ar-139 | Ar-2 |
| H | Ar-139 | Ar-3 | Phenyl | Ar-139 | Ar-3 |
| H | Ar-139 | Ar-4 | Phenyl | Ar-139 | Ar-4 |
| H | Ar-139 | Ar-16 | Phenyl | Ar-139 | Ar-16 |
| H | Ar-139 | Ar-64 | Phenyl | Ar-139 | Ar-64 |
| H | Ar-139 | Ar-66 | Phenyl | Ar-139 | Ar-66 |
| H | Ar-139 | Ar-69 | Phenyl | Ar-139 | Ar-69 |
| H | Ar-139 | Ar-74 | Phenyl | Ar-139 | Ar-74 |
| H | Ar-139 | Ar-78 | Phenyl | Ar-139 | Ar-78 |
| H | Ar-139 | Ar-82 | Phenyl | Ar-139 | Ar-82 |
| H | Ar-139 | Ar-89 | Phenyl | Ar-139 | Ar-89 |
| H | Ar-139 | Ar-99 | Phenyl | Ar-139 | Ar-99 |
| H | Ar-139 | Ar-117 | Phenyl | Ar-139 | Ar-117 |
| H | Ar-139 | Ar-134 | Phenyl | Ar-139 | Ar-134 |
| H | Ar-139 | Ar-139 | Phenyl | Ar-139 | Ar-139 |
| H | Ar-139 | Ar-141 | Phenyl | Ar-139 | Ar-141 |
| H | Ar-139 | Ar-143 | Phenyl | Ar-139 | Ar-143 |
| H | Ar-139 | Ar-150 | Phenyl | Ar-139 | Ar-150 |
| H | Ar-139 | Ar-155 | Phenyl | Ar-139 | Ar-155 |
| H | Ar-139 | Ar-172 | Phenyl | Ar-139 | Ar-172 |
| H | Ar-139 | Ar-177 | Phenyl | Ar-139 | Ar-177 |
| H | Ar-139 | Ar-213 | Phenyl | Ar-139 | Ar-213 |
| H | Ar-139 | Ar-216 | Phenyl | Ar-139 | Ar-216 |
| H | Ar-139 | Ar-222 | Phenyl | Ar-139 | Ar-222 |
| H | Ar-139 | Ar-247 | Phenyl | Ar-139 | Ar-247 |
| R-1 | Ar-1 | Ar-2 | R-1 | Ar-3 | Ar-2 |
| R-1 | Ar-1 | Ar-3 | R-1 | Ar-3 | Ar-3 |
| R-1 | Ar-1 | Ar-4 | R-1 | Ar-3 | Ar-4 |
| R-1 | Ar-1 | Ar-16 | R-1 | Ar-3 | Ar-16 |
| R-1 | Ar-1 | Ar-64 | R-1 | Ar-3 | Ar-64 |
| R-1 | Ar-1 | Ar-66 | R-1 | Ar-3 | Ar-66 |
| R-1 | Ar-1 | Ar-69 | R-1 | Ar-3 | Ar-69 |
| R-1 | Ar-1 | Ar-74 | R-1 | Ar-3 | Ar-74 |

-continued

| R | Ar¹ | Ar² | R | Ar¹ | Ar² |
|---|-----|-----|---|-----|-----|
| R-1 | Ar-1 | Ar-78 | R-1 | Ar-3 | Ar-78 |
| R-1 | Ar-1 | Ar-82 | R-1 | Ar-3 | Ar-82 |
| R-1 | Ar-1 | Ar-89 | R-1 | Ar-3 | Ar-89 |
| R-1 | Ar-1 | Ar-99 | R-1 | Ar-3 | Ar-99 |
| R-1 | Ar-1 | Ar-117 | R-1 | Ar-3 | Ar-117 |
| R-1 | Ar-1 | Ar-134 | R-1 | Ar-3 | Ar-134 |
| R-1 | Ar-1 | Ar-139 | R-1 | Ar-3 | Ar-139 |
| R-1 | Ar-1 | Ar-141 | R-1 | Ar-3 | Ar-141 |
| R-1 | Ar-1 | Ar-143 | R-1 | Ar-3 | Ar-143 |
| R-1 | Ar-1 | Ar-150 | R-1 | Ar-3 | Ar-150 |
| R-1 | Ar-1 | Ar-155 | R-1 | Ar-3 | Ar-155 |
| R-1 | Ar-1 | Ar-172 | R-1 | Ar-3 | Ar-172 |
| R-1 | Ar-1 | Ar-177 | R-1 | Ar-3 | Ar-177 |
| R-1 | Ar-1 | Ar-213 | R-1 | Ar-3 | Ar-213 |
| R-1 | Ar-1 | Ar-216 | R-1 | Ar-3 | Ar-216 |
| R-1 | Ar-1 | Ar-222 | R-1 | Ar-3 | Ar-222 |
| R-1 | Ar-1 | Ar-247 | R-1 | Ar-3 | Ar-247 |
| R-1 | Ar-2 | Ar-2 | R-1 | Ar-4 | Ar-2 |
| R-1 | Ar-2 | Ar-3 | R-1 | Ar-4 | Ar-3 |
| R-1 | Ar-2 | Ar-4 | R-1 | Ar-4 | Ar-4 |
| R-1 | Ar-2 | Ar-16 | R-1 | Ar-4 | Ar-16 |
| R-1 | Ar-2 | Ar-64 | R-1 | Ar-4 | Ar-64 |
| R-1 | Ar-2 | Ar-66 | R-1 | Ar-4 | Ar-66 |
| R-1 | Ar-2 | Ar-69 | R-1 | Ar-4 | Ar-69 |
| R-1 | Ar-2 | Ar-74 | R-1 | Ar-4 | Ar-74 |
| R-1 | Ar-2 | Ar-78 | R-1 | Ar-4 | Ar-78 |
| R-1 | Ar-2 | Ar-82 | R-1 | Ar-4 | Ar-82 |
| R-1 | Ar-2 | Ar-89 | R-1 | Ar-4 | Ar-89 |
| R-1 | Ar-2 | Ar-99 | R-1 | Ar-4 | Ar-99 |
| R-1 | Ar-2 | Ar-117 | R-1 | Ar-4 | Ar-117 |
| R-1 | Ar-2 | Ar-134 | R-1 | Ar-4 | Ar-134 |
| R-1 | Ar-2 | Ar-139 | R-1 | Ar-4 | Ar-139 |
| R-1 | Ar-2 | Ar-141 | R-1 | Ar-4 | Ar-141 |
| R-1 | Ar-2 | Ar-143 | R-1 | Ar-4 | Ar-143 |
| R-1 | Ar-2 | Ar-150 | R-1 | Ar-4 | Ar-150 |
| R-1 | Ar-2 | Ar-155 | R-1 | Ar-4 | Ar-155 |
| R-1 | Ar-2 | Ar-172 | R-1 | Ar-4 | Ar-172 |
| R-1 | Ar-2 | Ar-177 | R-1 | Ar-4 | Ar-177 |
| R-1 | Ar-2 | Ar-213 | R-1 | Ar-4 | Ar-213 |
| R-1 | Ar-2 | Ar-216 | R-1 | Ar-4 | Ar-216 |
| R-1 | Ar-2 | Ar-222 | R-1 | Ar-4 | Ar-222 |
| R-1 | Ar-2 | Ar-247 | R-1 | Ar-4 | Ar-247 |
| R-1 | Ar-78 | Ar-2 | R-1 | Ar-139 | Ar-2 |
| R-1 | Ar-78 | Ar-3 | R-1 | Ar-139 | Ar-3 |
| R-1 | Ar-78 | Ar-4 | R-1 | Ar-139 | Ar-4 |
| R-1 | Ar-78 | Ar-16 | R-1 | Ar-139 | Ar-16 |
| R-1 | Ar-78 | Ar-64 | R-1 | Ar-139 | Ar-64 |
| R-1 | Ar-78 | Ar-66 | R-1 | Ar-139 | Ar-66 |
| R-1 | Ar-78 | Ar-69 | R-1 | Ar-139 | Ar-69 |
| R-1 | Ar-78 | Ar-74 | R-1 | Ar-139 | Ar-74 |
| R-1 | Ar-78 | Ar-78 | R-1 | Ar-139 | Ar-78 |
| R-1 | Ar-78 | Ar-82 | R-1 | Ar-139 | Ar-82 |
| R-1 | Ar-78 | Ar-89 | R-1 | Ar-139 | Ar-89 |
| R-1 | Ar-78 | Ar-99 | R-1 | Ar-139 | Ar-99 |
| R-1 | Ar-78 | Ar-117 | R-1 | Ar-139 | Ar-117 |
| R-1 | Ar-78 | Ar-134 | R-1 | Ar-139 | Ar-134 |
| R-1 | Ar-78 | Ar-139 | R-1 | Ar-139 | Ar-139 |
| R-1 | Ar-78 | Ar-141 | R-1 | Ar-139 | Ar-141 |
| R-1 | Ar-78 | Ar-143 | R-1 | Ar-139 | Ar-143 |
| R-1 | Ar-78 | Ar-150 | R-1 | Ar-139 | Ar-150 |
| R-1 | Ar-78 | Ar-155 | R-1 | Ar-139 | Ar-155 |
| R-1 | Ar-78 | Ar-172 | R-1 | Ar-139 | Ar-172 |
| R-1 | Ar-78 | Ar-177 | R-1 | Ar-139 | Ar-177 |
| R-1 | Ar-78 | Ar-213 | R-1 | Ar-139 | Ar-213 |
| R-1 | Ar-78 | Ar-216 | R-1 | Ar-139 | Ar-216 |
| R-1 | Ar-78 | Ar-222 | R-1 | Ar-139 | Ar-222 |
| R-1 | Ar-78 | Ar-247 | R-1 | Ar-139 | Ar-247 |

The compounds of formula (1), (1-1) or (1-2) according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds of formula (1), (1-1) or (1-2) according to the invention in an electronic device, in particular in an organic electroluminescent device.

The present invention still furthermore relates to an electronic device comprising at least one compound according to the invention. The preferences stated above likewise apply to the electronic devices.

The electronic device is preferably selected from the group consisting of organic electroluminescent devices (organic light-emitting diodes, OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells (ODSSCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., *Nature Photonics* 2008, 1-4), but preferably organic electroluminescent devices (OLEDs), particularly preferably phosphorescent OLEDs.

The organic electroluminescent devices and the light-emitting electrochemical cells can be employed for various applications, for example for mono-chromatic or polychromatic displays, for lighting applications or for medical and/or cosmetic applications, for example in phototherapy.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present.

The organic electroluminescent device here may comprise one emitting layer or a plurality of emitting layers. If a plurality of emission layers is present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). It is possible here for all emitting layers to be fluorescent or for all emitting layers to be phosphorescent or for one or more emitting layers to be fluorescent and one or more other layers to be phosphorescent.

The compound according to the invention in accordance with the embodiments indicated above can be employed here in different layers, depending on the precise structure. Preference is given to an organic electroluminescent device comprising a compound of the formula (1), (1-1) or (1-2) or the preferred embodiments as hole-transport material in a hole-transport or hole-injection or exciton-blocking layer or as matrix material for fluorescent or phosphorescent emitters, in particular for phosphorescent emitters. The preferred embodiments indicated above also apply to the use of the materials in organic electronic devices.

In a preferred embodiment of the invention, the compound of the formula (1), (1-1) or (1-2) or the preferred embodiments is employed as hole-transport or hole-injection material in a hole-transport or hole-injection layer. The emitting layer here can be fluorescent or phosphorescent. A hole-injection layer in the sense of the present invention is a layer which is directly adjacent to the anode. A hole-transport layer in the sense of the present invention is a layer which is located between a hole-injection layer and an emitting layer.

In still a further preferred embodiment of the invention, the compound of the formula (1), (1-1) or (1-2) or the preferred embodiments is employed in an exciton-blocking layer. An exciton-blocking layer is taken to mean a layer which is directly adjacent to an emitting layer on the anode side.

The compound of the formula (1), (1-1) or (1-2) or the preferred embodiments is particularly preferably employed in a hole-transport or exciton-blocking layer.

If the compound of the formula (1), (1-1) or (1-2) is employed as a hole-transport material in a hole-transport layer, a hole-injection layer or an exciton-blocking layer, then the compound of formula (1) can be used in such a layer as a single material, i.e. in a proportion of 100%, or the compound of formula (1), (1-1) or (1-2) can be used in combination with one or more further compounds in such a layer. According to a preferred embodiment, the organic layer comprising the compound of formula (1), (1-1) or (1-2) additionally comprises one or more p-dopants. Preferred p-dopant for the present invention are organic compounds that can accept electrons (electron acceptors) and can oxidize one or more of the other compounds present in the mixture.

Particularly preferred embodiments of p-dopants are described in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600, WO 2012/095143 and DE 102012209523.

Particularly preferred as p-dopants are quinodimethane compounds, azaindenofluorendione, azaphenalene, azatriphenylene, $I_2$, metal halides, preferably transition metal halides, metal oxides, preferably metal oxides containing at least one transition metal or a metal of the 3rd main group and transition metal complexes, preferably complexes of Cu, Co, Ni, Pd and Pt with ligands containing at least one oxygen atom as binding site. Also preferred are transition metal oxides as dopants, preferably oxides of rhenium, molybdenum and tungsten, particularly preferably $Re_2O_7$, $MoO_3$, $WO_3$ and $ReO_3$.

The p-dopants are preferably distributed substantially uniformly in the p-doped layers. This can be achieved for example by co-evaporation of the p-dopant and of the hole-transport material matrix.

Particularly preferred p-dopants are selected from the compounds (D-1) to (D-13):

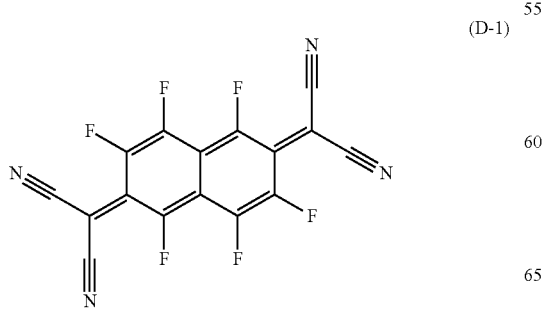
(D-1)

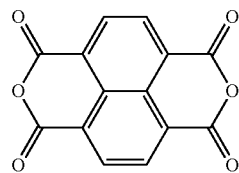
(D-2)

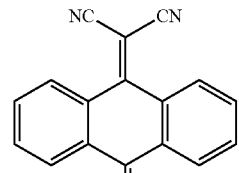
(D-3)

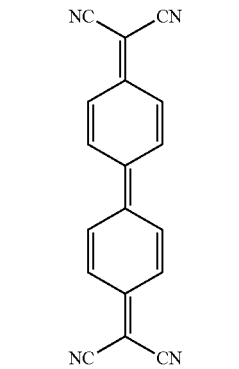
(D-4)

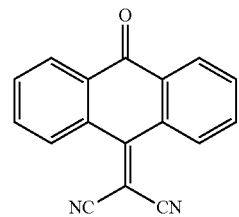
(D-5)

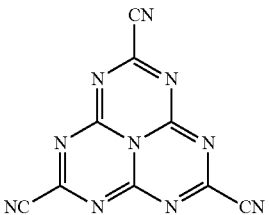
(D-6)

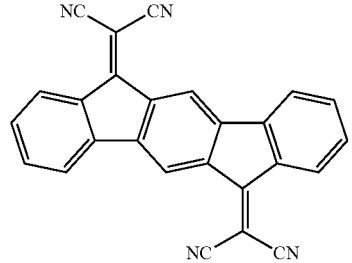
(D-7)

(D-8) 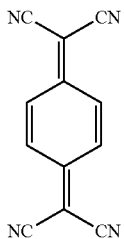

(D-9) 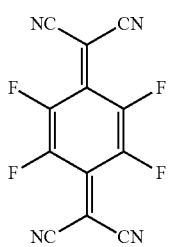

(D-10) 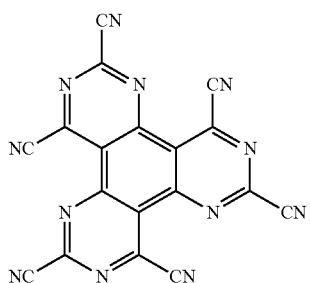

(D-11) 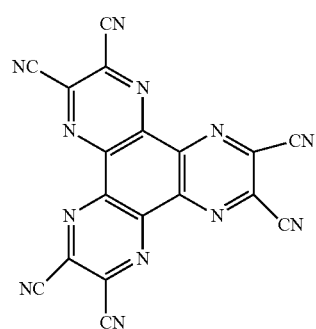

(D-12) 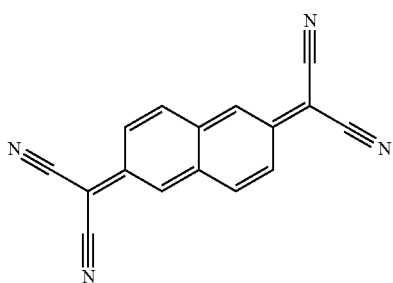

(D-13) 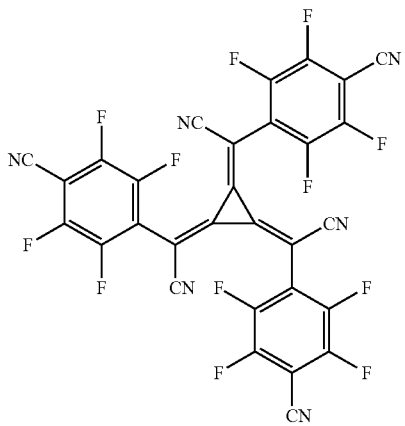

In an embodiment of the invention, the compound of the formula (1), (1-1) or (1-2) or the preferred embodiments is used in a hole-transport or -injection layer in combination with a layer which comprises a hexaazatriphenylene derivative, in particular hexacyanohexaazatriphenylene (for example in accordance with EP 1175470). Thus, for example, preference is given to a combination which looks as follows: anode-hexaazatriphenylene derivative-hole-transport layer, where the hole-transport layer comprises one or more compounds of the formula (1), (1-1) or (1-2) or the preferred embodiments. It is likewise possible in this structure to use a plurality of successive hole-transport layers, where at least one hole-transport layer comprises at least one compound of the formula (1), (1-1) or (1-2) or the preferred embodiments. A further preferred combination looks as follows: anode-hole-transport layer-hexaazatriphenylene derivative-hole-transport layer, where at least one of the two hole-transport layers comprises one or more compounds of the formula (1), (1-1) or (1-2) or the preferred embodiments. It is likewise possible in this structure to use a plurality of successive hole-transport layers instead of one hole-transport layer, where at least one hole-transport layer comprises at least one compound of the formula (1), (1-1) or (1-2) or the preferred embodiments.

In a further preferred embodiment of the invention, the compound of the formula (1), (1-1) or (1-2) or the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1), (1-1) or (1-2) or the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having a spin multiplicity>1, in particular from an excited triplet state. For the purposes of this application, all luminescent complexes containing transition metals or lanthanoids, in particular all luminescent iridium, platinum and copper complexes, are to be regarded as phosphorescent compounds.

The mixture comprising the matrix material, which comprises the compound of the formula (1), (1-1) or (1-2) or the preferred embodiments, and the emitting compound comprises between 99.9 and 1% by weight, preferably between 99 and 10% by weight, particularly preferably between 97 and 60% by weight, in particular between 95 and 80% by weight, of the matrix material, based on the entire mixture comprising emitter and matrix material. Correspondingly, the mixture comprises between 0.1 and 99% by weight, preferably between 1 and 90% by weight, particularly preferably between 3 and 40% by weight, in particular between 5 and 20% by weight, of the emitter, based on the entire mixture comprising emitter and matrix material.

The limits indicated above apply, in particular, if the layer is applied from solution. If the layer is applied by vacuum evaporation, the same numerical values apply, with the percentage in this case being indicated in % by vol. in each case.

A particularly preferred embodiment of the present invention is the use of the compound of the formula (1), (1-1) or (1-2) or the preferred embodiments as matrix material for a phosphorescent emitter in combination with a further matrix material. Particularly suitable matrix materials which can be employed in combination with the compounds of the formula (1), (1-1) or (1-2) or the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 or WO 2011/000455, aza-carbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 08/056746, zinc complexes, for example in accordance with EP 652273 or WO 2009/062578, fluorene derivatives, for example in accordance with WO 2009/124627, diazasilole or tetraazasilole derivatives, for example in accordance with WO 2010/054729, diazaphosphole derivatives, for example in accordance with WO 2010/054730, or bridged carbazole derivatives, for example in accordance with US 2009/0136779, WO 2010/050778, WO 2011/042107 or WO 2011/088877. It is furthermore possible to use an electronically neutral co-host which has neither hole-transporting nor electron-transporting properties, as described, for example, in WO 2010/108579.

It is likewise possible to use two or more phosphorescent emitters in the mixture. In this case, the emitter which emits at shorter wavelength acts as co-host in the mixture.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

Examples of the emitters described above are revealed by the applications WO 2000/70655, WO 2001/41512, WO 2002/02714, WO 2002/15645, EP 1191613, EP 1191612, EP 1191614, WO 2005/033244, WO 2005/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/157339 or WO 2012/007086. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to use the compound of the formula (1), (1-1) or (1-2) or the preferred embodiments both in a hole-transport layer or exciton-blocking layer and as matrix in an emitting layer.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1), (1-1) or (1-2) according to the invention or the preferred embodiments.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, LITI (light induced thermal imaging, thermal transfer printing), ink-jet printing, screen printing, flexographic printing, offset printing or nozzle printing.

Soluble compounds, which are obtained, for example, by suitable substitution, are necessary for this purpose. These processes are also particularly suitable for the compounds according to the invention, since these generally have very good solubility in organic solvents.

Also possible are hybrid processes, in which, for example, one or more layers are applied from solution and one or more further layers are applied by vapour deposition. Thus, for example, the emitting layer can be applied from solution and the electron-transport layer by vapour deposition.

These processes are generally known to the person skilled in the art and can be applied by him without inventive step to organic electroluminescent devices comprising the compounds according to the invention.

The processing of the compounds according to the invention from the liquid phase, for example by spin coating or by printing processes, requires formulations of the compounds according to the invention. These formulations can be, for example, solutions, dispersions or mini-emulsions. It may be preferred to use mixtures of two or more solvents for this purpose. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, dispersion or mini-emulsion, comprising at least one compound of the formula (1), (1-1) or (1-2) or the preferred embodiments indicated above and at least one solvent, in particular an organic solvent. The way in which solutions of this type can be prepared is known to the person skilled in the art and is described, for example, in WO 2002/072714, WO 2003/019694 and the literature cited therein.

The present invention furthermore relates to mixtures comprising at least one compound of the formula (1), (1-1) or (1-2) or the preferred embodiments indicated above and at least one further compound. The further compound can be, for example, a fluorescent or phosphorescent dopant if the compound according to the invention is used as matrix material. The mixture may then also additionally comprise a further material as additional matrix material.

The invention is explained in greater detail by the following examples, without wishing to restrict it thereby. On the basis of the descriptions, the person skilled in the art will be able to carry out the invention throughout the range disclosed and prepare further compounds according to the invention without inventive step and use them in electronic devices or use the process according to the invention.

EXAMPLES

A) Synthesis Examples

A-1) Route (a-2)

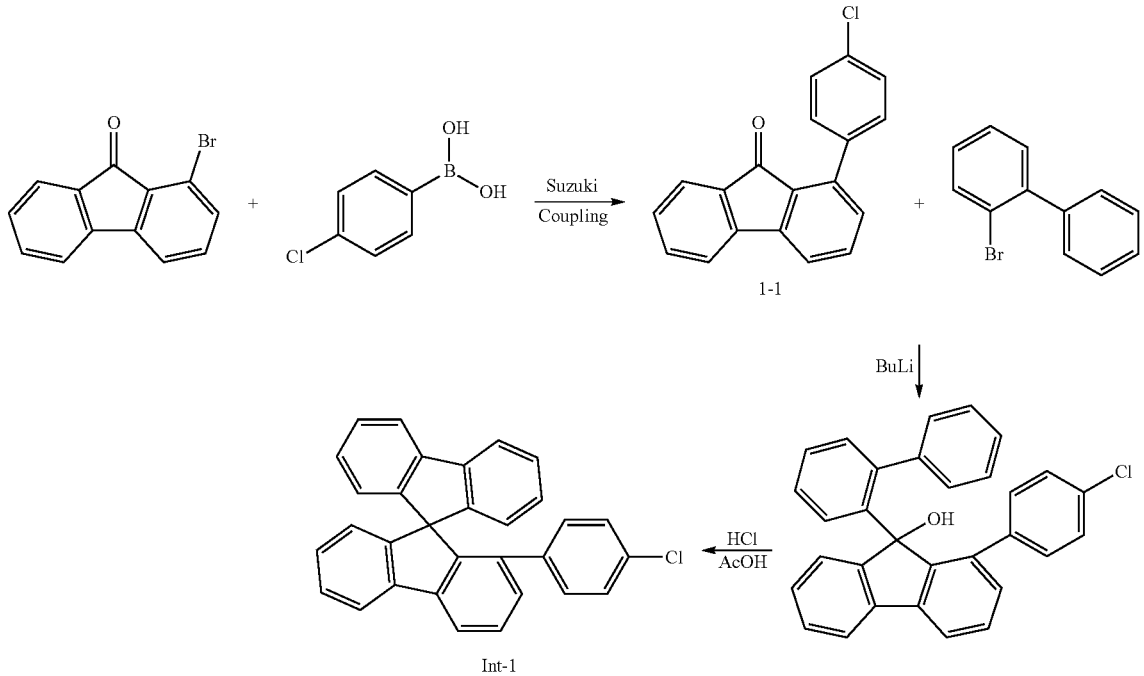

Route (a-2-1) with $X^3$ is —$B(OR^B)_2$ and $X^1$ is Br or I

Synthesis of 1-(4-chloro-phenyl)-fluoren-9-one 1-1 (Compound 1-1)

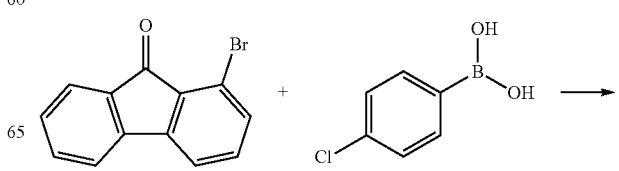

-continued

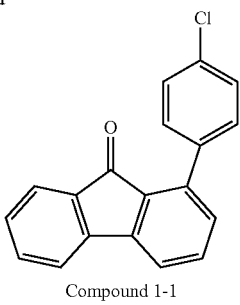
Compound 1-1

76 g (486 mmol) of 4-chlorophenylboronic acid, 120 g (463 mmol) of 1-Brom-fluoren-9-one and 16 g (14 mmol) of Pd(Ph$_3$P)$_4$ are suspended in 1900 ml of THF. 463 ml of 2 M potassium carbonate solution are slowly added to this suspension, and the reaction mixture is heated under reflux for 16 h. After cooling, the organic phase is separated off, filtered through silica gel, washed three times with 500 ml of water and subsequently evaporated to dryness. The residue is purified by crystallitation with MeOH. Yield: 125 g (420 mmol), 90% of theory, purity according to HPLC>98%.

| | Reactant 1 | Reactant 2 | Product | Yield |
|---|---|---|---|---|
| 1-2 | | | | 89% |
| 1-3 | | (63503-60-6) | | 88% |
| 1-4 | | (3900-89-8) | | 85% |
| 1-5 | | (147102-97-4) | | 89% |

-continued
| | Reactant 1 | Reactant 2 | Product | Yield |
|---|---|---|---|---|
| 1-6 | 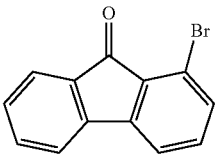 [SMILES: O=C1c2ccccc2-c2cccc(Br)c21] | 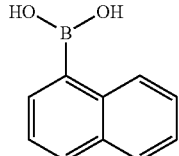<br>(145965-14-6) | 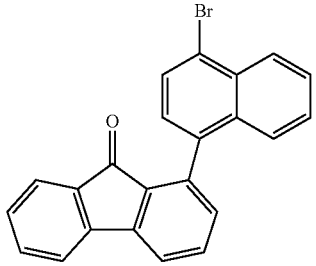 [SMILES: O=C1c2ccccc2-c2cccc(-c3ccc(Br)c4ccccc34)c21] | 78% |
| 1-7 | 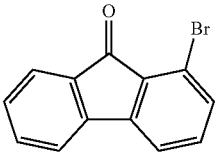 [SMILES: O=C1c2ccccc2-c2cccc(Br)c21] | 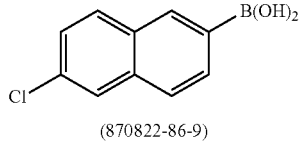 [SMILES: OB(O)c1ccc2cc(Cl)ccc2c1]<br>(870822-86-9) | 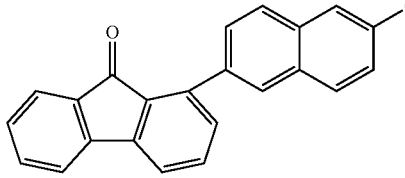 | 75% |
| 1-8 | 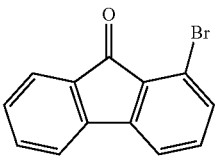 | 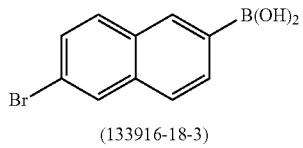 [SMILES: OB(O)c1ccc2cc(Br)ccc2c1]<br>(133916-18-3) | 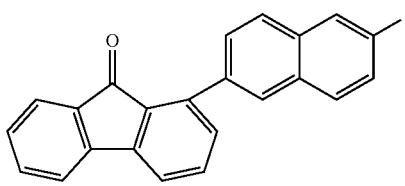 | 80% |
| 1-9 | 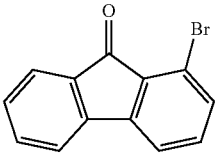 [SMILES: O=C1c2ccccc2-c2cccc(Br)c21] | 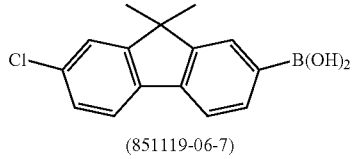 [SMILES: CC1(C)c2cc(Cl)ccc2-c2ccc(B(O)O)cc21]<br>(851119-06-7) | 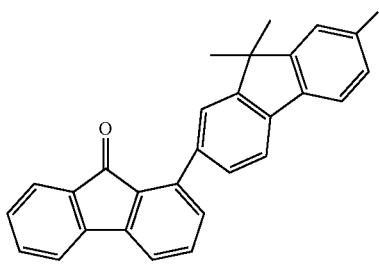 | 76% |
| 1-10 | 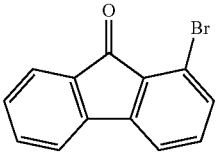 [SMILES: O=C1c2ccccc2-c2cccc(Br)c21] | 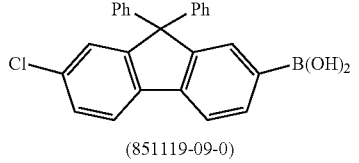 [SMILES: OB(O)c1ccc2c(c1)C(c1ccccc1)(c1ccccc1)c1cc(Cl)ccc1-2]<br>(851119-09-0) | 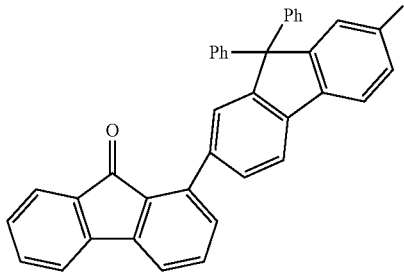 | 82% |
| 1-11 | 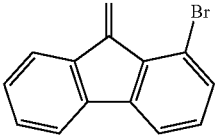 | 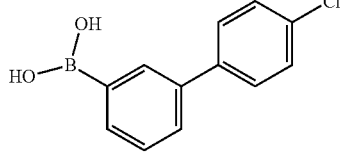<br>(180994-92-7) | 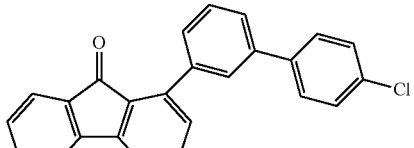 | 87% |

-continued
| | Reactant 1 | Reactant 2 | Product | Yield |
|---|---|---|---|---|
| 1-12 | 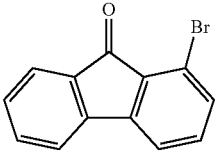 [SMILES: O=C1c2ccccc2-c2cccc(Br)c21] | 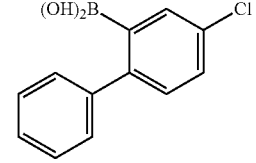 (544678-60-6) | 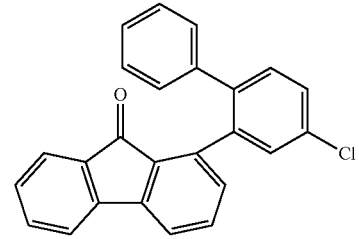 [SMILES: O=C1c2ccccc2-c2cccc(-c3cc(Cl)ccc3-c3ccccc3)c21] | 84% |
| 1-13 | 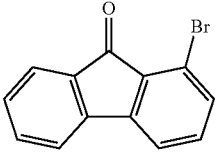 | 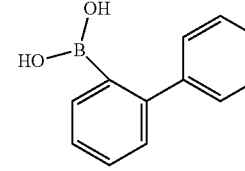 (179526-96-6) | 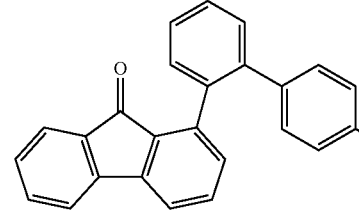 | 80% |
| 1-14 | 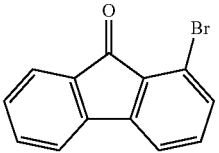 [SMILES: O=C1c2ccccc2-c2cccc(Br)c21] | 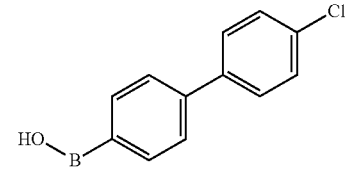 (364044-44-0) | 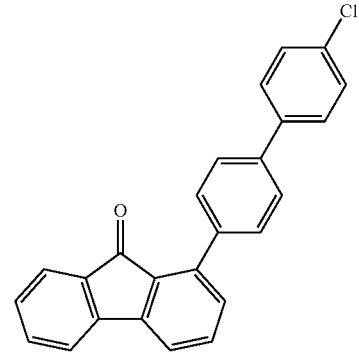 [SMILES: O=C1c2ccccc2-c2cccc(-c3ccc(-c4ccc(Cl)cc4)cc3)c21] | 77% |
| 1-15 | 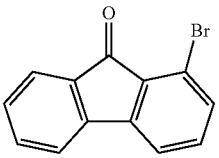 [SMILES: O=C1c2ccccc2-c2cccc(Br)c21] | 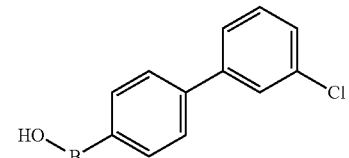 (1025496-32-5) | 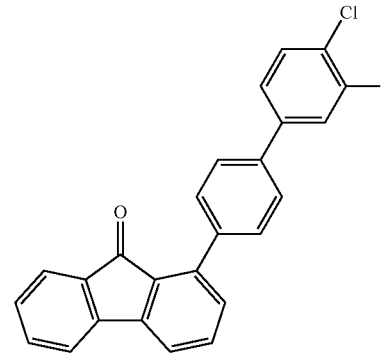 | 76% |
| 1-16 | 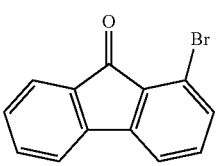 [SMILES: O=C1c2ccccc2-c2cccc(Br)c21] | 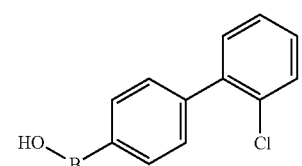 (1383531-51-8) | 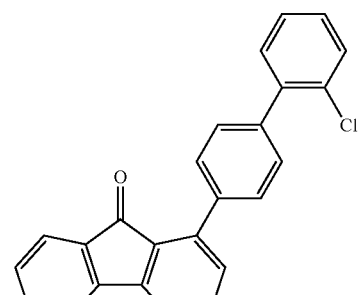 | 85% |

-continued
| | Reactant 1 | Reactant 2 | Product | Yield |
|---|---|---|---|---|
| 1-17 | 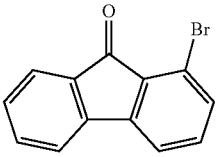 [SMILES: O=C1c2ccccc2-c2cccc(Br)c21] | 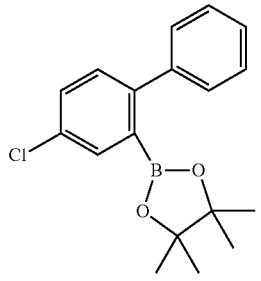 (1399362-31-2) | 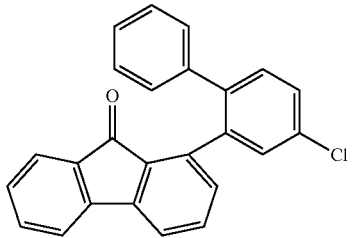 [SMILES: O=C1c2ccccc2-c2cccc(-c3cc(Cl)ccc3-c3ccccc3)c21] | 84% |
| 1-18 | 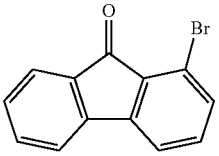 [SMILES: O=C1c2ccccc2-c2cccc(Br)c21] | 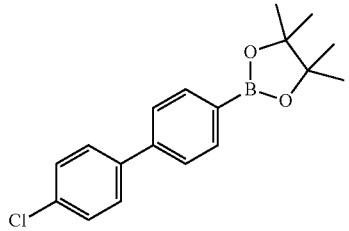 (942589-53-9) | 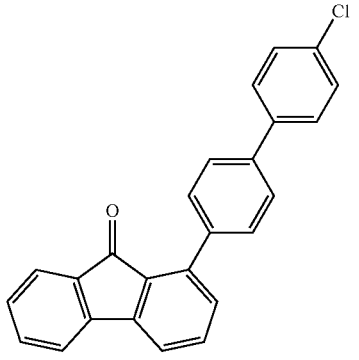 [SMILES: O=C1c2ccccc2-c2cccc(-c3ccc(-c4ccc(Cl)cc4)cc3)c21] | 81% |
| 1-19 | 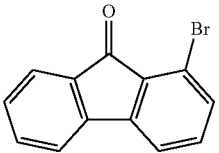 [SMILES: O=C1c2ccccc2-c2cccc(Br)c21] | 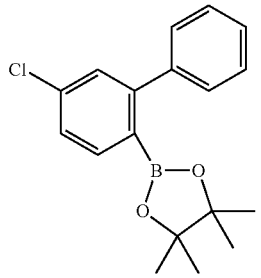 (1399362-32-3) | 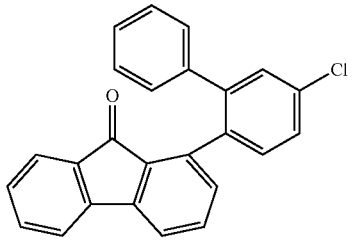 [SMILES: O=C1c2ccccc2-c2cccc(-c3ccc(Cl)cc3-c3ccccc3)c21] | 79% |
| 1-20 | 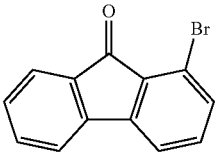 [SMILES: O=C1c2ccccc2-c2cccc(Br)c21] | 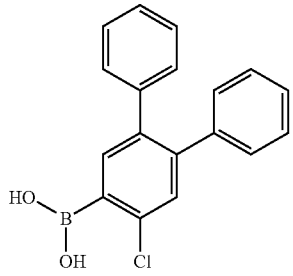 (101415-60-8) | 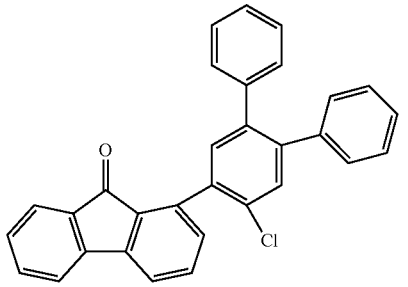 [SMILES: O=C1c2ccccc2-c2cccc(-c3cc(-c4ccccc4)c(-c4ccccc4)cc3Cl)c21] | 86% |

-continued
| | Reactant 1 | Reactant 2 | Product | Yield |
|---|---|---|---|---|
| 1-21 | 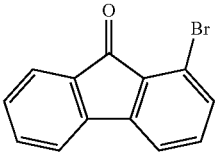 | 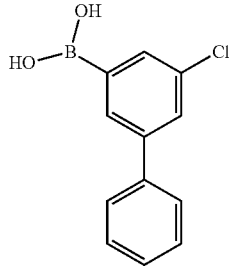 (1186403-21-3) | 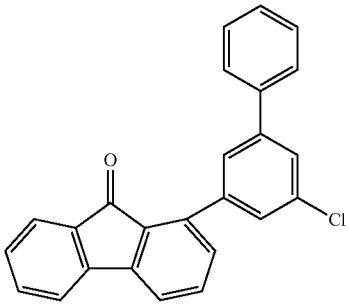 [SMILES: O=C1c2ccccc2-c2cccc(-c3cc(Cl)cc(-c4ccccc4)c3)c21] | 89% |
| 1-22 | 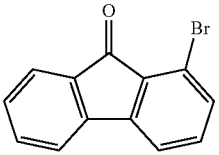 [SMILES: O=C1c2ccccc2-c2cccc(Br)c21] | 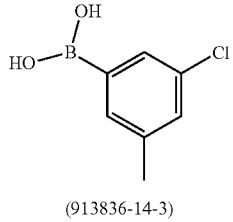 (913836-14-3) | 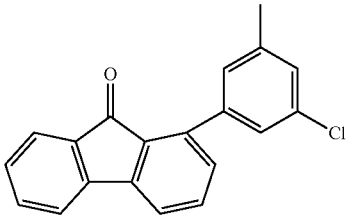 [SMILES: Cc1cc(Cl)cc(-c2cccc3c2C(=O)c2ccccc2-3)c1] | 83% |
| 1-23 | 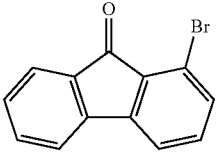 | 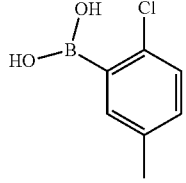 (193353-35-4) | 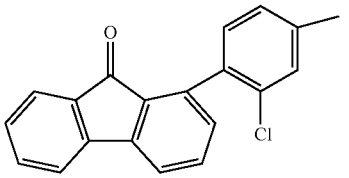 [SMILES: Cc1ccc(-c2cccc3c2C(=O)c2ccccc2-3)c(Cl)c1] | 83% |
| 1-24 | 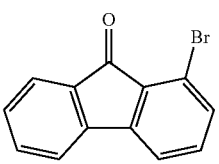 [SMILES: O=C1c2ccccc2-c2cccc(Br)c21] | 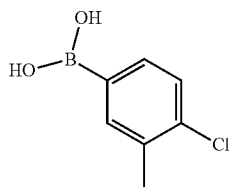 (161950-10-3) | 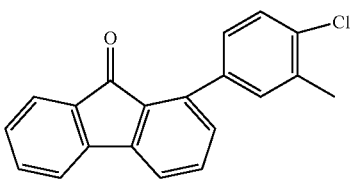 [SMILES: Cc1cc(-c2cccc3c2C(=O)c2ccccc2-3)ccc1Cl] | 82% |
| 1-25 | 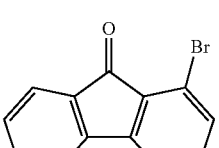 | 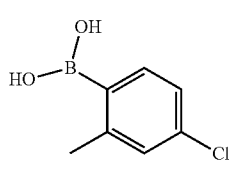 (209919-30-2) | 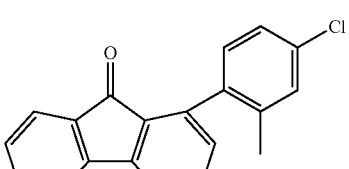 | 80% |
| 1-26 | 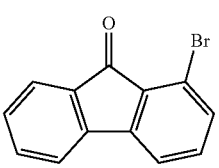 [SMILES: O=C1c2ccccc2-c2cccc(Br)c21] | 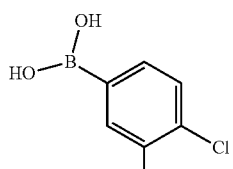 (918810-94-3) | 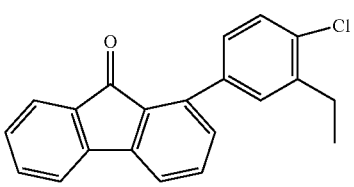 [SMILES: CCc1cc(-c2cccc3c2C(=O)c2ccccc2-3)ccc1Cl] | 85% |

-continued

| | Reactant 1 | Reactant 2 | Product | Yield |
|---|---|---|---|---|
| 1-27 | | (1350512-30-9) | | 84% |
| 1-28 | | (1395084-16-8) | | 83% |
| 1-29 | | (176976-42-4) | | 78% |
| 1-30 | | (313545-41-4) | | 85% |

Route (a-2-1) with $X^1$ is —$B(OR^B)_2$ and $X^3$ is Br, I or Cl

Synthesis of 1-(4-chloro-phenyl)-fluoren-9-one 1-1 (Compound 2-1)

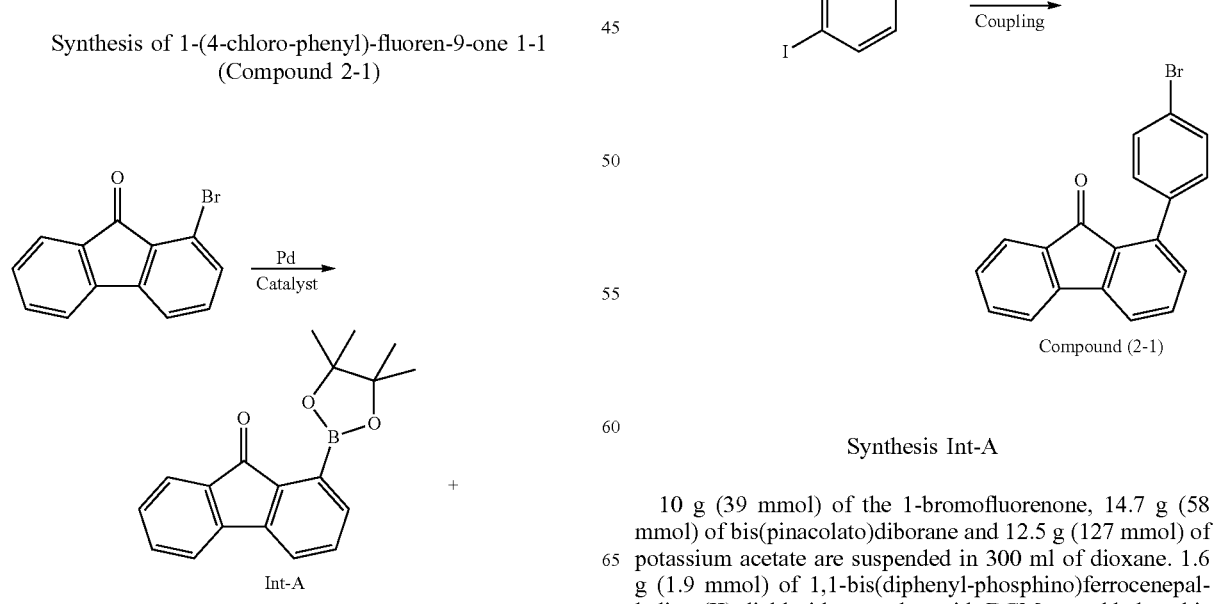

Synthesis Int-A 10 g (39 mmol) of the 1-bromofluorenone, 14.7 g (58 mmol) of bis(pinacolato)diborane and 12.5 g (127 mmol) of potassium acetate are suspended in 300 ml of dioxane. 1.6 g (1.9 mmol) of 1,1-bis(diphenyl-phosphino)ferrocenepalladium(II) dichloride complex with DCM are added to this suspension. The reaction mixture is heated under reflux for 16 h. After cooling, the organic phase is separated off, washed three times with 400 ml of water and subsequently evaporated to dryness. The residue is recrystallised from toluene (6 g, 51% yield).

Synthesis of Compound 2-1

20 g (69 mmol) of 1-Bromo-4-iodo-benzene, 21.1 g (69 mmol) of 1-pinacolboron ester-fluoren-9-one and 2.4 g (2.1 mmol) of Pd(Ph$_3$P)$_4$ are suspended in 300 ml of THF. 283 ml of 2 M potassium carbonate solution are slowly added to this suspension, and the reaction mixture is heated under reflux for 16 h. After cooling, the organic phase is separated off, filtered through silica gel, washed three times with 300 ml of water and subsequently evaporated to dryness. The residue is purified by crystallitation with MeOH. Yield: 19 g (54 mmol), 78% of theory, purity according to HPLC>98%.

The following compounds are prepared analogously:

-continued
| Reactant 1 | Reactant 2 | Reactant 3 | Int-B | Yield |
|---|---|---|---|---|
| 2-6 | | | | 61% |
| 2-7 | | | | 53% |
| 2-8 | | | | 50% |
| 2-9 | | | | 55% |
Synthesis of Intermediate Int-1
Route (a-2-2): Synthesis of 1-(4-chloro-phenyl)-spirofluorene
Compound (3-1)
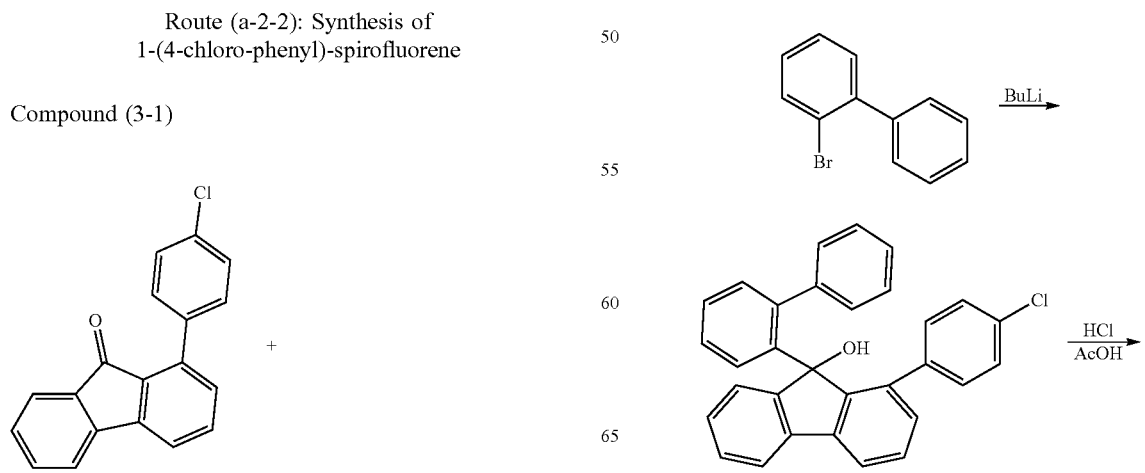

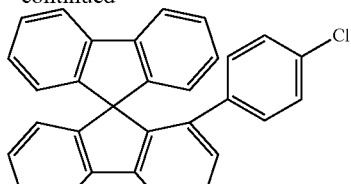

Compound 3-1

16 g (64 mmol) of 2-bromo-biphenyl are initially introduced in 400 ml of THF at −78° C. 30 ml of BuLi (2 M in hexane) are added dropwise at this temperature. After 1 hour, 16.9 g (94 mmol) of 1-(4-Chloro-phenyl)-fluoren-9-one in 200 ml of THF are added dropwise. The batch is left to stir overnight at room temperature, added to ice-water and extracted with dichloromethane. The combined organic phases are washed with water and dried over sodium sulfate. The solvent is removed in vacuo, and the residue is, without further purification, heated under reflux at 100° C. overnight with 30 ml of HCl and 300 ml of AcOH. After cooling, the precipitated solid is filtered off with suction, washed once with 100 ml of water, three times with 100 ml of ethanol each time and subsequently recrystallised from heptane. Yield: 17 g (56 mmol), 60%; purity approx. 98% according to $^1$H-NMR.

| | Reactant 1 | Reactant 2 | Product | Yield |
|---|---|---|---|---|
| 3-2 | | | | 80% |
| 3-3 | | | | 78% |
| 3-4 | | | | 60% |

| | Reactant 1 | Reactant 2 | Product | Yield |
|---|---|---|---|---|
| 3-5 | 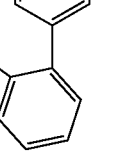 | 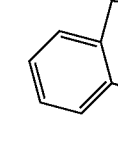 | 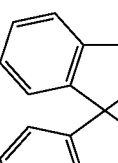 | 65% |
| 3-6 | 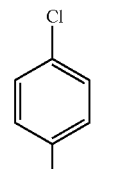 | 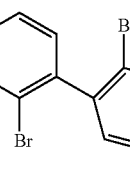 | 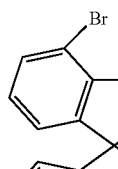 | 72% |
| 3-7 | 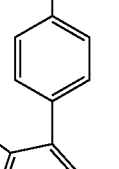 | 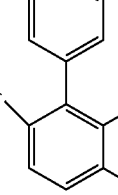 | 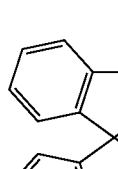 | 70% |
| 3-8 | 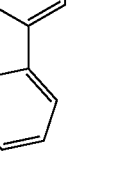 | 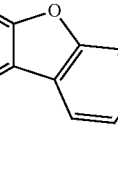 | 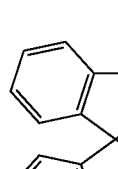 | 78% |
| 3-9 | 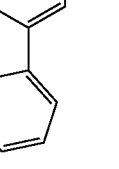 | 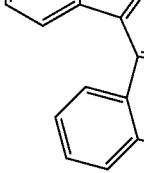 | 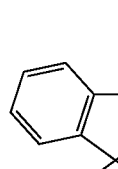 | 73% |

-continued
| | Reactant 1 | Reactant 2 | Product | Yield |
|---|---|---|---|---|
| 3-10 | 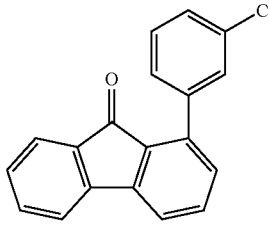 | 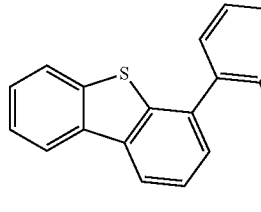 | 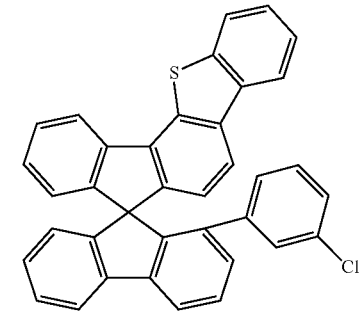 | 79% |
| 3-11 | 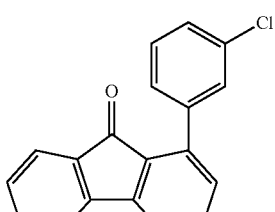 | 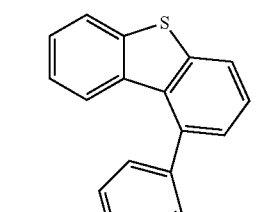 | 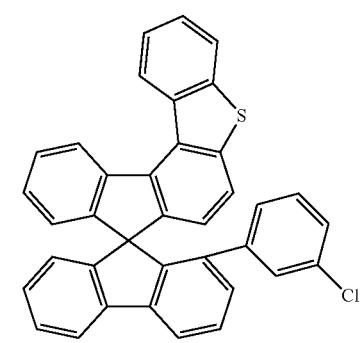 [SMILES: Clc1cccc(-c2cccc3c2C2(c4ccccc4-3)c3ccccc3-c3c2ccc2oc4ccccc4c32)c1] | 72% |
| 3-12 | 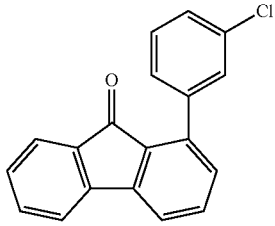 [SMILES: O=C1c2ccccc2-c2cccc(-c3cccc(Cl)c3)c21] | 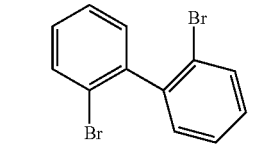 [SMILES: Brc1ccccc1-c1ccccc1Br] | 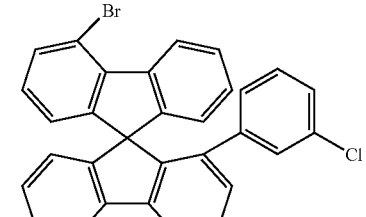 | 75% |
| 3-13 | 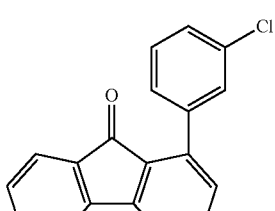 | 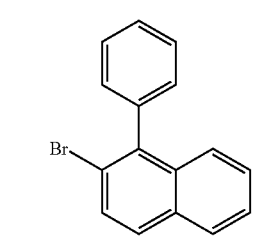 [SMILES: Brc1ccc2ccccc2c1-c1ccccc1] | 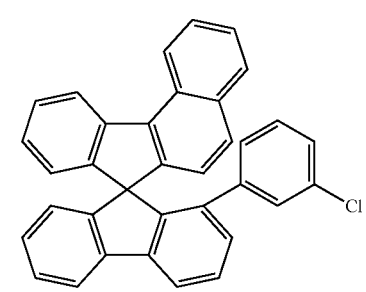 [SMILES: Clc1cccc(-c2cccc3c2C2(c4ccccc4-3)c3ccccc3-c3c2ccc2ccccc32)c1] | 80% |
| 3-14 | 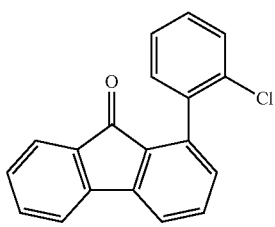 [SMILES: O=C1c2ccccc2-c2cccc(-c3ccccc3Cl)c21] | 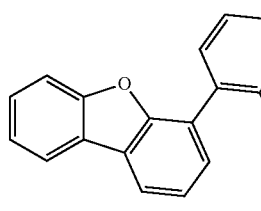 | 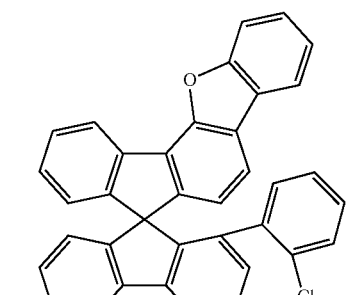 | 75% |

-continued
| | Reactant 1 | Reactant 2 | Product | Yield |
|---|---|---|---|---|
| 3-15 | 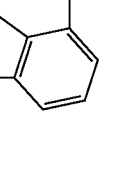 | 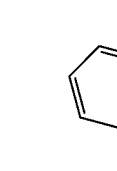 | 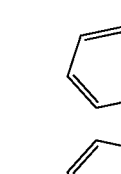 | 73% |
| 3-16 | 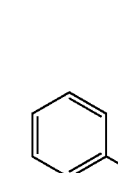 |  | 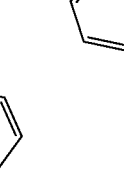 | 70% |
| 3-17 | 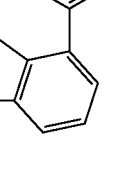 | 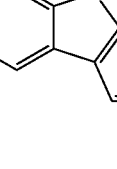 | 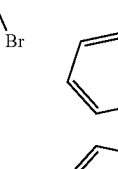 | 75% |
| 3-18 | 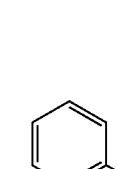 | 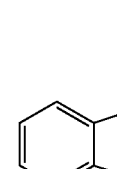 | 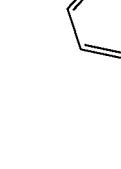 | 65% |
| 3-19 | 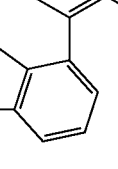 | 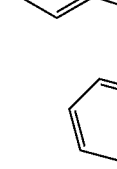 | 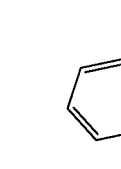 | 58% |

-continued

| | Reactant 1 | Reactant 2 | Product | Yield |
|---|---|---|---|---|
| 3-20 | | | | 80% |
| 3-21 | | | | 72% |
| 3-22 | | | | 75% |
| 3-23 | | | | 67% |
| 3-24 | | | | 75% |
| 3-25 | | | | 70% |

-continued
| | Reactant 1 | Reactant 2 | Product | Yield |
|---|---|---|---|---|
| 3-26 | 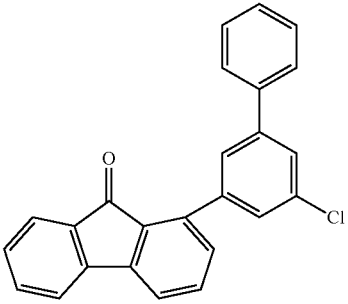 [SMILES: O=C1c2ccccc2-c2cccc(-c3cc(Cl)cc(-c4ccccc4)c3)c21] | 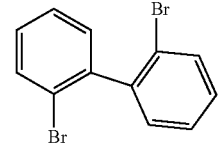 [SMILES: Brc1ccccc1-c1ccccc1Br] | 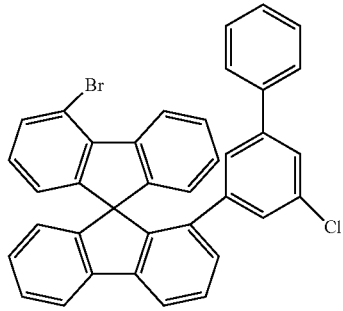 [SMILES: Clc1cc(-c2ccccc2)cc(-c2cccc3c2C2(c4ccccc4-3)c3ccccc3-c3c(Br)cccc32)c1] | 65% |
| 3-27 | 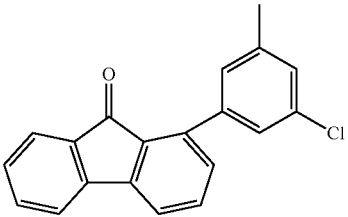 [SMILES: Cc1cc(Cl)cc(-c2cccc3c2C(=O)c2ccccc2-3)c1] | 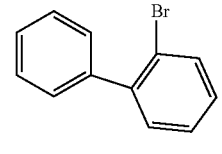 [SMILES: Brc1ccccc1-c1ccccc1] | 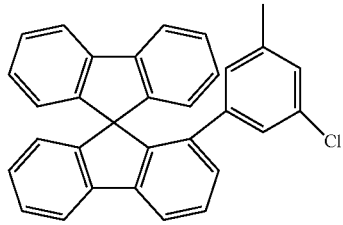 [SMILES: Cc1cc(Cl)cc(-c2cccc3c2C2(c4ccccc4-c4ccccc42)c2ccccc2-3)c1] | 75% |
| 3-28 | 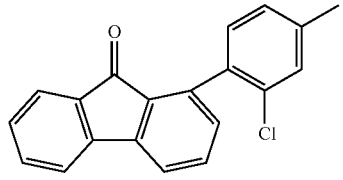 [SMILES: Cc1ccc(-c2cccc3c2C(=O)c2ccccc2-3)c(Cl)c1] | 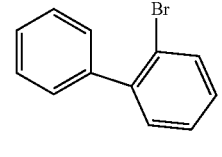 [SMILES: Brc1ccccc1-c1ccccc1] | 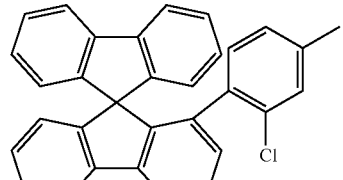 | 80% |
| 3-29 | 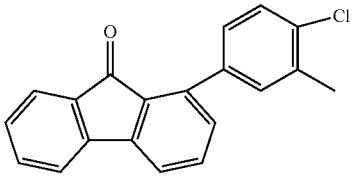 [SMILES: Cc1cc(-c2cccc3c2C(=O)c2ccccc2-3)ccc1Cl] | 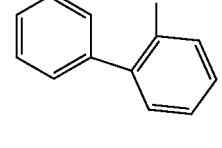 | 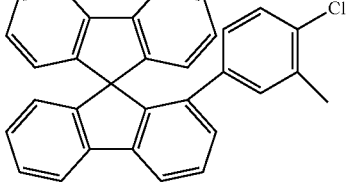 | 70% |
| 3-30 | 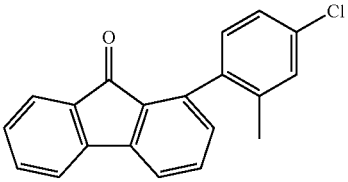 | 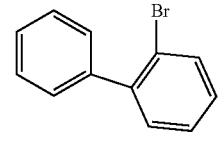 [SMILES: Brc1ccccc1-c1ccccc1] | 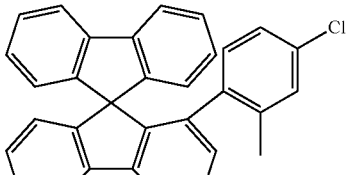 | 65% |
| 3-31 | 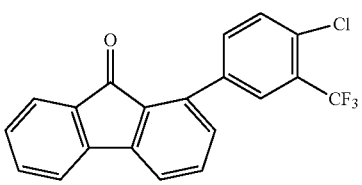 [SMILES: O=C1c2ccccc2-c2cccc(-c3ccc(Cl)c(C(F)(F)F)c3)c21] | 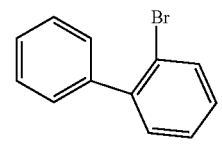 [SMILES: Brc1ccccc1-c1ccccc1] | 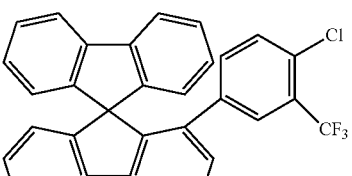 | 70% |

-continued
| | Reactant 1 | Reactant 2 | Product | Yield |
|---|---|---|---|---|
| 3-32 | 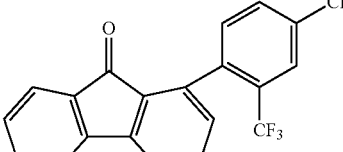 | 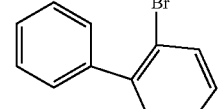 | 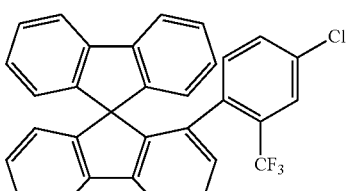 | 81% |
| 3-33 | 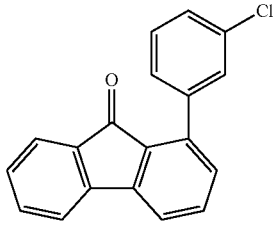 [SMILES: O=C1c2ccccc2-c2cccc(-c3cccc(Cl)c3)c21] | 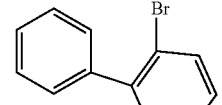 | 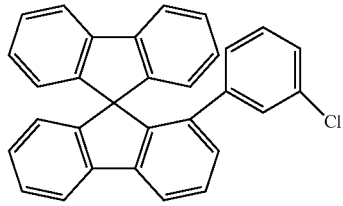 [SMILES: Clc1cccc(-c2cccc3c2C2(c4ccccc4-c4ccccc42)c2ccccc2-3)c1] | 79% |
| 3-34 | 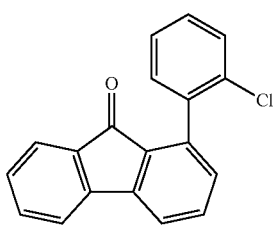 [SMILES: O=C1c2ccccc2-c2cccc(-c3ccccc3Cl)c21] | 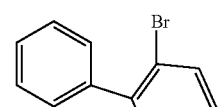 | 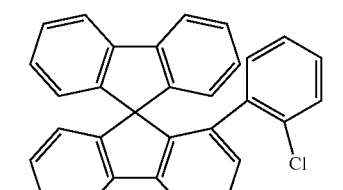 | 83% |
| 2-35 | 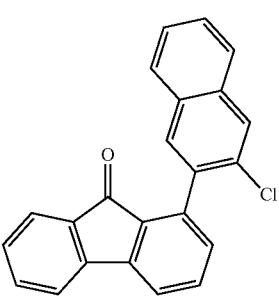 [SMILES: O=C1c2ccccc2-c2cccc(-c3cc4ccccc4cc3Cl)c21] | 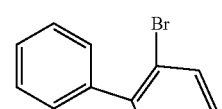 | 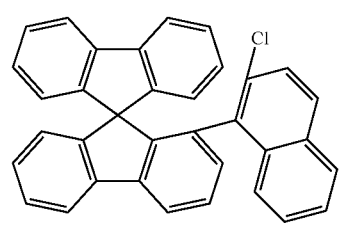 [SMILES: Clc1ccc2ccccc2c1-c1cccc2c1C1(c3ccccc3-c3ccccc31)c1ccccc1-2] | 77% |
| 3-36 | 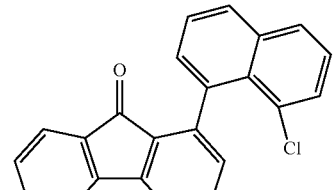 | 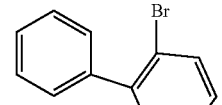 | 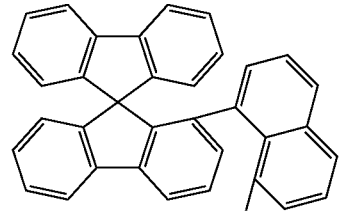 | 85% |
| 3-37 | 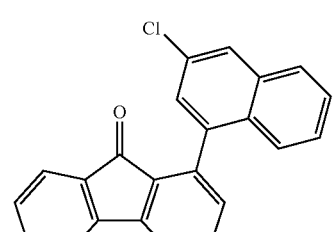 | 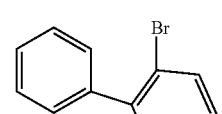 | 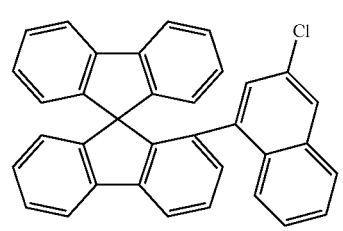 [SMILES: Clc1cc(-c2cccc3c2C2(c4ccccc4-c4ccccc42)c2ccccc2-3)c2ccccc2c1] | 80% |

Route (a-1-2): Synthesis of
1-(4-chloro-phenyl)-Spirofluorene

Compound (4-1)

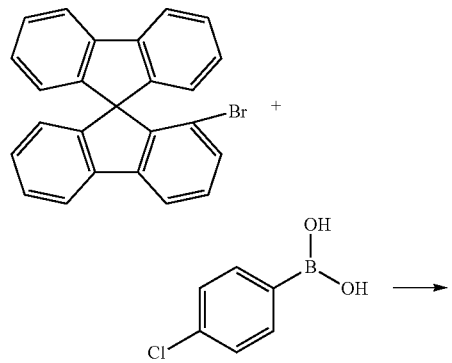

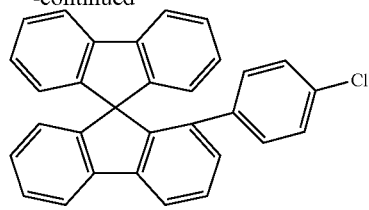

Compound 4-1

16 g (103 mmol) of 4-chlorophenylboronic acid, 37 g (94 mmol) of 1-Brom-spirofluorene and 5.4 g (5 mmol) of Pd(Ph$_3$P)$_4$ are suspended in 600 ml of THF. 155 ml of 2 M potassium carbonate solution are slowly added to this suspension, and the reaction mixture is heated under reflux for 16 h. After cooling, the organic phase is separated off, filtered through silica gel, washed three times with 500 ml of water and subsequently evaporated to dryness. The residue is purified by crystallitation with MeOH. Yield: 29 g (65 mmol), 72% of theory, purity according to HPLC>98%.

| | Reactant 1 | Reactant 2 | Product | Yield |
|---|---|---|---|---|
| 4-2 | | | | 80% |
| 4-3 | | | | 75% |
| 4-4 | | | | 76% |

| | Reactant 1 | Reactant 2 | Product | Yield |
|---|---|---|---|---|
| 4-5 | | (63503-60-6) | | 82% |
| 4-6 | | | | 78% |
| 4-7 | | | | 81% |
| 4-8 | | (3900-89-8) | | 72% |
| 4-9 | | | | 80% |

| | Reactant 1 | Reactant 2 | Product | Yield |
|---|---|---|---|---|
| 4-10 | 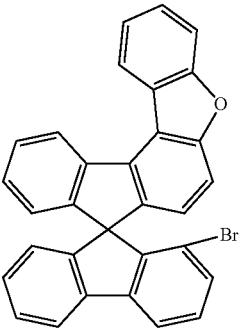 [SMILES: Brc1cccc2c1C1(c3ccccc3-2)c2ccccc2-c2c1ccc1oc3ccccc3c21] | 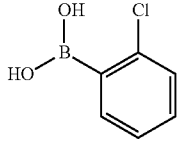 | 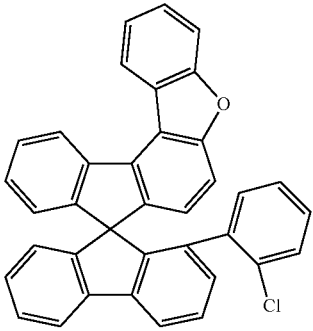 [SMILES: Clc1ccccc1-c1cccc2c1C1(c3ccccc3-2)c2ccccc2-c2c1ccc1oc3ccccc3c21] | 70% |
Route (a-1-1): Synthesis of 1-(4-chloro-phenyl)-spirofluorene
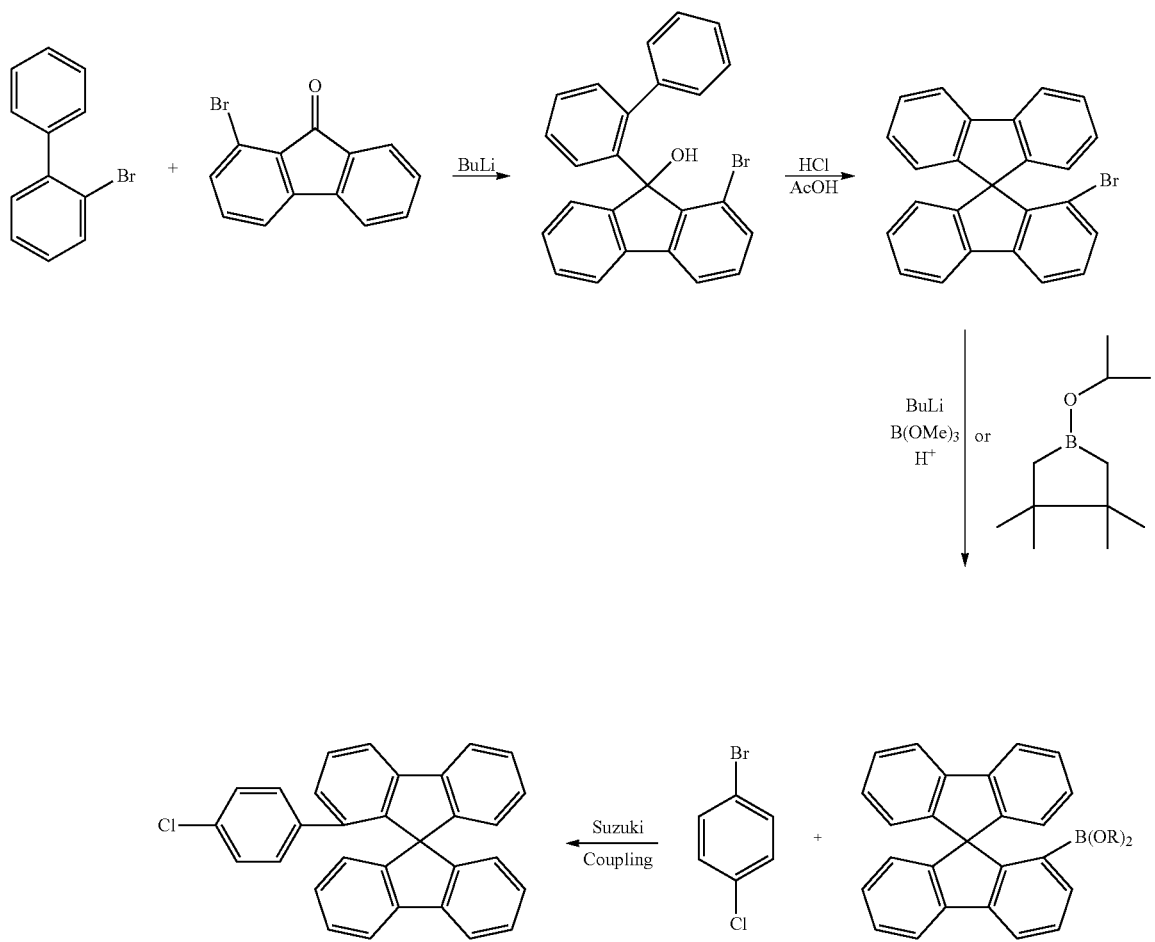

Synthesis of 1-Spirofluorenepinacolboronic ester (Compound 5-1) Using a Pd Catalysator

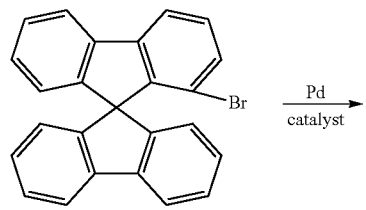

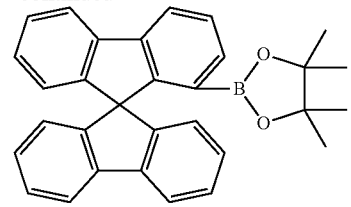

Compound 5-1

50 g (103 mmol) of the bromospirofluorene derivative, 32 g (123 mmol) of bis(pinacolato)diborane and 30 g (309 mmol) of potassium acetate are suspended in 800 ml of dioxane. 2.5 g (3.09 mmol) of 1,1-bis(diphenyl-phosphino)ferrocenepalladium(II) dichloride complex with DCM are added to this suspension. The reaction mixture is heated under reflux for 16 h. After cooling, the organic phase is separated off, washed three times with 400 ml of water and subsequently evaporated to dryness. The residue is recrystallised from toluene (52 g, 95% yield).

The following compounds are prepared analogously:

| | Starting material 1 | Product | Yield |
|---|---|---|---|
| 5-2 | 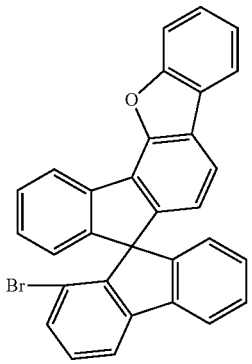 [SMILES: Brc1cccc2c1C1(c3ccccc3-2)c2ccccc2-c2c1ccc1c2oc2ccccc21] | 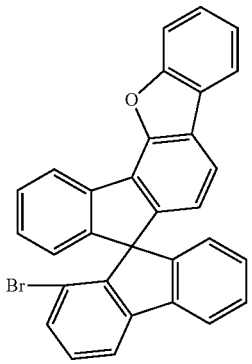 [SMILES: Brc1cccc2c1C1(c3ccccc3-2)c2ccccc2-c2c1ccc1c2oc2ccccc21] | 90% |
| 5-3 | 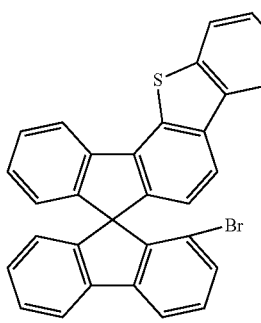 | 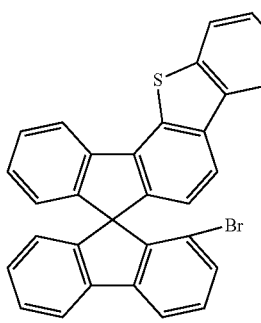 | 88% |
| 5-4 | 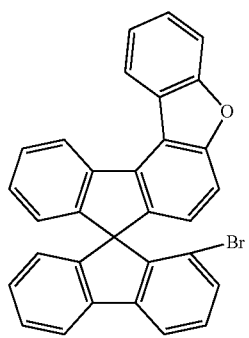 [SMILES: Brc1cccc2c1C1(c3ccccc3-2)c2ccccc2-c2c1ccc1oc3ccccc3c21] | 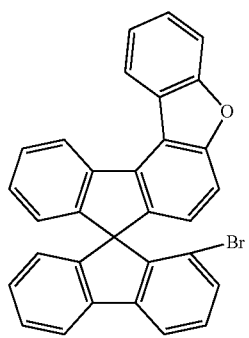 [SMILES: Brc1cccc2c1C1(c3ccccc3-2)c2ccccc2-c2c1ccc1oc3ccccc3c21] | 91% |

| | Starting material 1 | Product | Yield |
|---|---|---|---|
| 5-5 | 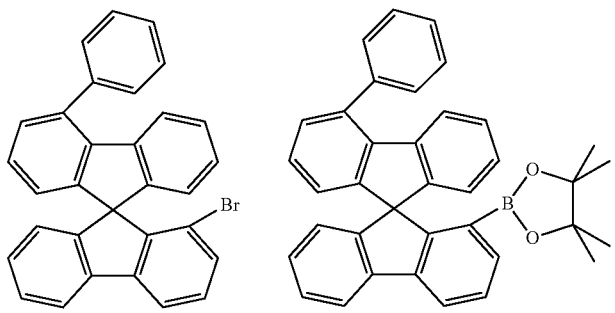 | | 87% |

Synthesis of 1-Spirofluorenepinacolboronic ester (Compound 6-1) Using BuLi

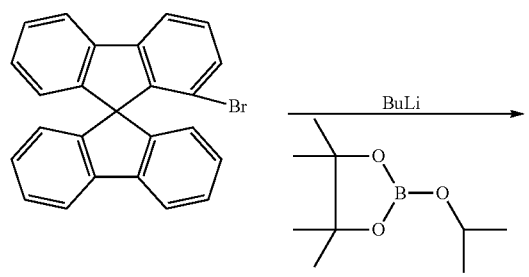

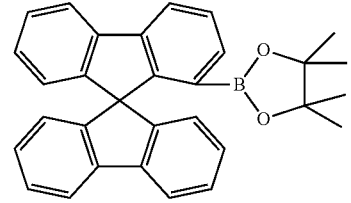

Compound 6-1

50 g (126 mmol) of 1-Bromo-spirofluorene are initially introduced in 1500 ml of THF at −20° C. 56 ml of BuLi (2 M in hexane) are added dropwise at this temperature. After 4 hours, 49 g (300 mmol) of isopropoxytetramethyl-dioxaborolane are added dropwise. The batch is left to stir overnight at room temperature. When the reaction is complete, water and ethyl acetate are added, and the organic phase is separated off, dried and evaporated. The residue is purified by chromatography on silica gel. Yield: 44 g (100 mmol), 80% of theory, purity according to HPLC>98%.

| | Starting material 1 | Borylating reagent | Product | Yield |
|---|---|---|---|---|
| 6-1 | 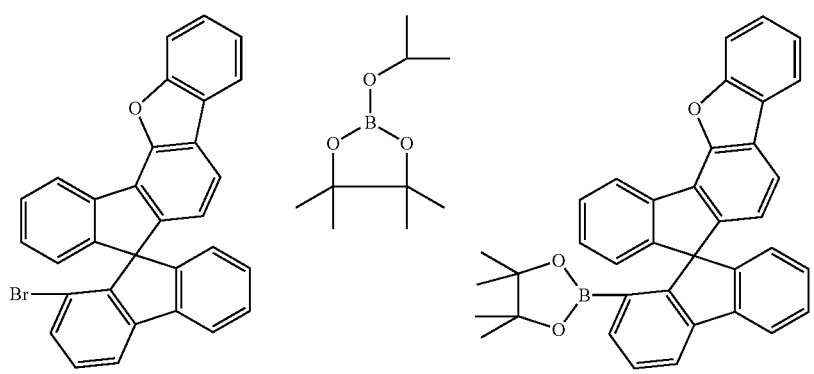 | | | 85% |

-continued

| | Starting material 1 | Borylating reagent | Product | Yield |
|---|---|---|---|---|
| 6-2 | | | | 80% |
| 6-3 | | | | 75% |
| 6-4 | | | | 78% |

Route (a-1-2): Synthesis of Compounds 7-1

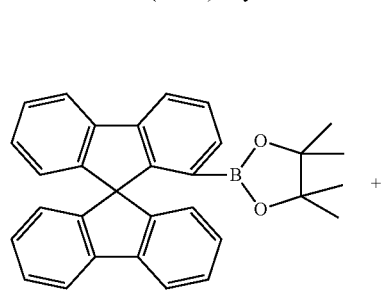

+

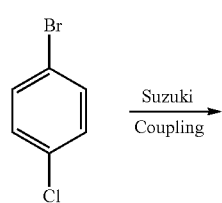

→ Suzuki Coupling →

-continued

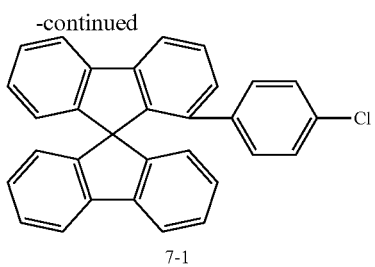

7-1

20.3 g (46.3 mmol) of spirofluorene pinacoleboronic ester derivative and 8.8 g (46.3 mmol) of chlorine derivative are suspended in 300 ml of dioxane and 14.1 g of caesium fluoride (92.6 mmol). 4.1 g (5.56 mmol) of bis-(tricyclohexylphosphine)palladium dichloride are added to this suspension, and the reaction mixture is heated under reflux for 24 h. After cooling, the organic phase is separated off, filtered through silica gel, washed three times with 100 ml of water and subsequently evaporated to dryness. The crude product is recrystallised from heptane/toluene. The yield is 15.8 g (80% of theory).

The following compounds are prepared analogously:
| | Reagent1 | Reagent 2 |
|---|---|---|
| 7-2 | 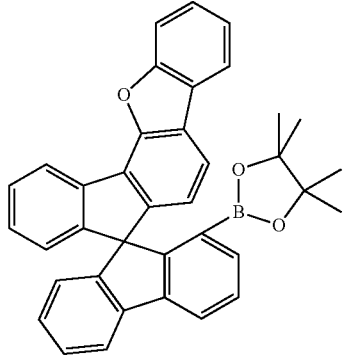 [SMILES: CC1(C)OB(c2cccc3c2C2(c4ccccc4-3)c3ccccc3-c3c2ccc2c3oc3ccccc32)OC1(C)C] | 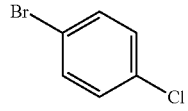 |
| 7-3 | 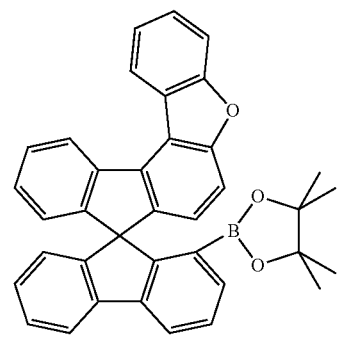 [SMILES: CC1(C)OB(c2cccc3c2C2(c4ccccc4-3)c3ccccc3-c3c2ccc2oc4ccccc4c32)OC1(C)C] | 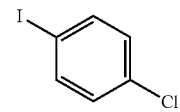 |
| 7-4 | 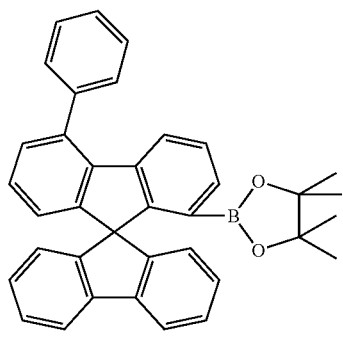 [SMILES: CC1(C)OB(c2cccc3c2C2(c4ccccc4-c4ccccc42)c2cccc(-c4ccccc4)c2-3)OC1(C)C] | 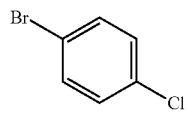 |
| 7-5 | 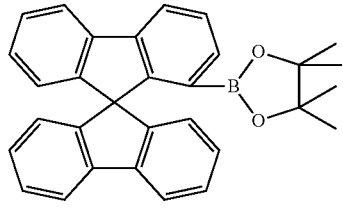 [SMILES: CC1(C)OB(c2cccc3c2C2(c4ccccc4-c4ccccc42)c2ccccc2-3)OC1(C)C] | 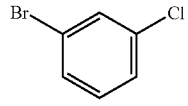 |

-continued
| | | |
|---|---|---|
| 7-6 | 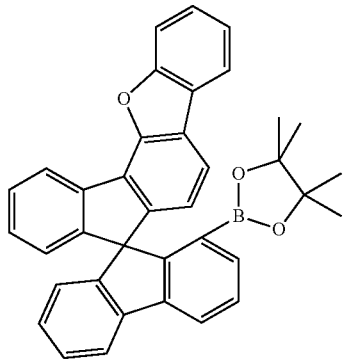 [SMILES: CC1(C)OB(c2cccc3c2C2(c4ccccc4-3)c3ccccc3-c3c2ccc2c3oc3ccccc32)OC1(C)C] | 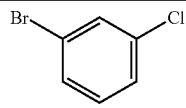 |
| 7-7 | 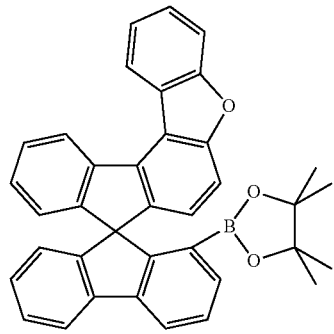 | 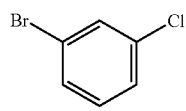 |
| 7-8 | 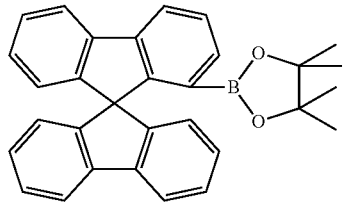 [SMILES: CC1(C)OB(c2cccc3c2C2(c4ccccc4-c4ccccc42)c2ccccc2-3)OC1(C)C] | 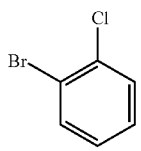 |
| 7-9 | 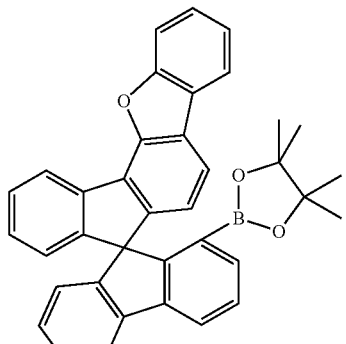 | 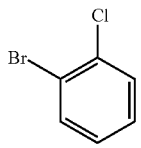 |
| 7-10 | 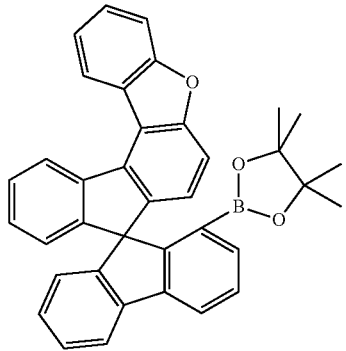 [SMILES: CC1(C)OB(c2cccc3c2C2(c4ccccc4-3)c3ccccc3-c3c2ccc2oc4ccccc4c32)OC1(C)C] | 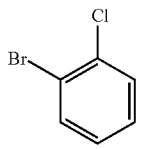 |

-continued
| Product | Yield |
|---|---|
| 7-2 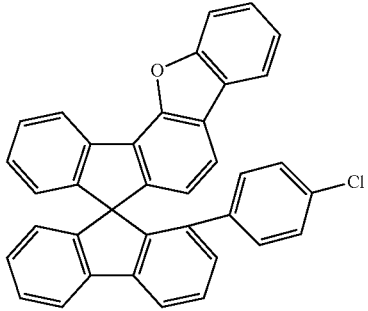 [SMILES: Clc1ccc(-c2cccc3c2C2(c4ccccc4-3)c3ccccc3-c3c2ccc2c3oc3ccccc32)cc1] | 80% |
| 7-3 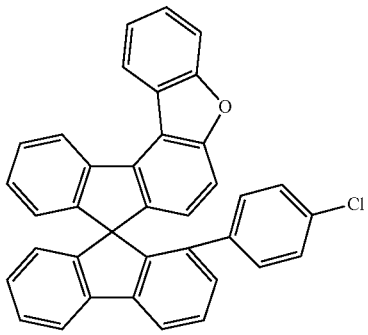 | 75% |
| 7-4 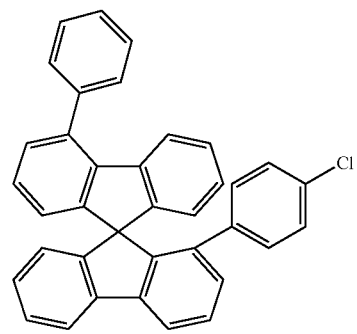 [SMILES: Clc1ccc(-c2cccc3c2C2(c4ccccc4-3)c3ccccc3-c3c(-c4ccccc4)cccc32)cc1] | 76% |
| 7-5 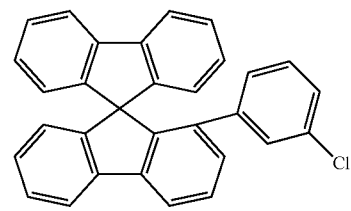 [SMILES: Clc1cccc(-c2cccc3c2C2(c4ccccc4-c4ccccc42)c2ccccc2-3)c1] | 82% |
| 7-6 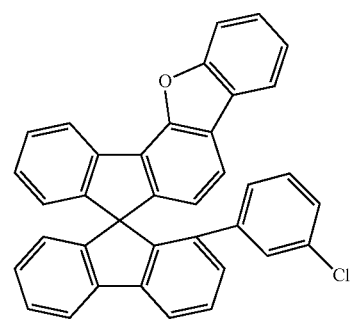 | 78% |

| | | -continued | |
|---|---|---|---|
| 7-7 | 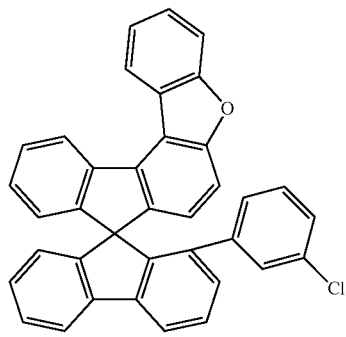 | | 81% |
| 7-8 | 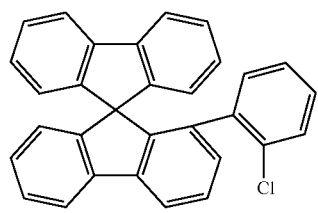 [SMILES: Clc1ccccc1-c1cccc2c1C1(c3ccccc3-c3ccccc31)c1ccccc1-2] | | 72% |
| 7-9 | 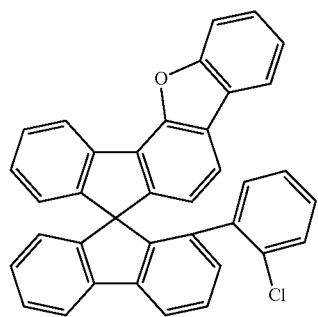 | | 80% |
| 7-10 | 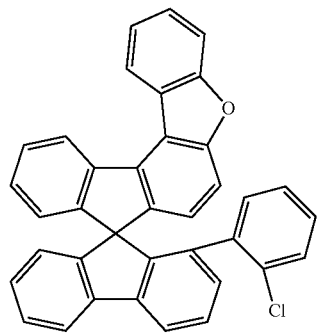 | | 70% |
Synthesis of Compound 8-1
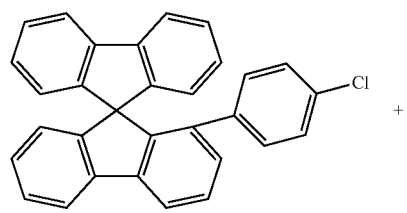 +
-continued
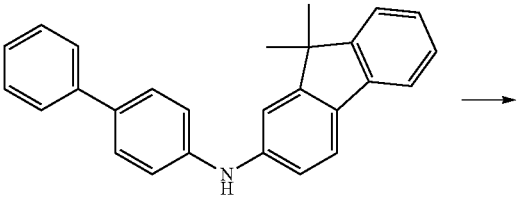

Synthesis of Compound 8-1

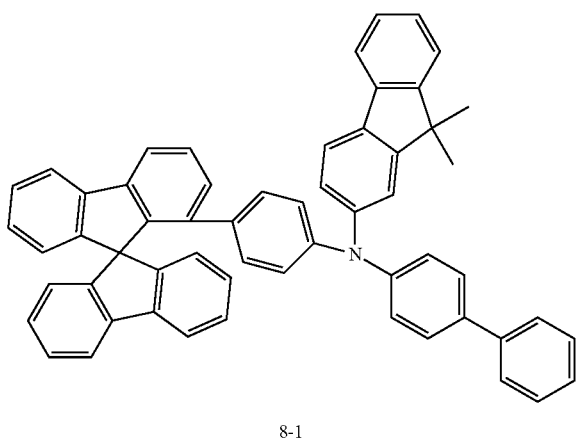

8-1

10.1 g (28 mmol) of biphenyl-4-yl-(9,9-dimethyl-9H-fluoren-2-yl)amine and 11.7 g (27 mol) of the 1'-(4-chlorophenyl)-9,9'spirobifluorene are dissolved in 225 ml of toluene. The solution is degassed and saturated with $N_2$. 2.1 ml (2.1 mmol) of a 10% tri-tert-butylphosphine solution and 0.98 g (1 mmol) of $Pd_2(dba)_3$ are then added, and 5.1 g of sodium tert-butoxide (53 mmol) are subsequently added. The reaction mixture is heated at the boil under a protective atmosphere for 5 h. The mixture is subsequently partitioned between toluene and water, the organic phase is washed three times with water and dried over $Na_2SO_4$ and evaporated in a rotary evaporator. After filtration of the crude product through silica gel with toluene, the residue which remains is recrystallised from heptane/toluene and finally sublimed in a high vacuum. The purity is 99.9% (HPLC). The yield of compound is 11.5 g (57% of theory).

The following compounds are also prepared analogously to the synthesis of compound 1.

| | Reactant 1 | Reactant 2 |
|---|---|---|
| 8-2 | 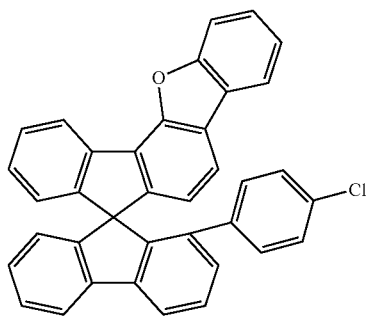 [SMILES: Clc1ccc(-c2cccc3c2C2(c4ccccc4-3)c3ccccc3-c3c2ccc2c3oc3ccccc32)cc1] | 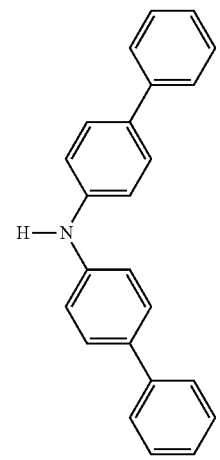 [SMILES: c1ccc(-c2ccc(Nc3ccc(-c4ccccc4)cc3)cc2)cc1] |
| 8-3 | 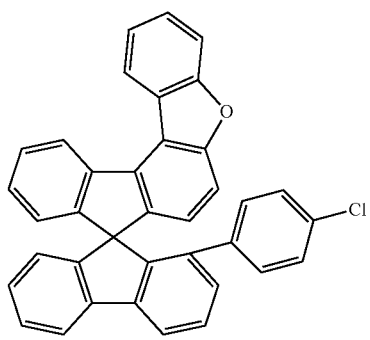 [SMILES: Clc1ccc(-c2cccc3c2C2(c4ccccc4-3)c3ccccc3-c3c2ccc2oc4ccccc4c32)cc1] | 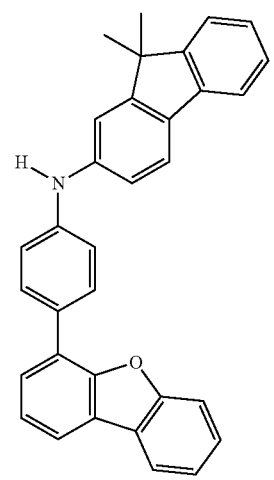 |

8-4
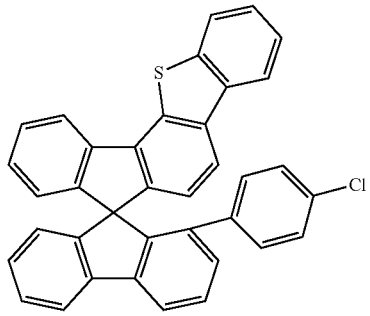
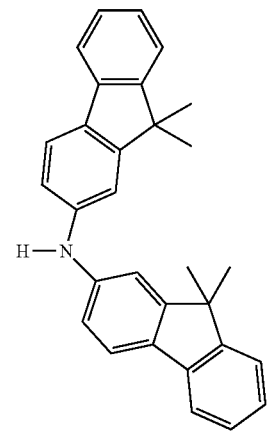
[500717-23-7]
8-5
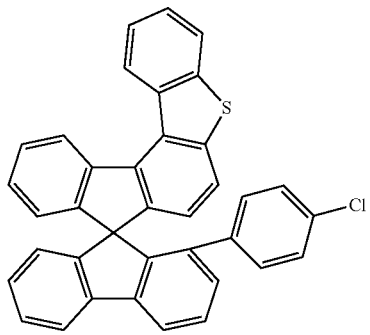
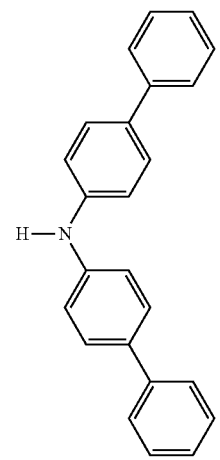
[102113-98-4]
8-6
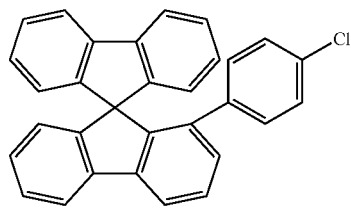 [SMILES: Clc1ccc(-c2cccc3c2C2(c4ccccc4-c4ccccc42)c2ccccc2-3)cc1]
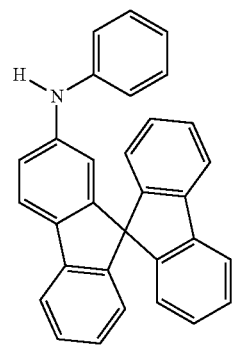 [SMILES: c1ccc(Nc2ccc3c(c2)C2(c4ccccc4-c4ccccc42)c2ccccc2-3)cc1]

| | | | |
|---|---|---|---|
| 8-7 | 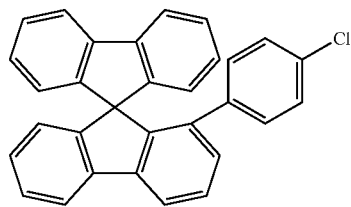 [SMILES: Clc1ccc(-c2cccc3c2C2(c4ccccc4-c4ccccc42)c2ccccc2-3)cc1] | | 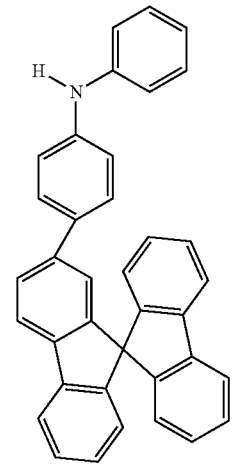 [SMILES: c1ccc(Nc2ccc(-c3ccc4c(c3)C3(c5ccccc5-c5ccccc53)c3ccccc3-4)cc2)cc1] |
| 8-8 | 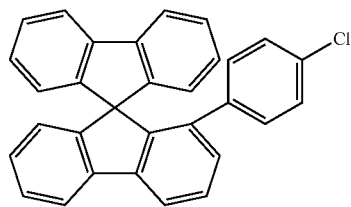 [SMILES: Clc1ccc(-c2cccc3c2C2(c4ccccc4-c4ccccc42)c2ccccc2-3)cc1] | | 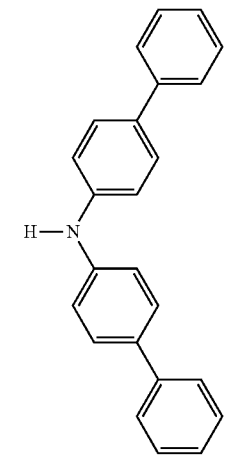 [SMILES: c1ccc(-c2ccc(Nc3ccc(-c4ccccc4)cc3)cc2)cc1] |
| 8-9 | 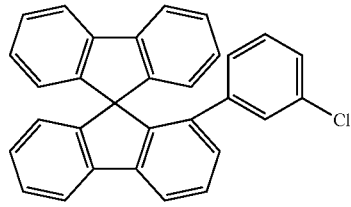 [SMILES: Clc1cccc(-c2cccc3c2C2(c4ccccc4-c4ccccc42)c2ccccc2-3)c1] | | 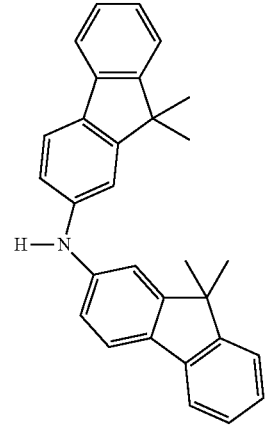 [SMILES: CC1(C)c2ccccc2-c2ccc(Nc3ccc4c(c3)C(C)(C)c3ccccc3-4)cc21] |

8-10 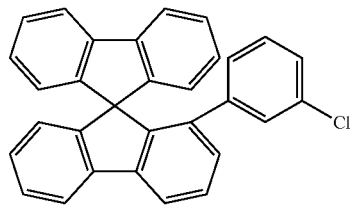 [SMILES: Clc1cccc(-c2cccc3c2C2(c4ccccc4-c4ccccc42)c2ccccc2-3)c1] 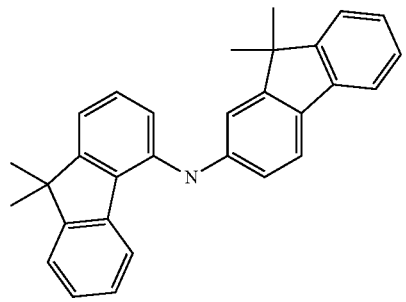 [SMILES: CC1(C)c2ccccc2-c2ccc(Nc3cccc4c3-c3ccccc3C4(C)C)cc21]
8-11 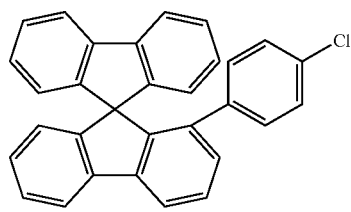 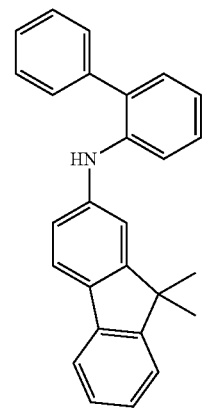 [SMILES: CC1(C)c2ccccc2-c2ccc(Nc3ccccc3-c3ccccc3)cc21]
8-12 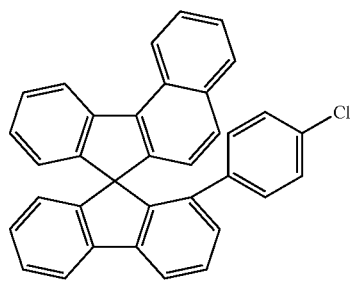 [SMILES: Clc1ccc(-c2cccc3c2C2(c4ccccc4-3)c3ccccc3-c3c2ccc2ccccc32)cc1] 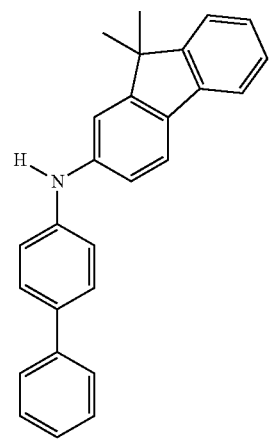 [SMILES: CC1(C)c2ccccc2-c2ccc(Nc3ccc(-c4ccccc4)cc3)cc21]
8-13 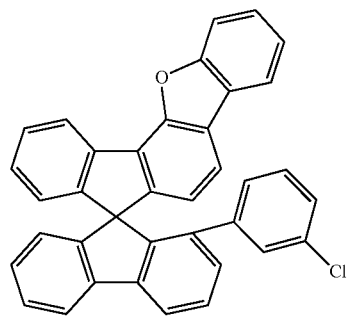 [SMILES: Clc1cccc(-c2cccc3c2C2(c4ccccc4-3)c3ccccc3-c3c2ccc2c3oc3ccccc32)c1] 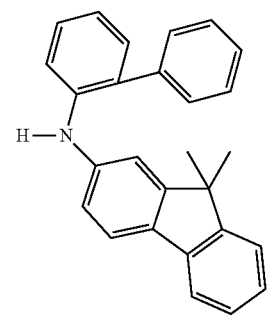
[1198395-24-2]

| | | | |
|---|---|---|---|
| 8-14 | 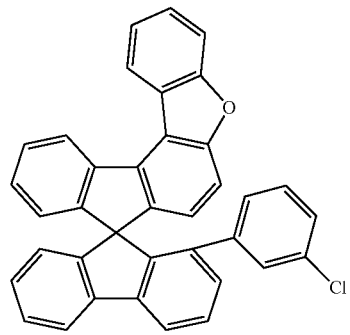 | 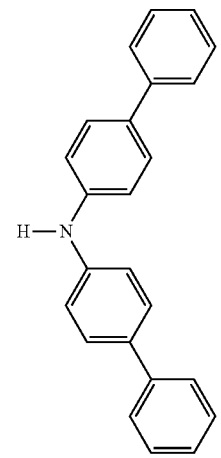 [102113-98-4] | |
| 8-15 | 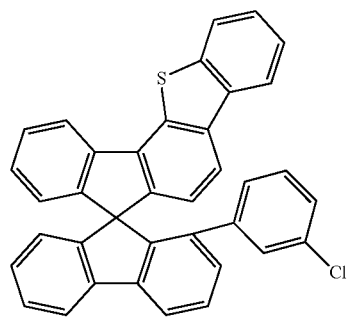 | 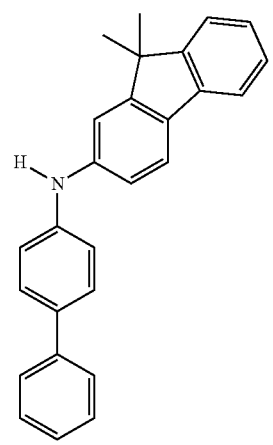 [SMILES: CC1(C)c2ccccc2-c2ccc(Nc3ccc(-c4ccccc4)cc3)cc21] | |
| 8-16 | 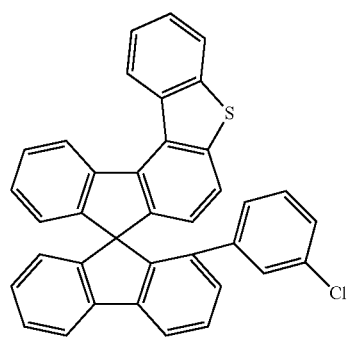 | 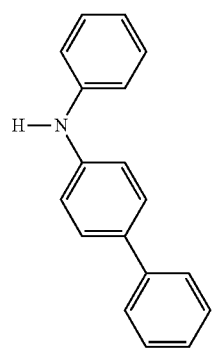 [SMILES: c1ccc(Nc2ccc(-c3ccccc3)cc2)cc1] | |

| | | | |
|---|---|---|---|
| 8-17 | 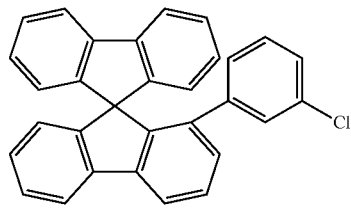 [SMILES: Clc1cccc(-c2cccc3c2C2(c4ccccc4-c4ccccc42)c2ccccc2-3)c1] | | 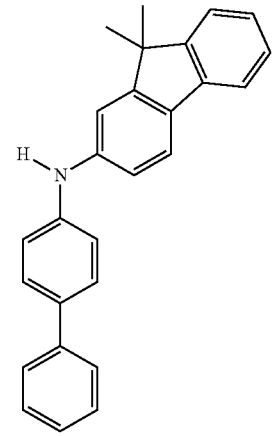 [SMILES: CC1(C)c2ccccc2-c2ccc(Nc3ccc(-c4ccccc4)cc3)cc21] |
| 8-18 | 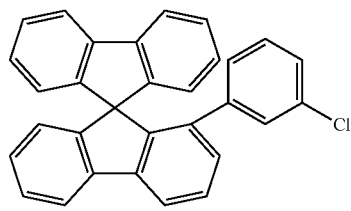 [SMILES: Clc1cccc(-c2cccc3c2C2(c4ccccc4-c4ccccc42)c2ccccc2-3)c1] | | 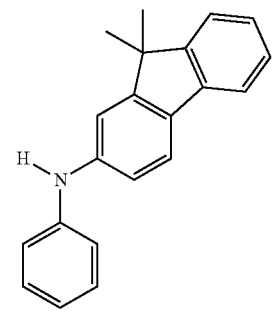 |
| 8-18 | 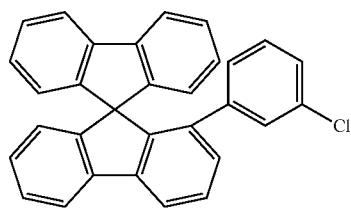 [SMILES: Clc1cccc(-c2cccc3c2C2(c4ccccc4-c4ccccc42)c2ccccc2-3)c1] | | 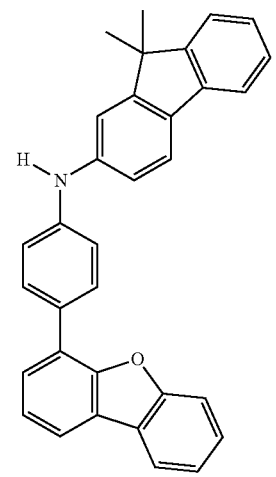 [SMILES: CC1(C)c2ccccc2-c2ccc(Nc3ccc(-c4cccc5c4oc4ccccc45)cc3)cc21] |

| | | | |
|---|---|---|---|
| 8-19 | 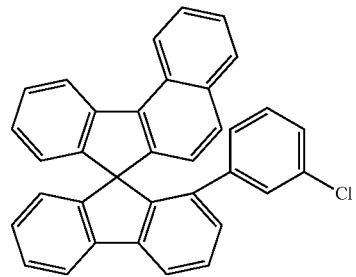 [SMILES: Clc1cccc(-c2cccc3c2C2(c4ccccc4-3)c3ccccc3-c3c2ccc2ccccc32)c1] | | 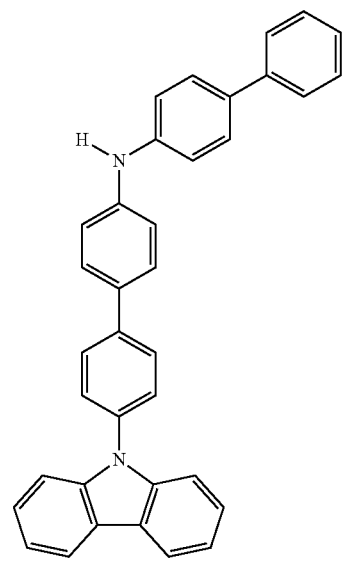 [SMILES: c1ccc(-c2ccc(Nc3ccc(-c4ccc(-n5c6ccccc6c6ccccc65)cc4)cc3)cc2)cc1] |
| 8-20 | 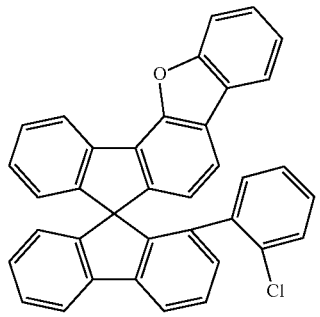 [SMILES: Clc1ccccc1-c1cccc2c1C1(c3ccccc3-2)c2ccccc2-c2c1ccc1c2oc2ccccc21] | | 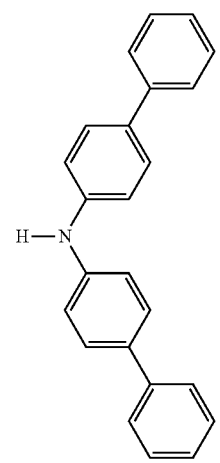 [SMILES: c1ccc(-c2ccc(Nc3ccc(-c4ccccc4)cc3)cc2)cc1] |
| 8-21 | 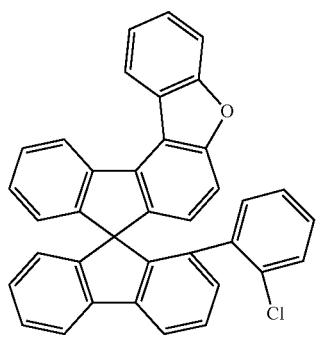 | | 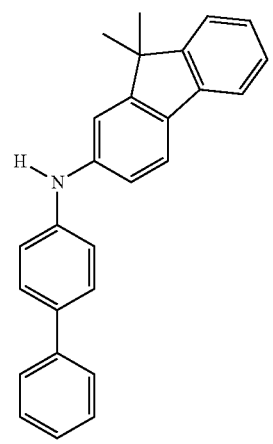 [SMILES: CC1(C)c2ccccc2-c2ccc(Nc3ccc(-c4ccccc4)cc3)cc21] |

| | | |
|---|---|---|
| 8-22 | 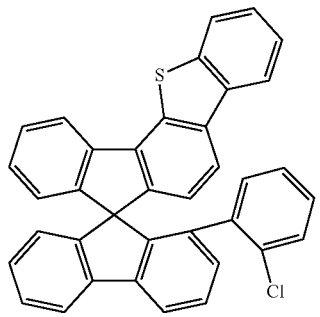 | 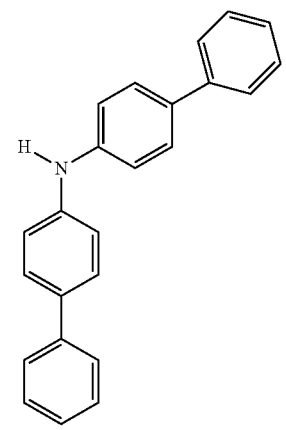 [SMILES: c1ccc(-c2ccc(Nc3ccc(-c4ccccc4)cc3)cc2)cc1] |
| 8-23 | 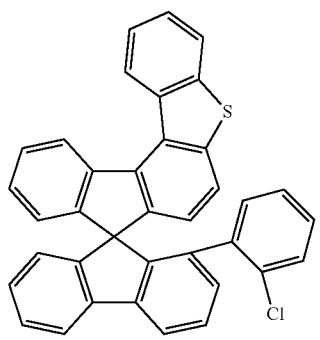 [SMILES: Clc1ccccc1-c1cccc2c1C1(c3ccccc3-2)c2ccccc2-c2c1ccc1sc3ccccc3c21] | 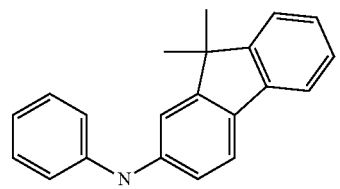 [SMILES: CC1(C)c2ccccc2-c2ccc(Nc3ccccc3)cc21] |
| 8-24 | 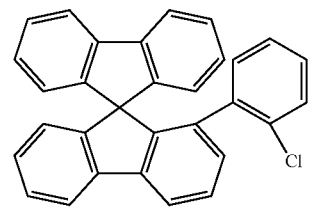 [SMILES: Clc1ccccc1-c1cccc2c1C1(c3ccccc3-c3ccccc31)c1ccccc1-2] | 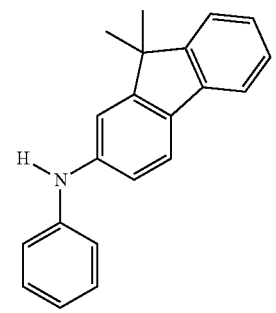 [SMILES: CC1(C)c2ccccc2-c2ccc(Nc3ccccc3)cc21] |
| 8-25 | 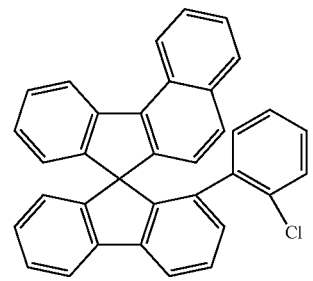 [SMILES: Clc1ccccc1-c1cccc2c1C1(c3ccccc3-2)c2ccccc2-c2c1ccc1ccccc21] | 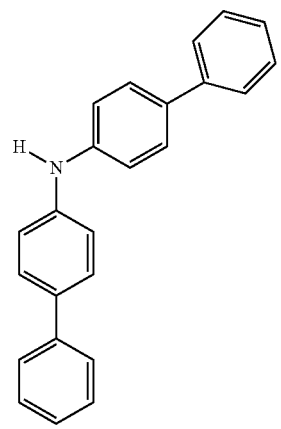 [SMILES: c1ccc(-c2ccc(Nc3ccc(-c4ccccc4)cc3)cc2)cc1] |

| | | |
|---|---|---|
| 8-26 | 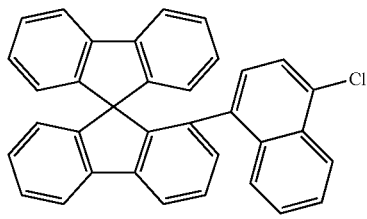 [SMILES: Clc1ccc(-c2cccc3c2C2(c4ccccc4-c4ccccc42)c2ccccc2-3)c2ccccc12] | 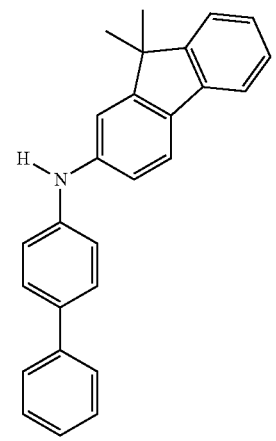 [SMILES: CC1(C)c2ccccc2-c2ccc(Nc3ccc(-c4ccccc4)cc3)cc21] |
| 8-27 | 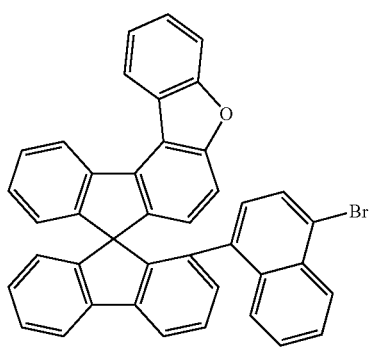 [SMILES: Brc1ccc(-c2cccc3c2C2(c4ccccc4-3)c3ccccc3-c3c2ccc2oc4ccccc4c32)c2ccccc12] | 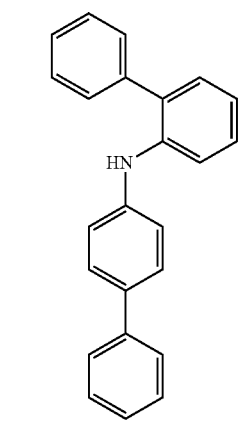 [SMILES: c1ccc(-c2ccc(Nc3ccccc3-c3ccccc3)cc2)cc1] |
| 8-28 | 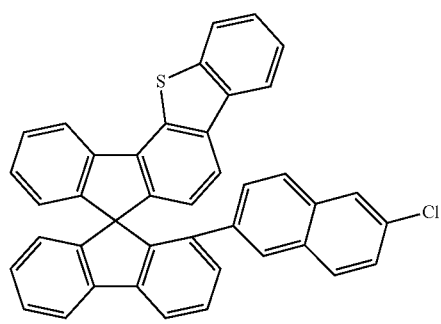 [SMILES: Clc1ccc2cc(-c3cccc4c3C3(c5ccccc5-4)c4ccccc4-c4c3ccc3c4sc4ccccc43)ccc2c1] | 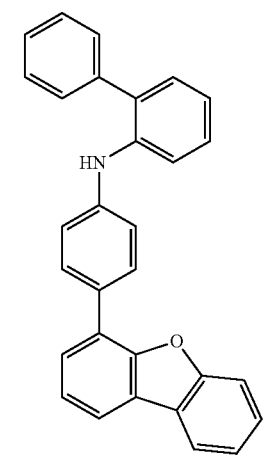 [SMILES: c1ccc(-c2ccccc2Nc2ccc(-c3cccc4c3oc3ccccc34)cc2)cc1] |
| 8-29 | 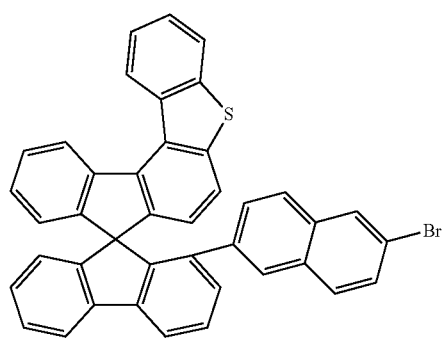 [SMILES: Brc1ccc2cc(-c3cccc4c3C3(c5ccccc5-4)c4ccccc4-c4c3ccc3sc5ccccc5c43)ccc2c1] | 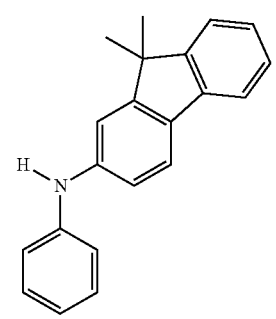 [SMILES: CC1(C)c2ccccc2-c2ccc(Nc3ccccc3)cc21] |

8-30 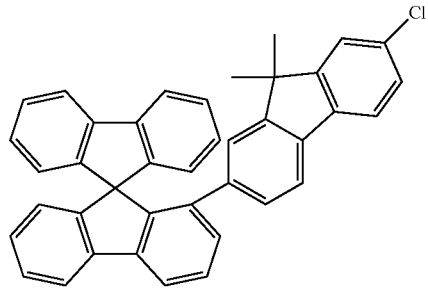 [SMILES: CC1(C)c2cc(Cl)ccc2-c2ccc(-c3cccc4c3C3(c5ccccc5-c5ccccc53)c3ccccc3-4)cc21] 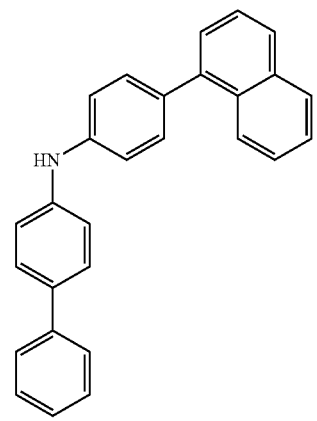 [SMILES: c1ccc(-c2ccc(Nc3ccc(-c4cccc5ccccc45)cc3)cc2)cc1]
8-31 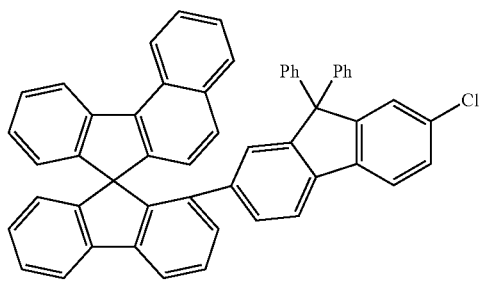 [SMILES: Clc1ccc2c(c1)C(c1ccccc1)(c1ccccc1)c1cc(-c3cccc4c3C3(c5ccccc5-4)c4ccccc4-c4c3ccc3ccccc43)ccc1-2] 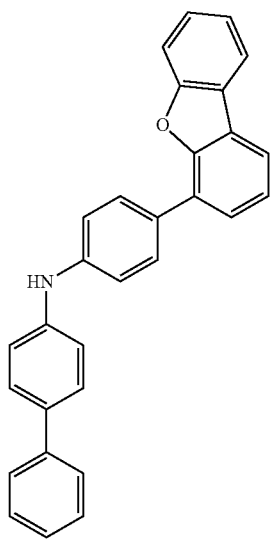 [SMILES: c1ccc(-c2ccc(Nc3ccc(-c4cccc5c4oc4ccccc45)cc3)cc2)cc1]
8-32 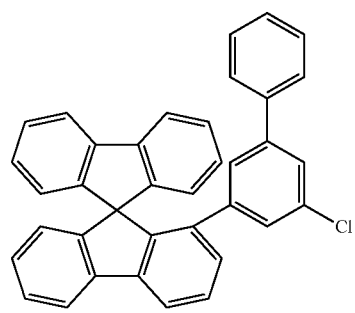 [SMILES: Clc1cc(-c2ccccc2)cc(-c2cccc3c2C2(c4ccccc4-c4ccccc42)c2ccccc2-3)c1] 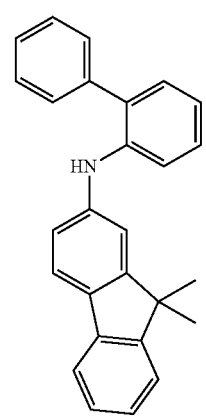 [SMILES: CC1(C)c2ccccc2-c2ccc(Nc3ccccc3-c3ccccc3)cc21]

| | | |
|---|---|---|
| 8-33 | 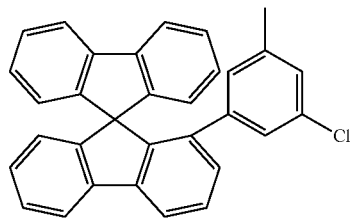 [SMILES: Cc1cc(Cl)cc(-c2cccc3c2C2(c4ccccc4-c4ccccc42)c2ccccc2-3)c1] | 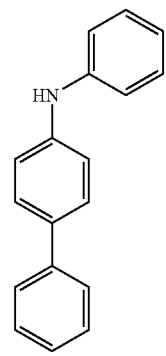 [SMILES: c1ccc(Nc2ccc(-c3ccccc3)cc2)cc1] |
| 8-34 | 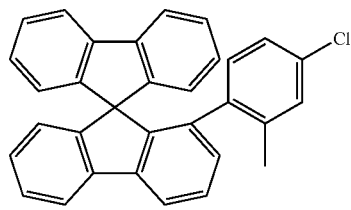 [SMILES: Cc1cc(Cl)ccc1-c1cccc2c1C1(c3ccccc3-c3ccccc31)c1ccccc1-2] | 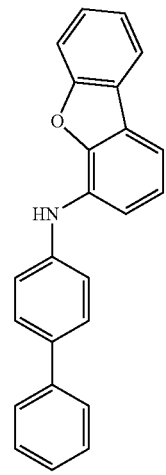 [SMILES: c1ccc(-c2ccc(Nc3cccc4c3oc3ccccc34)cc2)cc1] |
| 8-35 | 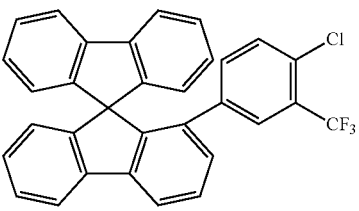 [SMILES: FC(F)(F)c1cc(-c2cccc3c2C2(c4ccccc4-c4ccccc42)c2ccccc2-3)ccc1Cl] | 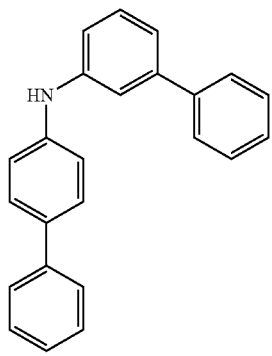 [SMILES: c1ccc(-c2ccc(Nc3cccc(-c4ccccc4)c3)cc2)cc1] |
| 8-36 | 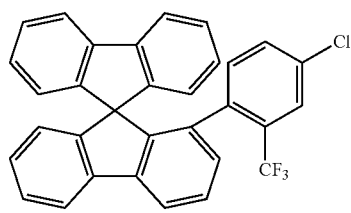 [SMILES: FC(F)(F)c1cc(Cl)ccc1-c1cccc2c1C1(c3ccccc3-c3ccccc31)c1ccccc1-2] | 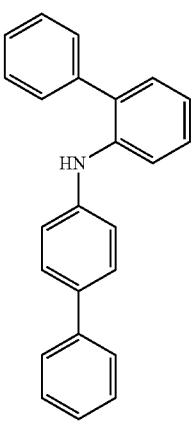 [SMILES: c1ccc(-c2ccc(Nc3ccccc3-c3ccccc3)cc2)cc1] |

| | | |
|---|---|---|
| 8-37 | 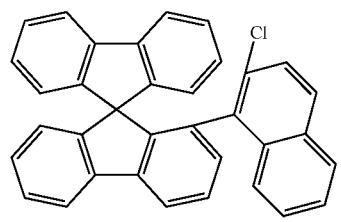 [SMILES: Clc1ccc2ccccc2c1-c1cccc2c1C1(c3ccccc3-c3ccccc31)c1ccccc1-2] | 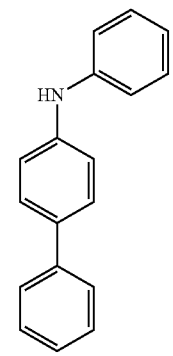 [SMILES: c1ccc(Nc2ccc(-c3ccccc3)cc2)cc1] |
| 8-38 | 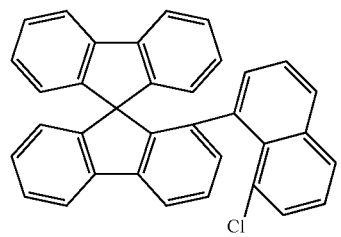 [SMILES: Clc1cccc2cccc(-c3cccc4c3C3(c5ccccc5-c5ccccc53)c3ccccc3-4)c12] | 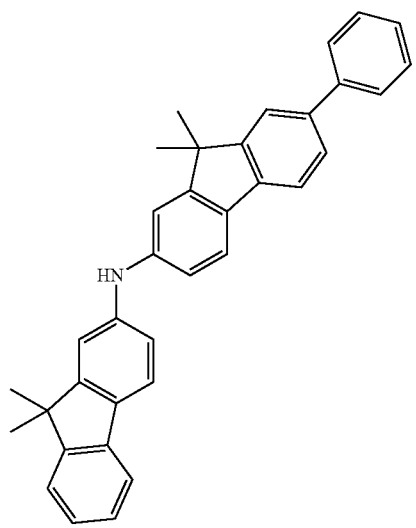 [SMILES: CC1(C)c2ccccc2-c2ccc(Nc3ccc4c(c3)C(C)(C)c3cc(-c5ccccc5)ccc3-4)cc21] |
| 8-39 | 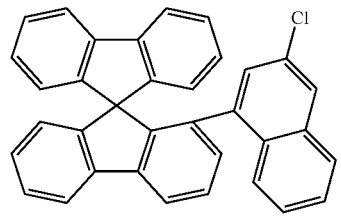 [SMILES: Clc1cc(-c2cccc3c2C2(c4ccccc4-c4ccccc42)c2ccccc2-3)c2ccccc2c1] | 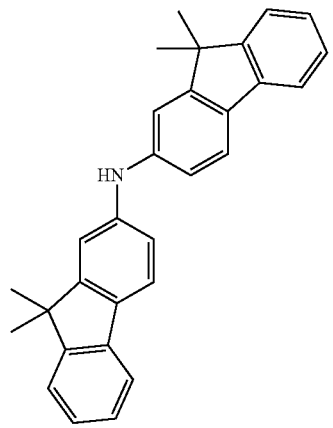 [SMILES: CC1(C)c2ccccc2-c2ccc(Nc3ccc4c(c3)C(C)(C)c3ccccc3-4)cc21] |

-continued
| Product | | Yield |
|---|---|---|
| 8-2 | 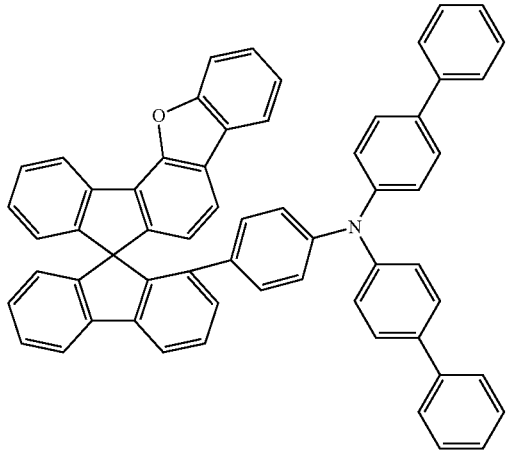 [SMILES: c1ccc(-c2ccc(N(c3ccc(-c4ccccc4)cc3)c3ccc(-c4cccc5c4C4(c6ccccc6-5)c5ccccc5-c5c4ccc4c5oc5ccccc54)cc3)cc2)cc1] | 78% |
| 8-3 | 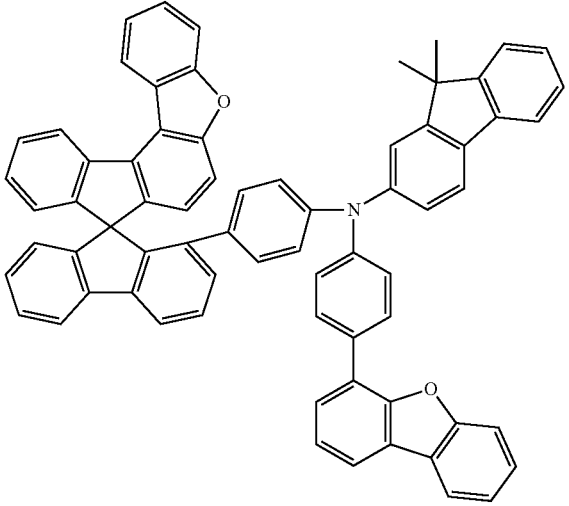 [SMILES: CC1(C)c2ccccc2-c2ccc(N(c3ccc(-c4cccc5c4C4(c6ccccc6-5)c5ccccc5-c5c4ccc4oc6ccccc6c54)cc3)c3ccc(-c4cccc5c4oc4ccccc45)cc3)cc21] | 82% |
| 8-4 | 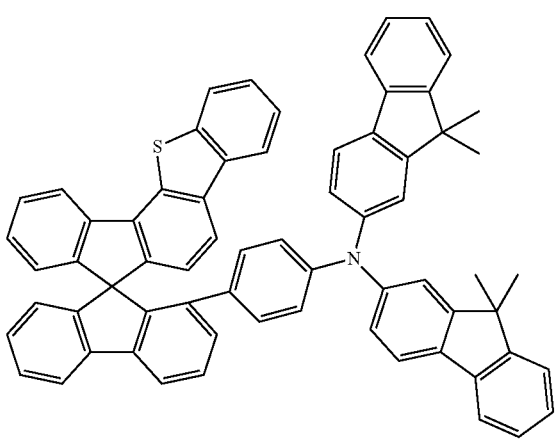 [SMILES: CC1(C)c2ccccc2-c2ccc(N(c3ccc(-c4cccc5c4C4(c6ccccc6-5)c5ccccc5-c5c4ccc4c5sc5ccccc54)cc3)c3ccc4c(c3)C(C)(C)c3ccccc3-4)cc21] | 88% |

| | | |
|---|---|---|
| 8-5 | 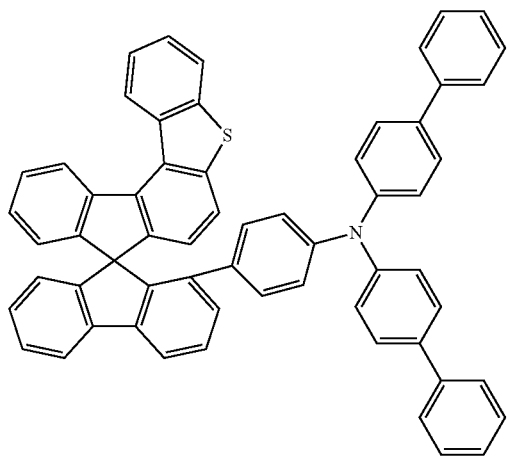 [SMILES: c1ccc(-c2ccc(N(c3ccc(-c4ccccc4)cc3)c3ccc(-c4cccc5c4C4(c6ccccc6-5)c5ccccc5-c5c4ccc4sc6ccccc6c54)cc3)cc2)cc1] | 67% |
| 8-6 | 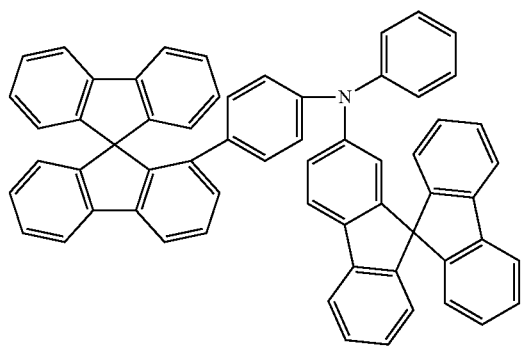 [SMILES: c1ccc(N(c2ccc(-c3cccc4c3C3(c5ccccc5-c5ccccc53)c3ccccc3-4)cc2)c2ccc3c(c2)C2(c4ccccc4-c4ccccc42)c2ccccc2-3)cc1] | 76% |
| 8-7 | 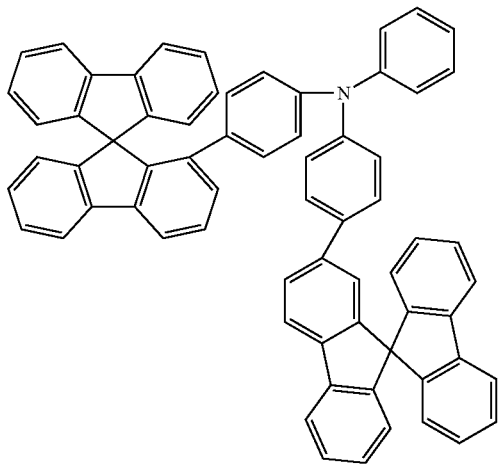 [SMILES: c1ccc(N(c2ccc(-c3ccc4c(c3)C3(c5ccccc5-c5ccccc53)c3ccccc3-4)cc2)c2ccc(-c3cccc4c3C3(c5ccccc5-c5ccccc53)c3ccccc3-4)cc2)cc1] | 70% |

| | | |
|---|---|---|
| 8-8 | 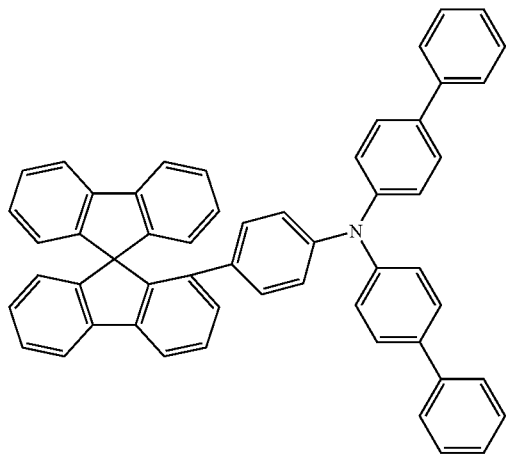 [SMILES: c1ccc(-c2ccc(N(c3ccc(-c4ccccc4)cc3)c3ccc(-c4cccc5c4C4(c6ccccc6-c6ccccc64)c4ccccc4-5)cc3)cc2)cc1] | 65% |
| 8-9 | 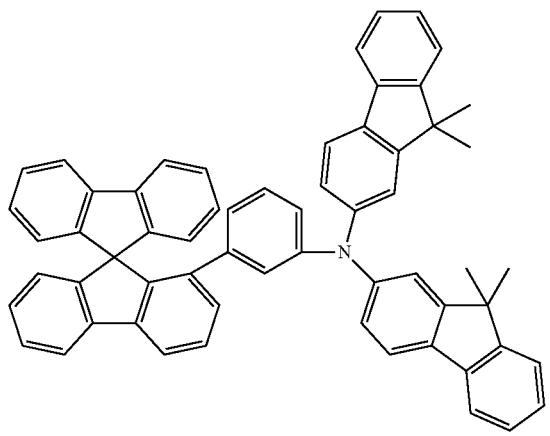 [SMILES: CC1(C)c2ccccc2-c2ccc(N(c3cccc(-c4cccc5c4C4(c6ccccc6-c6ccccc64)c4ccccc4-5)c3)c3ccc4c(c3)C(C)(C)c3ccccc3-4)cc21] | 60% |
| 8-10 | 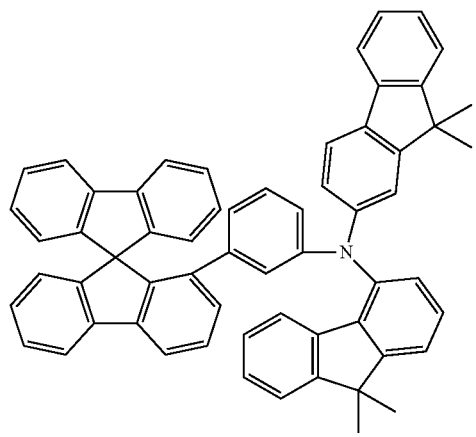 [SMILES: CC1(C)c2ccccc2-c2ccc(N(c3cccc(-c4cccc5c4C4(c6ccccc6-c6ccccc64)c4ccccc4-5)c3)c3cccc4c3-c3ccccc3C4(C)C)cc21] | 70% |

| | | |
|---|---|---|
| 8-11 | 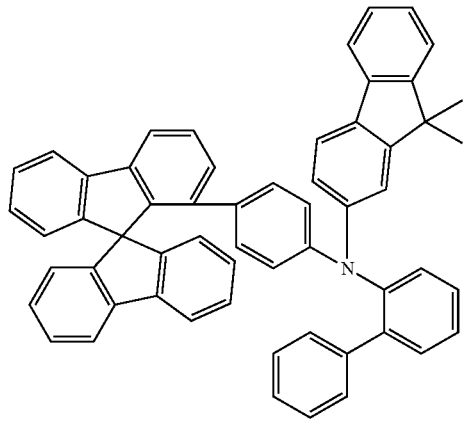 [SMILES: CC1(C)c2ccccc2-c2ccc(N(c3ccc(-c4cccc5c4C4(c6ccccc6-c6ccccc64)c4ccccc4-5)cc3)c3ccccc3-c3ccccc3)cc21] | 68% |
| 8-12 | 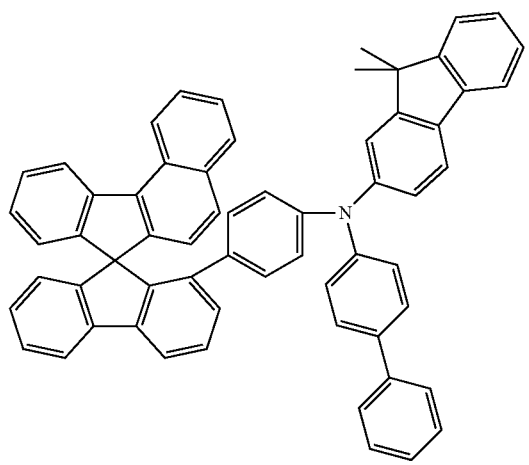 [SMILES: CC1(C)c2ccccc2-c2ccc(N(c3ccc(-c4ccccc4)cc3)c3ccc(-c4cccc5c4C4(c6ccccc6-5)c5ccccc5-c5c4ccc4ccccc54)cc3)cc21] | 80% |
| 8-13 | 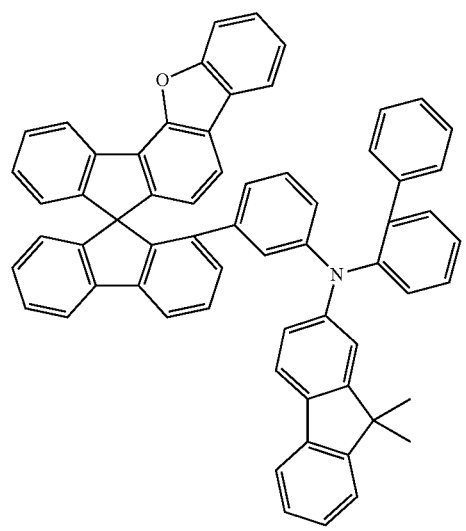 [SMILES: CC1(C)c2ccccc2-c2ccc(N(c3cccc(-c4cccc5c4C4(c6ccccc6-5)c5ccccc5-c5c4ccc4c5oc5ccccc54)c3)c3ccccc3-c3ccccc3)cc21] | 78% |

| | | |
|---|---|---|
| 8-14 | 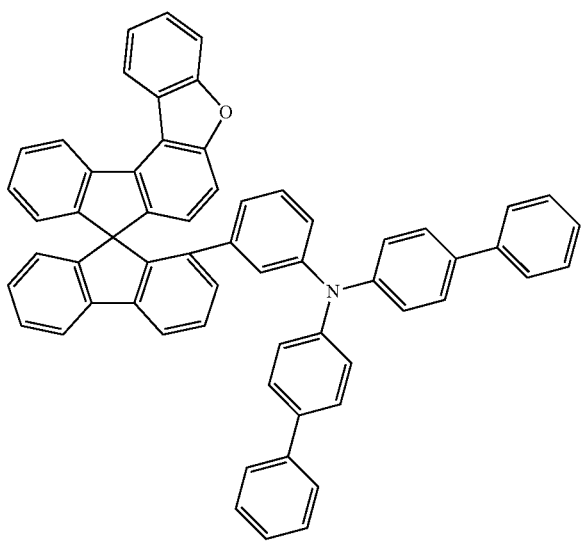 [SMILES: c1ccc(-c2ccc(N(c3ccc(-c4ccccc4)cc3)c3cccc(-c4cccc5c4C4(c6ccccc6-5)c5ccccc5-c5c4ccc4oc6ccccc6c54)c3)cc2)cc1] | 72% |
| 8-15 | 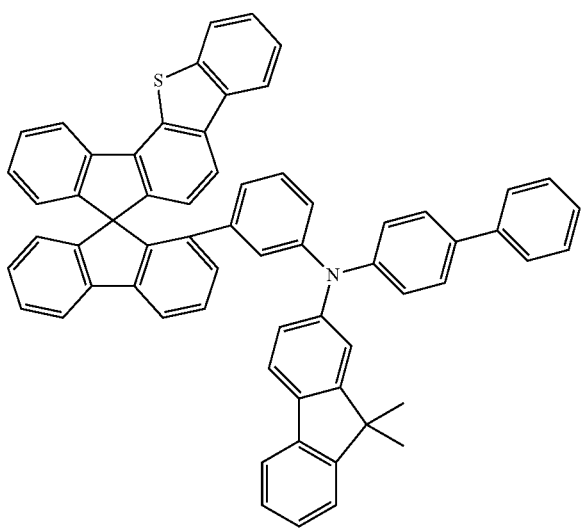 [SMILES: CC1(C)c2ccccc2-c2ccc(N(c3ccc(-c4ccccc4)cc3)c3cccc(-c4cccc5c4C4(c6ccccc6-5)c5ccccc5-c5c4ccc4c5sc5ccccc54)c3)cc21] | 83% |
| 8-16 | 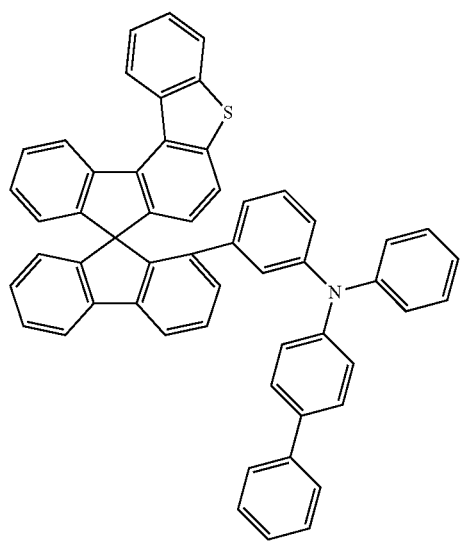 [SMILES: c1ccc(-c2ccc(N(c3ccccc3)c3cccc(-c4cccc5c4C4(c6ccccc6-5)c5ccccc5-c5c4ccc4sc6ccccc6c54)c3)cc2)cc1] | 75% |

| | | |
|---|---|---|
| 8-17 | 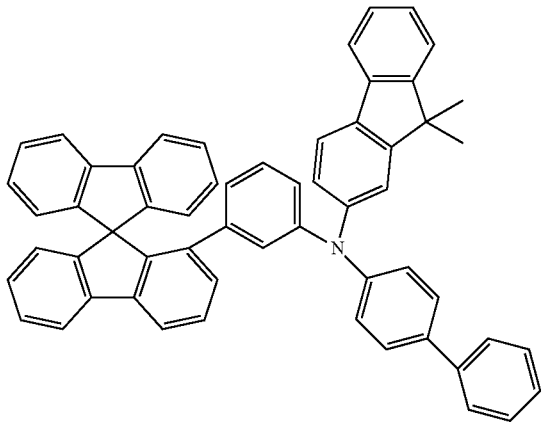 [SMILES: CC1(C)c2ccccc2-c2ccc(N(c3ccc(-c4ccccc4)cc3)c3cccc(-c4cccc5c4C4(c6ccccc6-c6ccccc64)c4ccccc4-5)c3)cc21] | 70% |
| 8-18 | 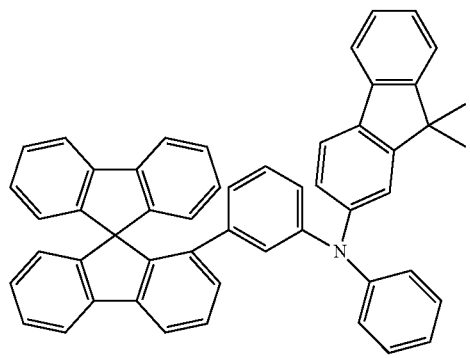 [SMILES: CC1(C)c2ccccc2-c2ccc(N(c3ccccc3)c3cccc(-c4cccc5c4C4(c6ccccc6-c6ccccc64)c4ccccc4-5)c3)cc21] | 65% |
| 8-18 | 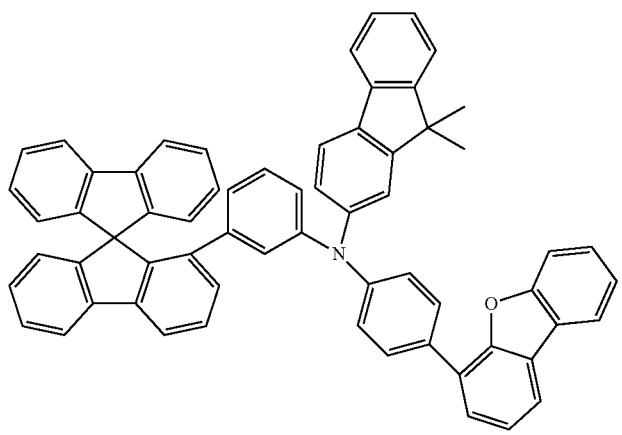 [SMILES: CC1(C)c2ccccc2-c2ccc(N(c3ccc(-c4cccc5c4oc4ccccc45)cc3)c3cccc(-c4cccc5c4C4(c6ccccc6-c6ccccc64)c4ccccc4-5)c3)cc21] | 76% |

| | | |
|---|---|---|
| 8-19 | 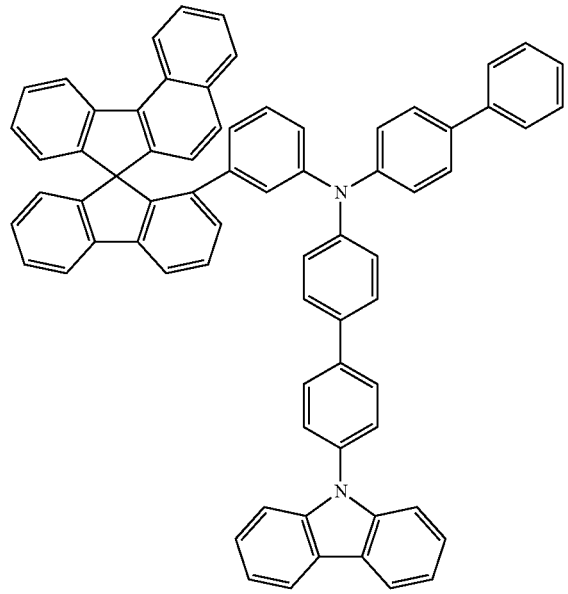 [SMILES: c1ccc(-c2ccc(N(c3ccc(-c4ccc(-n5c6ccccc6c6ccccc65)cc4)cc3)c3cccc(-c4cccc5c4C4(c6ccccc6-5)c5ccccc5-c5c4ccc4ccccc54)c3)cc2)cc1] | 81% |
| 8-20 | 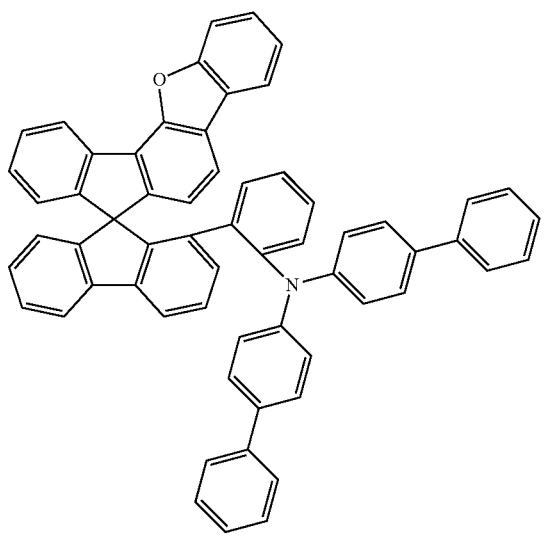 | 65% |

| | | |
|---|---|---|
| 8-21 | 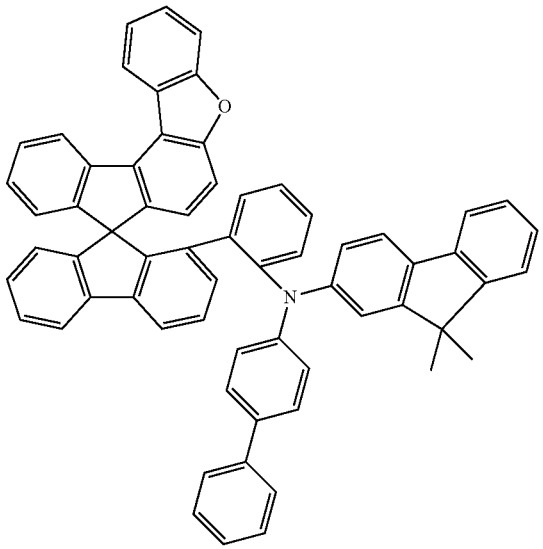 [SMILES: CC1(C)c2ccccc2-c2ccc(N(c3ccc(-c4ccccc4)cc3)c3ccccc3-c3cccc4c3C3(c5ccccc5-4)c4ccccc4-c4c3ccc3oc5ccccc5c43)cc21] | 55% |
| 8-22 | 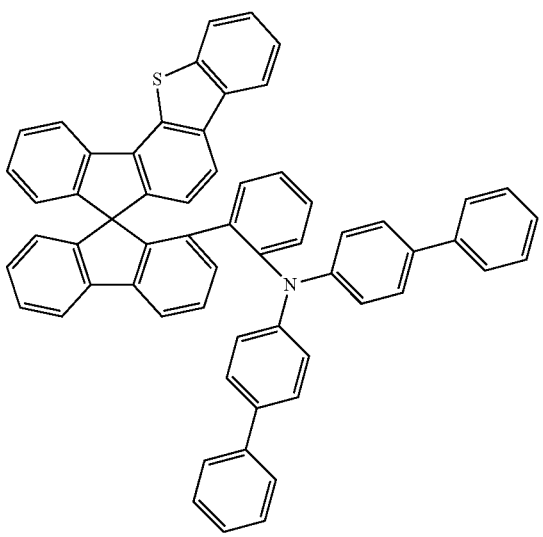 [SMILES: c1ccc(-c2ccc(N(c3ccc(-c4ccccc4)cc3)c3ccccc3-c3cccc4c3C3(c5ccccc5-4)c4ccccc4-c4c3ccc3c4sc4ccccc43)cc2)cc1] | 73% |
| 8-23 | 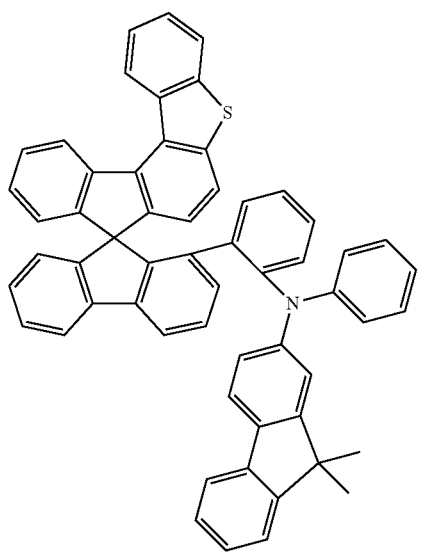 [SMILES: CC1(C)c2ccccc2-c2ccc(N(c3ccccc3)c3ccccc3-c3cccc4c3C3(c5ccccc5-4)c4ccccc4-c4c3ccc3sc5ccccc5c43)cc21] | 64% |

-continued
| | | |
|---|---|---|
| 8-24 | 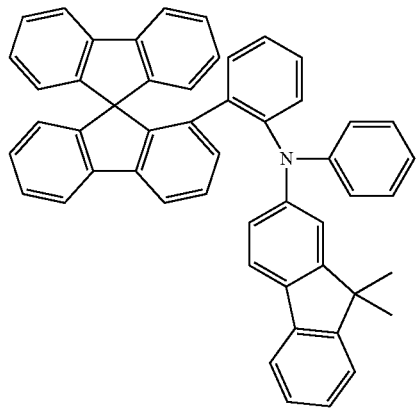 [SMILES: CC1(C)c2ccccc2-c2ccc(N(c3ccccc3)c3ccccc3-c3cccc4c3C3(c5ccccc5-c5ccccc53)c3ccccc3-4)cc21] | 59% |
| 8-25 | 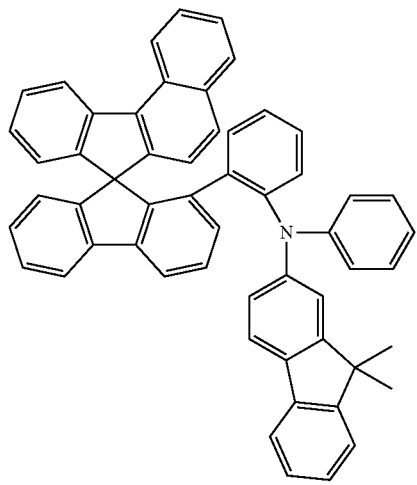 [SMILES: CC1(C)c2ccccc2-c2ccc(N(c3ccccc3)c3ccccc3-c3cccc4c3C3(c5ccccc5-4)c4ccccc4-c4c3ccc3ccccc43)cc21] | 72% |
| 8-26 | 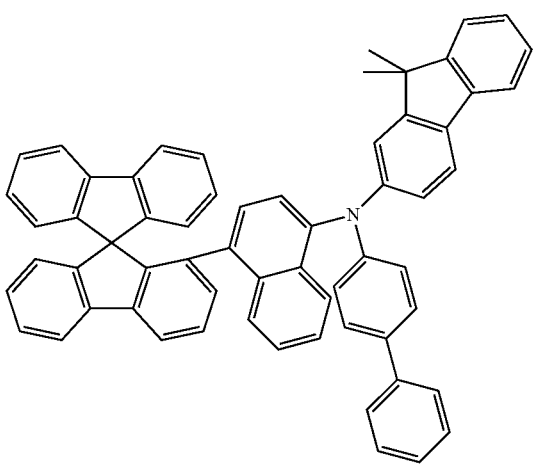 [SMILES: CC1(C)c2ccccc2-c2ccc(N(c3ccc(-c4ccccc4)cc3)c3ccc(-c4cccc5c4C4(c6ccccc6-c6ccccc64)c4ccccc4-5)c4ccccc34)cc21] | 67% |

| | | |
|---|---|---|
| 8-27 | 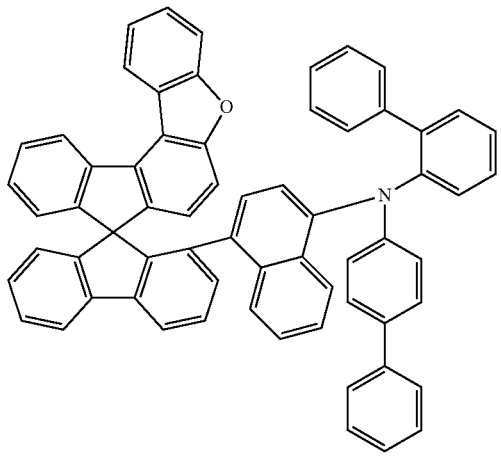 [SMILES: c1ccc(-c2ccc(N(c3ccccc3-c3ccccc3)c3ccc(-c4cccc5c4C4(c6ccccc6-5)c5ccccc5-c5c4ccc4oc6ccccc6c54)c4ccccc34)cc2)cc1] | 60% |
| 8-28 | 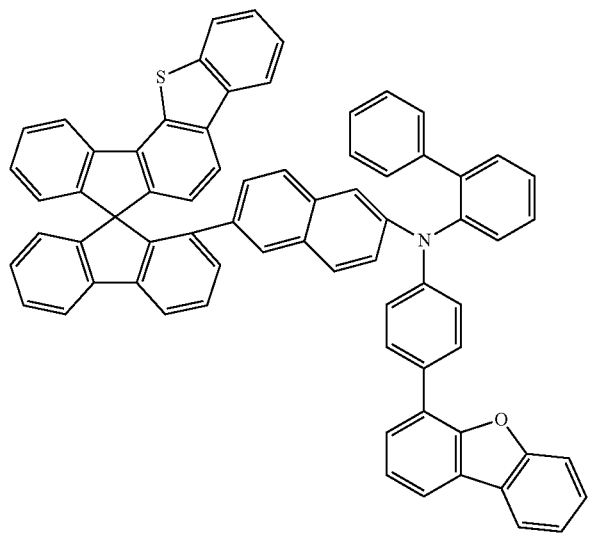 [SMILES: c1ccc(-c2ccccc2N(c2ccc(-c3cccc4c3oc3ccccc34)cc2)c2ccc3cc(-c4cccc5c4C4(c6ccccc6-5)c5ccccc5-c5c4ccc4c5sc5ccccc54)ccc3c2)cc1] | 71% |
| 8-29 | 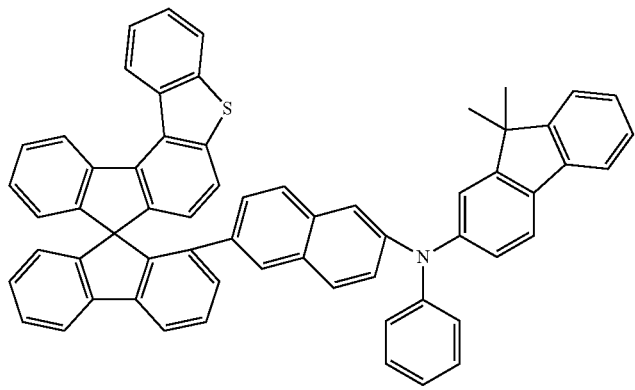 [SMILES: CC1(C)c2ccccc2-c2ccc(N(c3ccccc3)c3ccc4cc(-c5cccc6c5C5(c7ccccc7-6)c6ccccc6-c6c5ccc5sc7ccccc7c65)ccc4c3)cc21] | 67% |

| | | |
|---|---|---|
| 8-30 | 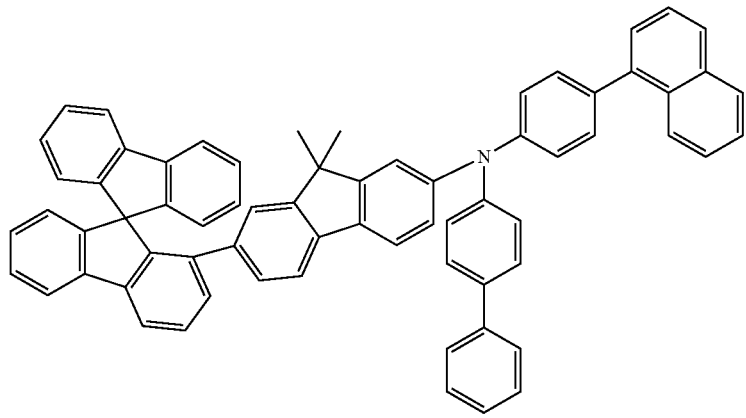 [SMILES: CC1(C)c2cc(-c3cccc4c3C3(c5ccccc5-c5ccccc53)c3ccccc3-4)ccc2-c2ccc(N(c3ccc(-c4ccccc4)cc3)c3ccc(-c4cccc5ccccc45)cc3)cc21] | 78% |
| 8-31 | 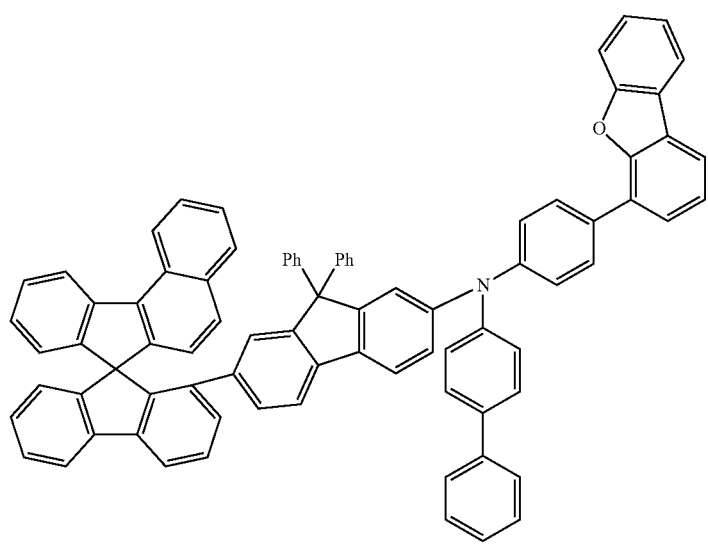 [SMILES: c1ccc(-c2ccc(N(c3ccc(-c4cccc5c4oc4ccccc45)cc3)c3ccc4c(c3)C(c3ccccc3)(c3ccccc3)c3cc(-c5cccc6c5C5(c7ccccc7-6)c6ccccc6-c6c5ccc5ccccc65)ccc3-4)cc2)cc1] | 74% |
| 8-32 | 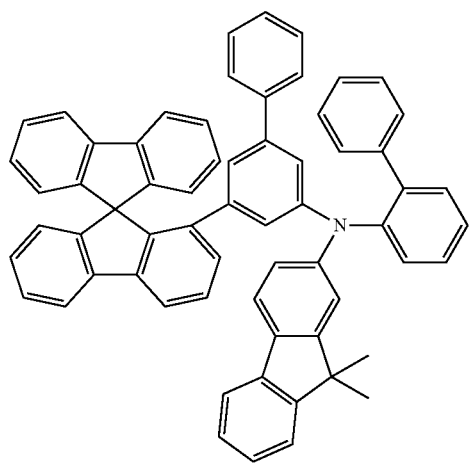 [SMILES: CC1(C)c2ccccc2-c2ccc(N(c3cc(-c4ccccc4)cc(-c4cccc5c4C4(c6ccccc6-c6ccccc64)c4ccccc4-5)c3)c3ccccc3-c3ccccc3)cc21] | 67% |

| | | |
|---|---|---|
| 8-33 | 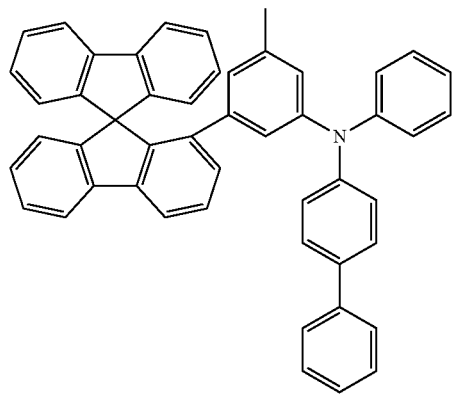 [SMILES: Cc1cc(-c2cccc3c2C2(c4ccccc4-c4ccccc42)c2ccccc2-3)cc(N(c2ccccc2)c2ccc(-c3ccccc3)cc2)c1] | 72% |
| 8-34 | 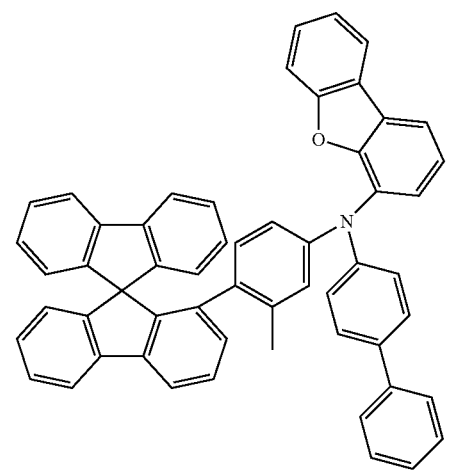 [SMILES: Cc1cc(N(c2ccc(-c3ccccc3)cc2)c2cccc3c2oc2ccccc23)ccc1-c1cccc2c1C1(c3ccccc3-c3ccccc31)c1ccccc1-2] | 66% |
| 8-35 | 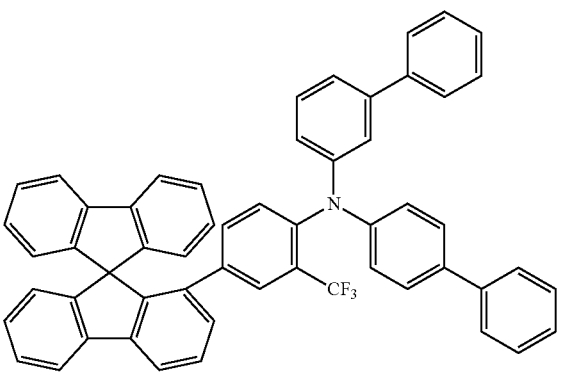 [SMILES: FC(F)(F)c1cc(-c2cccc3c2C2(c4ccccc4-c4ccccc42)c2ccccc2-3)ccc1N(c1ccc(-c2ccccc2)cc1)c1cccc(-c2ccccc2)c1] | 79% |
| 8-36 | 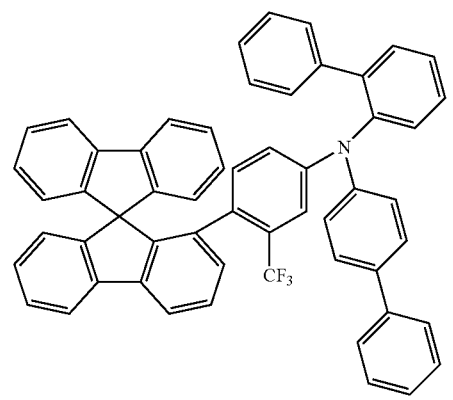 [SMILES: FC(F)(F)c1cc(N(c2ccc(-c3ccccc3)cc2)c2ccccc2-c2ccccc2)ccc1-c1cccc2c1C1(c3ccccc3-c3ccccc31)c1ccccc1-2] | 80% |

| | | |
|---|---|---|
| 8-37 | 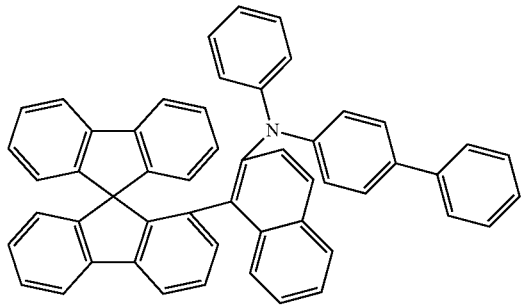 [SMILES: c1ccc(-c2ccc(N(c3ccccc3)c3ccc4ccccc4c3-c3cccc4c3C3(c5ccccc5-c5ccccc53)c3ccccc3-4)cc2)cc1] | 56% |
| 8-38 | 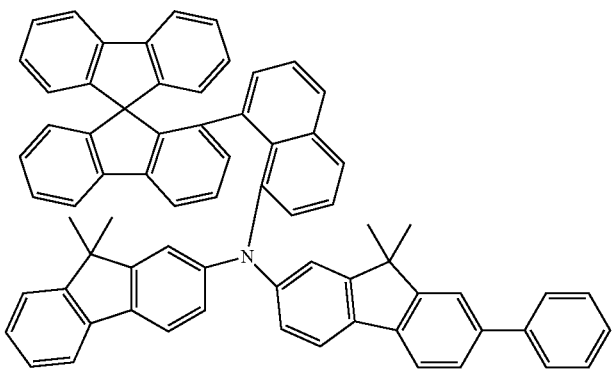 [SMILES: CC1(C)c2ccccc2-c2ccc(N(c3ccc4c(c3)C(C)(C)c3cc(-c5ccccc5)ccc3-4)c3cccc4cccc(-c5cccc6c5C5(c7ccccc7-c7ccccc75)c5ccccc5-6)c34)cc21] | 62% |
| 8-39 | 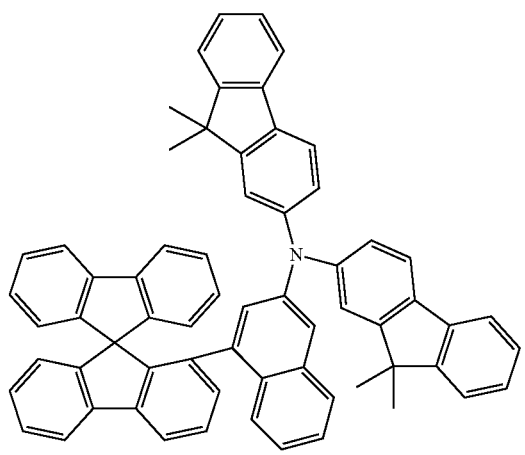 [SMILES: CC1(C)c2ccccc2-c2ccc(N(c3ccc4c(c3)C(C)(C)c3ccccc3-4)c3cc(-c4cccc5c4C4(c6ccccc6-c6ccccc64)c4ccccc4-5)c4ccccc4c3)cc21] | 70% |

B) Device Examples

OLEDs according to the invention and OLEDs in accordance with the prior art are produced by a general process in accordance with WO 2004/058911, which is adapted to the circumstances described here (layer-thickness variation, materials).

The data for various OLEDs are presented in Examples below (see Tables 1 to 2). The substrates used are glass plates coated with structured ITO (indium tin oxide) in a thickness of 50 nm. The OLEDs basically have the following layer structure: substrate/hole-injection layer (HIL)/hole-transport layer (HTL)/electron-blocking layer (EBL)/emission layer (EML)/electron-transport layer (ETL)/electron-injection layer (EIL) and finally a cathode. The cathode is formed by an aluminium layer with a thickness of 100 nm. The precise structure of the OLEDs is shown in table 1. The materials required for the production of the OLEDs are shown in table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as H1:SEB (5%) here means that material H1 is present in the layer in a proportion by volume of 95% and SEB is present in the layer in a proportion of 5%. Analogously, other layers may also consist of a mixture of two or more materials.

The OLEDs are characterised by standard methods. For this purpose, the electroluminescence spectra and the external quantum efficiency (EQE, measured in percent) as a function of the luminous density, calculated from current/voltage/luminous density characteristic lines (IUL characteristic lines) assuming Lambert emission characteristics, and the lifetime are determined. The expression EQE @ 10 mA/cm$^2$ denotes the external quantum efficiency at an operating current density of 10 mA/cm². LT80 @ 6000 cd/m² is the lifetime until the OLED has dropped from its initial luminance of 6000 cd/m² to 80% of the initial intensity to 4800 cd/m² calculated with an acceleration factor of 1.8.

The data for the various OLEDs containing inventive and comparative materials are summarised in table 2.

Use of Compounds According to the Invention as Hole-Transport Materials in Fluorescent OLEDs In particular, compounds according to the invention are suitable as HIL, HTL, EBL or matrix material in the EML in OLEDs. They are suitable as a single layer, but also as mixed component as HIL, HTL, EBL or within the EML. Compared with components from prior art (V1 to V9), the samples comprising the compounds according to the invention exhibit higher efficiencies and/or improved lifetimes both in singlet blue and also in triplet green.

TABLE 1

Structure of the OLEDs

| Ex. | HIL Thickness/nm | HTL Thickness/nm | IL Thickness/nm | EBL Thickness/nm | EML Thickness/nm | ETL Thickness/nm | EIL Thickness/nm |
|---|---|---|---|---|---|---|---|
| V1 | HIM: F4TCNQ(5%) 20 nm | HIM 180 nm | HTMV1: F4TCNQ(5%) 20 nm | HTMV1 10 nm | H1: SEB(5%) 20 nm | ETM: LiQ(50%) 30 nm | LiQ 1 nm |
| E1 | HIM: F4TCNQ(5%) 20 nm | HIM 180 nm | HTM1: F4TCNQ(5%) 20 nm | HTM1 10 nm | H1: SEB(5%) 20 nm | ETM: LiQ(50%) 30 nm | LiQ 1 nm |
| E2 | HIM: F4TCNQ(5%) 20 nm | HIM 180 nm | HTM2: F4TCNQ(5%) 20 nm | HTM2 10 nm | H1: SEB(5%) 20 nm | ETM: LiQ(50%) 30 nm | LiQ 1 nm |

TABLE 2

Data for the OLEDs

| Ex. | U @ 10 mA/cm² [V] | EQE @ 10 mA/cm² % | LT80 @ 6000 cd/m² [h] |
|---|---|---|---|
| V1 | 3.4 | 6.8 | 130 |
| E1 | 3.4 | 7.2 | 130 |
| E2 | 3.3 | 7.1 | 140 |

TABLE 3

Structures of the materials used

F4TCNQ

HIM

TABLE 3-continued

Structures of the materials used

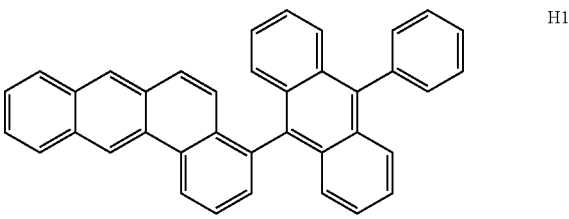

H1

TABLE 3-continued

Structures of the materials used

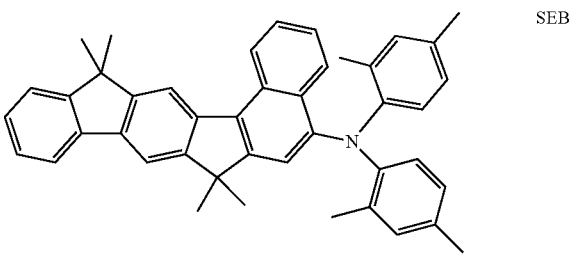

SEB

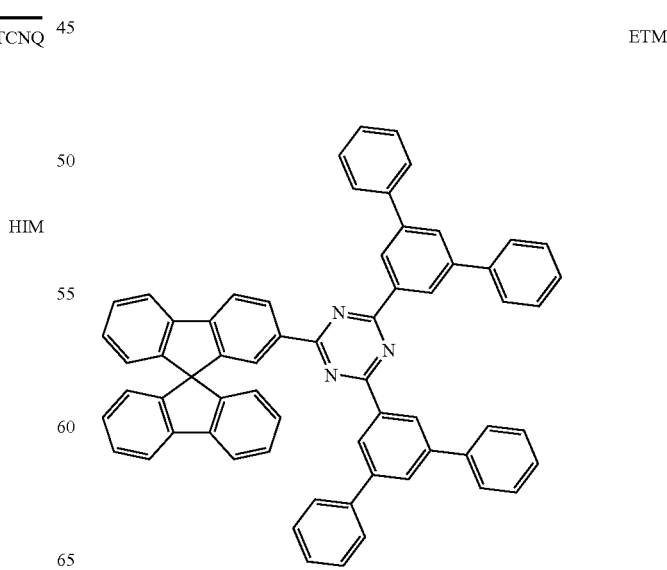

ETM

TABLE 3-continued

Structures of the materials used

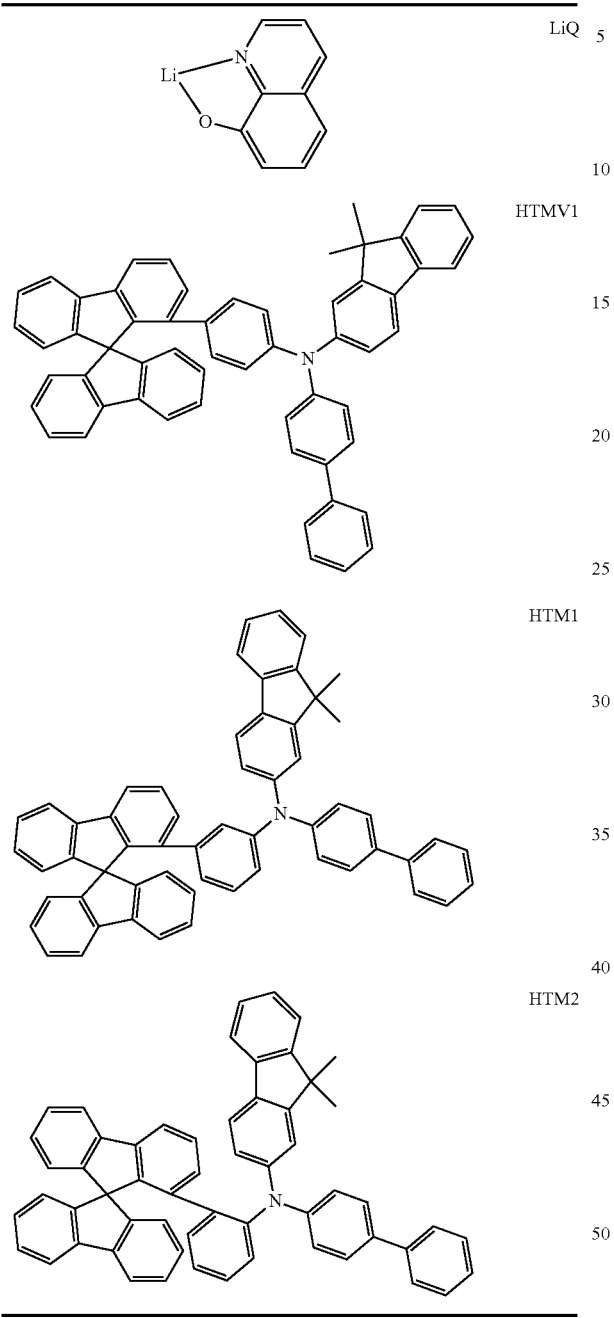

LiQ

HTMV1

HTM1

HTM2

Examples

OLED devices with the structures shown in table 1 are produced. Table 2 shows the performance data of the examples described. The device is a fluorescent blue device with comparison of HTMV1 and HTM1 as material in the electron blocking layer (EBL). It can be shown, that efficiency of device E1 is better than the comparative example V1, whereas the LT is comparable. Compared to HTMV1 (V1) as EBL HTM2 (E2) shows better efficiency and better lifetime.

The invention claimed is:
1. A compound of formula (Int-1),

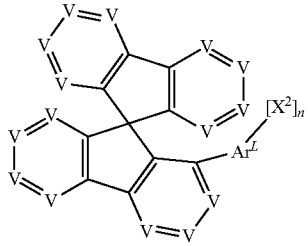

formula (Int-1)

where the following applies to the symbols used:

V is CR or N, with the proviso that there are maximum three N per 6-membered-ring, or two adjacent groups V (V—V or V=V) stand for a group of the formula (V-1) or (V-2),

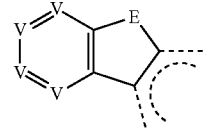

formula (V-1)

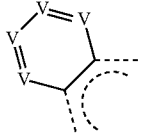

formula (V-2)

in which the dashed bonds indicate the linking to the spirobifluorene skeleton;

E is a divalent bridge selected from $N(R^0)$, $B(R^0)$, O, $C(R^0)_2$, $Si(R^0)_2$, $C=NR^0$, $C=C(R^0)_2$, S, S=O, $SO_2$, $P(R^0)$ and $P(=O)R^0$;

$X^2$ is Cl, Br, I, trifluoromethanesulfonate ($CF_3SO_3-$), tosylate ($CH_3C_6H_4SO_3-$) or mesylate ($CH_3SO_3-$);

$Ar^L$ is an aromatic or heteroaromatic ring system having 5 to 40 aromatic ring atoms, which may be substituted by one or more radicals $R^1$;

$R^0$, R, $R^2$ are selected on each occurrence, identically or differently, from the group consisting of H, D, F, CHO, CN, $C(=O)Ar^3$, $P(=O)(Ar^3)_2$, $S(=O)Ar^3$, $S(=O)_2Ar^3$, $N(Ar^3)_2$, $Si(R^3)_3$, $B(OR^3)_2$, $OSO_2R^3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^3$, where one or more non-adjacent $CH_2$ groups may be replaced by $R^3C=CR^3$, $C\equiv C$, $Si(R^3)_2$, $Ge(R^3)_2$, $Sn(R^3)_2$, C=O, C=S, C=Se, $P(=O)(R^3)$, SO, $SO_2$, O, S or $CONR^3$ and where one or more H atoms may be replaced by D, F or CN, an aromatic or heteroaromatic ring system having 5 to 60 aromatic ring atoms, which may be substituted by one or more radicals $R^3$, and an aryloxy group having 5 to 60 aromatic ring atoms, which may be substituted by one or more radicals $R^3$, where two adjacent substituents $R^0$, two adjacent substituents R or two adjacent substituents $R^2$ may form a mono- or polycyclic, aliphatic ring system or aromatic ring system, which may be substituted by one or more radicals $R^3$;

R¹ is selected on each occurrence, identically or differently, from the group consisting of H, D, F, CHO, CN, C(=O)Ar³, P(=O)(Ar³)$_2$, S(=O)Ar³, S(=O)Ar³, Si(R³)$_3$, B(OR³)$_2$, OSO$_2$R³, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals R³, where one or more non-adjacent CH$_2$ groups may be replaced by R³C=CR³, C≡C, Si(R³)$_2$, Ge(R³)$_2$, Sn(R³)$_2$, C=O, C=S, C=Se, P(=O)(R³), SO, SO$_2$, O, S or CONR³ and where one or more H atoms may be replaced by D, F or CN, an aromatic or heteroaromatic ring system having 5 to 60 aromatic ring atoms, which may be substituted by one or more radicals R³, and an aryloxy group having 5 to 60 aromatic ring atoms, which may be substituted by one or more radicals R³, where two adjacent substituents R¹ may form a mono- or polycyclic, aliphatic ring system or aromatic ring system, which may be substituted by one or more radicals R³;

R³ is selected on each occurrence, identically or differently, from the group consisting of H, D, F, CHO, CN, C(=O)Ar³, P(=O)(Ar³)$_2$, S(=O)Ar³, S(=O)Ar³, Si(R⁴)$_3$, B(OR⁴)$_2$, OSO$_2$R⁴, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals R⁴, where one or more non-adjacent CH$_2$ groups may be replaced by R⁴C=CR⁴, C≡C, Si(R⁴)$_2$, Ge(R⁴)$_2$, Sn(R⁴)$_2$, C=O, C=S, C=Se, P(=O)(R⁴), SO, SO2, O, S or CONR4 and where one or more H atoms may be replaced by D, F, or CN, an aromatic or heteroaromatic ring system having 5 to 60 aromatic ring atoms, which may be substituted by one or more radicals R4, and an aryloxy group having 5 to 60 aromatic ring atoms, which may be substituted by one or more radicals R4, where two adjacent substituents R3 may form a mono- or polycyclic, aliphatic ring system or aromatic ring system, which may be substituted by one or more radicals R⁴;

R⁴ is selected on each occurrence, identically or differently, from the group consisting of H, D, F, CN, a straight-chain alkyl, alkoxy or thioalkyl group having 1 to 20 C atoms or a branched or cyclic alkyl, alkoxy or thioalkyl group having 3 to 20 C atoms, where one or more non-adjacent CH$_2$ groups may be replaced by SO, SO$_2$, O, S and where one or more H atoms may be replaced by D or F, and aromatic or heteroaromatic ring system having 5 to 24 C atoms;

Ar³ is selected, identically or differently on each occurrence, from the group consisting of an aromatic or heteroaromatic ring system having 5 to 24 aromatic ring atoms, which may be substituted by one or more radicals R⁴;

n is 1, 2, or 3;

X² is Cl, Br, I, trifluoromethanesulfonate (CF$_3$SO$_3$—), tosylate (CH$_3$C$_6$H$_4$SO$_3$—) or mesylate (CH$_3$SO$_3$—);

X³ is Cl, Br, I or —B(OR$^B$)$_2$; with the proviso that one of the group X¹ or X³ must stand for —B(OR$^B$)$_2$ but not both groups stand for —B(OR$^B$)$_2$ at the same time.

2. The compound according to claim 1, characterized in that X² is Br, Cl or I.

3. The compound according to claim 1, selected from formulae (Int-2) to (Int-9),

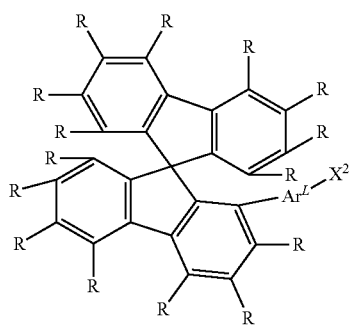

formula (Int-2)

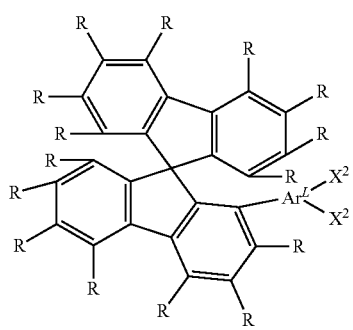

formula (Int-3)

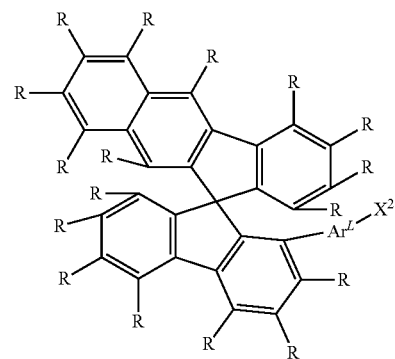

formula (Int-4)

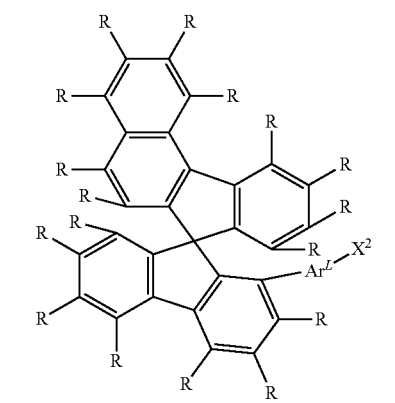

formula (Int-5)

-continued
formula (Int-6)
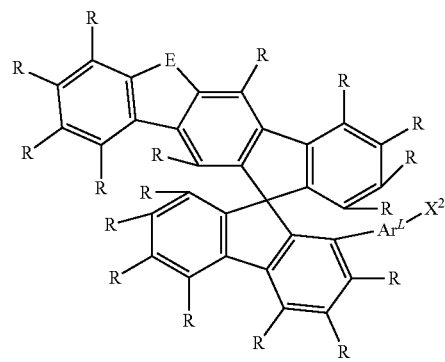
formula (Int-7)
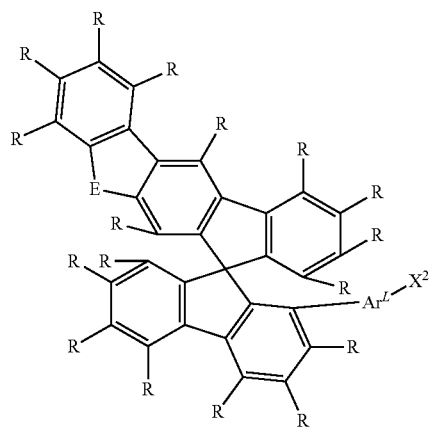
formula (Int-8)
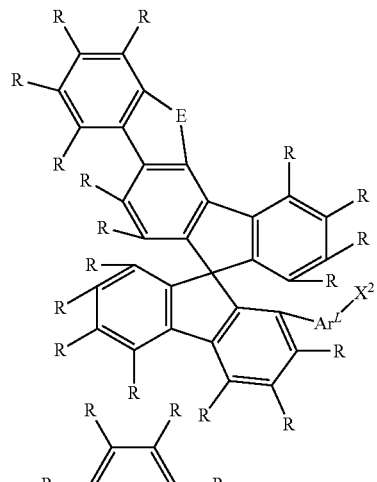
formula (Int-9)
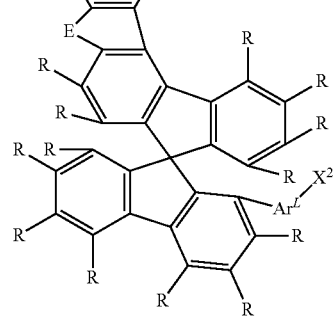
where the symbols have the same meaning as defined in claim 1.
4. The compound according to claim 1, selected from the compounds of formulae (Int-2-1) to (Int-2-8),
formula (Int-2-1)
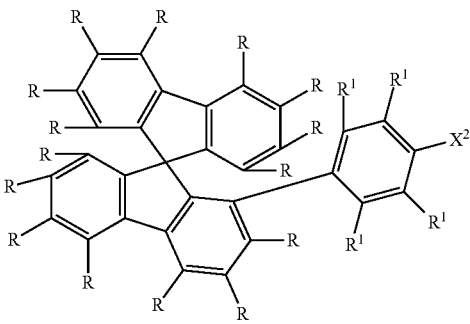
formula (Int-2-2)
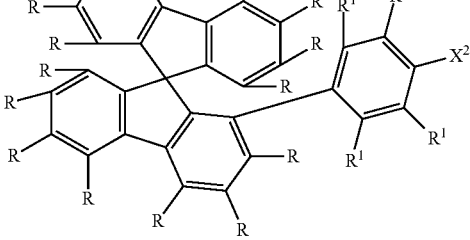
formula (Int-2-3)
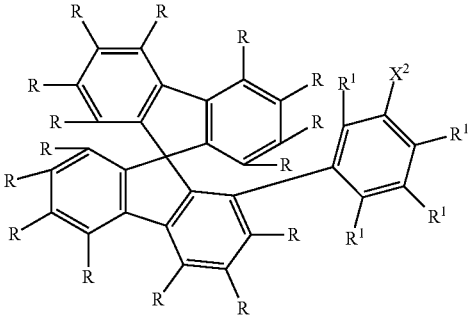
formula (Int-2-4)
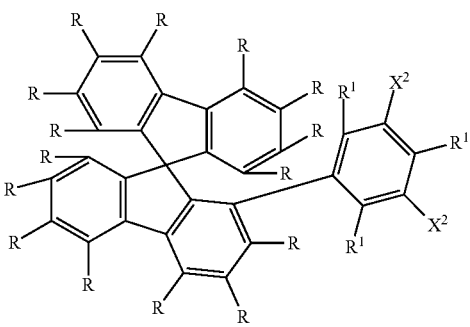

313
-continued
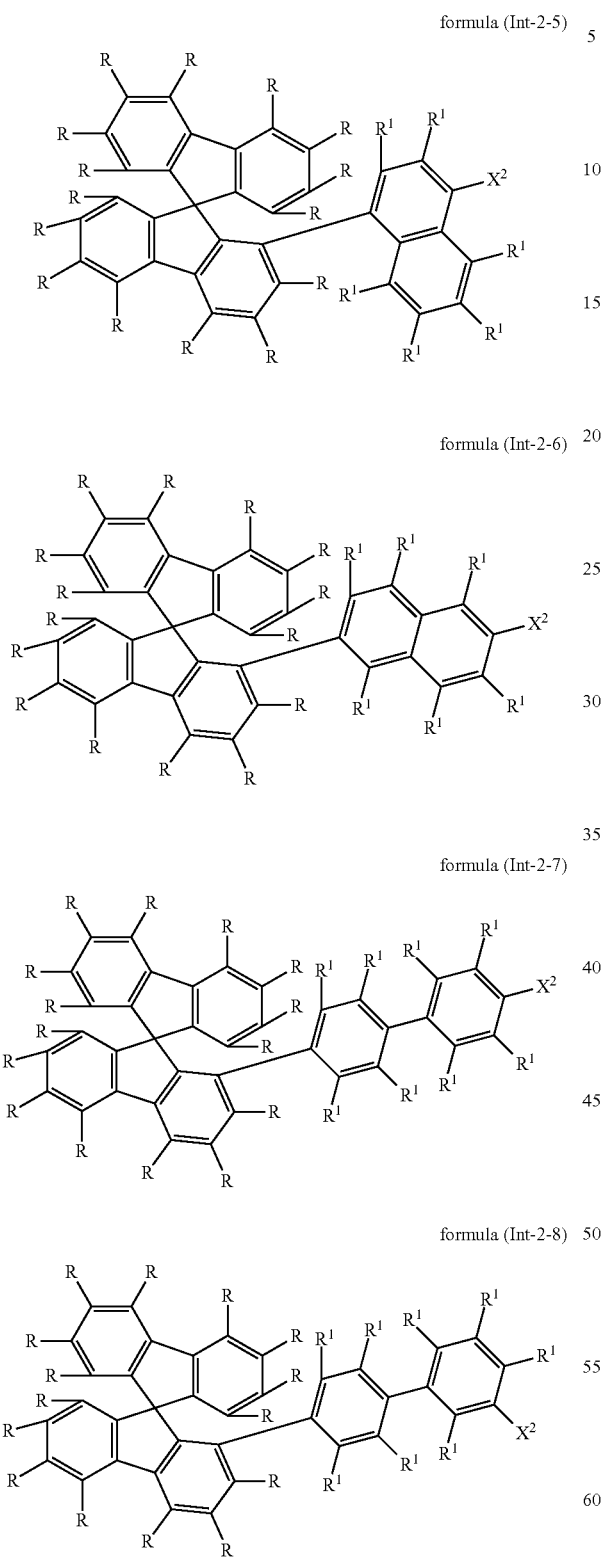
formula (Int-2-5)
formula (Int-2-6)
formula (Int-2-7)
formula (Int-2-8)
where the symbols have the same meaning as in claim 1.
5. The compound according to claim 1, selected from the compounds of formulae (Int-2-1-1) to (Int-2-8-1),
314
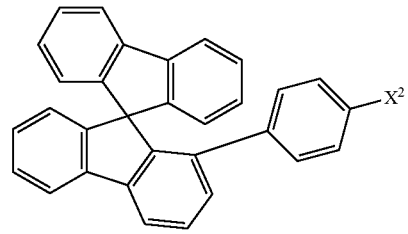
formula (Int-2-1-1)
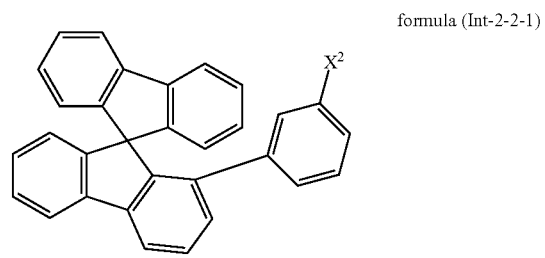
formula (Int-2-2-1)
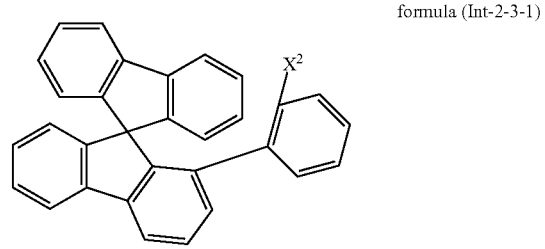
formula (Int-2-3-1)
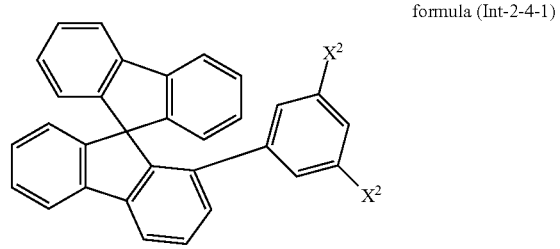
formula (Int-2-4-1)
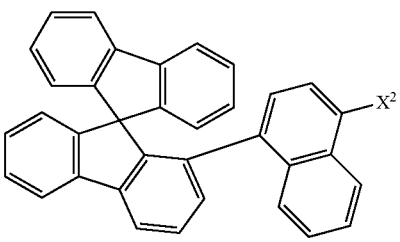
formula (Int-2-5-1)
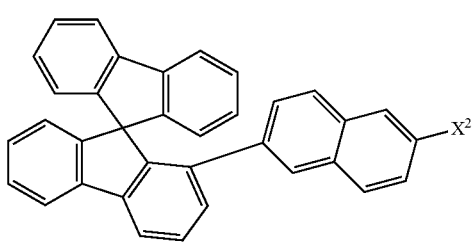
formula (Int-2-6-1)

-continued formula (Int-2-7-1)

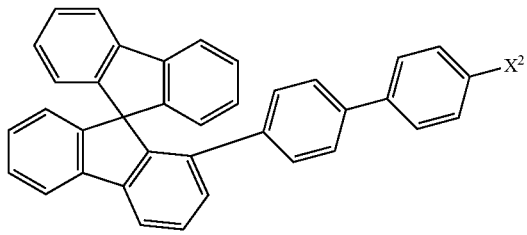

formula (Int-2-8-1)

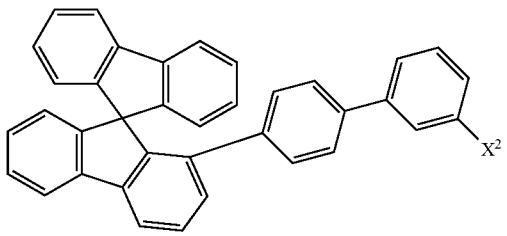

where X² has the same meaning as in claim 1.

6. A compound of formula (1-1) or (1-2), formula (1-1)

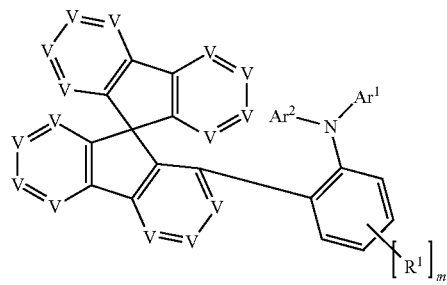

formula (1-2)

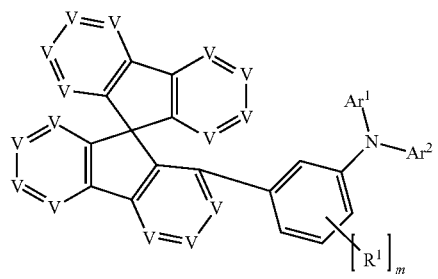

where the symbols V, $R^1$ have the same meaning as in claim 1, $Ar^1$, $Ar^2$ are, identically or differently, an aromatic or heteroaromatic ring system having 5 to 60 aromatic ring atoms, which may be substituted by one or more radicals $R^2$; $Ar^1$ and $Ar^2$ here may be connected via a single bond or a divalent bridge selected from —N($R^2$)—, —O—, —S—, —C($R^2$)$_2$—, —C($R^2$)$_2$—C($R^2$)$_2$—, —Si($R^2$)$_2$— and —B($R^2$)—; and where m is 0, 1, 2, 3 or 4.

7. The compound according to claim 6, selected from the compounds of formulae (1-1-1) and (1-2-1), formula (1-1-1)

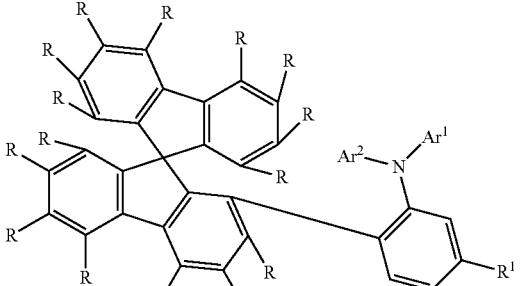

formula (1-2-1)

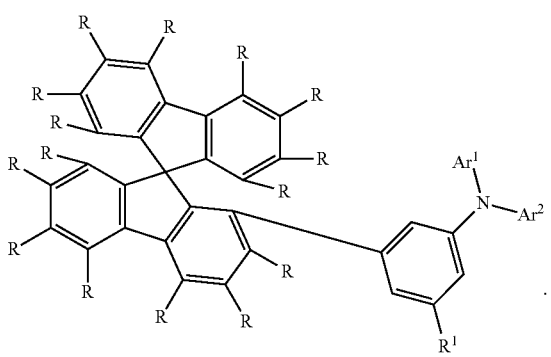

8. The compound according to claim 6, selected from the compounds of formula (1-1-1a) and (1-2-1a), formula (1-1-1a)

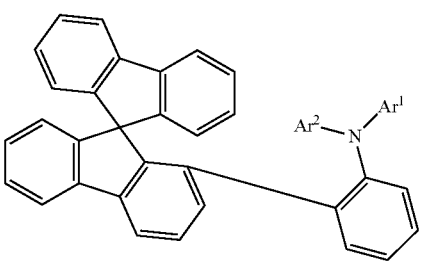

formula (1-2-1a)

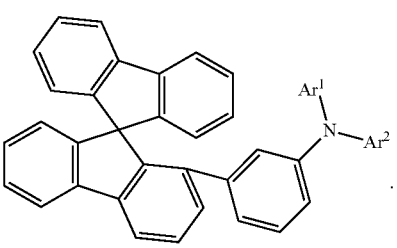

9. The compound according to claim 6, wherein $Ar^1$ and $Ar^2$ are selected, identically or differently on each occurrence from the groups of the following formulae (A-1) to (A-48),

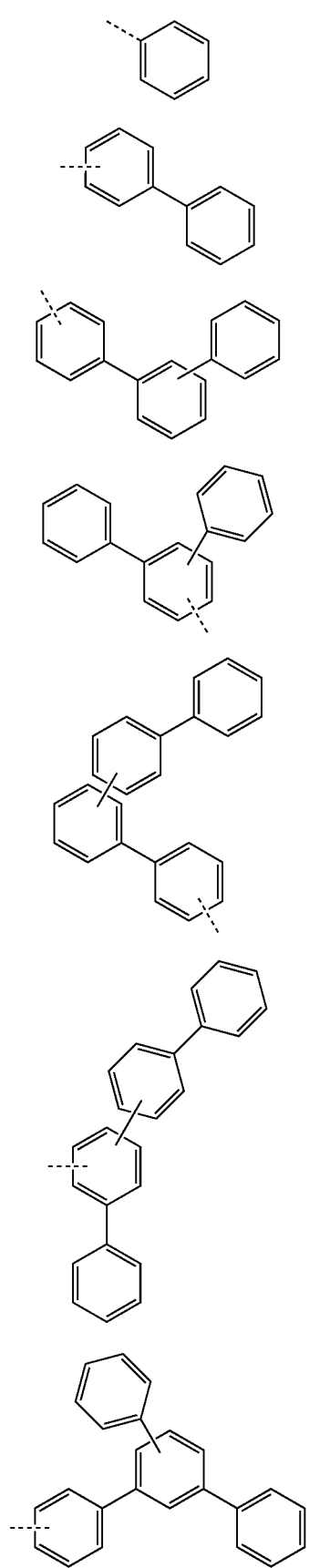
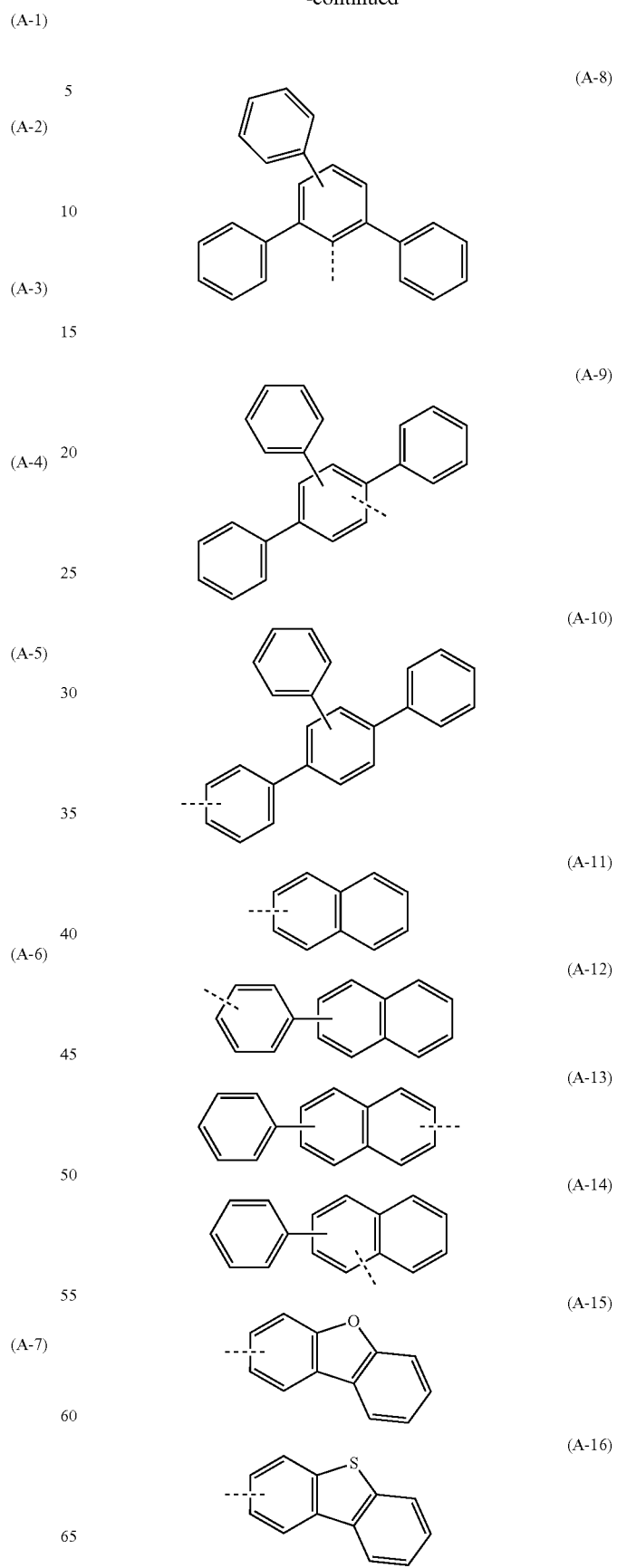

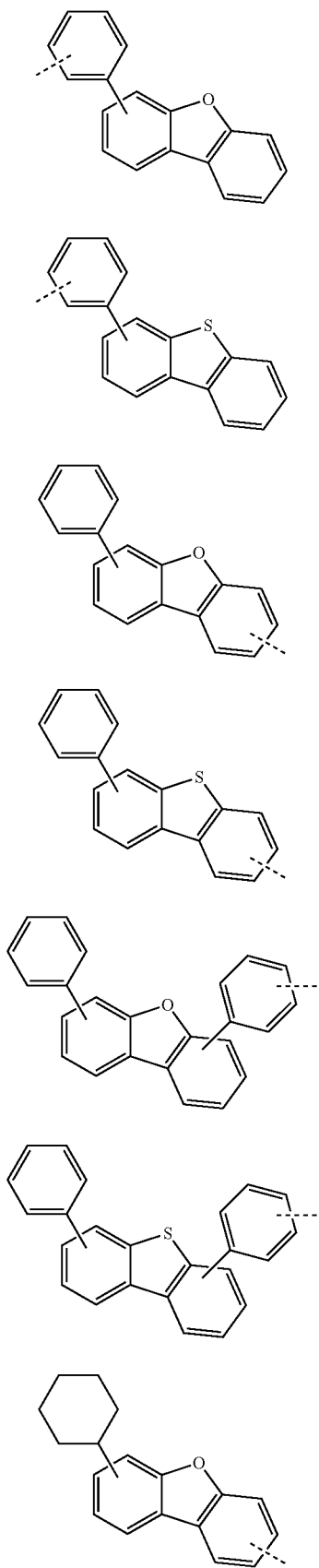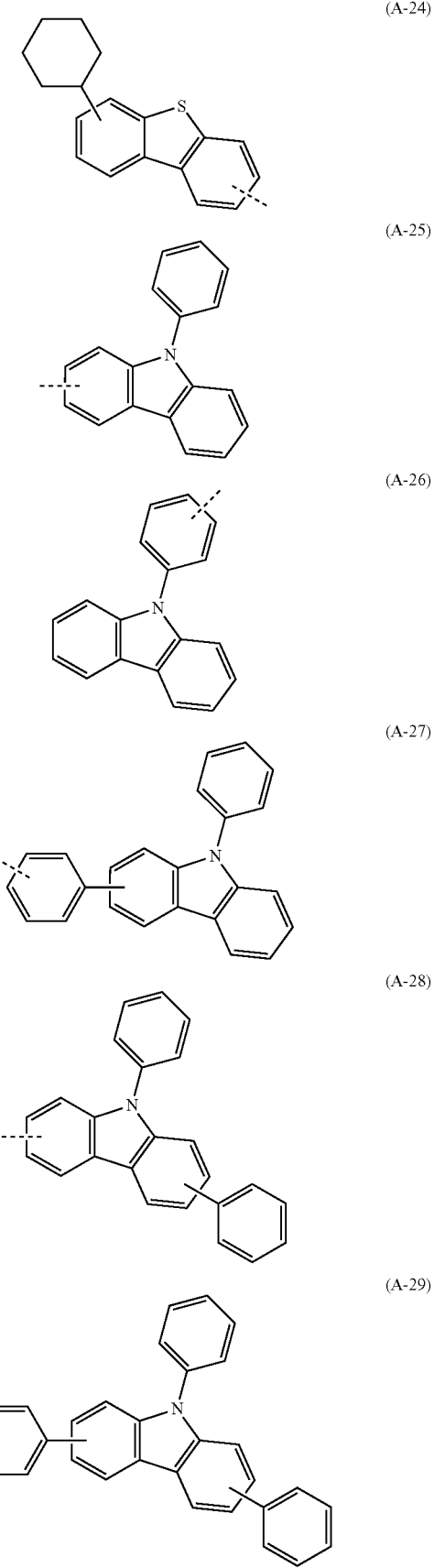

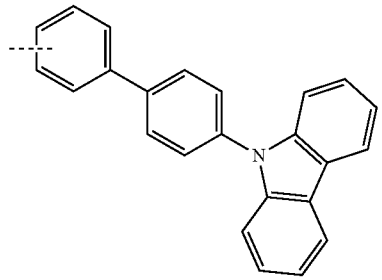
(A-30)
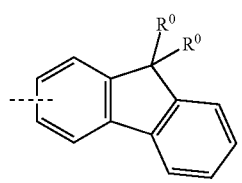
(A-31)
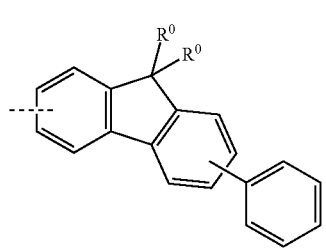
(A-32)
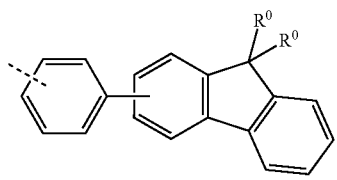
(A-33)
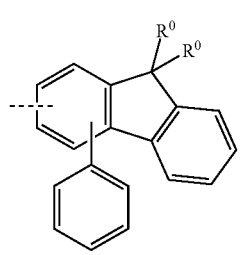
(A-34)
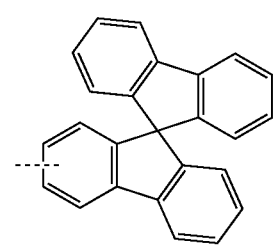
(A-35)
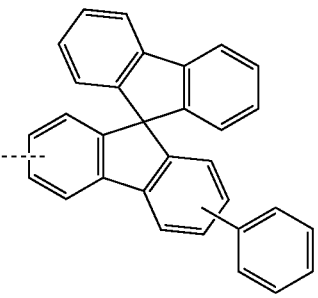
(A-36)
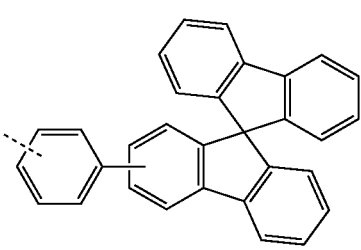
(A-37)
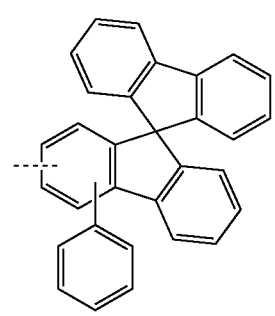
(A-38)
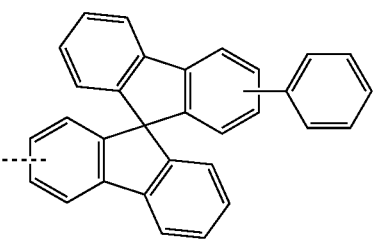
(A-39)
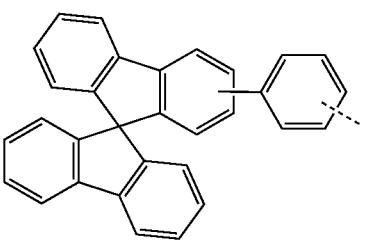
(A-40)
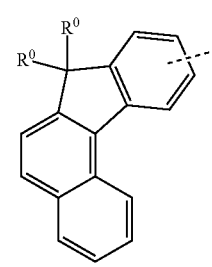
(A-41)

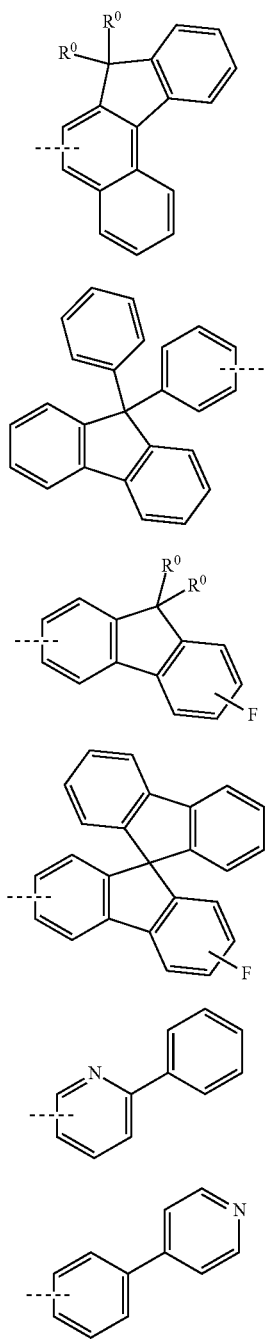
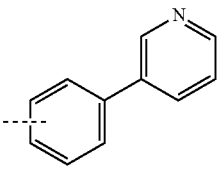

where the dashed bonds indicate the bonds to the nitrogen atom, where the groups of formulae (A-1) to (A-48) may further be substituted at each free position by a group $R^2$ as defined in claim 1, where the group $R^0$, in formulae (A-31) to (A-34), (A-41), (A-42) and (A-44), is selected on each occurrence, identically or differently, from the group consisting of H, D, F, CN, $Si(R^3)_3$, a straight-chain alkyl group having 1 to 10 C atoms or a branched or cyclic alkyl group having 3 to 10 C atoms, each of which may be substituted by one or more radicals $R^3$, an aryl or heteroaryl group having 5 to 18 aromatic ring atoms, which may be substituted by one or more radicals $R^3$, where two adjacent substituents $R^0$ may form a mono- or polycyclic, aliphatic ring system or aromatic ring system, which may be substituted by one or more radicals $R^3$.

10. Electronic device comprising at least one compound according to claim 6, selected from the group consisting of organic electroluminescent devices, organic integrated circuits, organic field-effect transistors, organic thin-film transistors, organic light-emitting transistors, organic solar cells, dye-sensitised organic solar cells, organic optical detectors, organic photoreceptors, organic field-quench devices, light-emitting electrochemical cells, organic laser diodes and organic plasmon emitting devices.

11. Electronic device according to claim 10, which is an organic electroluminescent device, characterised in that the at least one compound is employed as hole-transport material in a hole-transport or hole-injection or exciton-blocking or electron-blocking layer or as matrix material for fluorescent or phosphorescent emitters.

12. A formulation comprising at least one compound according to claim 6 and at least one solvent.

13. A mixture comprising at least one compound according to claim 6 and at least one further compound.

* * * * *